United States Patent
Akritopoulou-Zanze et al.

(10) Patent No.: US 9,187,483 B2
(45) Date of Patent: Nov. 17, 2015

(54) MODULATORS OF 5-HT RECEPTORS AND METHODS OF USE THEREOF

(75) Inventors: Irini Akritopoulou-Zanze, Libertyville, IL (US); Wilfried Braje, Mannheim (DE); Stevan W. Djuric, Libertyville, IL (US); Noel S. Wilson, Kenosha, WI (US); Sean C. Turner, Mannheim (DE); Albert W. Kruger, Pleasant Prairie, WI (US); Ana-Lucia Relo, Gönnheim (DE); Shashank Shekhar, Highland Park, IL (US); Dennie S. Welch, Lake Bluff, IL (US); Hongyu Zhao, Libertyville, IL (US); Jorge Gandarilla, North Riverside, IL (US); Alan F. Gasiecki, Vernon Hills, IL (US); Huanqiu Li, Wilmette, IL (US); Christina M. Thompson, Evanston, IL (US); Min Zhang, Libertyville, IL (US)

(73) Assignees: AbbVie Inc., North Chicago, IL (US); AbbVie Deutschland GmbH & Co. KG, Wiesbaden (DE)

( * ) Notice: Subject to any disclaimer, the term of this patent is extended or adjusted under 35 U.S.C. 154(b) by 296 days.

(21) Appl. No.: 12/784,624

(22) Filed: May 21, 2010

(65) Prior Publication Data

US 2010/0298292 A1 Nov. 25, 2010

Related U.S. Application Data

(60) Provisional application No. 61/180,569, filed on May 22, 2009.

(51) Int. Cl.
*A61K 31/55* (2006.01)
*C07D 487/04* (2006.01)
*C07D 491/04* (2006.01)
*C07D 495/04* (2006.01)

(52) U.S. Cl.
CPC ............ *C07D 487/04* (2013.01); *C07D 491/04* (2013.01); *C07D 495/04* (2013.01)

(58) Field of Classification Search
CPC .............................. A61K 31/55; C07D 487/04
USPC ...................... 514/211.04; 540/521
See application file for complete search history.

(56) References Cited

U.S. PATENT DOCUMENTS

| | | | |
|---|---|---|---|
| 4,268,513 A | 5/1981 | Shapiro | |
| 4,350,814 A | 9/1982 | Shapiro | |
| 4,440,768 A | 4/1984 | Shapiro | |
| 5,049,564 A | 9/1991 | DeBernardis et al. | |
| 5,317,017 A | 5/1994 | Ok et al. | |
| 5,491,141 A | 2/1996 | Warshawsky et al. | |
| 5,491,142 A | 2/1996 | Warshawsky et al. | |
| 5,597,922 A | 1/1997 | Cai et al. | |
| 5,880,122 A | 3/1999 | Trybulski et al. | |
| 7,572,805 B2 | 8/2009 | Fevig et al. | |
| 7,618,980 B2 | 11/2009 | Fevig et al. | |
| 2005/0033053 A1 | 2/2005 | Lee et al. | |
| 2007/0015746 A1 | 1/2007 | Martin et al. | |
| 2007/0049574 A1 | 3/2007 | Amrein et al. | |
| 2007/0155718 A1 | 7/2007 | Durrant et al. | |
| 2007/0191337 A1 | 8/2007 | Ivashchenko et al. | |
| 2007/0197594 A1 | 8/2007 | Hayashibe et al. | |
| 2007/0225274 A1 | 9/2007 | Jacobson | |
| 2007/0225277 A1 | 9/2007 | Rosenzweig-Lipson | |
| 2008/0146583 A1 | 6/2008 | McMurray et al. | |
| 2008/0161292 A1 | 7/2008 | Giranda et al. | |
| 2009/0221561 A1 | 9/2009 | Schor et al. | |
| 2010/0210680 A1 | 8/2010 | Grove et al. | |

FOREIGN PATENT DOCUMENTS

| | | |
|---|---|---|
| EP | 415634 A | 3/1991 |
| JP | 09221475 A | 8/1997 |
| SU | 327678 | 1/1972 |
| WO | 9006927 A | 6/1990 |
| WO | 9404531 A1 | 3/1994 |
| WO | 9407483 A1 | 4/1994 |

(Continued)

OTHER PUBLICATIONS

Montoya et al., Novel Medications to Treat Addictive Disorders, Curren Psychiatry Report, vol. 10, No. 5, pp. 392-398, Oct. 2008.*

(Continued)

*Primary Examiner* — Brenda Coleman
(74) *Attorney, Agent, or Firm* — Lisa V. Mueller; Michael Best & Friedrich LLP

(57) ABSTRACT

The present application relates to aryl- and heteroaryl-fused decahydropyrroloazepine, octahydrooxepinopyrrole, octahydropyrrolothiazepine dioxide, decahydrocyclohepta[c]pyrrole, and octahydrocyclohepta[c]pyrrole derivatives of formula (I)

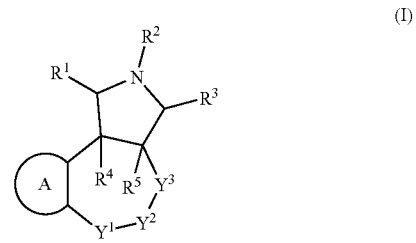

wherein $R^1$, $R^2$, $R^3$, $R^4$, $R^5$, A, $Y^1$, $Y^2$, and $Y^3$ are as defined in the specification. The present application also relates to compositions comprising such compounds, processes for making such compounds, and methods of treating disease conditions using such compounds and compositions, and methods for identifying such compounds.

13 Claims, 20 Drawing Sheets

(56) References Cited

FOREIGN PATENT DOCUMENTS

| WO | 9604288 | A2 | 2/1996 |
|---|---|---|---|
| WO | 9638435 | A1 | 12/1996 |
| WO | 9940093 | A2 | 8/1999 |
| WO | 200147510 | A2 | 7/2001 |
| WO | 02100350 | A2 | 12/2002 |
| WO | 2005009387 | A2 | 2/2005 |
| WO | 2005105805 | A1 | 11/2005 |
| WO | 2006033318 | A1 | 3/2006 |
| WO | 2006071740 | A2 | 7/2006 |
| WO | 2006134163 | | 12/2006 |
| WO | WO2007006566 | A1 | 1/2007 |
| WO | 2007015931 | A2 | 2/2007 |
| WO | 2007023273 | A1 | 3/2007 |
| WO | 2007053725 | A2 | 5/2007 |
| WO | 2007067781 | A2 | 6/2007 |
| WO | 2009037220 | A1 | 3/2009 |
| WO | 2009120733 | A1 | 10/2009 |
| WO | 2010135560 | A1 | 11/2010 |

OTHER PUBLICATIONS

Ahmed A., et al., "Synthesis of a potent (±)-4-(2-hydroxyphenyl) analogue of the acromelic acids by dearomatising cyclisation of a lithiated N-p-methoxybenzy1-4-methoxy-l-naphthamide", 2001, 42, 3407-3410.
"Antipsychotic Dopamine D2 Receptor Antagonist 5-HT2 Receptor Antagonist", Drugs Of The Future, 1993, 18, 1117-1123.
International Search Report and Written Opinion for PCT/US2010/035626 mailed on Aug. 31, 2010, 12 pages.
Arjona A. A., et al., "Effect of a 5-HT(2C) serotonin agonist, dexnorfenfluramine, on amyloid precursor protein metabolism in guinea pigs", Brain Res, 2002, 951 (1), 135-140.
Barr A. M., et al., "The selective serotonin-2A receptor antagonist M100907 reverses behavioral deficits in dopamine transporter knockout mice", Neuropsychopharmacology, 2004, 29 (2), 221-228.
Berge S. M., et al., "Pharmaceutical Salts," J Pharmaceutical Sciences, 1977, 66 (1), 1-19.
Bitner et al., "Broad-spectrum efficacy across cognitive domains by alpha7 nicotinic acetylcholine receptor agonism correlates with activation of ERK1/2 and CREB phosphorylation pathways," J. Neurosci., 2007, vol. 27 (39), pp. 10578-10587.
Brennan P. E., et al., "Discovery of a novel azepine series of potent and selective 5-HT2C agonists as potential treatments for urinary incontinence", Bioorg Med Chem Lett, 2009, 19 (17), 4999-5003.
Brus R., et al., "Influence of 5,7-dihydroxytryptamine (5,7-DHT) on the antinociceptive effect of serotonine (5-HT) 5-HT 2C receptor agonist in male and female rats", Med Sci Monit, 1997, 3 (5), 654-656.
Bryant H. U., et al., "A novel class of 5-HT2A receptor antagonists: aryl aminoguanidines", Life Sci., 1996, 59 (15), 1259-1268.
Bubar M. J., et al., "Prospects for serotonin 5-HT2R pharmacotherapy in psychostimulant abuse", Prog Brain Res, 2008, 172, 319-346.
Cheng,Y. et al., "Relationship Between the Inhibition Constant (KI) and the Concentration of Inhibitor Which Causes 50 Per Cent Inhibition (I.sub.50) of An Enzymatic Reaction," Biochemical Pharmacology, vol. 22, pp. 3099-3108, 1973.
Chou-Green J. M., et al., "Compulsive behavior in the 5-HT2C receptor knockout mouse", Physiol Behav, 2003, 78 (4-5), 641-649.
Chou-Green J. M., et al., "Repeated stress in young and old 5-HT(2C) receptor knockout mice", Physiol Behav, 2003, 79 (2), 217-226.
Cryan J. F., et al., "Antidepressant-like behavioral effects mediated by 5- Hydroxytryptamine(2C) receptors", J Pharmacol Exp Ther, 2000, 295 (3), 1120-1126.
Davis K. L., et al., "Dopamine in schizophrenia: a review and reconceptualization", Am J Psychiatry, 1991, 148 (11), 1474-1486.
Dekeyne A., et al., "S32006, a novel 5-HT2C receptor antagonist displaying broad-based antidepressant and anxiolytic properties in rodent models", Psychopharmacology, 2008, 199 (4), 549-568.

Di Giovanni G., et al., "Preferential modulation of mesolimbic vs. nigrostriatal dopaminergic function by serotonin(2C/2B) receptor agonists: a combined in vivo electrophysiological and microdialysis study", Synapse, 2000, 35 (1), 53-61.
Di Matteo V., et al., "SB 242084, a selective serotonin2C receptor antagonist, increases dopaminergic transmission in the mesolimbic system", Neuropharmacology, 1999, 38 (8), 1195-1205.
Du Y., et al., "Editing of the serotonin 2C receptor pre-mRNA: Effects of the Morris Water Maze", Gene, 2007, 391 (1-2), 186-197.
Dunlop J., et al., "Pharmacological Profile of the 5-HT2C Receptor Agonist WAY-163909; Therapeutic Potential in Multiple Indications", CNS Drug Rev, 2006, 12 (3-4), 167-177.
Dunlop J., et al., "WAY-163909 [(7bR,10aR)-1,2,3,4,8,9,10,10a-Octahydro-7bHcyclopenta-[ b][1,4]diazepino[6,7,1hi]indole], a Novel 5-Hydroxytryptamine 2C Receptor-Selective Agonist with Anorectic Activity", J Pharmacol Exp Ther, 2005, 313 (2), 862-869.
Esposito E., et al., "Role of central 5-HT2C receptor in the control of basal ganglia functions", The Basal Ganglia Pathophysiology, 2007, 97-127.
Fletcher P. J., et al., "Serotonin receptors as potential targets for modulation of nicotine use and dependence", Prog Brain Res, 2008, 172, 361-383.
Frank M. G. et al., "Sleep and sleep homeostasis in mice lacking the 5-HT2c receptor", Neuropsychopharmacology, 2002, 27 (5), 869-873.
Furniss B. S. et al, "Practical Organic Chemistry", 5th Ed., Longman Scientific & Technical & John Wiley & Sons, Inc., Table of Contents, 1989.
Greene T. W. et al., "Protective Groups in Organic Synthesis," 1999, Ed. 3, John Wiley & Sons, pp. 494-653.
Isaac M., "Serotonergic 5-HT2C receptors as a potential therapeutic target for the design antiepileptic drugs", Curr Top Med Chem, 2005, 5 (1), 59-67.
IUPAC Commission on Nomenclature of Organic Chemistry: Rules for the Nomenclature of Organic Chemistry Section E: Stereochemistry, Pure Appl Chem, 1976, 45, 13-30.
Iwamoto K., et al., "Altered RNA editing of serotonin 2C receptor in a rat model of depression", Neurosci Res, 2005, 53 (1), 69-76.
Iwamoto K., et al., "RNA editing of serotonin 2C receptor in human postmortem brains of major mental disorders", Neurosci Lett, 2003, 346 (3), 169-172.
Kao T., et al., "Role of the 5-HT2C receptor in improving weight-supported stepping in adult rats spinalized as neonates", Brain Res, 2006, 1112 (1), 159-168.
Kaufman M. J., et al., "Cyclic GMP inhibits phosphoinositide turnover in choroid plexus: evidence for interactions between second messengers concurrently triggered by 5-HT2C receptors", Neurosci Lett, 1996, 206 (2-3), 153-156.
Leone M., et al., "The serotonergic system in migraine", J Headache Pain, 2001, 2, S43-S46.
Lopez-Gimenez J. F., et al., "Regional distribution and cellular localization of 5-HT2C receptor mRNA in monkey brain: comparison with [3H]mesulergine binding sites and choline acetyltransferase mRNA", Synapse, 2001, 42 (1), 12-26.
Marquis K. L., et al., "WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity", J Pharmacol Exp Ther, 20, 2007.
Mbaki Y., et al., "Investigation of the role of 5-HT2 receptor subtypes in the control of the bladder and the urethra in the anaesthetized female rat", Br J Pharmacol, 2008, 155 (3), 343-356.
Monsma F. J. et al., "Cloning and expression of a novel serotonin receptor with high affinity for tricyclic psychotropic drugs", Mol Pharmacol, 1993, 43 (3), 320-327.
Motofei I. G. et al., "A dual physiological character for sexual function: the role of serotonergic receptors", BJU Int, 2008, 101 (5), 531-534.
Munson P. J. et al., "Ligand: a versatile computerized approach for characterization of ligand-binding systems," Anal Biochem, 1980, vol. 107, pp. 220-239.
Nakae A., et al., "Serotonin2C receptor mRNA editing in neuropathic pain model", Neurosci Res, 2008, 60 (2), 228-231.

(56) References Cited

OTHER PUBLICATIONS

Nakae A., et al., "The role of RNA editing of the serotonin 2C receptor in a rat model of oro-facial neuropathic pain", Eur J Neurosci, 2008, 27 (9), 2373-2379.
Niswender C. M., et al., "RNA editing of the human serotonin 5-HT2C receptor. alterations in suicide and implications for serotonergic pharmacotherapy", Neuropsychopharmacology, 2001, 24 (5), 478-491.
Nunes-De-Souza V., et al., "5-HT2 receptor activation in the midbrain periaqueductal grey (PAG) reduces anxiety-like behaviour in mice", Behav Brain Res., 2008, 187 (1), 72-79.
Obato H., et al., "Antiallodynic effects of intrathecally administered 5-HT(2C) receptor agonists in rats with nerve injury", Pain, 2004, 108 (1-2), 163-169.
Obato H., et al., "Possible involvement of spinal noradrenergic mechanisms in the antiallodynic effect of intrathecally administered 5-HT2C receptor agonists in the rats with peripheral nerve injury", Eur J Pharmacol, 2007, 567 (1-2), 89-94.
Olson J., et al., "Customization of a Commercially Available Prep Scale SFC System to Provide Enhanced Capabilities", JALA, 2002, 7 (4), 69-74.
Pompeiano M., et al., "Distribution of the serotonin 5-HT2 receptor family mRNAs: comparison between 5-HT2A and 5-HT2C receptors", Brain Res Mol Brain Res, 1994, 23 (1-2), 163-178.
Prescott et al., "Lipid Vesicles as Carriers for Introducing Biologically Active Materials into Cells," Methods in Cell Biology, 1976, vol. 14, Academic Press, pp. 33-71.
Remington G., et al., "Atypical antipsychotics: are some more atypical than others?", Psychopharmacology, 2000, 148, 3-15.
Rocha B. A., et al., "Enhanced locomotor, reinforcing, and neurochemical effects of cocaine in serotonin 5-hydroxytryptamine 2C receptor mutant mice", J Neurosci, 2002, 22 (22), 10039-10045.
Rosenzweig-Lipson S., et al., "5-HT2C receptor agonists as an innovative approach for psychiatric disorders", Drug News Perspect, 2007, 20 (9), 565-571.
Rosenzweig-Lipson S., et al., "Antidepressant-like effects of the novel, selective, 5-HT2C receptor agonist WAY-163909 in rodents", Psychopharmacology, 2007, 192 (2), 159-170.
Rosenzweig-Lipson S., et al., "Antiobesity-like effects of the 5-HT2C receptor agonist WAY-161503", Brain Res, 2006, 240-251.
Schmauss C., "Serotonin 2C receptors: suicide, serotonin, and runaway RNA editing", Neuroscientist, 2003, 9 (4), 237-242.
Sharif N. A., et al., "AL-34662: a potent, selective, and efficacious ocular hypotensive serotonin-2 receptor agonist", J Ocul Pharmacol Ther, 2007, 23 (1), 1-13.
Shimada I., et al., "Synthesis and structure-activity relationships of a series of benzazepine derivatives as 5-HT2C receptor agonists", Bioorg Med Chem, 2008, 16 (6), 3309-3320.
Siuciak J. A., et al., "CP-809,101, a selective 5-HT2C agonist, shows activity in animal models of antipsychotic activity", Neuropharmacology, 2007, 52 (2), 279-290.
Smith B. M., et al., "Discovery and structure-activity relationship of (1R)-8-chloro-2,3,4,5-tetrahydro-1-methyl-1H-3-benzazepine (Lorcaserin), a selective serotonin 5-HT2C receptor agonist for the treatment of obesity", J Med Chem, 2008, 51 (2), 305-313.
Tecott L. H., et al., "Eating disorder and epilepsy in mice lacking 5-HT2c serotonin receptors", Nature, 1995, 374 (6522), 542-546.
Thomsen W. J., et al., "Lorcaserin, a novel selective human 5-hydroxytryptamine2C agonist: in vitro and in vivo pharmacological characterization", J Pharmacol Exp Ther, 2008, 325 (2), 577-587.
Thorslund K., et al., "Serotonergic drugs—a possible role in the treatment of psoriasis?", Drug News Perspect, 2007, 20 (8), 521-525.
Weinberger D. R., et al, "Prefrontal function in schizophrenia: confounds and controversies", Philos Trans R Soc Lond B Biol Sci., 1996, 351 (1346), 1495-1503.
Werry T. D., et al., "RNA editing of the serotonin 5HT2C receptor and its effects on cell signalling, pharmacology and brain function", Pharmacol Ther, 2008, 119 (1), 7-23.
Feldman H.A., "Mathematical Theory of Complex Ligand-Binding at Equilibrium", Analytical Biochemistry, 1972, 48, 317-338.
Dezi, Modeling of 5-HT2A and 5-HT2C Receptors and of their Complexes with Actual and Potential Antipsychotic Drugs, PhD Thesis, Pompeu Fabra University, Barcelona, 2007, pp. 1-239; p. 72-p. 94; p. 113-p. 116; p. 149-p. 151; p. 208-p. 209.
Holenz J., et al., "Medicinal Chemistry Strategies To 5-HT(6) Receptor Ligands as Potential Cognitive Enhancers and Antiobesity Agents," Drug Discovery Today, 2006, vol. 11 (7-8), pp. 283-299.
Richter, H.G.F. et al., "Design, synthesis and evaluation of 2B-alkenyl penam sulfone acids as inhibitors of B-lacatamases," J. Med. Chem. (1996) 39:3712-3722.
"Antipsychotic Dopamine D2 receptor antagonist 5-HT2 receptor antagonist," Drugs of Future (1993) 18(12):1117-1123.
International Preliminary Report on Patentability and Written Opinion for Application No. PCT/US2010/057454, mailed on Nov. 27, 2012, 13 pages.
International Preliminary Report on Patentability for Application No. PCT/US2010/035626, mailed on Nov. 22, 2011, 1 page.
International Search Report for Application No. PCT/US2010/057454, mailed on Feb. 9, 2011, 2 pages.
Non-Final Office Action mailed Dec. 7, 2012 for U.S. Appl. No. 12/950,029, filed Nov. 19, 2010.
Notice of Allowance mailed Sep. 3, 2013 for U.S. Appl. No. 12/950,029, filed Nov. 19, 2010.
Ballaz et al., Neuroscience, 147: 428-438 (2007).
Rogers et al., Psychopharmacology, 158: 114-119 (2001).

\* cited by examiner

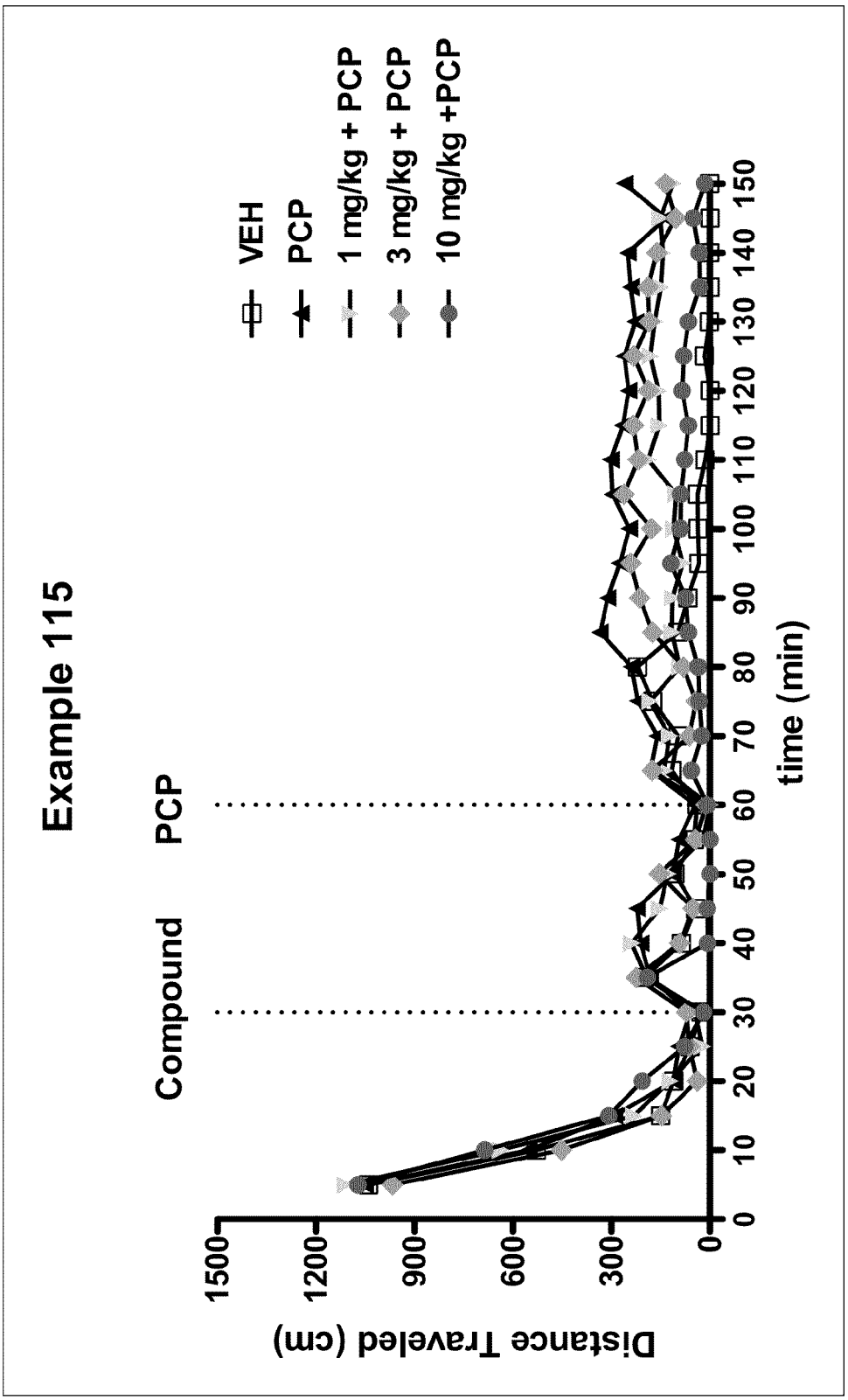
Figure 1B: Effects of Example 115 on PCP-induced hyperactivity in rats

*p<0.05, p<0.01 and *p<0.001, compared to VEH-treated group.
Mann-Whitney test

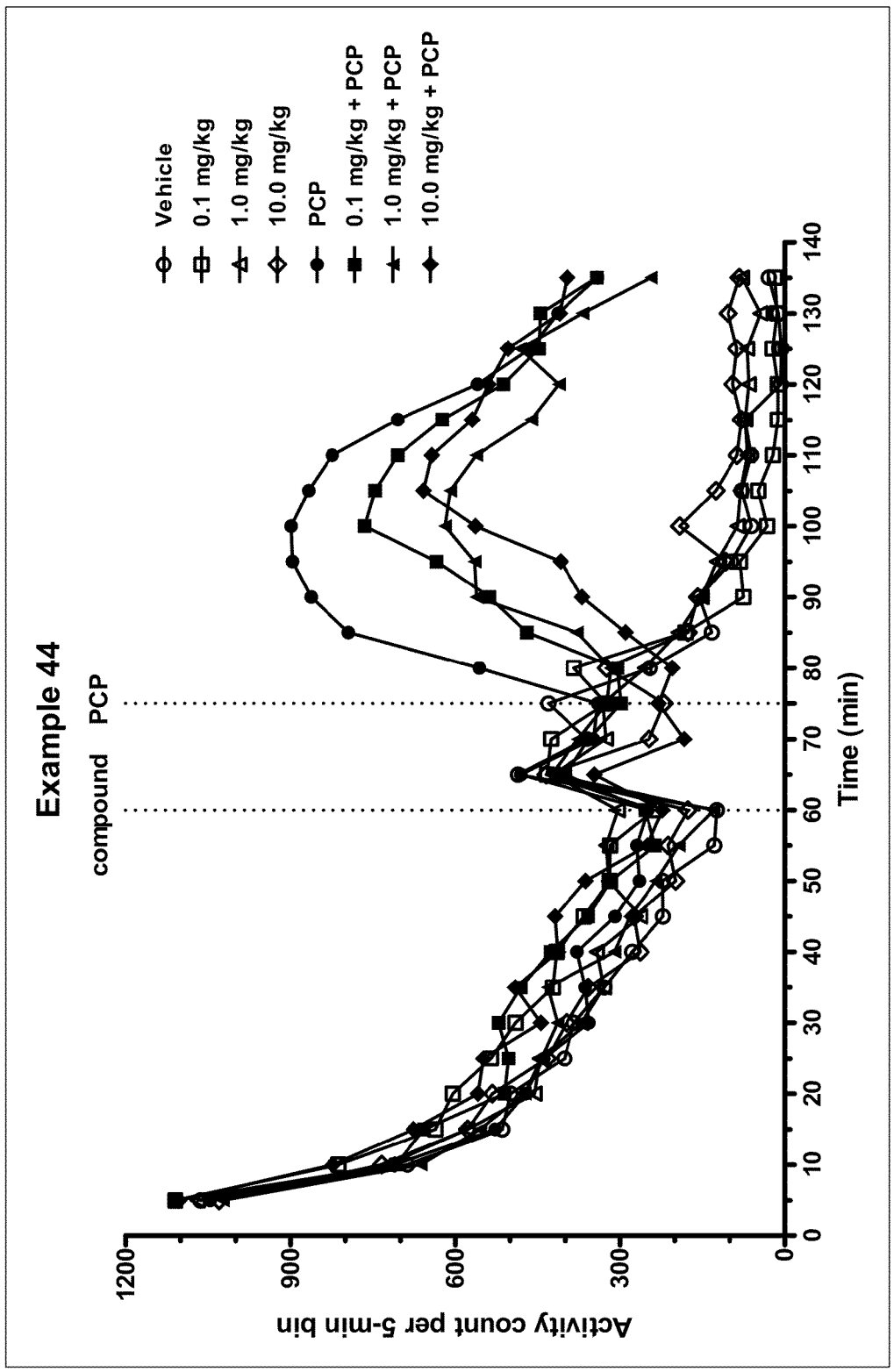
Figure 4A: Effects of Example 44 on PCP-induced hyperactivity in mice

Figure 4B: Effects of Example 44 on PCP-induced hyperactivity in mice
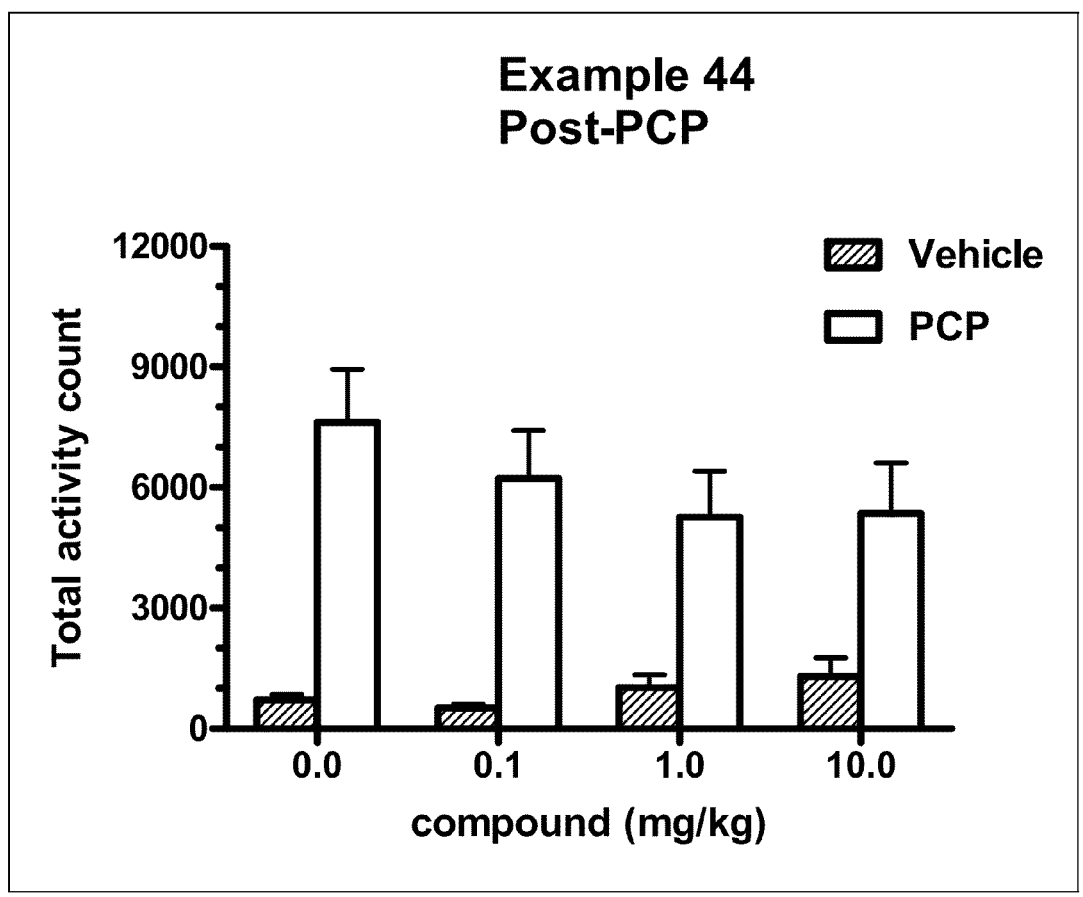

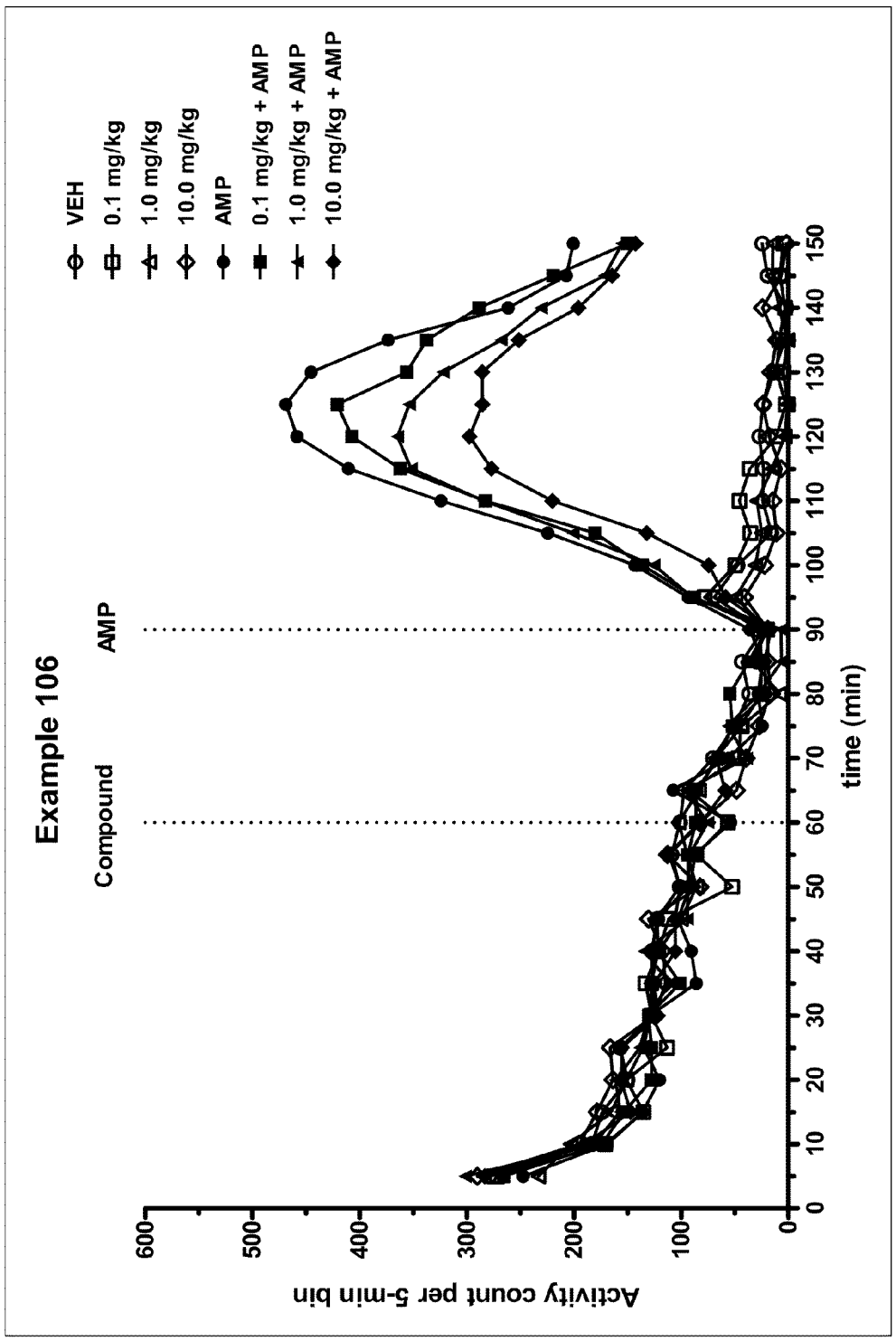
Figure 5A: Effects of Example 106 on AMP-induced hyperactivity in mice Figure 5B: Effects of Example 106 on AMP-induced hyperactivity in mice
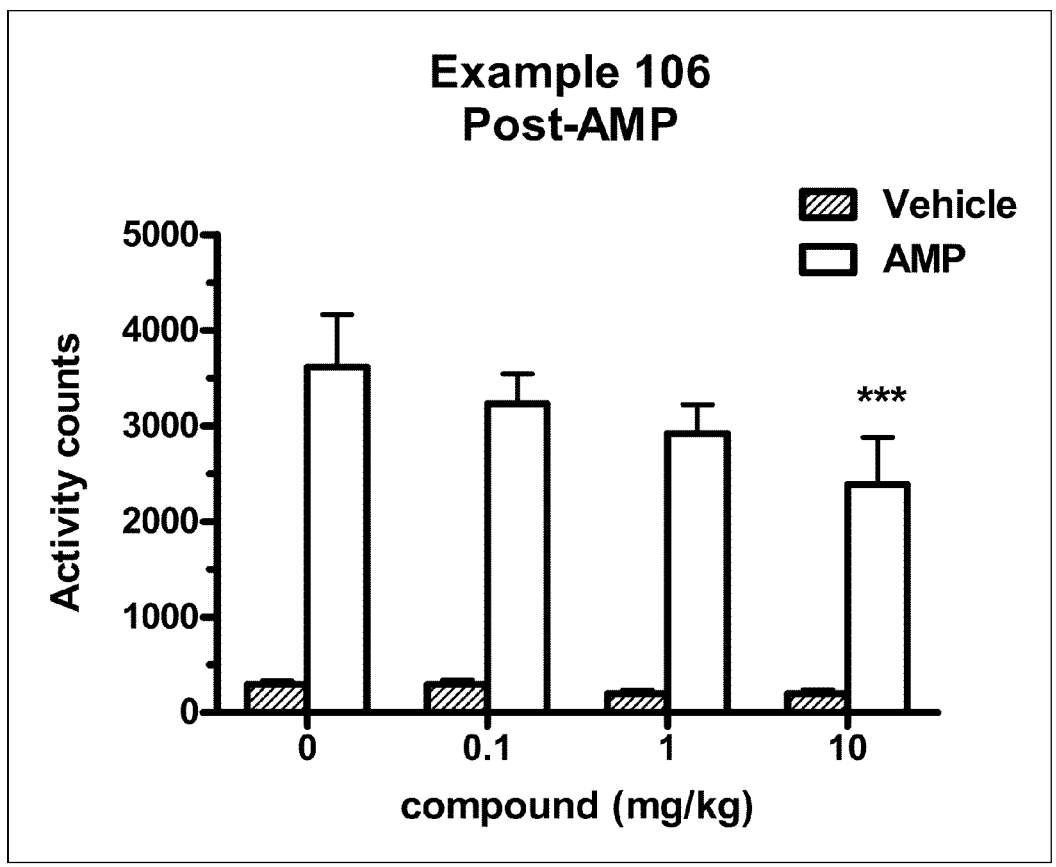

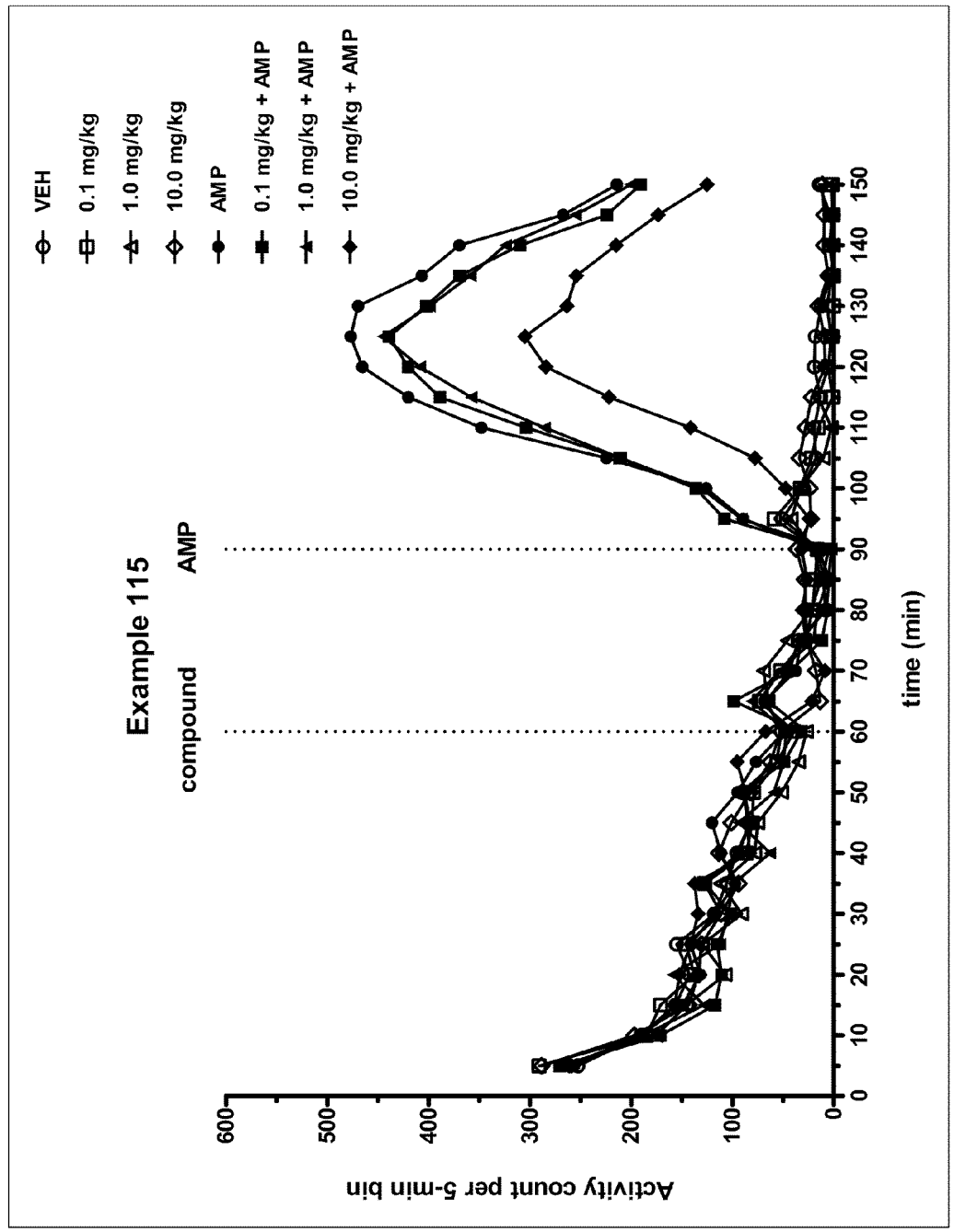
Figure 6A: Effects of Example 115 on AMP-induced hyperactivity in mice Figure 6B: Effects of Example 115 on AMP-induced hyperactivity in mice
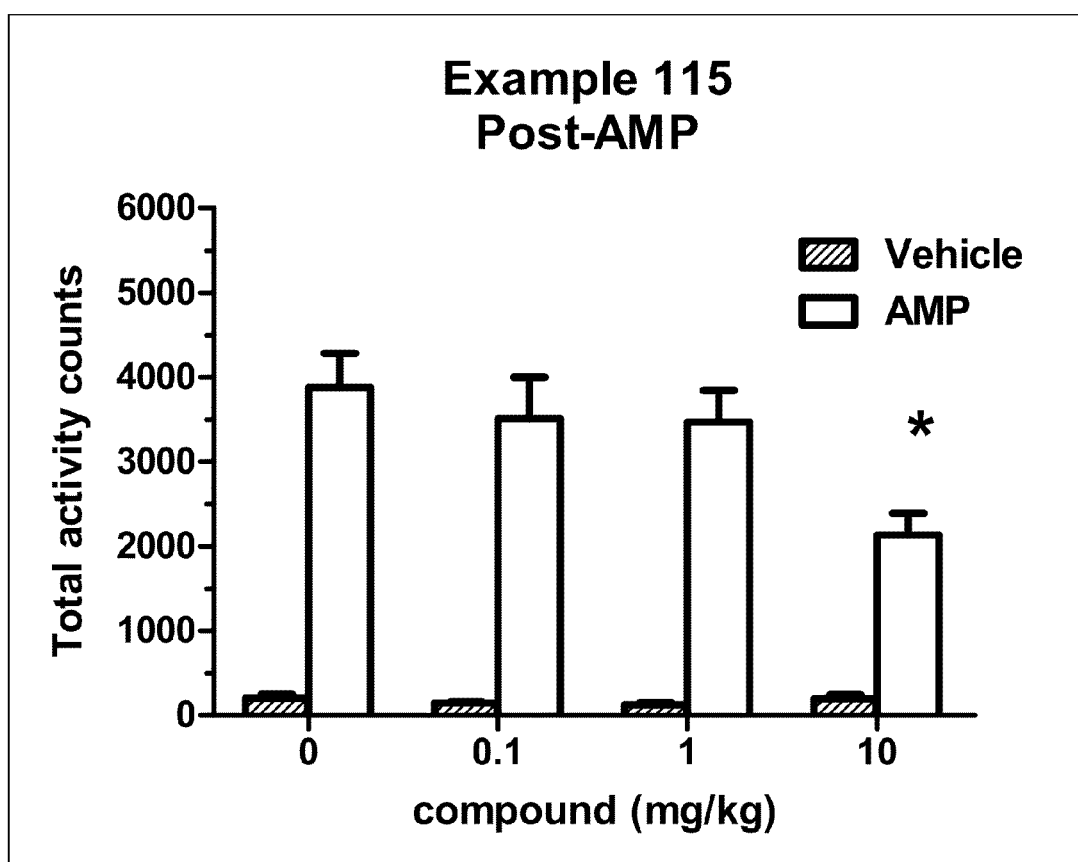

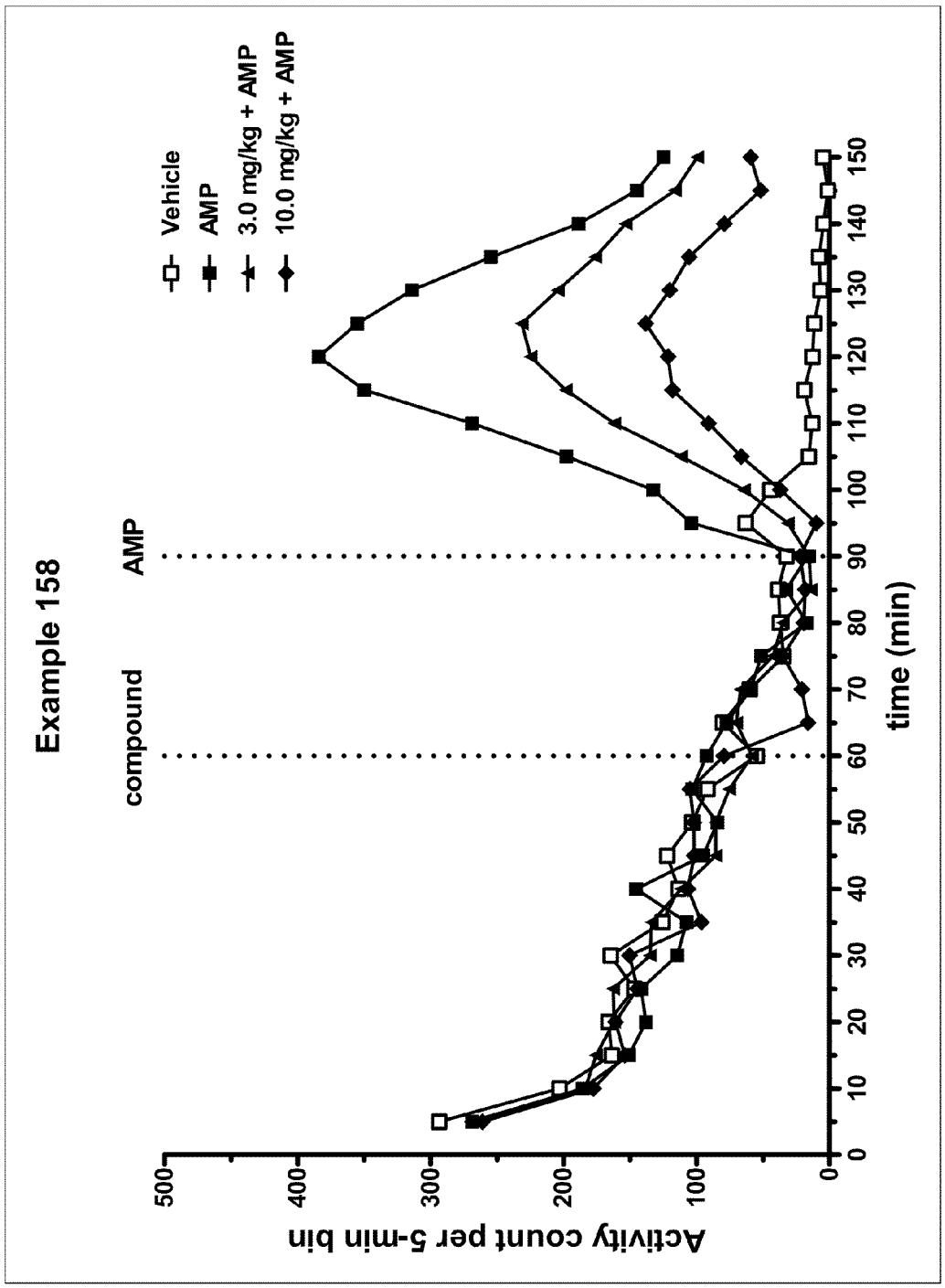
Figure 7A: Effects of Example 158 on AMP-induced hyperactivity in mice Figure 7B: Effects of Example 158 on AMP-induced hyperactivity in mice
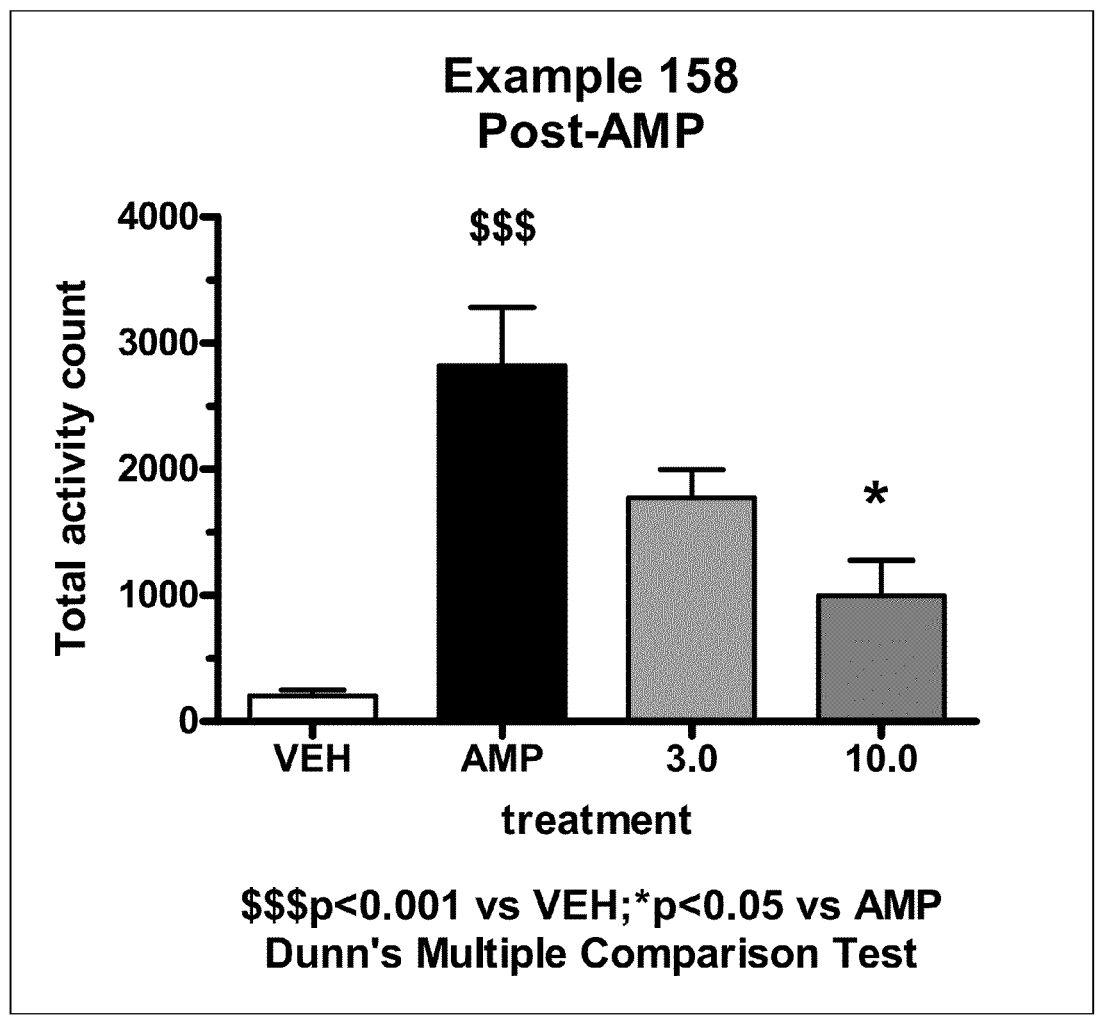

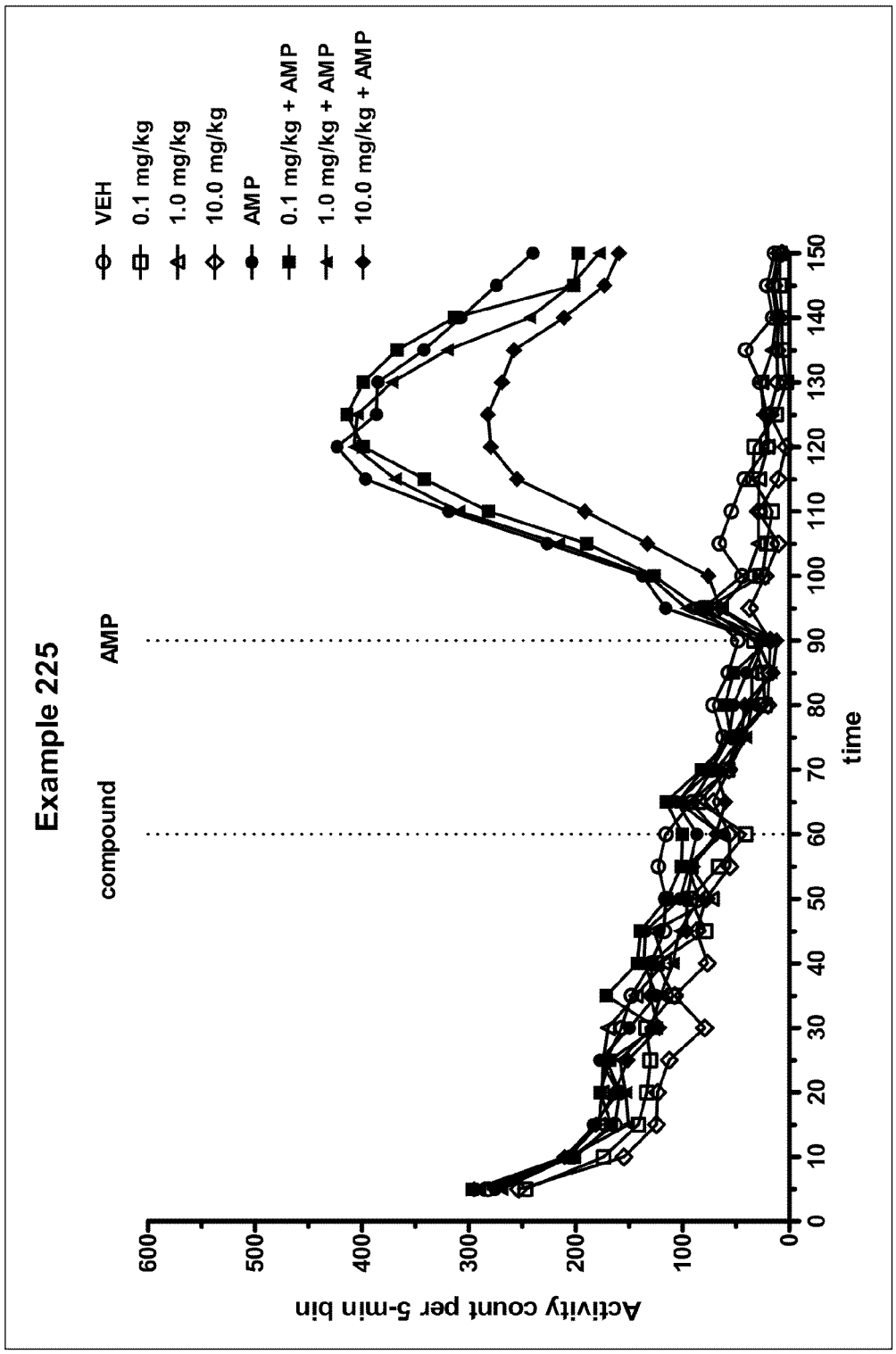
Figure 8A: Effects of Example 225 on AMP-induced hyperactivity in mice Figure 8B: Effects of Example 225 on AMP-induced hyperactivity in mice
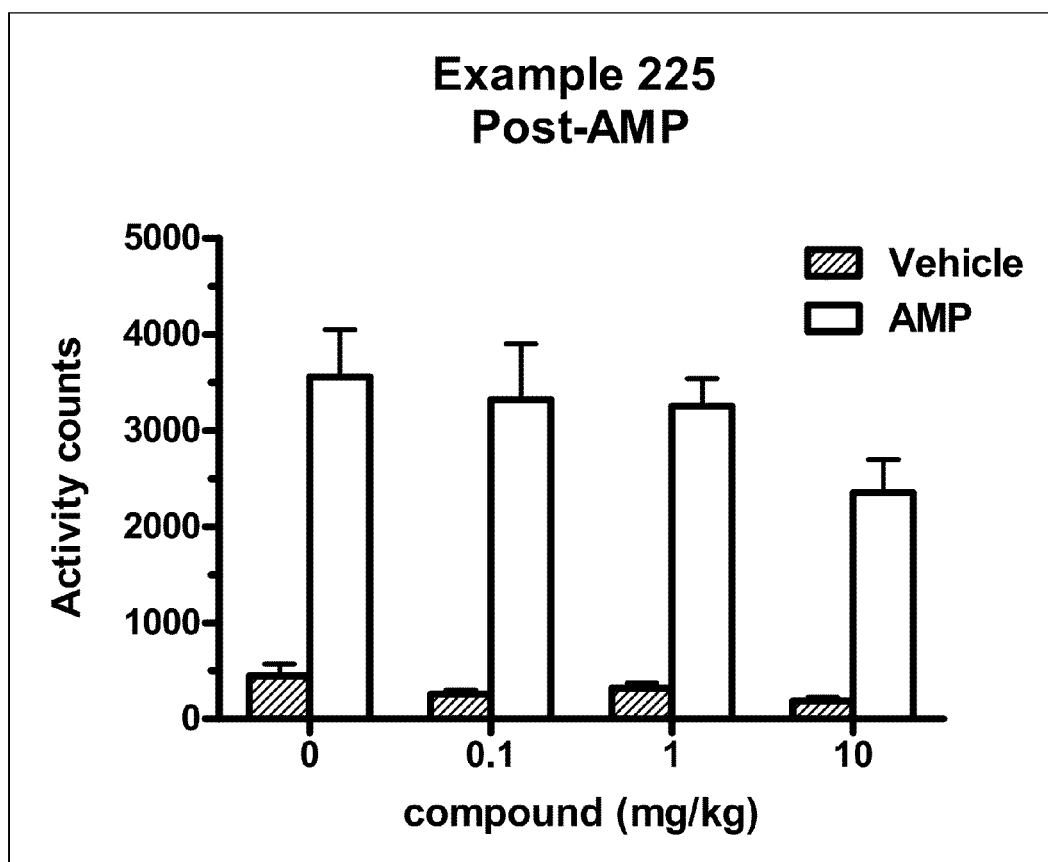

Figure 9A: Effects of Example 115 on conditioning avoidance responding in rats; avoided responses.
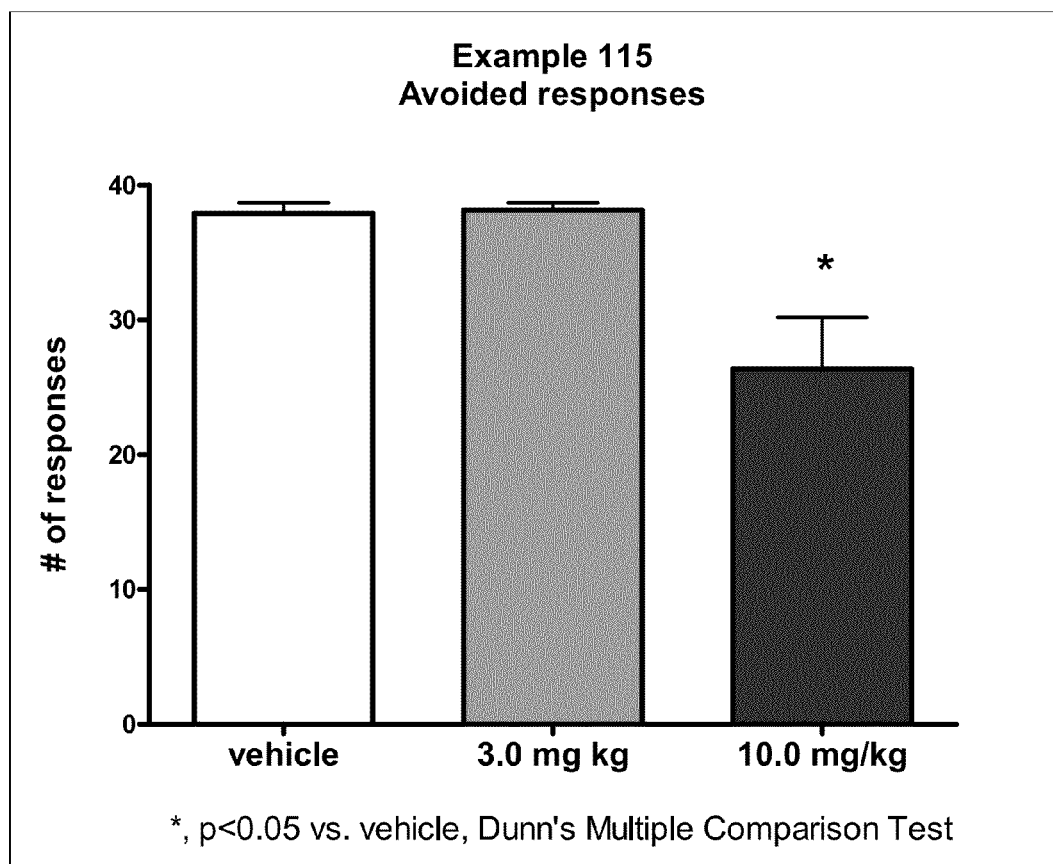

Figure 9B: Effects of Example 115 on conditioning avoidance responding in rats; escaped responses.
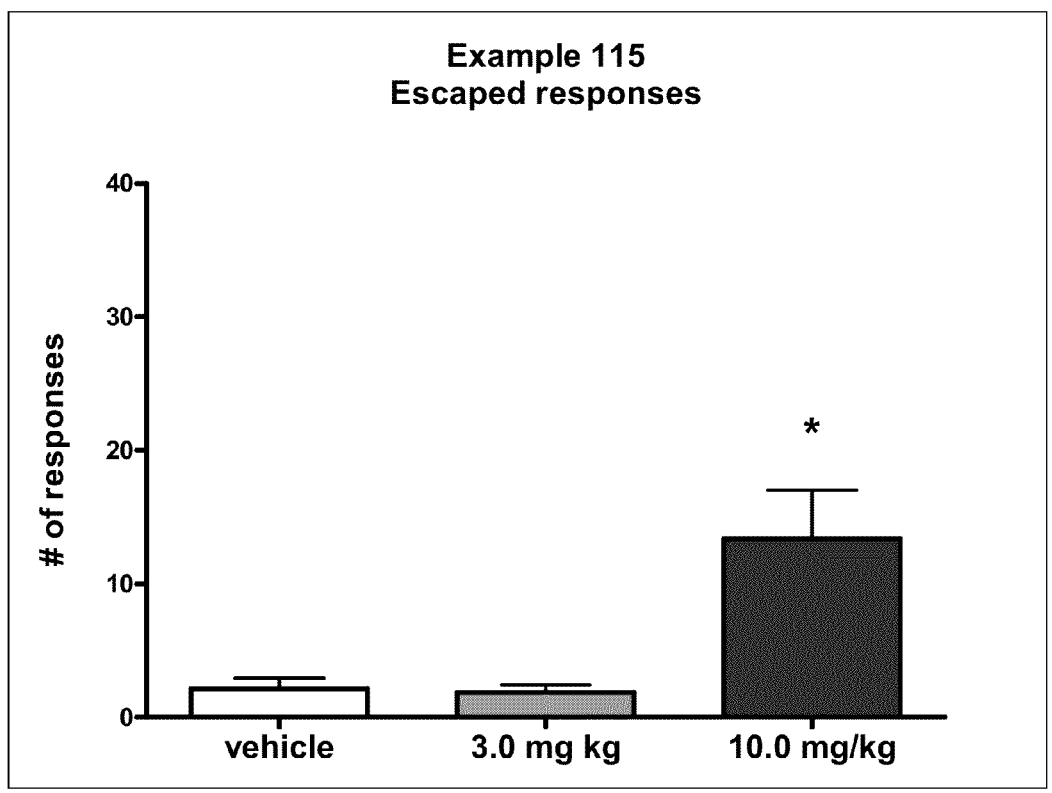

Figure 9C: Effects of Example 115 on conditioning avoidance responding in rats; failure responses.
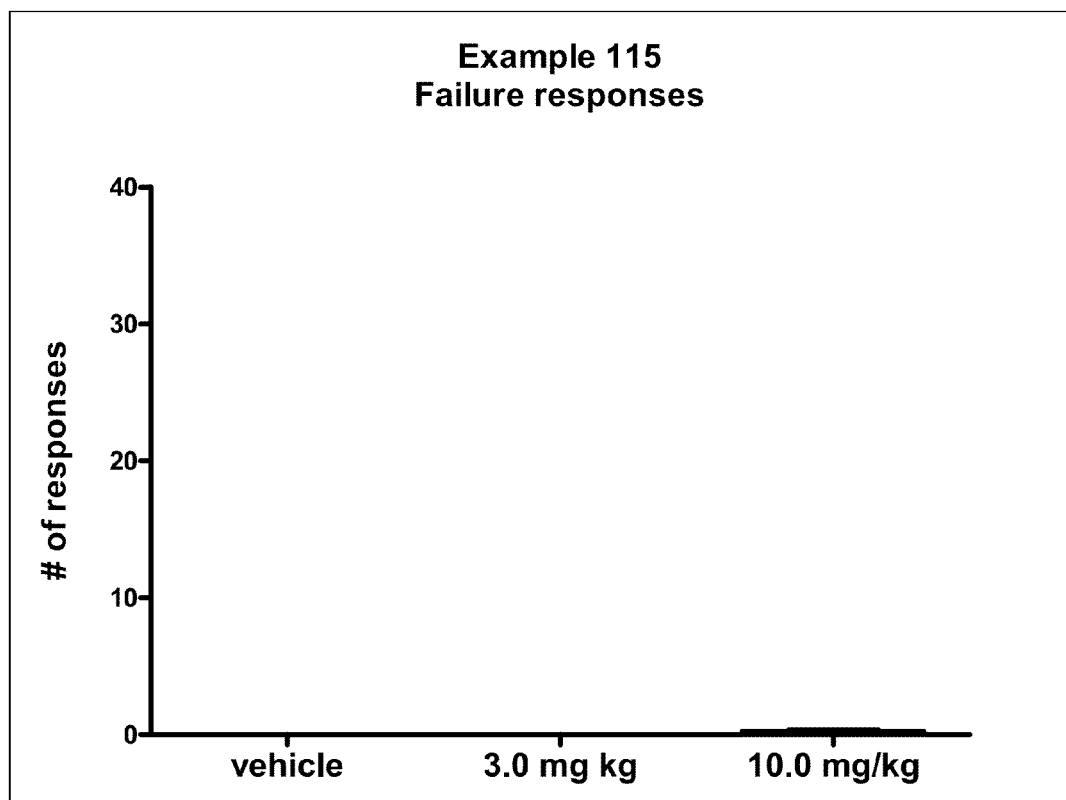

Figure 10A: Effects of Example 158 on conditioning avoidance responding in rats; avoided responses.
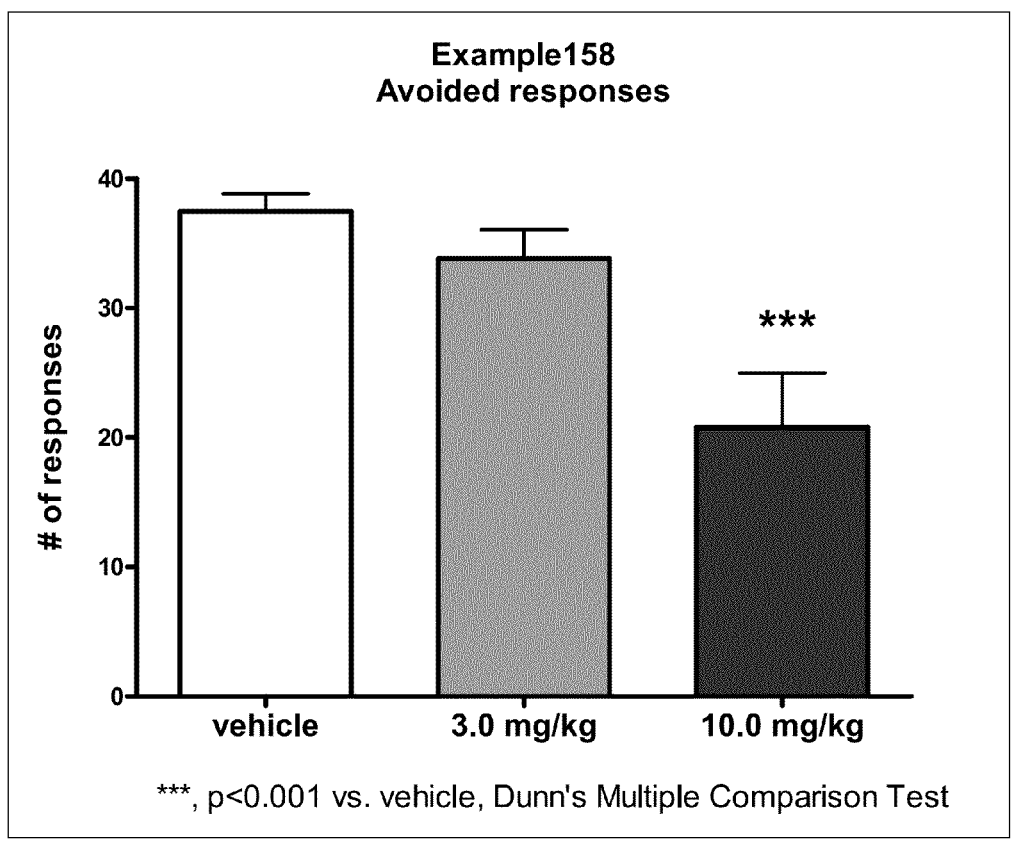

Figure 10B: Effects of Example 158 on conditioning avoidance responding in rats; escaped responses.
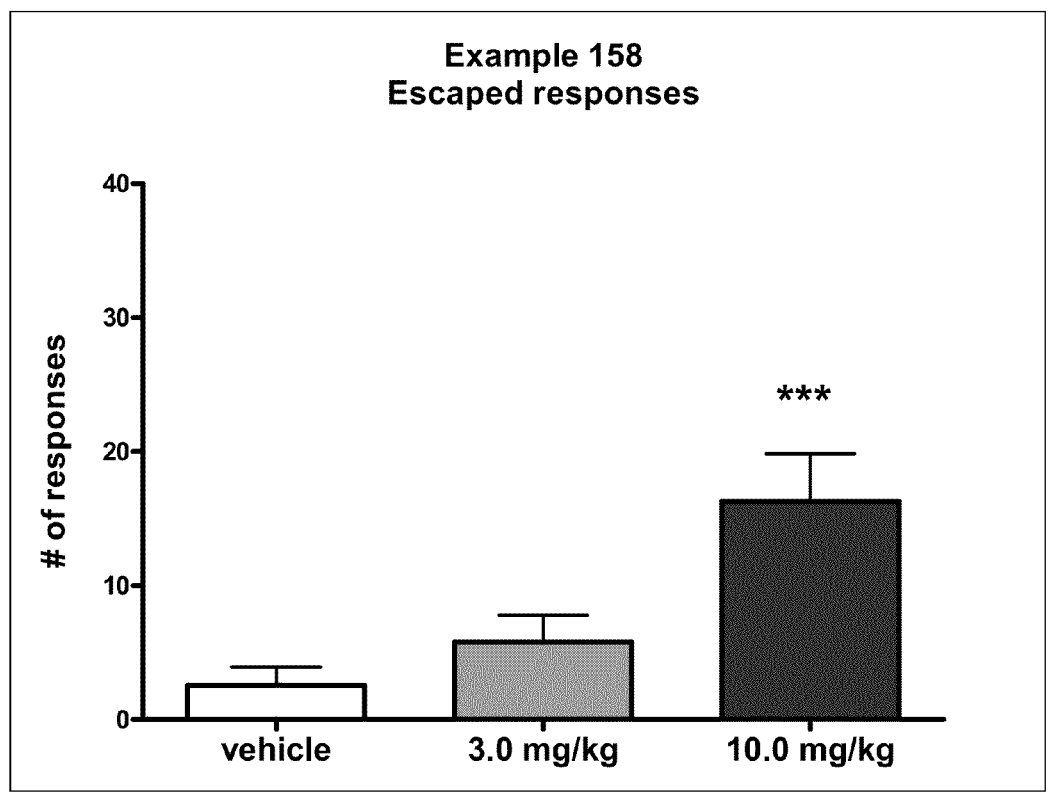

Figure 10C: Effects of Example 158 on conditioning avoidance responding in rats; failure responses.
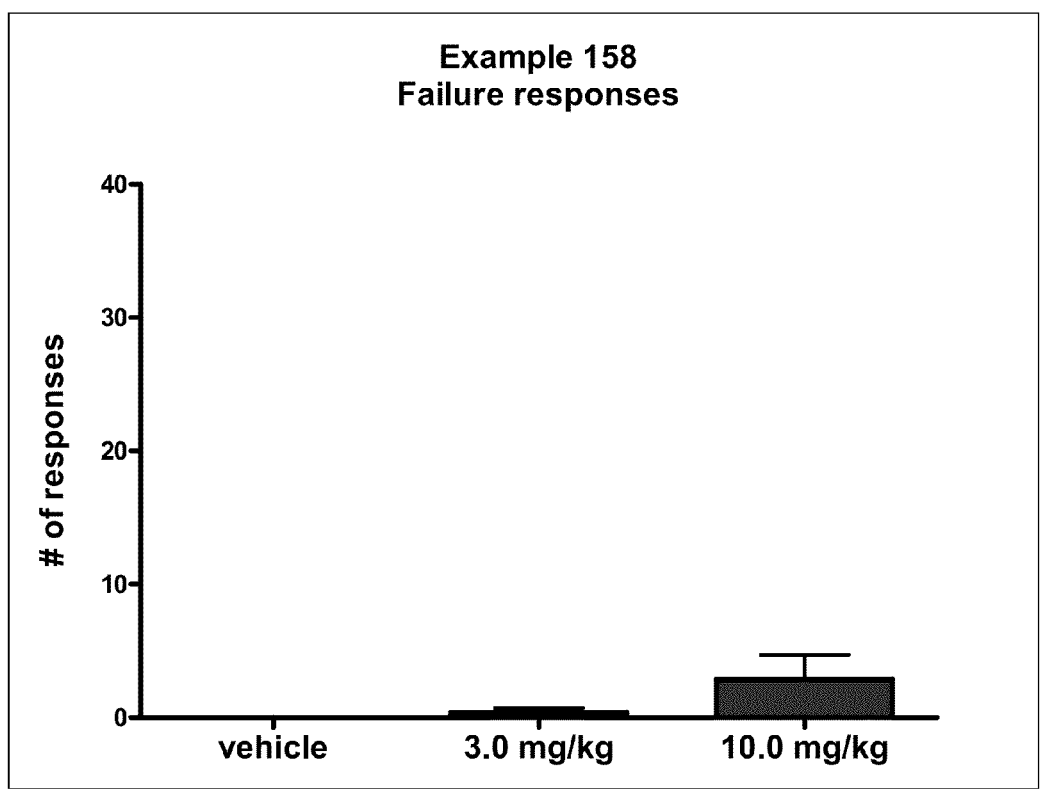

MODULATORS OF 5-HT RECEPTORS AND METHODS OF USE THEREOF

CROSS-REFERENCE TO RELATED APPLICATIONS

This patent application claims priority to U.S. Provisional Patent Application No. 61/180,569, filed on May 22, 2009, the entirety of which is incorporated herein by reference.

FIELD OF THE INVENTION

The present invention relates to aryl- and heteroaryl-fused decahydropyrroloazepine, octahydrooxepinopyrrole, octahydropyrrolothiazepine dioxide, decahydrocyclohepta[c]pyrrole, and octahydrocyclohepta[c]pyrrole derivatives, methods of modulating the $5\text{-HT}_{2C}$ receptor, the $5\text{-HT}_6$ receptor or both the $5\text{-HT}_{2C}$ and $5\text{-HT}_6$ receptor in the prevention or treatment of serotonin-related conditions and disorders using such compounds or compositions containing such compounds, and processes for preparing such compounds and compositions.

BACKGROUND OF THE INVENTION

The present invention relates to compounds and pharmaceutical compositions containing the compounds useful as $5\text{-HT}_{2C}$ receptor agonists or partial agonists, $5\text{-HT}_6$ antagonists or both $5\text{-HT}_{2C}$ receptor agonists or partial agonists and $5\text{-HT}_6$ antagonists for the treatment of diseases, disorders and conditions where $5\text{-HT}_{2C}$ or $5\text{-HT}_6$ modulation is desired such as depression, anxiety, schizophrenia, bipolar disorder, obsessive compulsive disorder, migraine, pain, epilepsy, substance abuse, eating disorders, obesity, diabetes, erectile dysfunction and others.

Serotonin (5-hydroxytryptamine, 5-HT), a monoamine neurotransmitter and local hormone, is formed by the hydroxylation and decarboxylation of tryptophan. The greatest concentration is found in the enterochromaffin cells of the gastrointestinal tract, the remainder being predominantly present in platelets and in the Central Nervous System (CNS). 5-HT is implicated in a vast array of physiological and pathophysiological pathways. In the periphery, it contracts a number of smooth muscles and induces endothelium-dependent vasodilation. In the CNS, it is believed to be involved in a wide range of functions, including the control of appetite, mood, anxiety, hallucinations, sleep, vomiting and pain perception.

Neurons that secrete 5-HT are termed serotonergic. The function of 5-HT is exerted upon its interaction with specific (serotonergic) neurons. Seven types of 5-HT receptors have been identified: $5\text{-HT}_1$ (with subtypes $5\text{-HT}_{1A}$, $5\text{-HT}_{1B}$, $5\text{-HT}_{1D}$, $5\text{-HT}_{1E}$ and $5\text{-HT}_{1F}$), $5\text{-HT}_2$ (with subtypes $5\text{-HT}_{2A}$, $5\text{-HT}_{2B}$ and $5\text{-HT}_{2C}$), $5\text{-HT}_3$, $5\text{-HT}_4$, $5\text{-HT}_5$ (with subtypes $5\text{-HT}_{5A}$ and $5\text{-HT}_{5B}$), $5\text{-HT}_6$ and $5\text{-HT}_7$. Most of these receptors are coupled to G-proteins that affect the activities of adenylate cyclase or phospholipase Cγ.

Alterations in the activity of multiple neurotransmitter receptor systems (dopamine, serotonin, glutamate, GABA, acetylcholine) have been implicated in the manifestation of the symptoms of schizophrenia. The most widely accepted "Dopamine Hypothesis of Schizophrenia" in its simplest form states that the positive symptoms of this pathology relate to a functional hyperactivity of the mesolimbic dopaminergic system, while the negative and cognitive aspects can be traced to a functional hypoactivity of the mesocortical dopaminergic projections. Atypical antipsychotics block the mesolimbic dopaminergic neurotransmission, thereby controlling positive symptoms, with little or no effect on the nigrostriatal system, leading to less induction of extrapyramidal side effects (EPS).

Primary negative and cognitive symptoms of schizophrenia reflect a dysfunction of the frontal cortex ("hypofrontality"), which is thought to be induced by a decreased tone in the mesocortical dopaminergic projection field [Davis K L, Kahn R S, Ko G and Davidson M (1991). Dopamine in schizophrenia: a review and re-conceptualization. *Am J Psychiatry* 148: 1474-86. Weinberger D R and Berman K F (1996). Prefrontal function in schizophrenia: confounds and controversies. *Philos Trans R Soc Lond B Biol Sci* 351: 1495-503]. Agents that selectively enhance dopamine levels in the cortex have the potential to address the negative symptoms of this disorder. Atypical antipsychotics lack robust efficacy against negative and cognitive components of the schizophrenic syndrome.

The schizophrenic symptomatology is further complicated by the occurrence of drug-induced so-called secondary negative symptoms and cognitive impairment, which are difficult to distinguish from primary negative and cognitive symptoms [Remington G and Kapur S (2000). Atypical antipsychotics: are some more atypical than others? *Psychopharmacol* 148: 3-15]. The occurrence of secondary negative symptoms not only limits therapeutic efficacy but also, together with these side effects, negatively affects patient compliance.

It may thus be hypothesized that a novel mechanistic approach that blocks dopaminergic neurotransmission in the limbic system but does not affect the striatal and pituitary projection fields, and stimulates frontocortical projection fields, would provide an efficacious treatment for all parts of the schizophrenic pathology, including its positive, negative and cognitive symptoms. Moreover, a selective compound that is substantially free of the ancillary pharmacology that characterizes current agents would be expected to avoid a variety of off-target side effects that plague current treatments such as extrapyramidal side effects (EPS) and weight gain.

The $5\text{-HT}_{2C}$ receptor, previously named 5-HT1C, is a G-protein-coupled receptor, which couples to multiple cellular effector systems including the phospholipase C, A and D pathways. It is found primarily in the brain and its distribution is particularly high in the plexus choroideus, where it is assumed to control cerebrospinal fluid production [Kaufman M J, Hirata F (1996) Cyclic GMP inhibits phosphoinositide turnover in choroid plexus: evidence for interactions between second messengers concurrently triggered by $5\text{-HT}_{2C}$ receptors. *Neurosci Leu* 206:153-156]. Very high levels were also found in the retrosplenial, piriform and entorhinal cortex, anterior olfactory nucleus, lateral septal nucleus, subthalamic nucleus, amygdala, subiculum and ventral part of CA3, lateral habenula, substantia nigra pars compacta, several brainstem nuclei and the whole grey matter of the spinal cord [Pompeiano M, Palacios J M, Mengod G (1994). Distribution of the serotonin 5-HT2 receptor family mRNAs: comparison between $5\text{-HT}_{2A}$ and $5\text{-HT}_{2C}$ receptors. *Brain Res Mol Brain Res* 23:163-178]. A comparison of the distribution of $5\text{-HT}_{2C}$ mRNA with that of $5\text{-HT}_{2C}$ protein in monkey and human brains has revealed both pre- and postsynaptic localization [Lopez-Gimenez J F, Mengod G, Palacios J M, Vilaro M T (2001) Regional distribution and cellular localization of $5\text{-HT}_{2C}$ receptor mRNA in monkey brain: comparison with [$^3$H]mesulergine binding sites and choline acetyltransferase mRNA. *Synapse* 42:12-26].

It is anticipated that modulation of the $5\text{-HT}_{2C}$ receptor will improve disorders such as depression, anxiety, schizophrenia, cognitive deficits of schizophrenia, obsessive compulsive disorder, bipolar disorder, migraine, epilepsy, substance abuse, eating disorders, obesity, diabetes, sexual dysfunction/erectile dysfunction, sleep disorders, psoriasis, Parkinson's disease, pain conditions and disorders, and spinal cord injury, smoking cessation, ocular hypertension and Alzheimer's disease. Modulators of the 5-HT$_{2C}$ receptor are also shown to be useful in the modulation of bladder function, including the prevention or treatment of urinary incontinence.

The modulation of the 5-HT$_6$ receptor by suitable substances is expected to improve certain disorders including cognitive dysfunctions, such as a deficit in memory, cognition and learning associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, drug addiction and obesity.

There is still an ongoing need for providing compounds having high affinity and selectivity for the 5-HT$_6$ receptor. In particular the compounds should have low affinity to adrenergic receptors, such as the $\alpha_1$-adrenergic receptor, histamine receptors, such as the H$_1$-receptor, and dopaminergic receptors, such as the D$_2$-receptor, in order to avoid or reduce side effects associated with modulation of these receptors, such as postural hypotension, reflex tachycardia, potentiation of the antihypertensive effect of prazosin, terazosin, doxazosin and labetalol or dizziness associated with the blockade of the $\alpha_1$-adrenergic receptor, weight gain, sedation, drowsiness or potentiation of central depressant drugs associated with the blockade of the H$_1$-receptor, or extrapyramidal movement disorder, such as dystonia, parkinsonism, akathisia, tardive dyskinesia or rabbit syndrome, or endocrine effects, such as prolactin elevation (galactorrhea, gynecomastia, mentstrual changes, sexual dysfunction in males), associated with the blockade of the D$_2$-receptor.

The present invention provides compounds which have an affinity for the 5-HT$_{2C}$ or 5-HT$_6$ receptor or both the 5-HT$_{2C}$ and 5-HT$_6$ receptors, thus allowing the treatment of disorders related to or affected by the 5-HT$_{2C}$ or 5-HT$_6$ receptors or both the 5-HT$_{2C}$ and 5-HT$_6$ receptors.

SUMMARY OF THE INVENTION

The invention is directed to aryl- and heteroaryl-fused decahydropyrroloazepine, and octahydro-1H-oxepino[4,5-c]pyrrole, octahydropyrrolothiazepine dioxide, decahydrocyclohepta[c]pyrrole, and octahydrocyclohepta[c]pyrrole derivatives, compositions comprising such compounds, and methods of using such compounds and compositions.

In one aspect, the present invention relates to compounds of having a formula of (I):

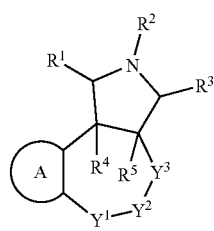

(I)

or a pharmaceutically acceptable salt or prodrug thereof, wherein

A is selected from the group consisting of

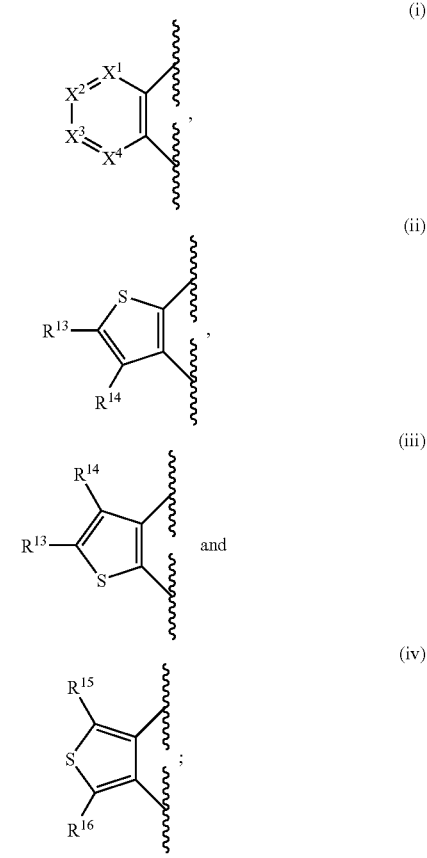

R$^1$, R$^3$, R$^4$, and R$^5$ are independently selected from the group consisting of hydrogen, alkenyl, alkyl, haloalkyl, G$^1$, G$^2$, —(CR$^{4a}$R$^{5a}$)$_m$-G$^1$, and —(CR$^{4a}$R$^{5a}$)$_m$-G$^2$;

R$^{4a}$ and R$^{5a}$, at each occurrence, are each independently hydrogen, halogen, alkyl, or haloalkyl;

G$^1$, at each occurrence, is independently aryl or heteroaryl, wherein each G$^1$ is independently unsubstituted or substituted with 1, 2, 3, 4, or 5 substituents selected from the group consisting of alkyl, alkenyl, alkynyl, halogen, cyano, —NO$_2$, —OR$^{1b}$, —OC(O)R$^{1b}$, —OC(O)N(R$^b$)(R$^{3b}$), —SR$^{1b}$, —S(O)R$^{2b}$, —S(O)$_2$R$^{2b}$, —S(O)$_2$N(R$^b$)(R$^{3b}$), —C(O)R$^{1b}$, —C(O)OR$^{1b}$, —C(O)N(R$^b$)(R$^{3b}$), —N(R$^b$)(R$^{3b}$), —N(R$^a$)C(O)R$^{1b}$, —N(R$^a$)C(O)OR$^{1b}$, —N(R$^a$)C(O)N(R$^b$)(R$^{3b}$), —(CR$^{4b}$R$^{5b}$)$_m$—NO$_2$, —N(R$^b$)S(O)$_2$(R$^{2b}$), —(CR$^{4b}$R$^{5b}$)$_m$—OR$^{1b}$, —C(OH)[(CR$^{4b}$R$^{5b}$)R$^{4b}$]$_2$, —(CR$^{4b}$R$^{5b}$)OC(O)R$^{1b}$, —(CR$^{4b}$R$^{5b}$)$_m$—OC(O)N(R$^b$)(R$^{3b}$), —(CR$^{4b}$R$^{5b}$)$_m$—SR$^{1b}$, —(CR$^{4b}$R$^{5b}$)$_m$—S(O)R$^{2b}$, —(CR$^{4b}$R$^{5b}$)$_m$—S(O)$_2$R$^{2b}$, —(CR$^{4b}$R$^{5b}$)$_m$—S(O)$_2$N(R$^b$)(R$^{3b}$), —(CR$^{4b}$R$^{5b}$)$_m$—C(O)R$^{1b}$, —(CR$^{4b}$R$^{5b}$)$_m$—C(O)OR$^{1b}$, —(CR$^{4b}$R$^{5b}$)$_m$—C(O)N(R$^b$)(R$^{3b}$), —(CR$^{4b}$R$^{5b}$)$_m$—N(R$^b$)(R$^{3b}$), —(CR$^{4b}$R$^{5b}$)$_m$—N(R$^a$)C(O)R$^{1b}$, —(CR$^{4b}$R$^{5b}$)$_m$—N(R$^a$)C(O)OR$^{1b}$, —(CR$^{4b}$R$^{5b}$)$_m$—N(R$^a$)C(O)N(R$^b$)(R$^{3b}$), —(CR$^{4b}$R$^{5b}$)$_m$—N(R$^b$)S(O)$_2$(R$^{2b}$), cyanoalkyl, and haloalkyl;

G$^2$ is cycloalkyl, cycloalkenyl, or heterocycle unsubstituted or substituted with 1, 2, 3, 4, or 5 substituents selected from the group consisting of alkyl, alkenyl, alkynyl, halogen, cyano, oxo, —$SR^{1b}$, —$S(O)R^{2b}$—$S(O)_2R^{2b}$—$S(O)_2N(R^b)(R^{3b})$—$C(O)R^{1b}$—$C(O)OR^{1b}$, —$C(O)N(R^b)(R^{3b})$, —$N(R^b)(R^{3b})$, —$N(R^a)C(O)R^{1b}$, —$N(R^a)C(O)O(R^{1b})$, —$N(R^a)C(O)N(R^b)(R^{3b})$, —$(CR^{4b}R^{5b})_m$—$NO_2$, —$N(R^b)S(O)_2(R^{2b})$, —$(CR^{4b}R^{5b})OR^{1b}$, —$(CR^{4b}R^{5b})_m$—$OC(O)R^{1b}$, —$(CR^{4b}R^{5b})_m$—$OC(O)N(R^b)(R^{3b})$, —$(CR^{4b}R^{5b})_m$—$SR^{1b}$, —$(CR^{4b}R^{5b})_m$—$S(O)R^{2b}$, —$(CR^{4b}R^{5b})_m$—$S(O)_2R^{2b}$, —$(CR^{4b}R^{5b})_m$—$S(O)_2N(R^b)(R^{3b})$, —$(CR^{4b}R^{5b})_m$—$C(O)R^{1b}$, —$(CR^{4b}R^{5b})_m$—$C(O)OR^{1b}$, —$(CR^{4b}R^{5b})_m$—$C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, —$(CR^{4b}R^{5b})_m$—$N(R^b)S(O)_2(R^{2b})$, cyanoalkyl, and haloalkyl;

$R^a$ and $R^b$, at each occurrence, are each independently hydrogen, alkyl, or haloalkyl;

$R^{1b}$ and $R^{3b}$, at each occurrence, are each independently hydrogen, alkyl, or haloalkyl;

$R^{2b}$, at each occurrence, is independently alkyl or haloalkyl;

$R^{4b}$ and $R^{5b}$, at each occurrence, are each independently hydrogen, halogen, alkyl, or haloalkyl;

m, at each occurrence, is independently 1, 2, 3, 4, or 5;

$R^2$ is selected from the group consisting of hydrogen, alkoxyalkyl, alkyl, alkylcarbonyl, haloalkyl, —$(CR^{4a}R^{5a})_m$-$G^1$, —$(CR^{4a}R^{5a})_p$—O-$G^1$, —$C(O)$-$G^1$, —$(CR^{4a}R^{5a})_m$-$G^2$, —$(CR^{4a}R^{5a})_p$—O-$G^2$, —$C(O)$-$G^2$, —$S(O)_2R^6$, and —$C(O)NR^7R^8$;

p, at each occurrence, is independently 2, 3, 4, or 5;

$R^6$ and $R^7$ are independently selected from the group consisting of alkyl, haloalkyl, $G^1$, —$(CR^{4a}R^{5a})_m$-$G^1$, $G^2$ and —$(CR^{4a}R^{5a})_m$-$G^2$;

$R^8$ is selected from the group consisting of hydrogen, alkyl, and haloalkyl; or $R^7$ and $R^8$ taken together with the nitrogen to which they are attached form a heterocycle;

$X^1$ is N or $CR^9$;

$X^2$ is N or $CR^{16}$;

$X^3$ is N or $CR^{11}$;

$X^4$ is N or $CR^{12}$;

provided that only one or two of $X^1$, $X^2$, $X^3$, or $X^4$ can be N;

$R^9$, $R^{10}$, $R^{11}$, $R^{12}$, $R^{13}$, $R^{14}$, $R^{15}$ and $R^{16}$ are each independently hydrogen, alkyl, alkenyl, alkynyl, halogen, cyano, -$G^1$, -$G^2$, —$NO_2$, —$OR^{1a}$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)G^3$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R^b)(R^{3a})$, —$N(R^a)S(O)_2(R^{2a})$, —$(CR^{4a}R^{5a})NO_2$, —$(CR^{4a}R^{5a})OR^{1a}$, —$(CR^{4a}R^{5a})OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, —$CR^{4a}$=$CR^{5a}$-$G^1$, —$(CR^{4a}R^{5a})_m$-$G^2$, —$CR^{4a}$=$CR^{5a}$-$G^2$, —$CR^{6a}$=$C(R^{7a})_2$, cyanoalkyl, haloalkyl, (v), (vi), (vii) or (viii); wherein (v) [structure: indanone with $R^{4a}$, $R^{5a}$ substituents, subscript q]

(vi) [structure: indandione with $R^{4a}$, $R^{5a}$ substituents, subscript q]

(vii) [structure: hydroxyindane with HO, $R^{4a}$, $R^{5a}$ substituents, subscript q]

(viii) [structure: hydroxyindane isomer with HO, $R^{4a}$, $R^{5a}$ substituents, subscript q]

$R^{1a}$ and $R^{3a}$, at each occurrence, are each independently hydrogen, alkyl, haloalkyl, $G^1$, —$(CR^{4a}R^{5a})_m$-$G^1$, $G^2$, or —$(CR^{4a}R^{5a})_m$-$G^2$;

$R^{2a}$, at each occurrence, is independently alkyl, haloalkyl, $G^1$, or —$(CR^{4a}R^{5a})_m$-$G^1$;

$R^{6a}$ is alkyl or haloalkyl;

$R^{7a}$, at each occurrence, is independently hydrogen, alkyl, or haloalkyl;

$G^3$ is a heterocyclic ring attached to the adjacent carbonyl moiety through a nitrogen atom contained within the heterocycle;

q is 1 or 2; or $R^9$ and $R^{10}$, $R^{10}$ and $R^{11}$, $R^{11}$ and $R^{12}$, or $R^{13}$ and $R^{14}$ taken together with the carbon atoms to which they are attached form a substituted or unsubstituted phenyl, cycloalkyl, heterocycle, or heteroaryl ring;

$Y^1$ is $NR^{17}$, $CR^{18}R^{19}$, C(O), S(O)$_n$, or O;

$Y^2$ is $NR^{20}$, $CR^{18}R^{19}$, C(O), or S(O)$_n$;

$Y^3$ is $NR^{17}$, $CR^{18}R^{19}$, C(O), or S(O)$_n$; or $Y^1$ and $Y^2$ together are $CR^{18}$=$CR^{19}$, provided $Y^3$ is other than $NR^{17}$; or $Y^2$ and $Y^3$ together are $CR^{18}$=$CR^{19}$, provided $Y^1$ is other than $NR^{17}$ or O;

n is 1 or 2;

provided that only one of $Y^1$ and $Y^3$ can be $NR^{17}$; or $Y^1$ and $Y^3$ are other than $NR^{17}$ when $Y^2$ is $NR^{20}$; or only one of $Y^1$, $Y^2$, or $Y^3$ can be C(O) or S(O)$_n$; or $Y^2$ is other than $NR^{20}$ or S(O)$_n$ when $Y^1$ is O; or $Y^3$ is other than $NR^{17}$ when $Y^1$ is O;

$R^{17}$ is selected from the group consisting of hydrogen, alkyl, alkylcarbonyl, haloalkyl, —C(O)-$G^1$, —$(CR^{4a}R^{5a})_m$-$G^1$, —C(O)-$G^2$, and —$(CR^{4a}R^{5a})_m$-$G^2$;

$R^{18}$ and $R^{19}$ are independently selected from the group consisting of hydrogen, alkyl, and haloalkyl; and $R^{20}$ is selected from the group consisting of hydrogen, alkyl, alkylcarbonyl, haloalkyl, —C(O)-$G^1$, —C(O)NR$^a$-$G^1$, —S(O)$_n$-G$^1$, —(CR$^{4a}$R$^{5a}$)$_m$-G$^1$, —C(O)-G$^2$, —C(O)NR$^a$-G$^2$, —S(O)$_n$-G$^2$, and —(CR$^{4a}$R$^{5a}$)$_m$-G$^2$.

In another aspect, the present invention relates to pharmaceutical compositions comprising a therapeutically effective amount of at least one compound having a formula of (I) described above or pharmaceutically acceptable salts thereof, in combination with at least one pharmaceutically acceptable carrier.

Another aspect of the invention relates to pharmaceutical compositions comprising compounds of the invention. Such compositions can be administered in accordance with a method of the invention, typically as part of a therapeutic regimen for treatment or prevention of conditions and disorders related to 5-HT activity, and more particularly 5-HT$_2$, activity, 5-HT$_6$ activity, or both 5-HT$_2$, activity and 5-HT$_6$ activity.

In yet another aspect, the present invention relates to a method of preventing or treating a cognitive dysfunction, attention deficit/hyperactivity syndrome, personality disorders, affective disorders, motion or motor disorders, migraine, pain, urinary incontinence, sleep disorders, feeding disorders, gastrointestinal disorders, diseases associated with neurodegeneration, addiction diseases, obesity, diabetes, psoriasis, or ocular hypertension disorder using a compound of formula (I). Such methods involve administering a therapeutically effective amount of at least one compound of formula (I) to a subject in need of treatment thereof. Examples of cognitive dysfunction are deficits in memory, cognition, and learning, Alzheimer's disease, age-related cognitive decline, and mild cognitive impairment, or any combinations thereof. Examples of personality disorders are schizophrenia and cognitive deficits related to schizophrenia. Examples of affective disorders are depression, anxiety, bipolar disorder and obsessive compulsive disorders, or any combination thereof. Examples of motion or motor disorders are Parkinson's disease and epilepsy. Examples of feeding disorders are anorexia and bulimia. Examples of gastrointestinal disorders are irritable bowel syndrome. Examples of diseases associated with neurodegeneration are stroke, spinal or head trauma, and head injuries.

In one embodiment of the present invention, a method of treating a mammal suffering from schizophrenia and/or cognitive deficits related to schizophrenia is provided that includes administering to the mammal at least one compound of formula (I) or a pharmaceutically acceptable salt thereof.

In still yet another aspect, the present invention relates to the use of a compound of formula (I) or a pharmaceutically acceptable salt thereof in the manufacture of a medicament for the prevention or treatment of the disorders described above, alone or in combination with at least one pharmaceutically acceptable carrier.

The compounds of formula (I), compositions comprising these compounds, and methods for preventing or treating cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension disorders by administering these compounds or pharmaceutical compositions are further described herein.

The compounds, compositions comprising the compounds, methods for using the compounds, and processes for preparing the compounds, as well as intermediates obtained in such processes, are further described herein.

These and other objects of the invention are described in the following paragraphs. These objects should not be deemed to narrow the scope of the invention.

BRIEF DESCRIPTION OF THE FIGURES

FIG. 1B shows a graphical representation of the dose-dependent effects of Example 115 in attenuating the affect of phencylidine (PCP). Rats were treated with the vehicle, PCP or a dose of Example 115 followed by phencylidine. The X-axis represents the time course of the experiment, and the Y-axis represents the distance traveled in the 5 minute time period.

FIG. 4A shows a graphical representation of the concentration-dependent effects of Example 44 attenuating the affect of phencyclidine (PCP). Mice were treated with vehicle, d-amphetamine or a dose of Example 44 followed by PCP. The X-axis represents time (minutes), and the Y-axis represents activity counts per 5 minute time period.

FIG. 4B shows a graphical representation of the concentration-dependent effects of Example 44 attenuating the affect of phencyclidine (PCP). Mice were treated with vehicle, d-amphetamine or a dose of Example 44 followed by PCP. FIG. 4B shows the total activity counts after PCP injection for the different groups.

FIG. 5A shows a graphical representation of the concentration-dependent effects of Example 106 attenuating the affect of d-amphetamine (AMP). Mice were treated with vehicle, AMP or a dose of Example 106 followed by AMP. The X-axis represents time (minutes), and the Y-axis represents activity counts per 5 minute time period.

FIG. 5B shows a graphical representation of the concentration-dependent effects of Example 106 attenuating the affect of d-amphetamine (AMP). Mice were treated with vehicle, AMP or a dose of Example 106 followed by AMP. FIG. 5B shows the total activity counts after AMP injection for the different groups.

FIG. 6A shows a graphical representation of the concentration-dependent effects of Example 115 attenuating the affect of d-amphetamine (AMP). Mice were treated with vehicle, AMP or a dose of Example 115 followed by AMP. The X-axis represents time (minutes), and the Y-axis represents activity counts per 5 minute time period.

FIG. 6B shows a graphical representation of the concentration-dependent effects of Example 115 attenuating the affect of d-amphetamine (AMP). Mice were treated with vehicle, AMP or a dose of Example 115 followed by AMP. FIG. 6B shows the total activity counts after AMP injection for the different groups.

FIG. 7A shows a graphical representation of the concentration-dependent effects of Example 158 attenuating the affect of d-amphetamine (AMP). Mice were treated with vehicle, AMP or a dose of Example 158 followed by AMP. The X-axis represents time (minutes), and the Y-axis represents activity counts per 5 minute time period.

FIG. 7B shows a graphical representation of the concentration-dependent effects of Example 158 attenuating the affect of d-amphetamine (AMP). Mice were treated with vehicle, AMP or a dose of Example 158 followed by AMP. FIG. 7B shows the total activity counts after AMP injection for the different groups.

FIG. 8A shows a graphical representation of the concentration-dependent effects of Example 225 attenuating the affect of d-amphetamine (AMP). Mice were treated with vehicle, AMP or a dose of Example 225 followed by AMP. The X-axis represents time (minutes), and the Y-axis represents activity counts per 5 minute time period.

FIG. 8B shows a graphical representation of the concentration-dependent effects of Example 225 attenuating the affect of d-amphetamine (AMP). Mice were treated with vehicle, AMP or a dose of Example 225 followed by AMP. FIG. 8B shows the total activity counts after AMP injection for the different groups.

FIG. 9A shows a graphical representation of avoided responses in conditioned avoidance response in rats following acute administration of Example 115. The X-axis indicates the dosage, and the Y-axis shows the number of this type of response.

FIG. 9B shows a graphical representation of escaped responses in conditioned avoidance response in rats following acute administration of Example 115. The X-axis indicates the dosage, and the Y-axis shows the number of this type of response.

FIG. 9C shows a graphical representation of failure responses in conditioned avoidance response in rats following acute administration of Example 115. The X-axis indicates the dosage, and the Y-axis shows the number of this type of response.

FIG. 10A shows a graphical representation of avoided responses in conditioned avoidance response in rats following acute administration of Example 158. The X-axis indicates the dosage, and the Y-axis shows the number of this type of response.

FIG. 10B shows a graphical representation of escaped responses in conditioned avoidance response in rats following acute administration of Example 158. The X-axis indicates the dosage, and the Y-axis shows the number of this type of response.

FIG. 10C shows a graphical representation of failure responses in conditioned avoidance response in rats following acute administration of Example 158. The X-axis indicates the dosage, and the Y-axis shows the number of this type of response.

DETAILED DESCRIPTION

Figure 1A:
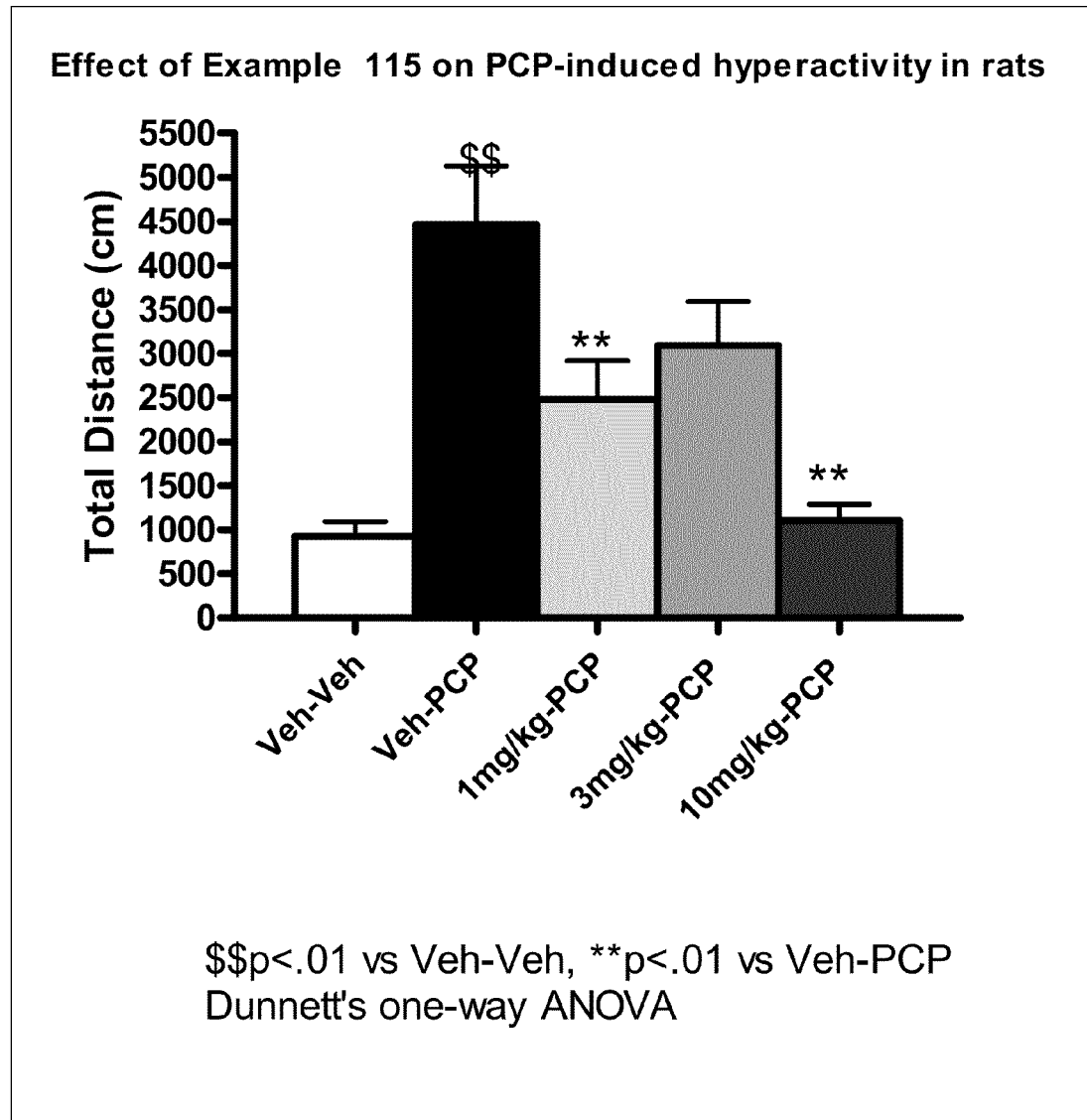
FIG. 1A shows a graphical representation of the dose-dependent effects of Example 115 in attenuating the affect of phencyclidine (PCP). Rats were treated with the vehicle, PCP or a dose of Example 115 followed by phencyclidine. The X-axis represents the dosing regimen, and the Y-axis represents activity as recorded by distance traveled by test animals during time period of the experiment.

In one aspect, the present invention relates to compounds having a formula (I) as shown below:

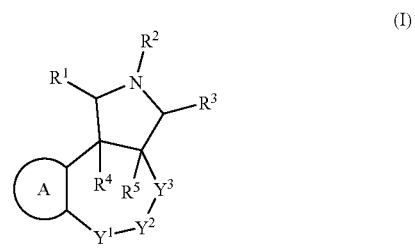

(I)

wherein $R^1$, $R^2$, $R^3$, $R^4$, $R^5$, A, $Y^1$, $Y^2$, and $Y^3$ are as defined above in the Summary of the Invention.

In another aspect, the present invention relates to compositions comprising compounds having a formula (I) as described above and at least one pharmaceutically acceptable carrier.

In still yet another aspect, the present invention relates to methods for preventing and treating disease conditions, such as treating cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension disorders, using compounds having a formula of formula (I) as described above.

In still yet another aspect, the present invention relates to the use of compounds having a formula (I) in the manufacture of a medicament for the prevention or treatment of the disease conditions, such as treating cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension disorders, described above, alone or in combination with at least one pharmaceutically acceptable carrier.

In various embodiments, the present invention provides at least one variable that occurs more than one time in any substituent or in the compound of the present invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylene" means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "carbonyl" as used herein means a —C(=O)— group.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, and 3-cyanopropyl.

The term "cycloalkenyl" as used herein means a cyclic hydrocarbon group containing from 3 to 10 carbons, containing 1 or 2 carbon-carbon double bonds. Examples of cycloalkenyl include cyclopropenyl, cyclobutenyl, cyclopentenyl, cyclohexenyl, cycloheptentyl, and cyclooctenyl.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1] nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, fluoromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-c]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, dihydropyranyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-admantane (1-azatricyclo[3.3.1.1$^{3,7}$]decane), and oxa-admantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "oxo" as used herein, means a =O moiety.

b. Compounds

Compounds of the present invention have the formula (I) as described above.

Particular values of variable groups in compounds of formula (I) are as follows. Such values may be used where appropriate with any of the other values, definitions, claims or embodiments defined hereinbefore or hereinafter.

In one embodiment, A is (i).

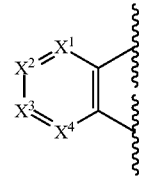

(i)

In one embodiment, $X^1$, $X^2$, $X^3$ and $X^4$ are N or $CR^9$, $CR^{10}$, $CR^{11}$, or $CR^{12}$, respectively, provided only one or two of $X^1$, $X^2$, $X^3$ or $X^4$ is N.

In one embodiment, $X^1$, $X^2$, $X^3$ and $X^4$ are $CR^9$, $CR^{10}$, $CR^{11}$, and $CR^{12}$, respectively.

In one embodiment, $X^1$ is N, and $X^2$, $X^3$ and $X^4$ are $CR^{10}$, $CR^{11}$, and $CR^{12}$, respectively.

In one embodiment, $X^2$ is N, and $X^1$, $X^3$ and $X^4$ are $CR^9$, $CR^{11}$, and $CR^{12}$, respectively.

In one embodiment, $X^3$ is N, and $X^1$, $X^2$ and $X^4$ are $CR^9$, $CR^{10}$, and $CR^{12}$, respectively.

In one embodiment, $X^4$ is N, and $X^1$, $X^2$ and $X^3$ are $CR^9$, $CR^{10}$, and $CR^{11}$, respectively.

In one embodiment, $R^9$, $R^{10}$, $R^{11}$, and $R^{12}$ are each independently hydrogen, alkyl, alkenyl, alkynyl, halogen, cyano, -G$^1$, -G$^2$, —NO$_2$, —OR$^{1a}$, —OC(O)R$^{1a}$, —OC(O)N(R$^b$)(R$^{3a}$), —SR$^{1a}$, —S(O)R$^{2a}$, —S(O)$_2$R$^{2a}$, —S(O)$_2$N(R$^b$)(R$^{3a}$), —C(O)R$^{1a}$, —C(O)G$^3$, —C(O)OR$^{1a}$, —C(O)N(R$^b$)(R$^{3a}$), —N(R$^b$)(R$^{3a}$), N(R$^a$)C(O)R$^{1a}$, N(R$^a$)C(O)O(R$^{1a}$), —N(R$^a$)C(O)N(R$^b$)(R$^{3a}$), —N(R$^a$)S(O)$_2$(R$^{2a}$), —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)R$^{2a}$, —(CR$^{4a}$R$^{5a}$)$_m$—S(O)$_2$R$^{2a}$, —(CR$^{4a}$R$^{5a}$)S(O)$_2$N(R$^b$)(R$^{3a}$), —(CR$^{4a}$R$^{5a}$)$_m$—C(O)R$^{1a}$, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R$^{1a}$, —(CR$^{4a}$R$^{5a}$)$_m$—N(R$^a$)C(O)O(R$^{1a}$), —(CR$^{4a}$R$^{5a}$)$_m$—N(R$^a$)C(O)N(R$^b$)(R$^{3a}$), —(CR$^{4a}$R$^{5a}$)$_m$-G$^1$, —CR$^{4a}$=CR$^{5a}$-G$^1$, —(CR$^{4a}$R$^{5a}$)$_m$-G$^2$, —CR$^{4a}$=CR$^{5a}$-G$^2$, —CR$^{6a}$=C(R$^{7a}$)$_2$, cyanoalkyl, haloalkyl, (v), (vi), (vii) or (viii); wherein

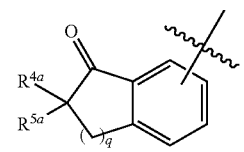

(v)

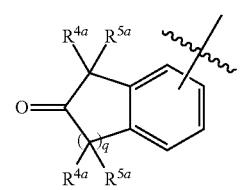

(vi)

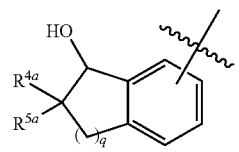

(vii)

(viii)

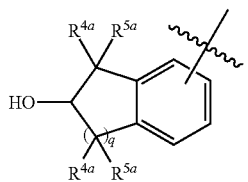

$R^{1a}$ and $R^{3a}$, at each occurrence, are each independently hydrogen, alkyl, haloalkyl, $G^1$, —$(CR^{4a}R^{5a})_m$-$G^1$, $G^2$, or —$(CR^{4a}R^{5a})_m$-$G^2$; $R^{2a}$, at each occurrence, is independently alkyl, haloalkyl, $G^1$, or —$(CR^{4a}R^{5a})_m$-$G^1$; $R^{6a}$ is alkyl or haloalkyl; $R^{7a}$, at each occurrence, is independently hydrogen, alkyl, or haloalkyl; $G^3$ is a heterocyclic ring attached to the adjacent carbonyl moiety through a nitrogen atom contained within the heterocycle; and q is 1 or 2.

In a further embodiment, one or two of $R^9$, $R^{10}$, $R^{11}$, and $R^{12}$ are each independently alkyl, alkenyl, alkynyl, halogen, cyano, -$G^1$, -$G^2$, —$NO_2$, —$OR^{1a}$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)G^3$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R^b)(R^{3a})$, —$N(R^a)S(O)_2(R^{2a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, $(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, —$CR^{4a}$=$CR^{5a}$-$G^1$, —$(CR^{4a}R^{5a})_m$-$G^2$, —$CR^{4a}$=$CR^{5a}$-$G^2$, cyanoalkyl, haloalkyl, (v), (vi), (vii) or (viii), and the others of $R^9$, $R^{10}$, $R^{11}$, and $R^{12}$ are hydrogen.

(v)

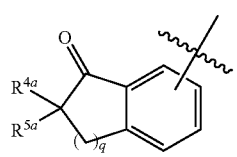

(vi)

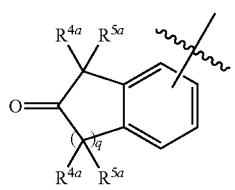

(vii)

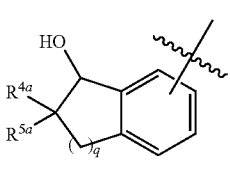

(viii)

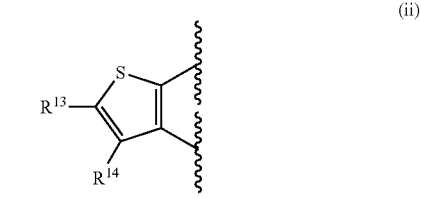

In another embodiment, $R^9$, $R^{10}$, $R^{11}$, and $R^{12}$ are each independently hydrogen, alkyl, alkenyl, halogen, -$G^1$, -$G^2$, —$OR^{1a}$, —$C(O)G^3$, —$C(O)OR^{1a}$, —$C(O)N(R^b)(R^{3a})$, —$N(R^b)(R^{3a})$, —$(CR^{4a}R^{5a})_m$—$OR^{1a}$, —$(CR^{4a}R^{5a})_m$-$G^1$-$CR^{4a}$=$CR^{5a}$-$G^1$, or (v), wherein $G^1$ is optionally substituted phenyl, naphthyl or heteroaryl.

In another embodiment, $R^9$ and $R^{10}$, $R^{10}$ and $R^{11}$, or $R^{11}$ and $R^{12}$ taken together with the carbon atoms to which they are attached form a substituted or unsubstituted phenyl, cycloalkyl, heterocycle, or heteroaryl ring.

In one embodiment, A is (ii).

(ii)

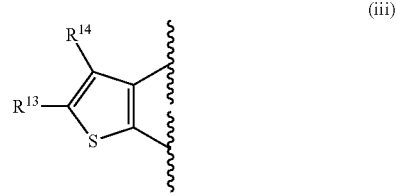

In one embodiment, A is (iii).

(iii)

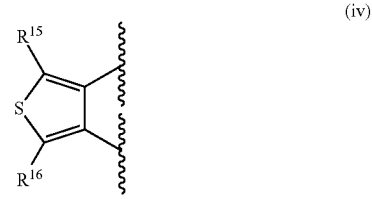

In one embodiment, A is (iv).

(iv)

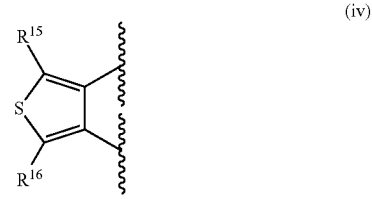

In one embodiment, $R^{13}$, $R^{14}$, $R^{15}$ and $R^{16}$ each independently hydrogen, alkyl, alkenyl, alkynyl, halogen, cyano, -$G^1$, -$G^2$, —$NO_2$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)G^3$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R^b)(R^{3a})$, —$N(R^a)S(O)_2(R^{2a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)$ $R^{1a}$, —$(CR^{4a}R^{5a})_m$—C(O)O$R^{1a}$, —$(CR^{4a}R^{5a})_m$—C(O)N($R^b$)($R^{3a}$), —$(CR^{4a}R^{5a})_m$—N($R^b$)($R^{3a}$), —$(CR^{4a}R^{5a})_m$—($R^a$)C(O)$R^{1a}$, —$(CR^{4a}R^{5a})_m$—($R^a$)C(O)O($R^{1a}$), —$(CR^{4a}R^{5a})_m$—N($R^a$)C(O)N($R^b$)($R^{3a}$), —$(CR^{4a}R^{5a})_m$-$G^1$, —$CR^{4a}$=$CR^{5a}$-$G^1$, —$(CR^{4a}R^{5a})_m$-$G^2$, —$CR^{4a}$=$CR^{5a}$-$G^2$, —$CR^{6a}$=C($R^{7a}$)$_2$, cyanoalkyl, haloalkyl, (v), (vi), (vii) or (viii); wherein

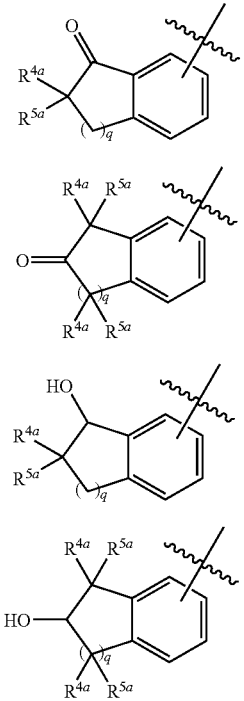

$R^{1a}$ and $R^{3a}$, at each occurrence, are each independently hydrogen, alkyl, haloalkyl, $G^1$, —$(CR^{4a}R^{5a})_m$-$G^1$, $G^2$, or —$(CR^{4a}R^{5a})_m$-$G^2$; $R^{2a}$, at each occurrence, is independently alkyl, haloalkyl, $G^1$, or —$(CR^{4a}R^{5a})_m$-$G^1$; $R^{6a}$ is alkyl or haloalkyl; $R^{7a}$, at each occurrence, is independently hydrogen, alkyl, or haloalkyl; $G^3$ is a heterocyclic ring attached to the adjacent carbonyl moiety through a nitrogen atom contained within the heterocycle; and q is 1 or 2.

In another embodiment, $R^{13}$, $R^{14}$, $R^{15}$ and $R^{16}$ each independently hydrogen, alkyl, or halogen.

In a further embodiment, $R^{13}$ and $R^{14}$ taken together with the carbon atoms to which they are attached form a substituted or unsubstituted phenyl or heteroaryl ring.

In one embodiment, $R^1$, $R^3$, $R^4$, and $R^5$ are independently selected from the group consisting of hydrogen, alkenyl, alkyl, haloalkyl, $G^1$, $G^2$, —$(CR^{4a}R^{5a})_m$-$G^1$, and —$(CR^{4a}R^{5a})_m$-$G^2$.

In another embodiment, $R^1$, $R^3$, $R^4$, and $R^5$ are independently selected from the group consisting of hydrogen and alkyl.

In a further embodiment, $R^1$, $R^3$, $R^4$, and $R^5$ are hydrogen.

In one embodiment, $R^2$ is hydrogen, alkoxyalkyl, alkyl, alkylcarbonyl, haloalkyl, —$(CR^{4a}R^{5a})_m$-$G^1$, —$(CR^{4a}R^{5a})_m$-$G^2$, —$(CR^{4a}R^{5a})_p$—O-$G^1$, —$(CR^{4a}R^{5a})_p$—O-$G^2$, —C(O)-$G^1$, —C(O)-$G^2$, —S(O)$_2R^6$, or —C(O)N$R^7R^8$; wherein $R^6$ and $R^7$ are independently selected from the group consisting of alkyl, haloalkyl, $G^1$, $G^2$, —$(CR^{4a}R^{5a})_m$-$G^1$, and —$(CR^{4a}R^{5a})_m$-$G^2$; wherein $R^8$ is selected from the group consisting of hydrogen, alkyl, and haloalkyl; or $R^7$ and $R^8$ taken together with the nitrogen to which they are attached form a heterocycle.

In another embodiment, $R^2$ is hydrogen, alkyl, haloalkyl, —$(CR^{4a}R^{5a})_m$-$G^1$, or —$S(O)_2R^6$; wherein $R^6$ is $G^1$.

In a further embodiment, $R^2$ is hydrogen or alkyl.

In one embodiment, $Y^1$ is $NR^{17}$, $CR^{18}R^{19}$, C(O), S(O)$_n$, or O.

In another embodiment, $Y^1$ is $CR^{18}R^{19}$, C(O) or O.

In another embodiment, $Y^1$ is $NR^{17}$.

In one embodiment, $Y^2$ is $NR^{20}$, $CR^{18}R^{19}$, C(O), or S(O)$_n$.

In another embodiment, $Y^2$ is $NR^{20}$, C(O), or $CR^{18}R^{19}$.

In one embodiment, $Y^3$ is $NR^{17}$, $CR^{18}R^{19}$, C(O), or S(O)$_n$.

In another embodiment, $Y^3$ is $NR^{17}$, $CR^{18}R^{19}$ or C(O).

In one embodiment, $Y^1$ is C(O), $Y^2$ is $NR^{20}$, and $Y^3$ is $CR^{18}R^{19}$.

In another embodiment, $Y^1$ is C(O), $Y^2$ is NCH$_3$, and $Y^3$ is CH$_2$.

In a further embodiment, $Y^1$ is C(O), $Y^2$ is NH, and $Y^3$ is CH$_2$.

In one embodiment $Y^1$ is $CR^{18}R^{19}$, $Y^2$ is $NR^{20}$, and $Y^3$ is C(O).

In a further embodiment, $Y^1$ is CH$_2$, $Y^2$ is NH, and $Y^3$ is C(O).

In one embodiment, $Y^1$ is $NR^{17}$, $Y^2$ is C(O), and $Y^3$ is $CR^{18}R^{19}$.

In a further embodiment, $Y^1$ is NH, $Y^2$ is C(O), and $Y^3$ is CH$_2$.

In one embodiment, $Y^1$ is $CR^{18}R^{19}$, $Y^2$ is C(O), and $Y^3$ is $NR^{17}$.

In a further embodiment, $Y^1$ is CH$_2$, $Y^2$ is C(O), and $Y^3$ is NH.

In one embodiment, $Y^1$ is S(O)$_n$, wherein n is 2, $Y^2$ is $NR^{20}$, and $Y^3$ is $CR^{18}R^{19}$.

In a further embodiment, $Y^1$ is S(O)$_2$, $Y^2$ is NH, and $Y^3$ is CH$_2$.

In one embodiment, $Y^1$ is C(O), and $Y^2$ and $Y^3$ are each $CR^{18}R^{19}$.

In another embodiment, $Y^1$ is C(O), and $Y^2$ and $Y^3$ are each CH$_2$.

In one embodiment, $Y^1$ is $CR^{18}R^{19}$, $Y^2$ is $NR^{20}$, and $Y^3$ is $CR^{18}R^{19}$.

In another embodiment, $Y^1$ is CH$_2$, $Y^2$ is $NR^{20}$, and $Y^3$ is CH$_2$.

In a further embodiment, $Y^1$ is CH$_2$, $Y^2$ is $NR^{20}$, and $Y^3$ is CH$_2$; wherein $R^{20}$ is selected from the group consisting of hydrogen, alkyl, alkylcarbonyl, haloalkyl, —C(O)-$G^1$, —C(O)N$R^a$-$G^1$, —S(O)$_n$-$G^1$, and —$(CR^{4a}R^{5a})_m$-$G^1$.

In yet a further embodiment, $Y^1$ is CH$_2$, $Y^2$ is $NR^{20}$, and $Y^3$ is CH$_2$; wherein $R^{20}$ is —S(O)$_n$-$G^1$; wherein n and $G^1$ are as described above.

In one embodiment, $Y^1$ is $NR^{17}$, and $Y^2$ and $Y_3$ are each $CR^{18}R^{19}$.

In another embodiment, $Y^1$ is NH, and $Y^2$ and $Y_3$ are each CH$_2$.

In one embodiment, $Y^1$ is O, $Y^2$ is $CR^{18}R^{19}$, and $Y^3$ is $CR^{18}R^{19}$.

In another embodiment, $Y^1$ is O, $Y^2$ is CH$_2$, and $Y^3$ is CH$_2$.

In one embodiment, $Y^1$ and $Y^2$ together are $CR^{18}$=$CR^{19}$, and $Y^3$ is $CR^{18}R^{19}$.

In a further embodiment, $Y^1$ and $Y^2$ together are CH=CH, and $Y^3$ is CH$_2$.

In one embodiment, $Y^1$ is $CR^{18}R^{19}$, and $Y^2$ and $Y^3$ together are $CR^{18}$=$CR^{19}$.

In another embodiment, $Y^1$ is $CH_2$, and $Y^2$ and $Y^3$ together are CH=CH.

In one embodiment, $Y^1$, $Y^2$, and $Y^3$ are each $CR^{18}R^{19}$.

In another embodiment, $Y^1$, $Y^2$, and $Y^3$ are each $CH_2$.

In one embodiment, compounds of formula (I) can include compounds of formula (Ia):

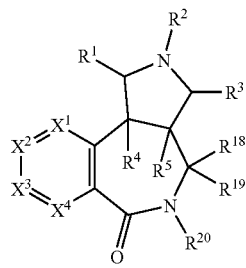

(Ia)

wherein $R^1$, $R^2$, $R^3$, $R^4$, $R^5$, $R^{18}$, $R^{19}$, $R^{20}$, $X^1$, $X^2$, $X^3$, and $X^4$ are as described above.

In one embodiment, compounds of formula (I) can include compounds of formula (Ib):

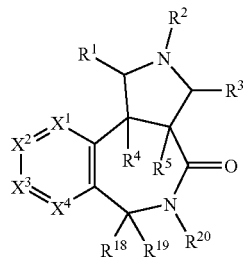

(Ib)

wherein $R^1$, $R^2$, $R^3$, $R^4$, $R^5$, $R^{18}$, $R^{19}$, $R^{20}$, $X^1$, $X^2$, $X^3$, and $X^4$ are as described above.

In one embodiment, compounds of formula (I) can include compounds of formula (Ic):

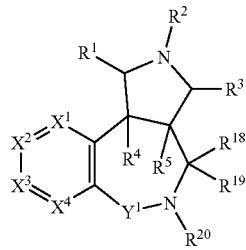

(Ic)

wherein $R^1$, $R^2$, $R^3$, $R^4$, $R^5$, $R^{18}$, $R^{19}$, $R^{20}$, $X^1$, $X^2$, $X^3$, and $X^4$ are as described above and $Y^1$ is $S(O)_2$ or $CR^{18}R^{19}$.

In one embodiment, compounds of formula (I) can include compounds of formula (Id):

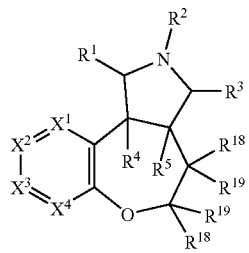

(Id)

wherein $R^1$, $R^2$, $R^3$, $R^4$, $R^5$, $R^{18}$, $R^{19}$, $R^{20}$, $X^1$, $X^2$, $X^3$, and $X^4$ are as described above.

In one embodiment, compounds of formula (I) can include compounds of formula (Ie):

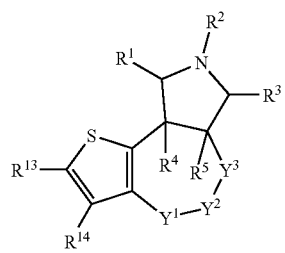

(Ie)

wherein $R^1$, $R^2$, $R^3$, $R^4$, $R^5$, $R^{13}$, $R^{14}$, $Y^1$, $Y^2$, and $Y^3$ are as described above.

In one embodiment, compounds of formula (I) can include compounds of formula (If):

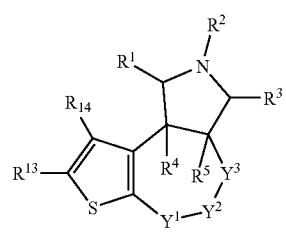

(If)

wherein $R^1$, $R^2$, $R^3$, $R^4$, $R^5$, $R^{13}$, $R^{14}$, $Y^1$, $Y^2$ and $Y^3$ are as described above.

In one embodiment, compounds of formula (I) can include compounds of formula (Ig):

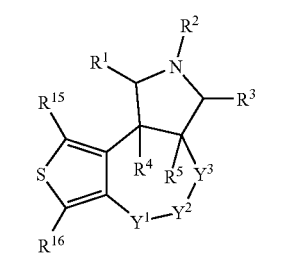

(Ig)

wherein $R^1$, $R^2$, $R^3$, $R^4$, $R^5$, $R^{15}$, $R^{16}$, $Y^1$, $Y^2$, and $Y^3$ are as described above.

In one embodiment, compounds of formula (I) can include compounds of formula (Ih):

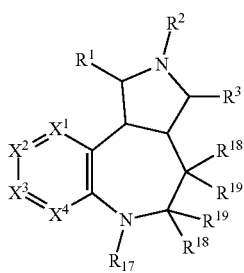

(Ih)

wherein $R^1$, $R^2$, $R^3$, $R^{17}$, $R^{18}$, $R^{19}$, $X^1$, $X^2$, $X^3$, and $X^4$ are as described above.

In one embodiment, compounds of formula (I) can include compounds of formula (Ii):

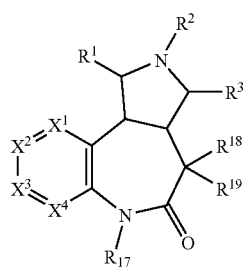

(Ii)

wherein $R^1$, $R^2$, $R^3$, $R^{17}$, $R^{18}$, $R^{19}$, $X^1$, $X^2$, $X^3$, and $X^4$ are as described above.

Specific embodiments of compounds contemplated as part of the invention include, but are not limited to:

trans-2-benzyl-1,2,3,3a,4,5-hexahydrobenzo[c]pyrrolo[3,4-e]azepin-6(10bH)-one;
trans-1,2,3,3a,4,5-hexahydrobenzo[c]pyrrolo[3,4-e]azepin-6(10bH)-one;
cis-2-benzyl-1,2,3,3a,4,5-hexahydrobenzo[c]pyrrolo[3,4-e]azepin-6(10bH)-one;
cis-1,2,3,3a,4,5-hexahydrobenzo[c]pyrrolo[3,4-e]azepin-6(10bH)-one;
trans-2-benzyl-1,2,3,3a,5,6-hexahydrobenzo[c]pyrrolo[3,4-e]azepin-4(10bH)-one;
trans-1,2,3,3a,5,6-hexahydrobenzo[c]pyrrolo[3,4-e]azepin-4(10bH)-one;
trans-2-benzyl-1,2,3,3a,4,5,6,10b-octahydrobenzo[c]pyrrolo[3,4-e]azepine;
trans-2-benzyl-5-(3-fluorophenylsulfonyl)-1,2,3,3a,4,5,6,10b-octahydrobenzo[c]pyrrolo[3,4-e]azepine;
trans-2-benzyl-5-(2,3-dichlorophenylsulfonyl)-1,2,3,3a,4,5,6,10b-octahydrobenzo[c]pyrrolo[3,4-e]azepine;
trans-2-benzyl-5-(2,5-dichlorophenylsulfonyl)-1,2,3,3a,4,5,6,10b-octahydrobenzo[c]pyrrolo[3,4-e]azepine;
trans-2-benzyl-5-(2-bromophenylsulfonyl)-1,2,3,3a,4,5,6,10b-octahydrobenzo[c]pyrrolo[3,4-e]azepine;
trans-2-benzyl-5-(3-bromophenylsulfonyl)-1,2,3,3a,4,5,6,10b-octahydrobenzo[c]pyrrolo[3,4-e]azepine;
trans-2-benzyl-5-(naphthalen-1-ylsulfonyl)-1,2,3,3a,4,5,6,10b-octahydrobenzo[c]pyrrolo[3,4-e]azepine;
trans-2-benzyl-5-(3-chloro-4-fluorophenylsulfonyl)-1,2,3,3a,4,5,6,10b-octahydrobenzo[c]pyrrolo[3,4-e]azepine;
trans-2-benzyl-5-(2,5-dimethoxyphenylsulfonyl)-1,2,3,3a,4,5,6,10b-octahydrobenzo[c]pyrrolo[3,4-e]azepine;
trans-2-benzyl-5-(3-(trifluoromethyl)phenylsulfonyl)-1,2,3,3a,4,5,6,10b-octahydrobenzo[c]pyrrolo[3,4-e]azepine;
trans-2-benzyl-5-(2,5-dimethylphenylsulfonyl)-1,2,3,3a,4,5,6,10b-octahydrobenzo[c]pyrrolo[3,4-e]azepine;
trans-2-benzyl-5-(3-methoxyphenylsulfonyl)-1,2,3,3a,4,5,6,10b-octahydrobenzo[c]pyrrolo[3,4-e]azepine;
trans-2-benzyl-5-(2-dichlorophenylsulfonyl)-1,2,3,3a,4,5,6,10b-octahydrobenzo[c]pyrrolo[3,4-e]azepine;
trans-2-benzyl-5-(3-chlorophenylsulfonyl)-1,2,3,3a,4,5,6,10b-octahydrobenzo[c]pyrrolo[3,4-e]azepine;
trans-2-benzyl-5-(2-cyanophenylsulfonyl)-1,2,3,3a,4,5,6,10b-octahydrobenzo[c]pyrrolo[3,4-e]azepine;
trans-2-(3,5-dimethylbenzyl)-1,2,3,3a,4,5-hexahydrobenzo[c]pyrrolo[3,4-e]azepin-6(10bH)-one;
trans-2-(2,5-dimethylbenzyl)-1,2,3,3a,4,5-hexahydrobenzo[c]pyrrolo[3,4-e]azepin-6(10bH)-one;
trans-2-(2,4-dimethylbenzyl)-1,2,3,3a,4,5-hexahydrobenzo[c]pyrrolo[3,4-e]azepin-6(10bH)-one;
trans-2-(3,4-dimethylbenzyl)-1,2,3,3a,4,5-hexahydrobenzo[c]pyrrolo[3,4-e]azepin-6(10bH)-one;
trans-2-(3-methylbenzyl)-1,2,3,3a,4,5-hexahydrobenzo[c]pyrrolo[3,4-e]azepin-6(10bH)-one;
trans-2-(2,3-dimethylbenzyl)-1,2,3,3a,4,5-hexahydrobenzo[c]pyrrolo[3,4-e]azepin-6(10bH)-one;
trans-2-(3-methoxybenzyl)-1,2,3,3a,4,5-hexahydrobenzo[c]pyrrolo[3,4-e]azepin-6(10bH)-one;
trans-2-(2-methoxybenzyl)-1,2,3,3a,4,5-hexahydrobenzo[c]pyrrolo[3,4-e]azepin-6(10bH)-one;
trans-2-(3,5-dichlorobenzyl)-1,2,3,3a,4,5-hexahydrobenzo[c]pyrrolo[3,4-e]azepin-6(10bH)-one;
trans-2-(2,5-dichlorobenzyl)-1,2,3,3a,4,5-hexahydrobenzo[c]pyrrolo[3,4-e]azepin-6(10bH)-one;
trans-2-(3-chlorobenzyl)-1,2,3,3a,4,5-hexahydrobenzo[c]pyrrolo[3,4-e]azepin-6(10bH)-one;
trans-2-(2-chlorobenzyl)-1,2,3,3a,4,5-hexahydrobenzo[c]pyrrolo[3,4-e]azepin-6(10bH)-one;
trans-2-(3-fluorobenzyl)-1,2,3,3a,4,5-hexahydrobenzo[c]pyrrolo[3,4-e]azepin-6(10bH)-one;
trans-2-(2-fluorobenzyl)-1,2,3,3a,4,5-hexahydrobenzo[c]pyrrolo[3,4-e]azepin-6(10bH)-one;
3-((trans-6-oxo-1,3a,4,5,6,10b-hexahydrobenzo[c]pyrrolo[3,4-e]azepin-2(3H)-yl)methyl)benzonitrile;
trans-2-(2,5-dimethoxybenzyl)-1,2,3,3a,4,5-hexahydrobenzo[c]pyrrolo[3,4-e]azepin-6(10bH)-one;
trans-2-(3,5-dimethoxybenzyl)-1,2,3,3a,4,5-hexahydrobenzo[c]pyrrolo[3,4-e]azepin-6(10bH)-one;
trans-2-(2,3-dichlorophenylsulfonyl)-1,2,3,3a,5,6-hexahydrobenzo[c]pyrrolo[3,4-e]azepin-4(10bH)-one;
cis-2-(3,5-dichlorobenzyl)-1,2,3,3a,4,5-hexahydrobenzo[c]pyrrolo[3,4-e]azepin-6(10bH)-one;
cis-2-(3-chlorobenzyl)-1,2,3,3a,4,5-hexahydrobenzo[c]pyrrolo[3,4-e]azepin-6(10bH)-one;
cis-2-(3-fluorobenzyl)-1,2,3,3a,4,5-hexahydrobenzo[c]pyrrolo[3,4-e]azepin-6(10bH)-one;
cis-2-(naphthalen-1-ylmethyl)-1,2,3,3a,4,5-hexahydrobenzo[c]pyrrolo[3,4-e]azepin-6(10bH)-one;
(3aR,10bS)-1,2,3,3a,4,5-hexahydrobenzo[c]pyrrolo[3,4-e]azepin-6(10bH)-one;
trans-2-benzyl-8-chloro-1,2,3,3a,4,5-hexahydrobenzo[c]pyrrolo[3,4-c]azepin-6(10bH)-one;
trans-8-chloro-1,2,3,3a,4,5-hexahydrobenzo[e]pyrrolo[3,4-c]azepin-6(10bH)-one;
(3aR,10bS)-1,2,3,3a,4,5-hexahydrobenzo[e]pyrrolo[3,4-c]azepin-6(10bH)-one;
trans-2-benzyl-10-chloro-1,2,3,3a,4,5-hexahydrobenzo[e]pyrrolo[3,4-c]azepin-6(10bH)-one;

trans-7-chloro-1,2,3,3a,4,5-hexahydrobenzo[e]pyrrolo[3,4-c]azepin-6(10bH)-one;
trans-7-chloro-1,2,3,3a,4,5-hexahydrobenzo[e]pyrrolo[3,4-c]azepin-6(10bH)-one;
trans-2-benzyl-9-chloro-1,2,3,3a,4,5-hexahydrobenzo[e]pyrrolo[3,4-c]azepin-6(10bH)-one;
trans-9-chloro-1,2,3,3a,4,5-hexahydrobenzo[e]pyrrolo[3,4-c]azepin-6(10bH)-one;
trans-8-chloro-2-methyl-1,2,3,3a,4,5-hexahydrobenzo[e]pyrrolo[3,4-c]azepin-6(10bH)-one;
trans-5-(3-fluorophenylsulfonyl)-1,2,3,3a,4,5,6,10b-octahydrobenzo[c]pyrrolo[3,4-e]azepine;
trans-2-benzyl-8-fluoro-1,2,3,3a,4,5-hexahydrobenzo[e]pyrrolo[3,4-c]azepin-6(10bH)-one;
trans-2-benzyl-8,9-dichloro-1,2,3,3a,4,5-hexahydrobenzo[c]pyrrolo[3,4-e]azepin-6(10bH)-one;
trans-8-fluoro-1,2,3,3a,4,5-hexahydrobenzo[c]pyrrolo[3,4-e]azepin-6(10bH)-one;
trans-2-benzyl-7-fluoro-1,2,3,3a,4,5-hexahydrobenzo[e]pyrrolo[3,4-c]azepin-6(10bH)-one;
cis-2-benzyl-7-fluoro-1,2,3,3a,4,5-hexahydrobenzo[c]pyrrolo[3,4-e]azepin-6(10bH)-one;
trans-7-fluoro-1,2,3,3a,4,5-hexahydrobenzo[c]pyrrolo[3,4-e]azepin-6(10bH)-one;
(3aS,10bS)-2-benzyl-8-fluoro-1,2,3,3a,4,5-hexahydrobenzo[c]pyrrolo[3,4-e]azepin-6(10bH)-one;
trans-7-fluoro-1,2,3,3a,4,5-hexahydrobenzo[c]pyrrolo[3,4-c]azepin-6(10bH)-one;
trans-2-benzyl-9-fluoro-1,2,3,3a,4,5-hexahydrobenzo[c]pyrrolo[3,4-e]azepin-6(10bH)-one;
trans-9-fluoro-1,2,3,3a,4,5-hexahydrobenzo[c]pyrrolo[3,4-e]azepin-6(10bH)-one;
trans-2-benzyl-10-fluoro-1,2,3,3a,4,5-hexahydrobenzo[c]pyrrolo[3,4-e]azepin-6(10bH)-one;
cis-2-benzyl-10-fluoro-1,2,3,3a,4,5-hexahydrobenzo[c]pyrrolo[3,4-e]azepin-6(10bH)-one;
trans-10-fluoro-1,2,3,3a,4,5-hexahydrobenzo[c]pyrrolo[3,4-e]azepin-6(10bH)-one;
trans-methyl-3-((6-oxo-1,3a,4,5,6,10b-hexahydrobenzo[e]pyrrolo[3,4-c]azepin-2(3H)-yl)methyl)benzoate;
trans-2-methyl-1,2,3,3a,4,5-hexahydrobenzo[c]pyrrolo[3,4-e]azepin-6(10bH)-one;
trans-2-(5-chloro-2-fluorobenzyl)-1,2,3,3a,4,5-hexahydrobenzo[c]pyrrolo[3,4-c]azepin-6(10bH)-one;
trans-2-methyl-5-(phenylsulfonyl)-1,2,3,3a,4,5,6,10b-octahydrobenzo[c]pyrrolo[3,4-e]azepine;
cis-2-methyl-5-(phenylsulfonyl)-1,2,3,3a,4,5,6,10b-octahydrobenzo[c]pyrrolo[3,4-e]azepine;
trans-5-(3-fluorophenylsulfonyl)-2-(4-methoxybenzyl)-1,2,3,3a,4,5,6,10b-octahydrobenzo[c]pyrrolo[3,4-e]azepine;
trans-2-(4-fluorobenzyl)-5-(3-fluorophenylsulfonyl)-1,2,3,3a,4,5,6,10b-octahydrobenzo[c]pyrrolo[3,4-e]azepine;
trans-8-(4-fluorophenyl)-2-methyl-1,2,3,3a,4,5-hexahydrobenzo[e]pyrrolo[3,4-c]azepin-6(10bH)-one;
trans-8-(3-fluorophenyl)-2-methyl-1,2,3,3a,4,5-hexahydrobenzo[e]pyrrolo[3,4-c]azepin-6(10bH)-one;
trans-8-(2-fluorophenyl)-2-methyl-1,2,3,3a,4,5-hexahydrobenzo[e]pyrrolo[3,4-c]azepin-6(10bH)-one;
trans-8-(3,4-difluorophenyl)-2-methyl-1,2,3,3a,4,5-hexahydrobenzo[e]pyrrolo[3,4-c]azepin-6(10bH)-one;
trans-2-methyl-8-(4-(trifluoromethyl)phenyl)-1,2,3,3a,4,5-hexahydrobenzo[e]pyrrolo[3,4-c]azepin-6(10bH)-one;
trans-2-methyl-8-(naphthalen-2-yl)-1,2,3,3a,4,5-hexahydrobenzo[e]pyrrolo[3,4-c]azepin-6(10bH)-one;
trans-2-methyl-8-m-tolyl-1,2,3,3a,4,5-hexahydrobenzo[e]pyrrolo[3,4-c]azepin-6(10bH)-one;
trans-2-methyl-8-p-tolyl-1,2,3,3a,4,5-hexahydrobenzo[e]pyrrolo[3,4-c]azepin-6(10bH)-one;
trans-2-methyl-8-(4-(methylsulfonyl)phenyl)-1,2,3,3a,4,5-hexahydrobenzo[e]pyrrolo[3,4-c]azepin-6(10bH)-one;
trans-2-methyl-8-(3-(methylsulfonyl)phenyl)-1,2,3,3a,4,5-hexahydrobenzo[e]pyrrolo[3,4-c]azepin-6(10bH)-one;
trans-2-methyl-8-styryl-1,2,3,3a,4,5-hexahydrobenzo[e]pyrrolo[3,4-c]azepin-6(10bH)-one;
trans-2-methyl-8-phenyl-1,2,3,3a,4,5-hexahydrobenzo[e]pyrrolo[3,4-c]azepin-6(10bH)-one;
trans-2-methyl-8-phenethyl-1,2,3,3a,4,5-hexahydrobenzo[e]pyrrolo[3,4-c]azepin-6(10bH)-one;
trans-methyl 2-methyl-6-oxo-1,2,3,3a,4,5,6,10b-octahydrobenzo[e]pyrrolo[3,4-c]azepine-8-carboxylate;
trans-10-fluoro-2-methyl-1,2,3,3a,4,5-hexahydrobenzo[e]pyrrolo[3,4-c]azepin-6(10bH)-one;
trans-9-fluoro-2-methyl-1,2,3,3a,4,5-hexahydrobenzo[e]pyrrolo[3,4-c]azepin-6(10bH)-one;
trans-8-fluoro-2-methyl-1,2,3,3a,4,5-hexahydrobenzo[e]pyrrolo[3,4-c]azepin-6(10bH)-one;
trans-7-fluoro-2-methyl-1,2,3,3a,4,5-hexahydrobenzo[e]pyrrolo[3,4-c]azepin-6(10bH)-one;
trans-2-benzyl-2,3,3a,4,5,10b-hexahydro-1H-[1]benzoxepino[4,5-c]pyrrole;
trans-2,3,3a,4,5,10b-hexahydro-1H-[1]benzoxepino[4,5-c]pyrrole;
trans-9-chloro-2,3,3a,4,5,10b-hexahydro-1H-[1]benzoxepino[4,5-c]pyrrole;
cis-2,3,3a,4,5,10b-hexahydro-1H-[1]benzoxepino[4,5-c]pyrrole;
trans-2-benzyl-2,3,3a,4,5,11c-hexahydro[1]benzothieno[2,3-c]pyrrolo[3,4-e]azepin-6(1H)-one;
trans-2-benzyl-8,10-dimethoxy-1,2,3,3a,4,5-hexahydrobenzo[c]pyrrolo[3,4-e]azepin-6(10bH)-one;
trans-2,3,3a,4,5,11c-hexahydro[1]benzothieno[2,3-c]pyrrolo[3,4-e]azepin-6(1H)-one;
trans-8,10-dimethoxy-1,2,3,3a,4,5-hexahydrobenzo[c]pyrrolo[3,4-e]azepin-6(10bH)-one;
trans-8-benzyl-6,6a,7,8,9,9a-hexahydropyrrolo[3,4-e]thieno[3,2-c]azepin-4(5H)-one;
trans-2-benzyl-7-(trifluoromethoxy)-1,2,3,3a,4,5-hexahydrobenzo[c]pyrrolo[3,4-e]azepin-6(10bH)-one;
trans-7-(trifluoromethoxy)-1,2,3,3a,4,5-hexahydrobenzo[c]pyrrolo[3,4-e]azepin-6(10bH)-one;
trans-6,6a,7,8,9,9a-hexahydropyrrolo[3,4-e]thieno[3,2-c]azepin-4(5H)-one;
(3aS,10bS)-2-benzyl-8,10-difluoro-1,2,3,3a,4,5-hexahydrobenzo[c]pyrrolo[3,4-e]azepin-6(10bH)-one;
(3aR,10bS)-8,10-difluoro-1,2,3,3a,4,5-hexahydrobenzo[c]pyrrolo[3,4-e]azepin-6(10bH)-one;
trans-2-benzyl-8-fluoro-2,3,3a,4,5,10b-hexahydro-1H-[1]benzoxepino[4,5-c]pyrrole;
trans-8-phenyl-2,3,3a,4,5,10b-hexahydro-1H-[1]benzoxepino[4,5-c]pyrrole;
trans-8-fluoro-2,3,3a,4,5,10b-hexahydro-1H-[1]benzoxepino[4,5-c]pyrrole;
trans-2-methyl-7-(trifluoromethoxy)-1,2,3,3a,4,5-hexahydrobenzo[c]pyrrolo[3,4-e]azepin-6(10bH)-one;
trans-2,3,3a,4,5,10b-hexahydro-1H-pyrrolo[3,4-d][1,2]benzothiazepine 6,6-dioxide;
(3aR,10bR)-2-methyl-7-(trifluoromethoxy)-1,2,3,3a,4,5-hexahydrobenzo[c]pyrrolo[3,4-e]azepin-6(10bH)-one;
(3aS,10bS)-2-methyl-7-(trifluoromethoxy)-1,2,3,3a,4,5-hexahydrobenzo[c]pyrrolo[3,4-e]azepin-6(10bH)-one;
trans-2-methyl-7-phenyl-1,2,3,3a,4,5-hexahydrobenzo[c]pyrrolo[3,4-e]azepin-6(10bH)-one;

(3aS,10bS)-8-(4-fluorophenyl)-2-methyl-1,2,3,3a,4,5-hexahydrobenzo[e]pyrrolo[3,4-c]azepin-6(10bH)-one;
(3aR,10bR)-8-(4-fluorophenyl)-2-methyl-1,2,3,3a,4,5-hexahydrobenzo[e]pyrrolo[3,4-c]azepin-6(10bH)-one;
trans-2-benzyl-8-hydroxy-1,2,3,3a,4,5-hexahydrobenzo[e]pyrrolo[3,4-c]azepin-6(10bH)-one;
trans-2-benzyl-8-((R)-1-phenylpropan-2-yloxy)-1,2,3,3a,4,5-hexahydrobenzo[e]pyrrolo[3,4-c]azepin-6(10bH)-one;
trans-2-benzyl-8-(3-fluorophenethoxy)-1,2,3,3a,4,5-hexahydrobenzo[e]pyrrolo[3,4-c]azepin-6(10bH)-one;
trans-2-benzyl-8-((S)-1-phenylpropan-2-yloxy)-1,2,3,3a,4,5-hexahydrobenzo[e]pyrrolo[3,4-c]azepin-6(10bH)-one;
trans-2-benzyl-8-phenethoxy-1,2,3,3a,4,5-hexahydrobenzo[e]pyrrolo[3,4-c]azepin-6(10bH)-one;
trans-2-methyl-8-(piperidine-1-carbonyl)-1,2,3,3a,4,5-hexahydrobenzo[e]pyrrolo[3,4-c]azepin-6(10bH)-one;
trans-8-phenethoxy-1,2,3,3a,4,5-hexahydrobenzo[e]pyrrolo[3,4-c]azepin-6(10bH)-one;
trans-8-(3-fluorophenethoxy)-1,2,3,3a,4,5-hexahydrobenzo[e]pyrrolo[3,4-c]azepin-6(10bH)-one;
trans-N,2-dimethyl-6-oxo-1,2,3,3a,4,5,6,10b-octahydrobenzo[e]pyrrolo[3,4-c]azepine-8-carboxamide;
trans-2-methyl-6-oxo-N-phenethyl-1,2,3,3a,4,5,6,10b-octahydrobenzo[e]pyrrolo[3,4-c]azepine-8-carboxamide;
trans-2-methyl-6-oxo-N-(3-(trifluoromethyl)phenethyl)-1,2,3,3a,4,5,6,10b-octahydrobenzo[e]pyrrolo[3,4-c]azepine-8-carboxamide;
trans-2-methyl-6-oxo-N-phenyl-1,2,3,3a,4,5,6,10b-octahydrobenzo[e]pyrrolo[3,4-c]azepine-8-carboxamide;
trans-methyl 2-benzyl-6-oxo-1,2,3,3a,4,5,6,10b-octahydrobenzo[e]pyrrolo[3,4-c]azepine-8-carboxylate;
cis-2-benzyl-8-methoxy-1,2,3,3a,4,5-hexahydrobenzo[e]pyrrolo[3,4-c]azepin-6(10bH)-one;
trans-8-(4-methoxyphenyl)-2-methyl-1,2,3,3a,4,5-hexahydrobenzo[e]pyrrolo[3,4-c]azepin-6(10bH)-one;
trans-2-methyl-8-(3-(trifluoromethoxy)phenyl)-1,2,3,3a,4,5-hexahydrobenzo[e]pyrrolo[3,4-c]azepin-6(10bH)-one;
trans-8-(3-methoxyphenyl)-2-methyl-1,2,3,3a,4,5-hexahydrobenzo[e]pyrrolo[3,4-c]azepin-6(10bH)-one;
trans-8-(3-isobutoxyphenyl)-2-methyl-1,2,3,3a,4,5-hexahydrobenzo[e]pyrrolo[3,4-c]azepin-6(10bH)-one;
cis-8-methoxy-1,2,3,3a,4,5-hexahydrobenzo[e]pyrrolo[3,4-c]azepin-6(10bH)-one;
trans-2-benzyl-8-(1,3,4-oxadiazol-2-yl)-1,2,3,3a,4,5-hexahydrobenzo[e]pyrrolo[3,4-c]azepin-6(10bH)-one;
trans-8-(2-methoxyphenyl)-2-methyl-1,2,3,3a,4,5-hexahydrobenzo[e]pyrrolo[3,4-c]azepin-6(10bH)-one;
trans-8-(4-isopropylphenyl)-2-methyl-1,2,3,3a,4,5-hexahydrobenzo[e]pyrrolo[3,4-c]azepin-6(10bH)-one;
trans-8-(4-ethylphenyl)-2-methyl-1,2,3,3a,4,5-hexahydrobenzo[e]pyrrolo[3,4-c]azepin-6(10bH)-one;
trans-2-methyl-8-(4-(trifluoromethoxy)phenyl)-1,2,3,3a,4,5-hexahydrobenzo[e]pyrrolo[3,4-c]azepin-6(10bH)-one;
trans-8-amino-2-benzyl-1,2,3,3a,4,5-hexahydrobenzo[e]pyrrolo[3,4-c]azepin-6(10bH)-one;
cis-8-amino-2-benzyl-1,2,3,3a,4,5-hexahydrobenzo[e]pyrrolo[3,4-c]azepin-6(10bH)-one;
trans-2-methyl-8-(pyridin-3-yl)-1,2,3,3a,4,5-hexahydrobenzo[e]pyrrolo[3,4-c]azepin-6(10bH)-one;
trans-8-amino-1,2,3,3a,4,5-hexahydrobenzo[e]pyrrolo[3,4-c]azepin-6(10bH)-one;
cis-8-amino-1,2,3,3a,4,5-hexahydrobenzo[e]pyrrolo[3,4-c]azepin-6(10bH)-one;
trans-8-(3-fluorobenzyloxy)-1,2,3,3a,4,5-hexahydrobenzo[e]pyrrolo[3,4-c]azepin-6(10bH)-one;
trans-8-(2-fluorobenzyloxy)-1,2,3,3a,4,5-hexahydrobenzo[e]pyrrolo[3,4-c]azepin-6(10bH)-one;
trans-8-(2-(trifluoromethyl)benzyloxy)-1,2,3,3a,4,5-hexahydrobenzo[e]pyrrolo[3,4-c]azepin-6(10bH)-one;
trans-8-((S)-1-phenylpropan-2-yloxy)-1,2,3,3a,4,5-hexahydrobenzo[e]pyrrolo[3,4-c]azepin-6(10bH)-one;
trans-8-((R)-1-phenylethoxy)-1,2,3,3a,4,5-hexahydrobenzo[e]pyrrolo[3,4-c]azepin-6(10bH)-one;
trans-9-benzyl-7,7a,8,9,10,10a-hexahydropyrido[2,3-e]pyrrolo[3,4-c]azepin-5(6H)-one;
trans-2-benzyl-1,2,3,3a,4,5-hexahydropyrido[3,4-e]pyrrolo[3,4-c]azepin-6(10bH)-one;
trans-7,7a,8,9,10,10a-hexahydropyrido[2,3-e]pyrrolo[3,4-c]azepin-5(6H)-one; trans-2-benzyl-1,2,3,3a,4,5-hexahydropyrido[3,2-e]pyrrolo[3,4-c]azepin-6(10bH)-one;
trans-8-((S)-1-phenylethoxy)-1,2,3,3a,4,5-hexahydrobenzo[e]pyrrolo[3,4-c]azepin-6(10bH)-one;
trans-8-((R)-1-phenylpropan-2-yloxy)-1,2,3,3a,4,5-hexahydrobenzo[e]pyrrolo[3,4-c]azepin-6(10bH)-one;
trans-1,2,3,3a,4,5-hexahydropyrido[3,2-e]pyrrolo[3,4-c]azepin-6(10bH)-one;
(3aS,10bS)-8-(4-methoxyphenyl)-2-methyl-1,2,3,3a,4,5-hexahydrobenzo[e]pyrrolo[3,4-c]azepin-6(10bH)-one;
(3aR,10bR)-8-(4-methoxyphenyl)-2-methyl-1,2,3,3a,4,5-hexahydrobenzo[e]pyrrolo[3,4-c]azepin-6(10bH)-one;
(3aS,10bS)-8-(3-methoxyphenyl)-2-methyl-1,2,3,3a,4,5-hexahydrobenzo[e]pyrrolo[3,4-c]azepin-6(10bH)-one;
(3aR,10bR)-8-(3-methoxyphenyl)-2-methyl-1,2,3,3a,4,5-hexahydrobenzo[e]pyrrolo[3,4-c]azepin-6(10bH)-one;
(3aS,10bS)-8,10-difluoro-2-methyl-1,2,3,3a,4,5-hexahydrobenzo[e]pyrrolo[3,4-c]azepin-6(10bH)-one;
(3aR,10bS)-8-fluoro-2,5-dimethyl-1,2,3,3a,4,5-hexahydrobenzo[e]pyrrolo[3,4-c]azepin-6(10bH)-one;
trans-8-(2-fluorobenzyloxy)-2-methyl-1,2,3,3a,4,5-hexahydrobenzo[e]pyrrolo[3,4-c]azepin-6(10bH)-one;
trans-8-sec-butoxy-1,2,3,3a,4,5-hexahydrobenzo[e]pyrrolo[3,4-c]azepin-6(10bH)-one;
trans-8-isobutoxy-1,2,3,3a,4,5-hexahydrobenzo[e]pyrrolo[3,4-c]azepin-6(10bH)-one;
trans-8-(cyclohexylmethoxy)-1,2,3,3a,4,5-hexahydrobenzo[e]pyrrolo[3,4-c]azepin-6(10bH)-one;
trans-8-(2,6-difluorobenzyloxy)-1,2,3,3a,4,5-hexahydrobenzo[e]pyrrolo[3,4-c]azepin-6(10bH)-one;
trans-8-(isopentyloxy)-1,2,3,3a,4,5-hexahydrobenzo[e]pyrrolo[3,4-c]azepin-6(10bH)-one;
trans-8-sec-butoxy-2-methyl-1,2,3,3a,4,5-hexahydrobenzo[e]pyrrolo[3,4-c]azepin-6(10bH)-one;
trans-8-(isopentyloxy)-2-methyl-1,2,3,3a,4,5-hexahydrobenzo[e]pyrrolo[3,4-c]azepin-6(10bH)-one;
trans-8-isobutoxy-2-methyl-1,2,3,3a,4,5-hexahydrobenzo[e]pyrrolo[3,4-c]azepin-6(10bH)-one;
trans-8-(2-methoxyphenethoxy)-1,2,3,3a,4,5-hexahydrobenzo[e]pyrrolo[3,4-c]azepin-6(10bH)-one;
trans-8-(3-methoxyphenethoxy)-1,2,3,3a,4,5-hexahydrobenzo[e]pyrrolo[3,4-c]azepin-6(10bH)-one;
trans-8-(4-methoxyphenethoxy)-1,2,3,3a,4,5-hexahydrobenzo[e]pyrrolo[3,4-c]azepin-6(10bH)-one;
trans-8-(cyclohexylmethoxy)-2-methyl-1,2,3,3a,4,5-hexahydrobenzo[e]pyrrolo[3,4-c]azepin-6(10bH)-one;
trans-8-(pyridin-4-yl)-1,2,3,3a,4,5-hexahydrobenzo[e]pyrrolo[3,4-c]azepin-6(10bH)-one;
trans-8-(2-methoxypyrimidin-5-yl)-1,2,3,3a,4,5-hexahydrobenzo[e]pyrrolo[3,4-c]azepin-6(10bH)-one;
(3aR,10bS)-8-(2-fluorobenzyloxy)-1,2,3,3a,4,5-hexahydrobenzo[e]pyrrolo[3,4-c]azepin-6(10bH)-one;
(3aS,10bR)-8-(2-fluorobenzyloxy)-1,2,3,3a,4,5-hexahydrobenzo[e]pyrrolo[3,4-c]azepin-6(10bH)-one;
(3aR,10bS)-8-((R)-1-phenylpropan-2-yloxy)-1,2,3,3a,4,5-hexahydrobenzo[e]pyrrolo[3,4-c]azepin-6(10bH)-one;

(3aS,10bR)-8-((R)-1-phenylpropan-2-yloxy)-1,2,3,3a,4,5-hexahydrobenzo[e]pyrrolo[3,4-c]azepin-6(10bH)-one;
trans-8-(2-methoxyphenethoxy)-2-methyl-1,2,3,3a,4,5-hexahydrobenzo[e]pyrrolo[3,4-c]azepin-6(10bH)-one;
trans-8-(thiophen-3-yl)-1,2,3,3a,4,5-hexahydrobenzo[e]pyrrolo[3,4-c]azepin-6(10bH)-one;
trans-2-methyl-8-(3-(1,1,1-trifluoro-2-hydroxypropan-2-yl)phenyl)-1,2,3,3a,4,5-hexahydrobenzo[e]pyrrolo[3,4-c]azepin-6(10bH)-one;
trans-8-(3-(2-hydroxypropan-2-yl)phenyl)-2-methyl-1,2,3,3a,4,5-hexahydrobenzo[e]pyrrolo[3,4-c]azepin-6(10bH)-one;
trans-8-(3-acetylphenyl)-5-methyl-1,2,3,3a,4,5-hexahydrobenzo[e]pyrrolo[3,4-c]azepin-6(10bH)-one;
trans-8-methoxy-5-methyl-1,2,3,3a,4,5-hexahydrobenzo[e]pyrrolo[3,4-c]azepin-6(10bH)-one;
trans-8-(3-(2-hydroxyethyl)phenyl)-5-methyl-1,2,3,3a,4,5-hexahydrobenzo[e]pyrrolo[3,4-c]azepin-6(10bH)-one;
trans-8-methoxy-2,5-dimethyl-1,2,3,3a,4,5-hexahydrobenzo[e]pyrrolo[3,4-c]azepin-6(10bH)-one;
trans-8-(3-acetylphenyl)-2,5-dimethyl-1,2,3,3a,4,5-hexahydrobenzo[e]pyrrolo[3,4-c]azepin-6(10bH)-one;
trans-8-(3-(2-hydroxyethyl)phenyl)-2,5-dimethyl-1,2,3,3a,4,5-hexahydrobenzo[e]pyrrolo[3,4-c]azepin-6(10bH)-one;
trans-8-(3-(1-hydroxyethyl)phenyl)-2,5-dimethyl-1,2,3,3a,4,5-hexahydrobenzo[e]pyrrolo[3,4-c]azepin-6(10bH)-one;
trans-8-(3-(2-hydroxypropan-2-yl)phenyl)-2,5-dimethyl-1,2,3,3a,4,5-hexahydrobenzo[e]pyrrolo[3,4-c]azepin-6(10bH)-one;
trans-8-(benzo[e][1,2,5]oxadiazol-5-yl)-2-methyl-1,2,3,3a,4,5-hexahydrobenzo[e]pyrrolo[3,4-c]azepin-6(10bH)-one;
trans-8-isopropyl-2-methyl-1,2,3,3a,4,5-hexahydrobenzo[e]pyrrolo[3,4-c]azepin-6(10bH)-one;
trans-2-methyl-8-(2-methylprop-1-enyl)-1,2,3,3a,4,5-hexahydrobenzo[e]pyrrolo[3,4-c]azepin-6(10bH)-one;
trans-3-(2-methyl-6-oxo-1,2,3,3a,4,5,6,10b-octahydrobenzo[e]pyrrolo[3,4-c]azepin-8-yl)benzaldehyde;
(3aS,10bS)-8-chloro-2-methyl-1,2,3,3a,4,5-hexahydrobenzo[e]pyrrolo[3,4-c]azepin-6(10bH)-one;
(3aS,10bS)-8-hydroxy-2-methyl-1,2,3,3a,4,5-hexahydrobenzo[e]pyrrolo[3,4-c]azepin-6(10bH)-one;
trans-8-cyclopentenyl-2-methyl-1,2,3,3a,4,5-hexahydrobenzo[e]pyrrolo[3,4-c]azepin-6(10bH)-one;
trans-2-methyl-8-(3,3,3-trifluoroprop-1-en-2-yl)-1,2,3,3a,4,5-hexahydrobenzo[e]pyrrolo[3,4-c]azepin-6(10bH)-one;
trans-2-methyl-8-(5-methylfuran-2-yl)-1,2,3,3a,4,5-hexahydrobenzo[e]pyrrolo[3,4-c]azepin-6(10bH)-one;
trans-8-cyclohexyl-2-methyl-1,2,3,3a,4,5-hexahydrobenzo[e]pyrrolo[3,4-c]azepin-6(10bH)-one;
trans-8-cyclopentyl-2-methyl-1,2,3,3a,4,5-hexahydrobenzo[e]pyrrolo[3,4-c]azepin-6(10bH)-one;
(3aS,10bS)-8-(3-fluorobenzyloxy)-2-methyl-1,2,3,3a,4,5-hexahydrobenzo[e]pyrrolo[3,4-c]azepin-6(10bH)-one;
(3aS,10bS)-8-(2-fluorobenzyloxy)-2-methyl-1,2,3,3a,4,5-hexahydrobenzo[e]pyrrolo[3,4-c]azepin-6(10bH)-one;
(3aS,10bS)-8-(3,5-difluorobenzyloxy)-2-methyl-1,2,3,3a,4,5-hexahydrobenzo[e]pyrrolo[3,4-c]azepin-6(10bH)-one;
3aS,10bS)-8-(2,6-difluorobenzyloxy)-2-methyl-1,2,3,3a,4,5-hexahydrobenzo[e]pyrrolo[3,4-c]azepin-6(10bH)-one;
(3aS,10bS)-8-(3,4-difluorobenzyloxy)-2-methyl-1,2,3,3a,4,5-hexahydrobenzo[e]pyrrolo[3,4-c]azepin-6(10bH)-one;
(3aS,10bS)-8-(4-fluorobenzyloxy)-2-methyl-1,2,3,3a,4,5-hexahydrobenzo[e]pyrrolo[3,4-c]azepin-6(10bH)-one;
(3aS,10bS)-8-(2,3-difluorobenzyloxy)-2-methyl-1,2,3,3a,4,5-hexahydrobenzo[e]pyrrolo[3,4-c]azepin-6(10bH)-one;
(3aS,10bS)-2-methyl-8-(2,3,6-trifluorobenzyloxy)-1,2,3,3a,4,5-hexahydrobenzo[e]pyrrolo[3,4-c]azepin-6(10bH)-one;
trans-9-bromo-2,3,3a,4,5,10b-hexahydro-1H-[1]benzoxepino[4,5-c]pyrrole;
trans-9-phenyl-2,3,3a,4,5,10b-hexahydro-1H-[1]benzoxepino[4,5-c]pyrrole;
trans-8-(benzyloxy)-2-methyl-1,2,3,3a,4,5-hexahydrobenzo[e]pyrrolo[3,4-e]azepin-6(10bH)-one;
trans-8-(3-fluorobenzyloxy)-2-methyl-1,2,3,3a,4,5-hexahydrobenzo[e]pyrrolo[3,4-e]azepin-6(10bH)-one;
trans-2-benzyl-8-(4-fluorophenyl)-1,2,3,3a,4,5-hexahydrobenzo[e]pyrrolo[3,4-c]azepin-6(10bH)-one;
trans-8-(4-fluorophenyl)-1,2,3,3a,4,5-hexahydrobenzo[e]pyrrolo[3,4-c]azepin-6(10bH)-one;
(3aR,10bS)-8-(4-fluorophenyl)-1,2,3,3a,4,5-hexahydrobenzo[e]pyrrolo[3,4-c]azepin-6(10bH)-one;
(3aS,10bR)-8-(4-fluorophenyl)-1,2,3,3a,4,5-hexahydrobenzo[c]pyrrolo[3,4-c]azepin-6(10bH)-one;
trans-2-benzyl-1,2,3,3a,4,10b-hexahydrobenzo[b]pyrrolo[3,4-d]azepin-5(6H)-one;
trans-2-benzyl-1,2,3,3a,4,10b-hexahydrobenzo[d]pyrrolo[3,4-b]azepin-5(6H)-one;
trans-8-fluoro-5-methyl-1,2,3,3a,4,5-hexahydrobenzo[c]pyrrolo[3,4-e]azepin-6(10bH)-one;
(3aR,10bS)-8-fluoro-5-methyl-1,2,3,3a,4,5-hexahydrobenzo[c]pyrrolo[3,4-e]azepin-6(10bH)-one;
(3aS,10bR)-8-fluoro-5-methyl-1,2,3,3a,4,5-hexahydrobenzo[c]pyrrolo[3,4-e]azepin-6(10bH)-one;
trans-8-(3-(methylsulfonyl)phenyl)-1,2,3,3a,4,5-hexahydrobenzo[c]pyrrolo[3,4-e]azepin-6(10bH)-one;
(3aS,10bS)-2-methyl-8-(3-(methylsulfonyl)phenyl)-1,2,3,3a,4,5-hexahydrobenzo[c]pyrrolo[3,4-e]azepin-6(10bH)-one;
(3aR,10bR)-2-methyl-8-(3-(methylsulfonyl)phenyl)-1,2,3,3a,4,5-hexahydrobenzo[c]pyrrolo[3,4-e]azepin-6(10bH)-one;
N,N-dimethyl-3-(trans-6-oxo-1,2,3,3a,4,5,6,10b-octahydrobenzo[c]pyrrolo[3,4-e]azepin-8-yl)benzamide;
trans-8-(2-(methylsulfonyl)phenyl)-1,2,3,3a,4,5-hexahydrobenzo[c]pyrrolo[3,4-e]azepin-6(10bH)-one;
trans-2-methyl-8-(2-(methylsulfonyl)phenyl)-1,2,3,3a,4,5-hexahydrobenzo[c]pyrrolo[3,4-e]azepin-6(10bH)-one;
(3aR,10bS)-9-chloro-2,3,3a,4,5,10b-hexahydro-1H-[1]benzoxepino[4,5-c]pyrrole;
(3aR,10bS)-9-chloro-2-methyl-2,3,3a,4,5,10b-hexahydro-1H-[1]benzoxepino[4,5-c]pyrrole;
(3aR,10bS)-2-methyl-2,3,3a,4,5,10b-hexahydro-1H-[1]benzoxepino[4,5-c]pyrrole;
trans-8-(3-acetylphenyl)-1,2,3,3a,4,5-hexahydrobenzo[c]pyrrolo[3,4-e]azepin-6(10bH)-one hydrochloride;
trans-8-(3-acetylphenyl)-2-methyl-1,2,3,3a,4,5-hexahydrobenzo[c]pyrrolo[3,4-e]azepin-6(10bH)-one;
trans-8-(3-(1-hydroxyethyl)phenyl)-2-methyl-1,2,3,3a,4,5-hexahydrobenzo[c]pyrrolo[3,4-e]azepin-6(10bH)-one;
3-(trans-6-oxo-1,2,3,3a,4,5,6,10b-octahydrobenzo[c]pyrrolo[3,4-e]azepin-8-yl)benzonitrile;
3-(trans-2-methyl-6-oxo-1,2,3,3a,4,5,6,10b-octahydrobenzo[c]pyrrolo[3,4-e]azepin-8-yl)benzonitrile;
trans-8-(3,6-dihydro-2H-pyran-4-yl)-1,2,3,3a,4,5-hexahydrobenzo[c]pyrrolo[3,4-e]azepin-6(10bH)-one;
trans-8-(3,6-dihydro-2H-pyran-4-yl)-2-methyl-1,2,3,3a,4,5-hexahydrobenzo[c]pyrrolo[3,4-e]azepin-6(10bH)-one;
trans-8-(4-fluorophenoxy)-2-methyl-1,2,3,3a,4,5-hexahydrobenzo[c]pyrrolo[3,4-e]azepin-6(10bH)-one;

trans-8-isobutyl-2-methyl-1,2,3,3a,4,5-hexahydrobenzo[c] pyrrolo[3,4-c]azepin-6(10bH)-one;
trans-8-(3,5-dimethylisoxazol-4-yl)-1,2,3,3a,4,5-hexahydrobenzo[c]pyrrolo[3,4-c]azepin-6(10bH)-one;
trans-8-(4,4-dimethylcyclohexyloxy)-1,2,3,3a,4,5-hexahydrobenzo[c]pyrrolo[3,4-c]azepin-6(10bH)-one;
trans-8-(3-oxo-2,3-dihydro-1H-inden-5-yl)-1,2,3,3a,4,5-hexahydrobenzo[c]pyrrolo[3,4-e]azepin-6(10bH)-one;
(3aS,10bS)-8-(3-((S)-1-hydroxyethyl)phenyl)-2-methyl-1,2,3,3a,4,5-hexahydrobenzo[c]pyrrolo[3,4-c]azepin-6(10bH)-one;
(3aS,10bS)-8-(3-((R)-1-hydroxyethyl)phenyl)-2-methyl-1,2,3,3a,4,5-hexahydrobenzo[c]pyrrolo[3,4-c]azepin-6(10bH)-one;
trans-8-(3-(ethylsulfonyl)phenyl)-1,2,3,3a,4,5-hexahydrobenzo[c]pyrrolo[3,4-e]azepin-6(10bH)-one;
trans-2-methyl-8-(3-oxo-2,3-dihydro-1H-inden-5-yl)-1,2,3,3a,4,5-hexahydrobenzo[c]pyrrolo[3,4-e]azepin-6(10bH)-one;
trans-8-(3-(2-hydroxyethyl)phenyl)-1,2,3,3a,4,5-hexahydrobenzo[c]pyrrolo[3,4-e]azepin-6(10bH)-one;
trans-8-(3-(2-hydroxyethyl)phenyl)-2-methyl-1,2,3,3a,4,5-hexahydrobenzo[c]pyrrolo[3,4-e]azepin-6(10bH)-one;
trans-2-benzyl-1,2,3,3a,4,5,6,10b-octahydrobenzo[b]pyrrolo[3,4-d]azepine;
trans-8-(3-(ethylsulfonyl)phenyl)-2-methyl-1,2,3,3a,4,5-hexahydrobenzo[c]pyrrolo[3,4-e]azepin-6(10bH)-one;
trans-2-benzyl-1,2,3,3a,4,5-hexahydronaphtho[2,3-c]pyrrolo[3,4-e]azepin-6(12bH)-one;
trans-1,2,3,3a,4,5-hexahydronaphtho[2,3-c]pyrrolo[3,4-e]azepin-6(12bH)-one;
trans-1,2,3,3a,4,5,8,9,10,11-decahydronaphtho[2,3-c]pyrrolo[3,4-e]azepin-6(12bH)-one;
(3aR,10bS)-9-methoxy-2,3,3a,4,5,10b-hexahydrobenzo[3,4]cyclohepta[1,2-c]pyrrol-6(1H)-one;
2,3,3a,4,5,10b-hexahydro-1H-pyrrolo[3',4':4,5]oxepino[2,3-b]pyridine;
trans-2-benzyl-9-methoxy-2,3,3a,4,5,10b-hexahydrobenzo[3,4]cyclohepta[1,2-c]pyrrol-6(1H)-one;
trans-2-benzyl-2,3,3a,4,5,10b-hexahydro-1H-pyrrolo[3',4':4,5]oxepino[2,3-b]pyridine;
trans-9-methoxy-1,2,3,3a,4,5,6,10b-octahydrobenzo[3,4]cyclohepta[1,2-c]pyrrole;
trans-2,3,3a,4,5,10b-hexahydro-1H-pyrrolo[3',4':4,5]oxepino[2,3-b]pyridine;
trans-8-(tetrahydro-2H-pyran-4-yl)-1,2,3,3a,4,5-hexahydrobenzo[c]pyrrolo[3,4-e]azepin-6(10bH)-one;
trans-9-methoxy-1,2,3,3a,4,10b-hexahydrobenzo[3,4]cyclohepta[1,2-c]pyrrole;
trans-2-methyl-8-(tetrahydro-2H-pyran-4-yl)-1,2,3,3a,4,5-hexahydrobenzo[c]pyrrolo[3,4-e]azepin-6(10bH)-one;
trans-2-methyl-2,3,3a,4,5,10b-hexahydro-1H-pyrrolo[3',4':4,5]oxepino[2,3-b]pyridine;
cis-2-methyl-1,2,3,3a,4,5,6,10b-octahydrobenzo[3,4]cyclohepta[1,2-c]pyrrole;
(3aR,10bS)-2,3,3a,4,5,10b-hexahydro-1H-[1]benzoxepino[4,5-c]pyrrole;
(3aS,10bR)-2,3,3a,4,5,10b-hexahydro-1H-[1]benzoxepino[4,5-c]pyrrole;
trans-10-methoxy-2,3,3a,4,5,10b-hexahydro-1H-[1]benzoxepino[4,5-c]pyrrole;
trans-10-methoxy-2-methyl-2,3,3a,4,5,10b-hexahydro-1H-[1]benzoxepino[4,5-c]pyrrole;
(3aS,10bS)-8-(benzyloxy)-2-methyl-1,2,3,3a,4,5-hexahydrobenzo[c]pyrrolo[3,4-c]azepin-6(10bH)-one;
(3aS,10bS)-8-(2-methoxyphenyl)-2-methyl-1,2,3,3a,4,5-hexahydrobenzo[c]pyrrolo[3,4-c]azepin-6(10bH)-one;
trans-8-(2,6-difluorophenyl)-1,2,3,3a,4,5-hexahydrobenzo[c]pyrrolo[3,4-c]azepin-6(10bH)-one;
(3aS,10bS)-8-(cyclopropylmethoxy)-2-methyl-1,2,3,3a,4,5-hexahydrobenzo[c]pyrrolo[3,4-c]azepin-6(10bH)-one;
(3aS,10bS)-8-(3-acetylphenyl)-2-methyl-1,2,3,3a,4,5-hexahydrobenzo[c]pyrrolo[3,4-c]azepin-6(10bH)-one; or
cis-8-fluoro-9-methyl-1,2,3,3a,4,5-hexahydrobenzo[c]pyrrolo[3,4-e]azepin-6(10bH)-one.

Compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

In another embodiment of this invention, therefore, pertains to a process for making (3aS,10bS)-8-chloro-2-methyl-1,2,3,3a,4,5-hexahydrobenzo[e]pyrrolo[3,4-c]azepin-6(10bH)-one comprising:

(a) combining dibenzoyl-D-tartaric acid (1.05 equivalents) and methanol;

(b) adding a solution of trans-8-chloro-2-methyl-1,2,3,3a,4,5-hexahydrobenzo[e]pyrrolo[3,4-c]azepin-6(10bH)-one (0.10-0.15 equivalents) in methanol;

(c) seeding the solution with (3aS,10bS)-8-chloro-2-methyl-1,2,3,3a,4,5-hexahydrobenzo[e]pyrrolo[3,4-c]azepin-6(10bH)-one which are obtained in smaller batches of the same sequence iteratively increasing the enantiomeric excess in successive passage;

(d) slowly adding additional trans-8-chloro-2-methyl-1,2,3,3a,4,5-hexahydrobenzo[e]pyrrolo[3,4-c]azepin-6(10bH)-one (0.85-0.90 equivalents) dissolved in methanol; and (e) stirring the resultant mixture for a period of time resulting in crystallization and isolating the crystalline (3aS,10bS)-8-chloro-2-methyl-1,2,3,3a,4,5-hexahydrobenzo[e]pyrrolo[3,4-c]azepin-6(10bH)-one dibenzyoyl-D-tartrate.

Another embodiment of this invention pertains to a process for making (3aS,10bS)-8-hydroxy-2-methyl-1,2,3,3a,4,5-hexahydrobenzo[e]pyrrolo[3,4-c]azepin-6(10bH)-one comprising:

(a) combining palladium(II) acetate (0.04 equivalents), 2-di-tert-butylphosphino-3,4,5,6-tetramethyl-2',4',6'-triisopropyl-1,1'-biphenyl (0.05 equivalents), cesium carbonate (1.5 equivalents) and (3aS,10bS)-8-chloro-2-methyl-1,2,3,3a,4,5-hexahydrobenzo[e]pyrrolo[3,4-c]azepin-6(10bH)-one (1 equivalent);

(b) adding a solution of benzyl alcohol (20 equivalents) in toluene to the mixture of palladium(II) acetate, 2-di-tert-butylphosphino-3,4,5,6-tetramethyl-2',4',6'-triisopropyl-1,1'-biphenyl, cesium carbonate and (3aS,10bS)-8-chloro-2-methyl-1,2,3,3a,4,5-hexahydrobenzo[e]pyrrolo[3,4-c]azepin-6(10bH)-one;

(c) isolating the (3aS,10bS)-8-(benzyloxy)-2-methyl-1,2,3,3a,4,5-hexahydrobenzo[e]pyrrolo[3,4-c]azepin-6(10bH)-one;

(d) combining (3aS,10bS)-8-(benzyloxy)-2-methyl-1,2,3,3a,4,5-hexahydrobenzo[e]pyrrolo[3,4-c]azepin-6(10bH)-one with catalyst JM UK#3 (10 weight percent dry basis, catalyst in 50>9% water) and methanol and hydrogenating the mixture for 5 minutes to 24 hours; and (e) isolating the (3aS,10bS)-8-hydroxy-2-methyl-1,2,3,3a,4,5-hexahydrobenzo[e]pyrrolo[3,4-c]azepin-6(10bH)-one.

The present application contemplates various stereoisomers and mixtures thereof and these are specifically included within the scope of this application. Stereoisomers include enantiomers and diastereomers, and mixtures of enantiomers or diastereomers. Individual stereoisomers of compounds of the present application may be prepared synthetically from commercially available starting materials which contain asymmetric or chiral centers or by preparation of racemic mixtures followed by resolution which is well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary or (2) direct separation of the mixture of optical enantiomers on chiral chromatographic columns.

Geometric isomers may exist in the compounds of the present invention. The present invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the present invention encompasses any tautomeric or stereoisomeric form, and mixtures thereof, and is not to be limited merely to any one tautomeric or stereoisomeric form utilized within the naming of the compounds or formulae drawings.

The present invention also includes isotopically-labeled compounds, which are identical to those recited in Formula I, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, fluorine, and chlorine, such as, but not limited to $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

c. Biological Data

To determine the effectiveness of compounds having a formula (I), these compounds can be evaluated in a radioligand binding assay for the agonist site of the human serotonin 5-$HT_2$ receptor, the human 5-$HT_6$ receptor or in vitro models of cellular function.

Abbreviations which have been used in the descriptions of Biological Data that follow are: BSA for bovine serum albumin; CHO for Chinese hamster ovary; DMEM for Dulbecco's modified Eagle's medium; dFCS for dialyzed fetal calf serum; DMSO for dimethyl sulfoxide; EDTA for ethylenediaminetetraacetic acid; FLIPR for fluorometric imaging plate reader; HEPES for 4-(2-hydroxyethyl)-1-piperazineethanesulfonic acid; ip for intraperitoneal; PBS for phosphate buffered saline; PEI for polyethylenimine; rpm for revolutions per minute; RPMI for Roswell Park Memorial Institute; sc for subcutaneous; Tris for tris(hydroxymethyl)aminomethane; and Tris-Cl for tris(hydroxymethyl)aminomethane hydrochloride.

(i) Human 5-$HT_{2c}$ Receptor Radioligand Binding Assay

Affinity of compounds for the agonist site of the 5-$HT_{2c}$ receptor in transfected CHO cells was determined in a radioligand binding assay essentially as described by Bryant, H. U., et al., Life Sciences (1996) 59(15), 1259-1268. In brief, cell membrane homogenates with 40 mg of protein were incubated for 15 minutes at 37° C. with 0.2 nM $[^{125}I](\pm)(1$-(4-iodo-2,5-dimethoxyphenyl)isopropylamine (DOI) with or without test compounds in a buffer containing 50 mM Tris-HCl, 5 mM $MgCl_2$ and 0.3% BSA. Nonspecific binding was determined in the presence of 10 μM (±)DOI. The amount of binding was determined by radioactivity quantitation with scintillation counter. $IC_{50}$s were determined from a standard curve of the reference compound (±)DOI. Ki's as shown in Table 1 were derived from the $IC_{50}$s in the standard method.

TABLE 1

| 5-$HT_{2c}$ Agonist Site Radioligand Binding | |
|---|---|
| Example | Ki (μm) |
| 2 | 0.022 |
| 8 | 0.093 |
| 12 | 0.32 |
| 14 | 0.59 |
| 16 | 0.56 |
| 20 | 0.26 |
| 27 | 0.21 |
| 28 | 0.014 |
| 29 | 0.07 |
| 30 | 0.0034 |
| 38 | 0.0086 |
| 44 | 0.0095 |
| 45 | 0.0069 |
| 46 | 0.011 |
| 47 | 0.0061 |
| 48 | 0.022 |
| 49 | 0.17 |
| 51 | 0.11 |
| 52 | 0.86 |
| 53 | 0.0081 |
| 54 | 0.0091 |

TABLE 1-continued

5-HT$_{2C}$ Agonist Site Radioligand Binding

| Example | Ki (µm) |
|---|---|
| 55 | 0.0091 |
| 56 | 0.07 |
| 57 | 0.026 |
| 58 | 0.031 |
| 59 | 0.21 |
| 60 | 0.044 |
| 61 | 0.0064 |
| 62 | 0.0082 |
| 63 | 0.14 |
| 64 | 1 |
| 65 | 0.053 |
| 66 | 0.29 |
| 67 | 0.043 |
| 68 | 0.01 |
| 69 | 0.048 |
| 70 | 0.036 |
| 71 | 0.015 |
| 72 | 0.065 |
| 96 | 0.38 |

(ii) Human 5-HT$_{2C}$ Functional Assay in 1321N1 Cells

Functional activity was determined by testing the effect of the compounds on intracellular calcium levels in 1321N1 cells stably transfected with the human 5-HT$_{2C}$ receptor. Cells were seeded into 96-well plates at 50,000 cells/well and grown overnight in tissue culture medium (DMEM with Glutamax I (Invitrogen), containing 10% dFCS, 50 µg/mL Gentamicin, 400 µg/mL Geneticin) at 37° C. and 7% CO$_2$. Growth medium was replaced by medium without dFCS for overnight incubation. Cells were loaded with a fluorescent calcium-sensitive dye in the presence of 1% probenicid according to the manufacturer's protocol (Fluo4 AM, Molecular Devices). Serial compound dilutions (final concentrations $10^{-10}$ to $10^{-5}$M) were added to the cells either alone or in the presence of serotonin ($10^{-9}$M) and the maximum calcium response was determined using a FLIPR instrument (Molecular Devices). Concentration-response curves were fitted using a four-parameter logistic equation (GraphPad Prism). The concentration at which the compound exerts half its maximal effect is named the 'effective concentration 50' or 'EC$_{50}$' and is listed in Table 2.

TABLE 2

5-HT$_{2C}$ Agonist Activity

| Example | EC$_{50}$ (µM) |
|---|---|
| 1 | 0.0112 |
| 3 | 0.101 |
| 4 | 0.202 |
| 9 | >10 |
| 12 | >10 |
| 14 | >10 |
| 16 | >10 |
| 20 | >10 |
| 22 | 0.00522 |
| 23 | 0.00885 |
| 24 | 0.0456 |
| 25 | 0.0402 |
| 26 | 0.0103 |
| 27 | 0.266 |
| 28 | 0.00395 |
| 29 | 0.027 |
| 30 | 0.00211 |
| 31 | 0.00405 |
| 32 | 0.0193 |
| 33 | 0.0329 |
| 34 | 0.012 |
| 35 | 0.0123 |
| 36 | 0.0772 |
| 38 | 0.00624 |
| 40 | 0.0113 |
| 41 | 0.00494 |
| 42 | 0.0181 |
| 43 | 0.0819 |
| 44 | 0.00302 |
| 45 | 0.00595 |
| 46 | 0.00114 |
| 47 | 0.000575 |
| 48 | 0.0141 |
| 49 | 0.0483 |
| 51 | 0.084 |
| 52 | 0.158 |
| 54 | 0.0132 |
| 55 | 0.0106 |
| 56 | 0.0153 |
| 57 | 0.00767 |
| 58 | 0.029 |
| 59 | 0.115 |
| 60 | 0.00765 |
| 61 | 0.0032 |
| 65 | 0.0202 |
| 66 | 0.179 |
| 67 | 0.00655 |
| 68 | 0.00397 |
| 69 | 0.00878 |
| 70 | 0.00176 |
| 71 | 0.0142 |
| 72 | 0.0519 |

(iii) Human 5-HT$_{2C}$ and 5-HT$_{2B}$ Functional High Throughput Screening Assays in CHO-K1 Cells CHO-K1 cells over-expressing 5HT$_{2C}$ or 5HT$_{2B}$ receptors were grown in 1272 cm$^2$ flasks to 70-80% confluency in UltraCHO media (Lonza, Walkersville, Md.) supplemented with 1% dialyzed fetal bovine serum (FBS), 250 µg/mL zeocin, 100 U/mL penicillin and 100 µg/mL streptomycin, and 400 µg/mL geneticin. The cells were dissociated from the flasks using 0.05% trypsin, resuspended in Recovery™ cell culture freezing medium (Invitrogen, Carlsbad, Calif.) and stored in liquid nitrogen until use. The calcium flux experiments were done using frozen cells. The cells were diluted in media containing 1% dialyzed FBS and 100 U/mL pencillin and 100 µg/mL streptomycin and plated into 384-well poly-D-Lysine coated plates (15,000 cells/well). Then the plates were incubated overnight in a cell incubator at 37° C., 5% CO$_2$. On the next day, the growth media was replaced with media without FBS and further incubated overnight. On day three, the changes in intracellular Ca$^{2+}$ were determined using calcium sensitive fluorescent dye, Ca4 (MDS Analytical Technologies, Sunnyvale, Calif.) by loading 15 µL of diluted dye in Hank's Balanced Salt Solution and 20 mM Hepes buffer (pH 7.4) with final concentration of 2.5 mM probenecid into the cells containing media. Then the cells were incubated at room temperature for 60 minutes in dark.

After incubation, the cell plates were transferred to FLIPR™ (MDS) and their fluorescence measurements were read at an excitation wavelength of 480 nm and an emission wavelength of 530 nm at 25° C. The baseline fluorescence was measured for the first 10 seconds and then 15 µL of 4× concentration of serotonin/test compound was added to the cells. The fluorescence intensity was captured every second for the first 1 minute followed by every 5 seconds for an additional 2 minutes. The increase in fluorescent response by a test compound was normalized to the response of serotonin and used to determine agonist activity. The concentration response of compounds was done from a starting concentration of 10 μM, 1:10 dilution across 6 wells with a final dimethyl sulfoxide concentration of 0.2% and was fitted using a 4-parameter logistic equation. The concentration at which a compound exerts half its maximal effect was named as 'effective concentration 50' or '$EC_{50}$'. Emax is the maximum functional response or efficacy expressed as a percentage relative to the effect of serotonin.

TABLE 3

5-HT$_{2C}$ Agonist Activity

| Example | $EC_{50}$ (μM) | Emax |
|---|---|---|
| 1 | 0.02 | >120% |
| 28 | 0.001 | >120% |
| 44 | 0.001 | 100% |
| 47 | 0.0003 | >120% |
| 53 | 0.02 | 100% |
| 55 | 0.04 | 120% |
| 57 | 0.006 | 120% |
| 58 | 0.03 | 110% |
| 59 | 0.1 | 120% |
| 60 | 0.007 | 120% |
| 61 | 0.00582 | >120% |
| 62 | 0.0012 | >120% |
| 63 | 0.2 | 120% |
| 65 | 0.02 | 120% |
| 67 | 0.005 | >120% |
| 68 | 0.007 | 120% |
| 69 | 0.009 | 120% |
| 75 | 0.0021 | >120% |
| 76 | 0.011 | >120% |
| 77 | 0.0058 | >120% |
| 78 | 0.0066 | >120% |
| 79 | 0.03 | >120% |
| 80 | 0.022 | >120% |
| 81 | 0.0017 | >120% |
| 82 | 0.0042 | >120% |
| 83 | 0.2 | >120% |
| 84 | 0.05 | >120% |
| 85 | 0.12066 | 100% |
| 86 | 0.007 | 110% |
| 87 | 0.038 | 90% |
| 88 | 0.5 | >120% |
| 89 | 0.01149 | >120% |
| 90 | 0.3 | 85% |
| 91 | 0.02 | >120% |
| 92 | 0.05602 | >120 |
| 93 | 0.1 | >120% |
| 94 | 0.03 | >120% |
| 95 | 0.002 | >120% |
| 96 | 0.2 | 120% |
| 97 | 1 | 110% |
| 98 | 0.01 | >120% |
| 99 | 0.02 | >120% |
| 100 | 0.003 | >120% |
| 101 | 0.4 | >120% |
| 102 | 0.1 | >120% |
| 103 | 0.0007 | >120% |
| 104 | 0.9 | >120% |
| 105 | 0.02 | >120% |
| 106 | 0.0004 | >120% |
| 107 | 0.09 | 110% |
| 108 | 0.2 | 110% |
| 109 | 0.04 | >120% |
| 110 | 0.02 | >120% |
| 111 | 6 | 100% |
| 112 | 2 | 90% |
| 113 | 0.005 | 120% |
| 114 | 5 | 80% |
| 115 | 0.002 | >120% |
| 116 | 0.9 | 90% |
| 117 | 0.2 | >120% |
| 118 | 0.3 | >120% |
| 119 | 0.1 | >120% |
| 120 | 0.4 | 110% |

TABLE 3-continued

5-HT$_{2C}$ Agonist Activity

| Example | $EC_{50}$ (μM) | Emax |
|---|---|---|
| 121 | 0.2 | 120% |
| 122 | 6 | 100% |
| 123 | 0.01 | 120% |
| 124 | 0.02 | >120% |
| 125 | 2 | 90% |
| 126 | 6 | 60% |
| 127 | 1 | 80% |
| 128 | 2 | 50% |
| 129 | 0.2 | >120% |
| 130 | 0.9 | 100% |
| 131 | 0.008 | >120% |
| 132 | 0.02 | >120% |
| 133 | 0.008 | >120% |
| 134 | 0.06 | >120% |
| 135 | 0.8 | >120% |
| 136 | 2 | 110% |
| 137 | 0.1 | >120% |
| 138 | 0.1 | >120% |
| 139 | 0.03 | >120% |
| 140 | 0.06 | >120% |
| 141 | 0.6 | >120% |
| 142 | 2 | 80% |
| 143 | 0.3 | >120% |
| 144 | 0.1 | >120% |
| 145 | 3 | 15% |
| 146 | 0.0008 | >120% |
| 147 | 0.0006 | >120% |
| 148 | 0.0009 | >120% |
| 149 | 0.004 | 120% |
| 150 | 0.05 | >120% |
| 151 | 0.07 | >120% |
| 152 | 2 | 50% |
| 153 | 0.08 | >120% |
| 154 | 2 | 90% |
| 155 | 0.05 | >120% |
| 157 | 3 | 110% |
| 158 | 0.0006 | >120% |
| 159 | 1 | 110% |
| 160 | 0.0008 | >120% |
| 161 | 0.2 | 110% |
| 162 | 0.008 | >120% |
| 163 | 0.06 | >120% |
| 164 | 0.7 | 50% |
| 165 | 0.08 | >120% |
| 166 | 0.008 | >120% |
| 167 | 0.005 | >120% |
| 168 | 0.001 | >120% |
| 169 | 0.001 | >120% |
| 170 | 0.07 | 120% |
| 171 | 0.03 | >120% |
| 172 | 0.06 | >120% |
| 173 | 0.02 | >120% |
| 174 | 0.03 | 110% |
| 175 | 0.006 | >120% |
| 176 | 0.2 | >120% |
| 177 | 0.1 | >120% |
| 178 | 0.07 | >120% |
| 179 | 0.0003 | >120% |
| 180 | 0.03 | >120% |
| 181 | 0.01 | >120% |
| 182 | 5 | 70% |
| 183 | 0.04 | 65% |
| 184 | 0.0003 | >120% |
| 185 | 0.001 | 120% |
| 186 | 0.001 | >120% |
| 187 | 0.003 | >120% |
| 188 | 0.06 | >120% |
| 189 | 0.0009 | >120% |
| 190 | 0.1 | >120% |
| 191 | 0.04 | 110% |
| 192 | 0.008 | 120% |
| 193 | 0.02 | >120% |
| 194 | 0.02 | >120% |
| 195 | 0.01 | >120% |
| 196 | 0.5 | 30% |
| 197 | 0.003 | >120% |

TABLE 3-continued

5-HT$_{2C}$ Agonist Activity

| Example | EC$_{50}$ (μM) | Emax |
|---|---|---|
| 198 | 0.009 | >120% |
| 199 | 0.01 | >120% |
| 200 | 0.5 | 55% |
| 201 | 0.1 | 120% |
| 202 | 0.4 | 80% |
| 203 | 0.006 | >120% |
| 204 | 0.5 | 80% |
| 205 | 0.3 | 90% |
| 206 | 0.002 | >120% |
| 207 | 0.001 | >120% |
| 208 | 0.002 | >120% |
| 209 | 0.001 | >120% |
| 210 | 0.002 | >120% |
| 211 | 0.002 | >120% |
| 212 | 0.0009 | >120% |
| 213 | 0.001 | >120% |
| 214 | 0.002 | >120% |
| 215 | 0.6 | >120% |
| 216 | 0.002 | >120% |
| 217 | 0.002 | 120% |
| 218 | 0.04 | >120% |
| 219 | 0.0007 | >120% |
| 220 | <0.0001 | >120% |
| 221 | 0.2 | >120% |
| 222 | 0.4 | >120% |
| 223 | 5 | 60% |
| 224 | 0.04 | >120% |
| 225 | 0.02 | >120% |
| 226 | 1 | >120% |
| 227 | 0.0008 | >120% |
| 228 | 0.007 | >120% |
| 229 | 1 | 90% |
| 230 | 0.08 | >120% |
| 231 | 0.9 | 105% |
| 232 | 3 | 30% |
| 233 | 0.0006 | >120% |
| 234 | 0.01 | >120% |
| 235 | 0.04 | 120% |
| 236 | 0.0003 | >120% |
| 237 | 0.003 | >120% |
| 238 | 0.0007 | >120% |
| 239 | 0.0008 | >120% |
| 240 | 0.01 | >120% |
| 241 | 0.007 | >120% |
| 242 | 0.2 | >120% |
| 243 | 0.06 | >120% |
| 244 | 0.1 | 80% |
| 245 | 0.05 | 100% |
| 246 | 0.04 | 100% |
| 247 | 0.008 | >120% |
| 248 | 0.002 | 100% |
| 249 | 0.002 | 100% |
| 250 | 0.003 | 105% |
| 251 | 0.4 | >120% |
| 252 | 0.0004 | >120% |
| 253 | 0.007 | >120% |
| 254 | 1 | 105% |
| 255 | 0.03 | 90% |
| 256 | 0.1 | 90% |
| 257 | 0.02 | 120% |
| 258 | 0.01 | 100% |
| 259 | 0.06 | >120% |
| 260 | 1 | >120% |
| 261 | 0.04 | >120% |
| 262 | 2 | 90% |
| 263 | 0.1 | >120% |
| 264 | 1 | >120% |
| 265 | 0.1 | >120% |
| 266 | 0.01 | >120% |
| 267 | 1 | 90% |
| 268 | 7 | 70% |
| 269 | 0.1 | >120% |
| 270 | 0.01 | >120% |
| 271 | 0.4 | 120% |
| 272 | 0.007 | >120% |
| 273 | 0.01 | >120% |
| 274 | 0.003 | >120% |
| 275 | 0.02 | >120% |
| 276 | 0.008 | >120% |
| 277 | 0.01 | 100% |
| 278 | 0.002 | 120% |
| 279 | 0.06 | >120% |

TABLE 4

5-HT$_{2B}$ Agonist Activity

| Example | EC$_{50}$ (μM) | Emax |
|---|---|---|
| 1 | >10 | inactive |
| 28 | 0.07 | 55% |
| 44 | 0.5 | 100% |
| 47 | 0.02 | 100% |
| 53 | >10 | inactive |
| 55 | >10 | inactive |
| 57 | 0.7 | 100% |
| 58 | >10 | inactive |
| 59 | >10 | inactive |
| 60 | 0.9 | 80% |
| 61 | 0.2 | 10% |
| 62 | 0.7 | 80% |
| 63 | >10 | inactive |
| 65 | >10 | inactive |
| 67 | 1 | 110% |
| 67 | >10 | inactive |
| 68 | >10 | inactive |
| 69 | 0.5 | 70% |
| 75 | >10 | inactive |
| 76 | >10 | inactive |
| 77 | >10 | inactive |
| 78 | >10 | inactive |
| 79 | >10 | inactive |
| 80 | >10 | inactive |
| 81 | >10 | inactive |
| 82 | >10 | inactive |
| 83 | >10 | inactive |
| 84 | >10 | inactive |
| 85 | >10 | inactive |
| 86 | >10 | inactive |
| 87 | >10 | inactive |
| 88 | >10 | inactive |
| 89 | 0.56 | 33% |
| 90 | >10 | inactive |
| 91 | 3 | 25% |
| 92 | 1.35 | 34% |
| 93 | >10 | inactive |
| 94 | 0.5 | 45% |
| 95 | 0.1 | 35% |
| 96 | 1 | 50% |
| 97 | 4 | 40% |
| 98 | >10 | inactive |
| 99 | 1 | 90% |
| 100 | 0.9 | 70% |
| 101 | >10 | inactive |
| 102 | >10 | inactive |
| 103 | 0.08 | 110% |
| 104 | >10 | inactive |
| 105 | >10 | inactive |
| 106 | 0.1 | 95% |
| 107 | 0.7 | 15% |
| 108 | >10 | inactive |
| 109 | 0.3 | 55% |
| 110 | 0.9 | 15% |
| 111 | >10 | 20% |
| 112 | >10 | inactive |
| 113 | 2 | 20% |
| 114 | >10 | inactive |
| 115 | >10 | inactive |
| 116 | >10 | inactive |

TABLE 4-continued

5-HT$_{2B}$ Agonist Activity

| Example | EC$_{50}$ (μM) | Emax |
|---|---|---|
| 117 | >10 | inactive |
| 118 | >10 | inactive |
| 119 | >10 | inactive |
| 120 | >10 | inactive |
| 121 | >10 | inactive |
| 122 | >10 | inactive |
| 123 | >10 | inactive |
| 124 | >10 | inactive |
| 125 | >10 | inactive |
| 126 | >10 | inactive |
| 127 | >10 | inactive |
| 128 | >10 | inactive |
| 129 | >10 | inactive |
| 130 | >10 | inactive |
| 131 | >10 | inactive |
| 132 | >10 | inactive |
| 133 | >10 | inactive |
| 134 | >10 | inactive |
| 135 | >10 | inactive |
| 136 | >10 | inactive |
| 137 | >10 | inactive |
| 138 | >10 | inactive |
| 139 | >10 | inactive |
| 140 | >10 | inactive |
| 141 | >10 | inactive |
| 142 | >10 | inactive |
| 143 | >10 | inactive |
| 144 | 1 | 60% |
| 145 | >10 | inactive |
| 146 | 1 | 15% |
| 147 | >10 | inactive |
| 148 | >10 | inactive |
| 149 | >10 | inactive |
| 150 | >10 | inactive |
| 151 | >10 | inactive |
| 152 | >10 | inactive |
| 153 | >10 | 30% |
| 154 | >10 | inactive |
| 155 | >10 | inactive |
| 157 | >10 | inactive |
| 158 | >10 | inactive |
| 159 | >10 | inactive |
| 160 | >10 | inactive |
| 161 | >10 | inactive |
| 162 | 0.1 | 40% |
| 163 | 0.8 | 20% |
| 164 | >10 | inactive |
| 165 | >10 | inactive |
| 166 | >10 | inactive |
| 167 | >10 | inactive |
| 168 | >10 | inactive |
| 169 | >10 | inactive |
| 170 | >10 | inactive |
| 171 | >10 | inactive |
| 172 | >10 | inactive |
| 173 | >10 | inactive |
| 174 | >10 | inactive |
| 175 | >10 | inactive |
| 176 | >10 | inactive |
| 177 | >10 | inactive |
| 178 | >10 | inactive |
| 179 | >10 | inactive |
| 180 | >10 | inactive |
| 181 | >10 | inactive |
| 182 | >10 | inactive |
| 183 | >10 | inactive |
| 184 | >10 | inactive |
| 185 | >10 | inactive |
| 186 | >10 | inactive |
| 187 | >10 | inactive |
| 188 | 1 | 90% |
| 189 | >10 | inactive |
| 190 | >10 | inactive |
| 191 | >10 | inactive |
| 192 | >10 | inactive |
| 193 | >10 | inactive |
| 194 | >10 | inactive |
| 195 | >10 | inactive |
| 196 | >10 | inactive |
| 197 | >10 | inactive |
| 198 | >10 | inactive |
| 199 | >10 | inactive |
| 200 | >10 | inactive |
| 201 | >10 | inactive |
| 202 | >10 | inactive |
| 203 | >10 | inactive |
| 204 | >10 | inactive |
| 205 | >10 | inactive |
| 206 | >10 | inactive |
| 207 | >10 | inactive |
| 208 | >10 | inactive |
| 209 | >10 | inactive |
| 210 | >10 | inactive |
| 211 | >10 | inactive |
| 212 | >10 | inactive |
| 213 | >10 | inactive |
| 214 | 0.02 | 50% |
| 215 | 5 | 15% |
| 216 | >10 | inactive |
| 217 | >10 | inactive |
| 218 | >10 | inactive |
| 219 | >10 | inactive |
| 220 | >10 | inactive |
| 221 | >10 | inactive |
| 222 | >10 | inactive |
| 223 | >10 | inactive |
| 224 | 6 | 45% |
| 225 | 2 | 110% |
| 226 | >10 | inactive |
| 227 | >10 | inactive |
| 228 | >10 | inactive |
| 229 | >10 | inactive |
| 230 | >10 | inactive |
| 231 | >10 | inactive |
| 232 | >10 | inactive |
| 233 | 0.007 | 55% |
| 234 | 0.01 | 70% |
| 235 | 0.1 | 45% |
| 236 | >10 | inactive |
| 237 | >10 | inactive |
| 238 | >10 | inactive |
| 239 | 2 | 20% |
| 240 | >10 | inactive |
| 241 | >10 | inactive |
| 242 | >10 | inactive |
| 243 | >10 | inactive |
| 244 | >10 | inactive |
| 245 | 2 | 15% |
| 246 | >10 | inactive |
| 247 | >10 | inactive |
| 248 | >10 | inactive |
| 249 | >10 | inactive |
| 250 | >10 | inactive |
| 251 | >10 | inactive |
| 252 | >10 | inactive |
| 253 | >10 | inactive |
| 254 | 0.8 | 30% |
| 255 | >10 | inactive |
| 256 | >10 | inactive |
| 257 | 0.06 | 40% |
| 258 | >10 | inactive |
| 259 | 1 | 85% |
| 260 | 3 | 45% |
| 261 | >10 | inactive |
| 262 | >10 | inactive |
| 263 | 0.02 | 100% |
| 264 | 3 | 20% |
| 265 | >10 | inactive |
| 266 | 0.4 | 25% |
| 267 | >10 | inactive |
| 268 | >10 | inactive |
| 269 | 0.8 | 50% |

TABLE 4-continued

5-HT$_{2B}$ Agonist Activity

| Example | EC$_{50}$ (µM) | Emax |
|---|---|---|
| 270 | 0.2 | 50% |
| 271 | 5 | 30% |
| 272 | 0.2 | 20% |
| 273 | 0.1 | 35% |
| 274 | >10 | inactive |
| 275 | >10 | inactive |
| 276 | >10 | inactive |
| 277 | >10 | inactive |
| 278 | >10 | inactive |
| 279 | 0.9 | 90% |

(iv) Human 5-HT$_{2C}$ Functional Assay in CHO-K1 Cells

Functional activity was determined by testing the effect of the compounds on intracellular calcium levels in CHO-K1 cells stably transfected with the human 5-HT$_{2C}$ receptor. Cells were seeded into 96-well plates at 60,000 cells/well and grown overnight in tissue culture medium (UltraCHO™ (Lonza), containing 1% dFCS, 250 µg/mL Zeocin, 400 µg/mL Geneticin) at 37° C. and 5% CO$_2$. Growth medium was replaced by medium without dFCS for overnight incubation. Cells were loaded with a fluorescent calcium-sensitive dye in the presence of probenicid according to the manufacturer's protocol (FLIPR Ca4 Assay kit, Molecular Devices). Serial compound dilutions (final concentrations 10$^{-10}$ to 10$^{-5}$ M) were added to the cells and the maximum calcium response was determined using a FLIPR instrument (Molecular Devices). Concentration-response curves were fitted using a four-parameter logistic equation (GraphPad Prism). The concentration at which the compound exerts half its maximal effect is named the 'effective concentration 50' or 'EC$_{50}$' and is listed in Table 5.

TABLE 5

5-HT$_{2C}$ Agonist Activity

| Example | EC$_{50}$ (µM) |
|---|---|
| 8 | >1 |
| 53 | 0.00293 |
| 62 | 0.0003 |
| 63 | 0.145 |
| 64 | 0.017 |
| 67 | 0.0025 |
| 73 | >1 |
| 74 | >10 |
| 86 | 0.0037 |
| 90 | 0.0145 |
| 91 | 0.0015 |
| 93 | 0.0044 |
| 94 | 0.124 |
| 95 | 0.0017 |
| 96 | 0.0369 |
| 156 | 0.013 |

(v) Human 5-HT$_6$ Receptor Radioligand Binding Assay

Preparation of Membranes by Ultrasonic Treatment and Differential Centrifugation Cells from stable clonal cell lines expressing the corresponding receptor (5-HT$_6$) were washed with PBS (without Ca$^{++}$, Mg$^{++}$) and harvested in PBS with 0.02% EDTA. The cells were collected by centrifugation at 500 g for 10 minutes at 4° C., washed with PBS and centrifuged (500 g, 10 minutes at 4° C.). The pellets were stored at −80° C. until use. For membrane preparation, the thawed cell pellet was resuspended in ice-cold sucrose buffer (0.25 M sucrose, 10 mM HEPES (pH 7.4), 1 mM phenylmethylsulfonyl fluoride (PMSF) in DMSO, 5 µg/ml Pepstatin-A, 3 mM EDTA, 0.025% Bacitracin) and homogenized with a Branson Sonifier W-250 (Settings: Timer 4; Output Control 3; Duty Cycle constant; 2 to 3 cycles). Cell disruption was checked with the aid of a microscope. Remaining unbroken cells were pelleted at 1,000 g for 10 minutes at 4° C. The sucrose buffer supernatant was then centrifuged at 60,000 g for 1 hour at 4° C. (Beckman Ultracentrifuge XL 80). The pellet was resuspended in 30 mL of ice-cold Tris buffer (20 mM TRIS (pH 7.4), 5 µg/mL Pepstatin A, 0.1 mM PMSF, 3 mM EDTA) by pipetting through a 10 mL serological pipet and centrifuged for 1 hour at 4° C. at 60,000 g. A final resuspension was performed in a small volume of ice-cold Tris buffer (see above) by pressing through a serological pipet followed by ultrasonic treatment with a Branson Sonifier W-250 (Settings: Timer 1; Output Control 3; Duty Cycle constant; 1 cycle). Protein concentration was determined (BCA-Kit; Pierce) and aliquots stored at −80° C. or in liquid nitrogen for long-term storage.

Receptor Binding Experiments

All receptor binding experiments were carried out in the corresponding assay buffer in a total volume of 200 µL in the presence of various concentrations of test compound (10$^{-5}$ M to 10$^{-9}$ M, tenfold serial dilution, duplicate determinations). The assays were terminated by filtration on polyethylenimine (PEI 0.1% or 0.3%) presoaked Packard Unifilter Plates (GF/C or GF/B) with a Tomtec MachIII U 96 well-plate harvester. After the plates had been dried for 2 hours at 55° C. in a drying chamber scintillation cocktail (BetaPlate Scint; PerkinElmer) was added. Radioactivity was measured in a Microbeta Trilux two hours after the addition of the scintillation mixture.

5-HT$_6$ Receptor Binding Assay

HEK293 cells stably expressing the h-5-HT$_6$ receptor (NCBI Reference Sequence XM 001435) were cultured in RPMI1640 medium supplemented with 25 mM HEPES, 10% fetal calf serum and 1-2 mM glutamine. The membrane preparation was performed as described above. For these membranes a K$_D$ of 1.95 nM for [$^3$H]-LSD (Lysergic Acid Diethylamide; Amersham, TRK1038) was determined by means of saturation binding experiments. On the day of the assay, the membranes were thawed, diluted in assay buffer (50 mM Tris-HCl, 5 mM CaCl$_2$, 0.1% ascorbic acid, 10 µM pargyline, pH 7.4) to a concentration of 8 µg protein/assay and homogenized by gentle vortexing. For inhibition studies, 1 nM [$^3$H]-lysergic acid diethylamide was incubated in the presence of various concentrations of test compound in assay buffer. Non-specific binding was defined with 1 µM methiothepin. The binding reaction was carried out for 3.5 hours at room temperature. During the incubation, the plates were shaken on a plate shaker at 100 rpm and terminated by filtration on Packard Unifilter GF/C (0.1% PEI) plates, followed by 2 wash cycles with ice-cold 50 mM Tris-HCl, 5 mM CaCl$_2$.

Data Analysis

Data derived from liquid scintillation counting were analyzed by iterative non-linear regression analysis with the use of the Statistical Analysis System (SAS): a program similar to "LIGAND" as described by Munson and Rodbard (Anal. Biochem. 1980, 107, 220-239). Fitting was performed according to formulae described by Feldman (Anal. Biochem. 1972, 48, 317-338). IC$_{50}$ and K$_i$ values were expressed as geometrical mean. For receptors with a low affinity for the test compound, where the highest tested compound concentration inhibited less than 30% of specific radioligand binding, K$_i$-values were determined according to the equation of Cheng and Prusoff (Biochem. Pharmacol. 1973, 22, 2099-2108) and expressed as greater than (>).

The results of the receptor binding studies are expressed as receptor binding constants $K_i(5\text{-}HT_6)$ as described herein before, and given in Table 6.

TABLE 6

5-HT$_6$ Agonist Site Radioligand Binding

| Example | Ki (μM) |
|---|---|
| 8 | 0.0403 |
| 9 | 0.0171 |
| 10 | 0.174 |
| 11 | 0.0403 |
| 13 | 0.0375 |
| 15 | 0.49 |
| 17 | 0.0551 |
| 18 | 0.0231 |
| 19 | 0.0141 |
| 21 | 0.0361 |
| 39 | 0.207 |
| 54 | 0.121 |
| 71 | 0.00442 |
| 72 | 0.0717 |
| 73 | 0.0143 |
| 74 | 0.00981 |
| 217 | 3.18 |

In these tests, the compounds according to the invention exhibit good affinity for the 5-HT$_6$ receptor ($K_i$<1000 nM or <50 nM).

(vi) Human 5-HT$_6$ Receptor Radioligand Binding Assay

Affinity of compounds for the agonist site of the 5-HT$_6$ receptor in transfected CHO cells was determined in a radioligand binding assay essentially as described by Monsma, F. J., et al., *Mol. Pharmacol.* (1993) 43, 320-327. In brief, cell membrane homogenates were incubated for 120 minutes at 37° C. with 2 nM [$^3$H]lysergic acid diethylamide (LSD) with or without test compounds. Nonspecific binding was determined in the presence of 100 μM serotonin. The amount of binding was determined by radioactivity quantitation with scintillation counter. IC$_{50}$s were determined from a standard curve of the reference compound serotonin. Ki's as shown in Table 7 were derived from the IC$_{50}$s in the standard method.

TABLE 7

5-HT$_6$ Agonist Site Radioligand Binding

| Example | Ki (μM) |
|---|---|
| 8 | 0.028 |
| 12 | 0.057 |
| 14 | 0.25 |
| 16 | 0.14 |
| 20 | 0.043 |
| 39 | 0.275 |

(vii) Assessment of Effects on Psychostimulant-Induced Hyperlocomotion in Rat

In humans, phencyclidine (PCP) is known to produce a syndrome of behavioral effects which have many characteristics in common with schizophrenia. Therefore, antagonism of PCP effects might be evidence for antipsychotic efficacy of a compound.

Methods

Male CD rats with a body weight of 316-394 g from Charles River (Portage, Mich.) were used in this study. The rats were habituated to the test room for 60 minutes. The rats were then placed into the locomotor activity chambers (AccuScan Instruments) for 30 minutes and then were dosed i.p. with Example 115 at 0, 1, 3 and 10 mg/kg. The rats were dosed sc 30 minutes later with PCP at 0 or 2 mg/kg. The activity was measured for 150 minutes in total and 90 minutes post PCP.

Results

As shown in FIG. 1, the PCP-treated group showed significant hyperlocomotion (p<0.01, vs. Veh-Veh group). Example 115 at 1 mg/kg and 10 mg/kg was able to significantly attenuate the PCP-induced hyperlocomotion.

(viii) Inhibitory Avoidance in Mouse

Glutamate has been shown to play a pivotal role in neuroplasticity, learning, memory, and neurodegenerative diseases. Specifically in the hippocampus CA1 area, N-methyl-D-aspartic acid (NMDA) receptors are known to regulate synaptic plasticity, long term-potentiation (LTP), and learning and memory processes, including short- and long-term memories. The non-competitive NMDA antagonist MK-801 has been shown to impair learning and memory processes in various tasks. The inhibitory avoidance task involves the uses of a two-compartment step through apparatus (Ugo Basile, Collegeville, Pa.) that measures the animal's ability to remember a brief noxious stimulus (foot shock), and is considered a measure of trial learning, and memory. (Bitner, R. S., et al. J. Neurosci. 2007, 27(39), 10578-10587). The purpose of this experiment was to test the ability of a 5HTc agonist to attenuate MK-801-induced deficits in the 24-hour inhibitory avoidance test. Effects against MK-801-induced cognitive impairment may indicate a potential efficacy in treating cognitive deficits of schizophrenia.

Methods:

Following a 2 hour habituation period, CD1 mice first received i.p. treatment with the test compound at 0, 1, 3, 10 mg/kg. 20 minutes later mice then received either MK-801 at 0.1 mg/kg (dissolved in 0.3% tartaric acid) or vehicle (Veh, water). 20 minutes after MK-801 administration, mice began their training session. For the training session, mice were placed into the light side of a 2-chambered compartment. The latency to enter the adjoining dark chamber was recorded, and an inescapable foot shock (0.3 mA, 1 second duration) was presented to the mouse. The mouse was removed from the chamber and returned to the home cage. Twenty-four hours later, the mouse was tested using methods identical to those on the training day, without being dosed or shocked. The latency to enter the dark chamber was recorded and was the dependent variable measured for assessing memory retention. If the mouse did not enter the dark chamber after 180 seconds, the test trial was terminated and the mouse was given a score of 180 seconds.

Figure 2:
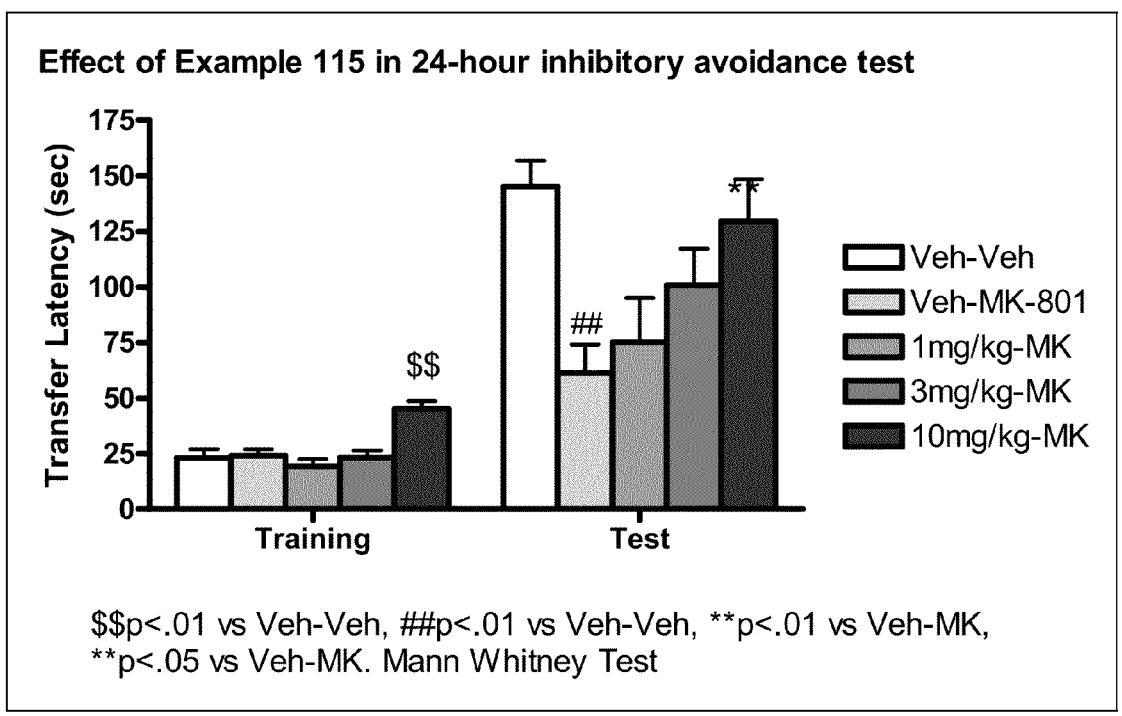
FIG. 2 shows a graphical representation of the dose-dependent improvement in mouse 24-hour inhibitory avoidance scores upon treatment with test compound (Example 115) followed by treatment with MK-801. Animals were treated with the vehicle or Example 115 followed by the vehicle or MK-801. The X-axis represents the dosing regiment for the day of exposure to condition and the same test groups 24 hours later, and the Y-axis represents the latency to cross to the punished side.

Results:

Acute administration of Example 115, at the high dose of 10 mg/kg, significantly increased transfer latencies compared to Veh-MK-801, indicating a procognitive effect (FIG. 2).

(ix) 5-Trial Inhibitory Avoidance/Impulsivity Model in the Pups of Spontaneously Hypertensive Rat Spontaneously hypertensive rats (SHR) exhibit many behavioral features characteristic of attention-deficit hyperactivity disorder (ADHD), including hyperactivity, impaired response inhibition, impaired sustained attention and decreased cognitive function compared with age- and sex-matched controls from the same genetic background or from other rat strains. However, the adult rats have spontaneous hypertension which may confound behavioral assessment. The juvenile SHRs were used in the current study since these pups show similar behavioral deficits while having not developed hypertension. The aim was to investigate the efficacy of 5-HT2c agonists in SHR pups in an inhibitory avoidance model, as indication of enhancement of inhibitory control/or anti-impulsivity.

Methods:

SHR pups at postnatal day 21-28 were sc dosed with either vehicle or Example 115 (1, 3, and 10 mg/kg; dissolved in tartaric acid/PH4-6) 30 minutes prior to the test. Upon testing initiation, pups were placed into the light side of a computer controlling 2-chambered compartment. The latency to enter the adjoining dark chamber was recorded, and an inescapable footshock (0.1 mA, 1 second duration) was presented to the pup. The pup was removed, placed back into the home cage for approximately 1 minute, and the process repeated for a total of 5 trials. The dependent variable used for data analysis was the total transfer latency of trial 2 to trial 5.

Figure 3:
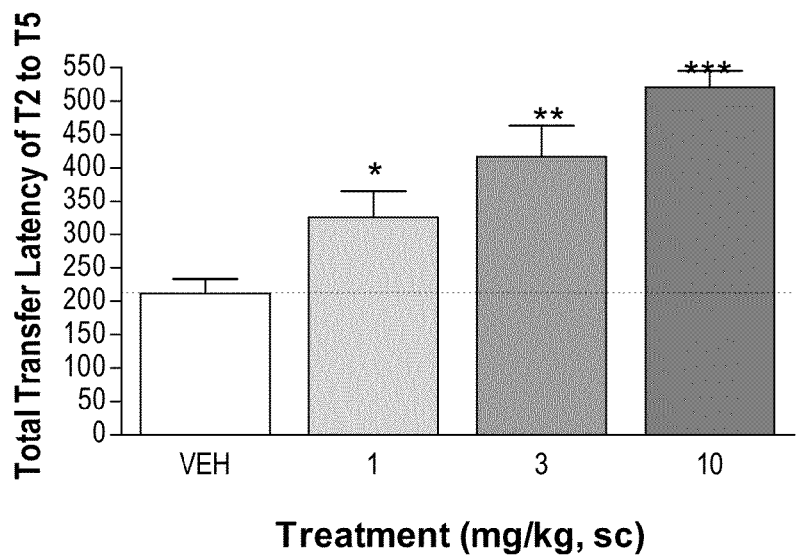
FIG. 3 shows a graphical representation of the dose-dependent improvement in 5-trial inhibitory avoidance scores in pups of spontaneously hypertensive rats (SHR) upon acute treatment with test compound (Example 115). The X-axis represents the dose of test compound, and the Y-axis represents the total transfer latency of trial 2 to trial 5 to cross to the punished side

Results:

The acute administration of Example 115 did result in a dose-dependent increase in transfer latencies across learning trials 2-5 at all three doses tested compared to vehicle (FIG. 3). The study demonstrated that Example 115 enhanced performance in the SHR pups in this 5-trial inhibitory avoidance/impulsivity model.

(x) Assessment of Effects on Psychostimulant-Induced Hyperlocomotion in Mice

In both humans and experimental animals amphetamine (AMP) profoundly affects motor activity, sensorimotor function, sleep, attention, aggressive and sexual behaviors, learning and memory, operant behaviors, appetite and food intake. In addition, amphetamine induces psychotic reactions in normal individuals and exacerbates symptoms of schizophrenia in patients. In experimental animals several distinct behaviors are considered to be correlates of amphetamine psychosis. For example, amphetamine-induced hyperactivity in rodents is believed to model the psychotic symptoms of schizophrenia. Reversal of these behaviors is used to predict potential antipsychotic activity of drugs in pre-clinical studies.

In humans, phencyclidine (PCP) is known to produce a syndrome of behavioral effects which have many characteristics in common with schizophrenia. Therefore, antagonism of PCP effects might be evidence for antipsychotic efficacy of a compound.

Animals

Male NMRI mice (5-week old, Janvier, France) or C57BL/6J mice (6-week old, Janvier, France) were group housed and allowed ad-libitum access to food and water. A 12 hour light/dark cycle was imposed with lights-on period between 0530 and 1730 hours. All testing occurred between 700 and 1300 hours. All procedures were approved by Abbott Institutional Animal Care and Use Committee (USA) or Animal Welfare Officer (Germany) and were conducted in accordance with the National Institutes of Health Guide for Care and Use of Laboratory Animals guidelines and applicable national laws in the facilities accredited by the Association for the Assessment and Accreditation of Laboratory Animal Care.

Methods

On the day of experiment, animals were brought from the animal facility into the experimental room and were allowed to acclimatize for at least 30 minutes. Animals were then placed in the test cages for a habituation period of 60 minutes. The animals were then injected ip with the test compound and returned to the test cage. 30 Minutes later the mice were injected with d-amphetamine (2.0 mg/kg, AMP, Sigma, #A5880, sc) or phencyclidine (2.0 mg/kg, PCP, Sigma, #P3029, sc) Sigma, and returned to the test cages for 90 minutes. Each treatment group consisted of 8-10 animals. The data was acquired by Cage rack Photobeam system (SDI, San Diego Instruments, CA). The analyzed data were: fine movements, ambulations and total movements (fine+ambulations). Data was subjected to one- or two-way distribution-free ANOVA followed by Dunnett's and Tukey's post hoc tests.

Results

Example 44 attenuated PCP-induced hyperactivity in mice significantly and in a dose dependent manner (treatment× time interaction $F(3,26)=1.47$, $p<0.01$), without affecting spontaneous activity (FIGS. 4A and 4B).

Example 106 modestly attenuated AMP-induced hyperactivity in mice in a dose dependent manner (time×treatment interaction $F(3, 29)=1.48$, $p<0.01$), without affecting spontaneous activity (FIGS. 5A and 5B).

Example 115 attenuated AMP-induced hyperactivity in mice significantly and in a dose dependent manner (treatment×time interaction $F(3,29)=2.65$, $p<0.001$), without affecting spontaneous activity (FIGS. 6A and 6B).

Example 158 attenuated AMP-induced hyperactivity in mice significantly and in a dose dependent manner (treatment×time interaction $F(3,29)=9.51$, $p<0.0001$) (FIGS. 7A and 7B).

Example 225 modestly attenuated AMP-induced hyperactivity in mice without affecting spontaneous activity (FIGS. 8A and 8B).

(xi) Assessment of Effects on Conditioning Avoidance Responding in Rats

Antipsychotics were found to have a unique ability to selectively suppress a conditioned avoidance response (CAR) behavior in rats. The fact that antipsychotics have the unique ability to selectively suppress CAR behavior, made the CAR test a useful tool for the screening of new, potentially antipsychotic compounds. All clinically effective antipsychotics (typical and atypical) have been shown to selectively suppress CAR.

Animals

Male Wistar rats (9-11 weeks old, Charles River, Germany) were pair-housed and allowed ad-libitum access to food and water. A 12-hour light/dark cycle was imposed with lights-on period between 0530 and 1730 hours. All testing occurred between 700 and 1300 hours. All procedures were approved by Abbott Institutional Animal Care and Use Committee (USA) or Animal Welfare Officer (Germany) and were conducted in accordance with the National Institutes of Health Guide for Care and Use of Laboratory Animals guidelines and applicable national laws in the facilities accredited by the Association for the Assessment and Accreditation of Laboratory Animal Care.

Methods

Wistar rats are exposed to a conditioned stimulus CS (a 2.9-kHz tone of 10 second duration), which is a signal for the animal that it must move into the other chamber in order to avoid an immediately ensuing footshock US (0.5 mA, 10 second, tone continues during shock presentation). Once the shock has begun, the animal can still escape it by moving to the other chamber. Each session is limited to a maximum of 40 trials (intertrial interval 10-90 seconds). The animals generally learn quickly to change chambers upon the conditioned stimulus and thus avoid further shocks. Scored are:

Avoided responses=crossings into other compartment within 10 seconds of tone presentation;

Escaped responses=crossings between 10-20 seconds of tone presentation;

Failures=crossings after cessation of tone-shock presentation or no crossing.

Animals are trained for 2 weeks, one session per day, or until they achieve a stable avoidance performance for at least 3 days of 75% (=30 avoided trials out of 40). At the test sessions (=CS-shock pairings), animals are pre-treated with a test drug or vehicle 30 minutes before commencement of the session.

Results

Example 115 significantly suppressed conditioned avoidance behavior in rats (p<0.05) without affecting the number of failures, indicating that the effect observed is not due to sedation or extrapyramidal side effects (FIG. 9A avoided responses; FIG. 9B escaped responses; FIG. 9C failure responses).

Example 158 significantly suppressed conditioned avoidance behavior in rats (p<0.01) without affecting the number of failures, indicating that the effect observed is not due to sedation or extrapyramidal side effects (FIG. 10A avoided responses; FIG. 10B escaped responses; FIG. 10C failure responses).

d. Methods of Using the Compounds

The compounds of this invention are modulators of the $5\text{-HT}_{2C}$ receptor or the $5\text{-HT}_6$ receptor or modulators of both the $5\text{-HT}_{2C}$ and $5\text{-HT}_6$ receptors. In certain embodiments of the invention, the compounds of formula (I) are agonists and partial agonists of the $5\text{-HT}_{2C}$ receptor or antagonists of the $5\text{-HT}_6$ receptor. In certain other embodiments of the invention, the compounds of formula (I) are agonists and partial agonists of the $5\text{-HT}_{2C}$ receptor and also antagonists of the $5\text{-HT}_6$ receptor. Thus, such compounds are of interest in the prevention or treatment of disease conditions associated with one of or both the $5\text{-HT}_{2C}$ and $5\text{-HT}_6$ receptors. Accordingly, the present invention provides a method for preventing or treating such a disease condition in a subject in need of treatment thereof. The subject in need of treatment thereof can be a mammal, such as, but not limited to, a human.

In one aspect, the disease condition is a cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension. Examples of cognitive dysfunction are deficits in memory, cognition, and learning, Alzheimer's disease, age-related cognitive decline, and mild cognitive impairment, or any combinations thereof. Examples of personality disorders are schizophrenia and cognitive deficits related to schizophrenia. Examples of affective disorders are depression, anxiety, bipolar disorder and obsessive compulsive disorders, or any combination thereof. Examples of motion or motor disorders are Parkinson's disease and epilepsy. Examples of feeding disorders are anorexia and bulimia. Examples of gastrointestinal disorders are irritable bowel syndrome. Examples of diseases associated with neurodegeneration are stroke, spinal or head trauma, and head injuries.

In certain embodiments, the disease condition is a pain condition including nociceptive pain, neuropathic pain or a combination thereof. Such pain conditions or disorders can include, but are not limited to, post-operative pain, osteoarthritis pain, pain due to inflammation, rheumatoid arthritis pain, musculoskeletal pain, burn pain (including sunburn), ocular pain, the pain associated with dental conditions (such as dental caries and gingivitis), post-partum pain, bone fracture, herpes, HIV, traumatic nerve injury, stroke, post-ischemia, fibromyalgia, reflex sympathetic dystrophy, complex regional pain syndrome, spinal cord injury, sciatica, phantom limb pain, diabetic neuropathy, hyperalgesia and cancer. In certain other embodiments, the disease condition is bladder dysfunction, including urinary incontinence.

In still yet another embodiment, the present invention relates to a method for preventing (the development of) a disease condition, such as cognitive dysfunction, attention deficit/hyperactivity syndrome, personality disorders, affective disorders, motion or motor disorders, migraine, pain, urinary incontinence, sleep disorders, feeding disorders, gastrointestinal disorders, diseases associated with neurodegeneration, addiction diseases, obesity, diabetes, psoriasis, or ocular hypertension. As used herein, the term "prevent" a disease condition, such as a cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, addiction diseases, obesity, diabetes, psoriasis, or ocular hypertension by administration of any of the compounds described herein means that the detectable physical characteristics or symptoms of the disease or condition do not develop following the administration of the compound described herein. Specifically, the method of the present invention comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof, in combination with a therapeutically effective amount of at least one cognitive enhancing drug.

In still yet another embodiment, the present invention relates to a method for preventing the progression (e.g., worsening) of a disease condition, such as a cognitive dysfunction, attention deficit/hyperactivity syndrome, personality disorders, affective disorders, motion or motor disorders, migraine, pain, urinary incontinence, sleep disorders, feeding disorders, gastrointestinal disorders, diseases associated with neurodegeneration, addiction diseases, obesity, diabetes, psoriasis, or ocular hypertension. The method comprises administering to the subject in need of treatment thereof (e.g., a mammal, such as a human) a therapeutically effective amount of any of the compounds as described herein, or a pharmaceutically acceptable salt thereof. Alternatively, the method comprises administering to the subject a therapeutically effective amount of any of the compounds as described herein, or a pharmaceutically acceptable salt thereof.

There are several lines of evidence suggesting that $5\text{-HT}_{2C}$ agonists or partial agonists would have therapeutic use in a variety of diseases, disorders and conditions.

Knockout mice models lacking the $5\text{-HT}_{2C}$ receptor exhibit hyperphagia, obesity and are more prone to seizures and sudden death [Tecott L H, Sun L M, Akana S F, Strack A M, Lowenstein D H, Dallman M F, Julius D (1995) Eating disorder and epilepsy in mice lacking $5\text{-HT}_{2C}$ serotonin receptors. *Nature* 374:542-546]. They also exhibit compulsive-like behavior [Chou-Green J M, Holscher T D, Dallman M F, Akana S F (2003). Compulsive behavior in the $5\text{-HT}_{2C}$ receptor knockout mouse. *Phys. Behav.* 78:641-649], hyperresponsiveness to repeated stress [Chou-Green J M, Holscher T D, Dallman M F, Akana S F (2003). Repeated stress in young and old $5\text{-HT}_{2C}$ receptor knockout mouse. *Phys. Behav.* 79:217-226], wakefulness [Frank M G, Stryker M P, Tecott L H (2002). Sleep and sleep homeostasis in mice lacking the $5\text{-HT}_{2C}$ receptor. *Neuropsychopharmacology* 27:869-873], hyperactivity and drug dependence [Rocha B A, Goulding E H, O'Dell L E, Mead A N, Coufal N G, Parsons L H, Tecott L H (2002). Enhanced locomotor, reinforcing and neurochemical effects of cocaine in serotonin 5-hydroxytryptamine 2C receptor mutant mice. *J. Neurosci.* 22:10039-10045].

5-HT$_{2C}$ is unique among other G-protein-coupled receptors (GPCRs) in that its pre-mRNA is a substrate for base modification via hydrolytic deamination of adenosines to yield inosines. Five adenosines, located within a sequence encoding the putative second intracellular domain can be converted to inosines. This editing can alter the coding potential of the triplet codons and allows for the generation of multiple different receptor isoforms. The edited receptor isoforms were shown to have reduced ability to interact with G-proteins in the absence of agonist stimulation [Werry, T D, Loiacono R, Sexton P A, Christopoulos A (2008). RNA editing of the serotonin 5-HT$_{2C}$ receptor and its effects on cell signaling, pharmacology and brain function. *Pharmac. Therap.* 119:7-23].

Edited 5-HT$_{2C}$ isoforms with reduced function are significantly expressed in the brains of depressed suicide victims [Schmauss C (2003) Serotonin 2C receptors: suicide, serotonin, and runaway RNA editing. *Neuroscientist* 9:237-242. Iwamoto K, Kato T (2003). RNA editing of serotonin 2C receptor in human postmortem brains of major mental disorders. *Neurosci. Lett.* 346:169-172] and in the learned helplessness rats (a well established animal model of depression) [Iwamotoa K, Nakatanib N, Bundoa M, Yoshikawab T, Katoa T (2005). Altered RNA editing of serotonin 2C receptor in a rat model of depression. *Neurosci. Res.* 53: 69-76] suggesting a link between 5-HT$_{2C}$ function and depression. There are also implications of edited 5-HT$_{2C}$ isoforms and spatial memory [Du Y, Stasko M, Costa A C, Davissone M T, Gardiner K J (2007). Editing of the serotonin 2C receptor pre-mRNA Effects of the Morris Water Maze. *Gene* 391:186-197]. In addition, fully edited isoforms of the human 5-HT$_{2C}$ receptor display a striking reduction in sensitivity to lysergic acid diethylamide (LSD) and to atypical antipsychotic drugs clozapine and loxapine, suggesting a possible role of the receptor in the etiology and pharmacology of schizophrenia [Niswender C M, Herrick-Davis K, Dilley G E, Meltzer H Y, Overholser J C, Stockmeier C A, Emeson R B, Sanders-Bush E (2001). RNA Editing of the Human Serotonin 5-HT$_{2C}$ Receptor: Alterations in Suicide and Implications for Serotonergic *Pharmacotherapy. Neuropsychopharm.* 24:478-491].

Recently, the availability of potent and selective 5-HT$_{2C}$ receptor agonists made it possible to directly investigate the effects of 5-HT$_{2C}$ agonists and their therapeutic potential. Thus recent studies demonstrated that selective 5-HT$_{2C}$ agonists resulted in decreased food intake and body weight gain in normal and obese rats [Smith B M, et al. (2008). Discovery and structure-activity relationship of (1R)-8-chloro-2,3,4,5-tetrahydro-1-methyl-1H-3-benzazepine (Lorcaserin), a selective serotonin 5-HT$_{2C}$ receptor agonist for the treatment of obesity. *J Med Chem* 51:305-313. Thomsen W J, Grottick A J, Menzaghi F, Reyes-Saldana H, Espitia S, Yuskin D, Whelan K, Martin M, Morgan M, Chen W, Al-Shama H, Smith B, Chalmers D, Behan D (2008) Lorcaserin, A Novel Selective Human 5-HT$_{2C}$ Agonist: In Vitro and In Vivo Pharmacological Characterization. *J Pharmacol Exp Ther.* 325: 577-587. Rosenzweig-Lipson S, Zhang J, Mazandarani H, Harrison B L, Sabb A, Sabalski J, Stack G, Welmaker G, Barrett J E, Dunlop J (2006) Antiobesity-like effects of the 5-HT$_{2C}$ receptor agonist WAY-161503. *Brain Res.* 1073-1074:240-251. Dunlop J, Sabb A L, Mazandarani H, Zhang J, Kalgaonker S, Shukhina E, Sukoff S, Vogel R L, Stack G, Schechter L, Harrison B L, Rosenzweig-Lipson S (2005). WAY-163909 [97bR,10aR)-1,2,3,4,8,9,10,10a-octahydro-7bH-cyclopenta-[b][1,4]diazepino[6,7,1hi]indole], a novel 5-hydroxytryptamine 2C receptor-selective agonist with anorectic activity. *J Pharmacol Exp Ther.* 313:862-869.].

Furthermore, selective 5-HT$_{2C}$ receptor agonists produce antidepressant effects in animal models of depression comparable to those of SSRIs but with a much faster onset of action and a therapeutic window that avoids antidepressant-induced sexual dysfunction. These agonists were also effective in animal models of compulsive behavior such as scheduled induced polydipsia and they also exhibited decreased hyperactivity and aggression in rodents [Rosenzweig-Lipson S, Sabb A, Stack G, Mitchell P, Lucki I, Malberg J E, Grauer S, Brennan J, Cryan J F, Sukoff Rizzo S J, Dunlop J, Barrett J E, Marquis K L (2007) Antidepressant-like effects of the novel, selective, 5-HT$_{2C}$ receptor agonist WAY-163909 in rodents. *Psychopharmacology* (Berlin) 192:159-170. Rosenzweig-Lipson S, Dunlop J, Marquis K L (2007) 5-HT$_{2C}$ receptor agonists as an innovative approach for psychiatric disorders. *Drug news Perspect,* 20: 565-571. Cryan, J F, Lucki I (2000). Antidepressant-like behavioral effects mediated by 5-Hydroxytryptamine 2C receptors. *J. Pharm. Exp. Ther.* 295:1120-1126.].

Acute or chronic administration of 5-HT$_{2C}$ agonists decreases the firing rate of ventral tegmental area dopamine neurons but not that of substantia nigra. In addition 5-HT$_{2C}$ agonists reduce dopamine levels in the nucleus accumbens but not in the striatum (the region of the brain mostly associated with extrapyramidal side effects) [Di Matteo, V., Di Giovanni, G., Di Mascio, M., & Esposito, E. (1999). SB 242084, a selective serotonin 2C receptor antagonist, increases dopaminergic transmission in the mesolimbic system. *Neuropharmacology* 38, 1195-1205. Di Giovanni, G., Di Matteo, V., Di Mascio, M., & Esposito, E. (2000). Preferential modulation of mesolimbic vs. nigrostriatal dopaminergic function by serotonin 2C/2B receptor agonists: a combined in vivo electrophysiological and microdialysis study. *Synapse* 35, 53-61. Marquis K L, Sabb A L, Logue S F, Brennan J A, Piesla M J, Comery T A, Grauer S M, Ashby C R, Jr., Nguyen H Q, Dawson L A, Barrett J E, Stack G, Meltzer H Y, Harrison B L, Rosenzweig-Lipson S (2007) WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. *J Pharmacol Exp Ther* 320:486-496.]. Therefore it is expected that 5-HT$_{2C}$ receptor agonists will selectively decrease mesolimibic dopamine levels without affecting the nigrostriatal pathway thus avoiding the EPS side effects of typical antipsychotics. Several 5-HT$_{2C}$ receptor agonists have shown antipsychotic activity in animal models of schizophrenia without EPS based on the lack of effect in catalepsy [Marquis K L, Sabb A L, Logue S F, Brennan J A, Piesla M J, Comery T A, Grauer S M, Ashby C R, Jr., Nguyen H Q, Dawson L A, Barrett J E, Stack G, Meltzer H Y, Harrison B L, Rosenzweig-Lipson S (2007) WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. *J Pharmacol Exp Ther* 320:486-496. Siuciak J A, Chapin D S, McCarthy S A, Guanowsky V, Brown J, Chiang P, Marala R, Patterson T, Seymour P A, Swick A, Iredale P A (2007) CP-809,101, a selective 5-HT$_{2C}$ agonist, shows activity in animal models of antipsychotic activity. *Neuropharmacology* 52:279-290]. The antipsychotic activity of 5-HT$_{2C}$ receptor agonists without EPS coupled with their beneficial effects in mood disorders and cognition and their antiobesity like effects render 5-HT$_{2C}$ receptor agonists as unique agents to treat schizophrenia [Rosenzweig-Lipson S, Dunlop J, Marquis K L (2007) 5-HT$_{2C}$ receptor agonists as an innovative approach for psychiatric disorders. *Drug news Perspect,* 20: 565-571. Dunlop J, Marquis K L, Lim H K, Leung L, Kao J, Cheesman C, Rosenzweig-Lipson S (2006). Pharmacological profile of the 5-HT$_{2C}$ receptor agonist WAY-163909; therapeutic potential in multiple indications. *CNS Dug Rev.* 12:167-177.].

In addition 5-HT$_{2C}$ modulation has been implicated in epilepsy [Isaac M (2005). Serotonergic 5-HT$_{2C}$ receptors as a potential therapeutic target for the antiepileptic drugs. *Curr. Topics Med. Chem.* 5:59:67], psoriasis [Thorslund K, Nordlind K (2007). Serotonergic drugs—a possible role in the treatment of psoriasis? *Drug News Perspect* 20:521-525], Parkinson's disease and related motor disorders [Esposito E, Di Matteo V, Pierucci M, Benigno A, Di Giavanni, G (2007). Role of central 5-HT$_{2C}$ receptor in the control of basal ganglia functions. *The Basal Ganglia Pathophysiology: Recent Advances* 97-127], behavioral deficits [Barr A M, Lahmann-Masten V, Paulus N I, Gainetdinov R P, Caron M G, Geyer M A (2004). The selective serotonin-2A receptor antagonist M100907 reverses behavioral deficits in dopamine transporter knockout mice. *Neuropsychopharmacology* 29:221-228], anxiety [Dekeyne A, Mannoury la Cour C, Gobert A, Brocco M, Lejuene F, Serres F, Sharp T, Daszuta A, Soumier A, Papp M, Rivet J M, Flik G, Cremers T I, Muller O, Lavielle G, Millan M J (2208). 532006, a novel 5-HT$_{2C}$ receptor antagonists displaying broad-based antidepressant and anxiolytic properties in rodent models. *Psychopharmacology* 199:549-568. Nunes-de-Souza V, Nunes-de-Souza R L, Rodgers R J, Canto-de-Souza A (2008). 5-HT2 receptor activation in the midbrain periaqueductal grey (PAG) reduces anxiety-like behavior in mice. *Behav. Brain Res.* 187:72-79.], migraine [Leone M, Rigamonti A, D'Amico D, Grazzi L, Usai S, Bussone G (2001). The serotonergic system in migraine. *Journal of Headache and Pain* 2(Suppl. 1):S43-S46], Alzheimer's disease [Arjona A A, Pooler A M, Lee R K, Wurtman R J (2002). Effect of a 5-HT$_{2C}$ serotonin agonist, dexnorfenfluramine, on amyloid precursor protein metabolism in guinea pigs. *Brain Res.* 951:135-140], pain and spinal cord injury [Nakae A, Nakai K, Tanaka T, Hagihira S, Shibata M, Ueda K, Masimo T (2008). The role of RNA editing of the serotonin 2C receptor in a rat model of oro-facial neuropathic pain. *The European Journal of Neuroscience* 27:2373-2379. Nakae A, Nakai K, Tanaka T, Takashina M, Hagihira S, Shibata M, Ueda K, Mashimo T (2008). Serotonin 2C receptor mRNA editing in neuropathic pain model. *Neurosci. Res.* 60:228-231. Kao T, Shumsky J S, Jacob-Vadakot S, Timothy H B, Murray M, Moxon, K A (2006). Role of the 5-HT$_{7C}$ receptor in improving weight-supported stepping in adult rats spinalized as neonates. *Brain Res.* 1112:159-168.], sexual dysfunction [Motofei IG (2008). A dual physiological character for sexual function: the role of serotonergic receptors. *BJU International* 101:531-534. Shimada I, Maeno K, Kondoh Y, Kaku H, Sugasawa K, Kimura Y, Hatanaka K, Naitou Y, Wanibuchi F, Sakamoto S, Tsukamoto S (2008). Synthesis and structure-activity relationships of a series of benzazepine derivatives as 5-HT$_2$ receptor agonists. *Bioorg. Med. Chem.* 16:3309-3320.], smoking cessation [Fletcher P J, Le A D, Higgins G A (2008). Serotonin receptors as potential targets for modulation of nicotine use and dependence. *Progress Brain Res.* 172:361-83], substance dependence [Bubar M J, Cunningham K A (2008). Prospects for serotonin 5-HT2R pharmacotherapy in psychostimulant abuse. *Progress Brain Res.* 172:319-46], and ocular hypertension [Sharif N A, McLaughlin M A, Kelly C R (2006). AL-34662: a potent, selective, and efficacious ocular hypotensive serotonin-2 receptor agonist. *J Ocul Pharmacol Ther.* 23:1-13].

Further, 5HT modulation can be useful in the treatment of pain, both neuropathic and nociceptive pain, see for example U.S. Patent application publication US2007/0225277. Obata, Hideaki; Ito, Naomi; Sasaki, Masayuki; Saito, Shigeru; Goto, Fumio. Possible involvement of spinal noradrenergic mechanisms in the antiallodynic effect of intrathecally administered 5-HT2C receptor agonists in the rats with peripheral nerve injury. *European Journal of Pharmacology* (2007), 567(1-2), 89-94. Serotonin 2C receptor mRNA editing in neuropathic pain model. Nakae, Aya; Nakai, Kunihiro; Tanaka, Tatsuya; Takashina, Masaki; Hagihira, Satoshi; Shibata, Masahiko; Ueda, Koichi; Mashimo, Takashi. Department of Anesthesiology & Intensive Care Medicine, Graduate School of Medicine, Osaka University, *Neuroscience Research* (Amsterdam, Netherlands) (2008), 60(2), 228-231. Antiallodynic effects of intrathecally administered 5-HT2C receptor agonists in rats with nerve injury. Obata, Hideaki; Saito, Shigeru; Sakurazawa, Shinobu; Sasaki, Masayuki; Usui, Tadashi; Goto, Fumio. Department of Anesthesiology, Gunma University Graduate School of Medicine, Maebashi, Gunma, Japan. *Pain* (2004), 108(1-2), 163-169. Influence of 5,7-dihydroxytryptamine (5,7-DHT) on the antinociceptive effect of serotonin (5-HT) 5-HT2C receptor agonist in male and female rats. Brus, Ryszard; Kasperska, Alicja; Oswiecimska, Joanna; Szkilnik, Ryszard. Department of Pharmacology, Silesian Medical University, Zabrze, Pol. *Medical Science Monitor* (1997), 3(5), 654-656.

Modulation of 5HT2 receptors may be beneficial in the treatment of conditions related to bladder function, in particular, urinary incontinence. [Discovery of a novel azepine series of potent and selective 5-HT2C agonists as potential treatments for urinary incontinence. Brennan, Paul E.; Whitlock, Gavin A.; Ho, Danny K. H.; Conlon, Kelly; McMurray, Gordon. *Bioorganic & Medicinal Chemistry Letters* (2009), 19(17), 4999-5003. Investigation of the role of 5-HT2 receptor subtypes in the control of the bladder and the urethra in the anesthetized female rat. Mbaki, Y.; Ramage, A. G. Department of Pharmacology, University College London, London, UK. *British Journal of Pharmacology* (2008), 155(3), 343-356.] In particular, compounds with agonist activity at 5-H$_{2C}$ have been shown to be useful in treating urinary incontinence, see for example U.S. patent application publications US2008/0146583 and US 2007/0225274.

Because of their binding profile, the compounds can be used for treating diseases which respond to 5-HT$_6$ receptor ligands (or which are susceptible to treatment with a 5-HT$_6$ receptor ligand), i.e. they are effective for treating those medical disorders or diseases in which exerting an influence on (modulating) the 5-HT$_6$ receptors leads to an improvement in the clinical picture or to the disease being cured. Examples of these diseases are disorders or diseases of the central nervous system.

Disorders or diseases of the central nervous system are understood as meaning disorders which affect the spinal cord and, in particular, the brain. Within the meaning of the invention, the term "disorder" denotes disturbances and/or anomalies which are as a rule regarded as being pathological conditions or functions and which can manifest themselves in the form of particular signs, symptoms and/or malfunctions. While the treatment according to the invention can be directed toward individual disorders, i.e. anomalies or pathological conditions, it is also possible for several anomalies, which may be causatively linked to each other, to be combined into patterns, i.e. syndromes, which can be treated in accordance with the invention.

The disorders which can be treated in accordance with the invention are in particular disorders which respond to a modulation of the 5-HT$_6$ receptor. They include cognitive dysfunctions, such as a deficit in memory, cognition and learning, in particular associated with Alzheimer's disease, age-related cognitive decline and mild cognitive impairment, attention deficit disorder/hyperactivity syndrome, personality disorders, such as schizophrenia, in particular cognitive deficits related with schizophrenia, affective disorders such as depression, anxiety and obsessive compulsive disorders, motion or motor disorders such as Parkinson's disease and epilepsy, migraine, sleep disorders (including disturbances of the Circadian rhythm), feeding disorders, such as anorexia and bulimia, certain gastrointestinal disorders such as Irritable Bowel Syndrome, diseases associated with neurodegeneration, such as stroke, spinal or head trauma and head injuries, such as hydrocephalus, drug addiction and obesity.

The addiction diseases include psychiatric disorders and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula (I) which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disorders whose causes can at least partially be attributed to an anomalous activity of 5-HT$_6$ receptors.

According to another aspect of the present invention, the treatment is directed, in particular, toward those disorders which can be influenced, within the sense of an expedient medicinal treatment, by the binding of preferably exogenously administered binding partners (ligands) to 5-HT$_6$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds of formula (I) can be used to treat a large number of signs, symptoms and/or malfunctions which are connected with the disorders of the central nervous system and, in particular, the above-mentioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disorders, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, more preferably for treating cognitive dysfunctions and in particular, for treating cognitive dysfunctions associated with schizophrenia or with Alzheimer's disease.

According to another aspect of the invention the compounds of formula (I) are particularly suitable for treating addiction diseases caused for instance by the abuse of psychotropic substances, such as pharmaceuticals, narcotics, nicotine or alcohol, including psychic disorders and behavioral disturbances related thereto.

According to another aspect of the invention the compounds of formula (I) are particularly suitable for treating nutritional disorders, such as obesity, as well as diseases related thereto, such as cardiovascular diseases, digestive diseases, respiratory diseases, cancer or type 2 diabetes.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

Actual dosage levels of active ingredients in the pharmaceutical compositions of the present invention can be varied so as to obtain an amount of the active compound(s) that is effective to achieve the desired therapeutic response for a particular subject (e.g., a mammal, preferably, a human (patient)), compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the present invention can also be administered to a subject as a pharmaceutical composition comprising the compounds of interest in combination with at least one pharmaceutically acceptable carriers. The phrase "therapeutically effective amount" of the compound of the present invention means a sufficient amount of the compound to treat disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a subject (namely, a mammal, such as a human) ranges from about 0.01 mg/kg body weight to about 100 mg/kg body weight. More preferable doses can be in the range of from about 0.01 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

In yet another embodiment, the present invention provides pharmaceutical compositions. The pharmaceutical compositions of the present invention comprise the compounds of the present invention or a pharmaceutically acceptable salt or solvate thereof. The pharmaceutical compositions of the present invention comprise compounds of the present invention that can be formulated together with at least one non-toxic pharmaceutically acceptable carrier.

In yet another embodiment, the present invention provides a pharmaceutical composition comprising compounds of the present invention, or a pharmaceutically acceptable salt thereof, and one or more pharmaceutically acceptable carriers, alone or in combination with one or more compounds that are not the compounds of the present invention. Examples of one or more compounds that can be combined with the compounds of the present invention in pharmaceutical compositions, include, but are not limited to, one or more cognitive enhancing drugs.

The pharmaceutical compositions of this present invention can be administered to a subject (e.g., a mammal, such as a human) orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of the present invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

Dosage forms for topical administration of a compound of the present invention include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (*J. Pharmaceutical Sciences*, 1977, 66: 1 et seq.). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention also contemplates compounds of the present invention formed by synthetic means or formed by in vivo biotransformation of a prodrug.

The compounds of the present invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the present invention whether prepared by synthetic processes or by metabolic processes. Preparation of the compounds by metabolic processes includes those occurring in the human or animal body (in vivo) or processes occurring in vitro.

The compounds of the present invention may be prepared by a variety of processes well known for the preparation of compounds of this class. For example, the compounds of the present invention wherein the groups A and $G^1$ have the meanings as set forth in the Summary of the Invention section unless otherwise noted, can be synthesized as shown in Schemes 1-25.

Abbreviations which have been used in the descriptions of the Schemes that follow are: Ac for acetyl; $Ac_2O$ for acetic anhydride; Bn for benzyl; Boc for t-butoxycarbonyl; $Boc_2O$ for di-tert-butyl dicarbonate; Bu for butyl; t-Bu for tert-butyl; $(CH_2O)_p$ for paraformaldehyde; DMAP for 4-(dimethylamino)pyridine; Et for ethyl; EtOH for ethanol; HOAc for acetic acid; KOtBu for potassium t-butoxide; LDA for lithium diisopropylamide; $MP-BH_3CN$ for macro-porous cyanoborohydride resin; $NEt_3$ for triethylamine, OAc for acetate; Ph for phenyl; TBAF for tetrabutylammonium fluoride; TBS for t-butyldimethylsilyl; TBTU for O-(benzotriazol-1-yl)-N,N,N',N'-tetramethyluronium tetrafluoroborate; TFA for trifluoroacetic acid; and Ts for p-toluenesulfonyl.

Scheme 1

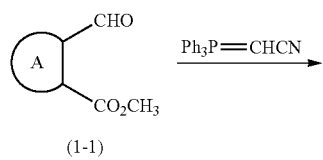

(1-1)

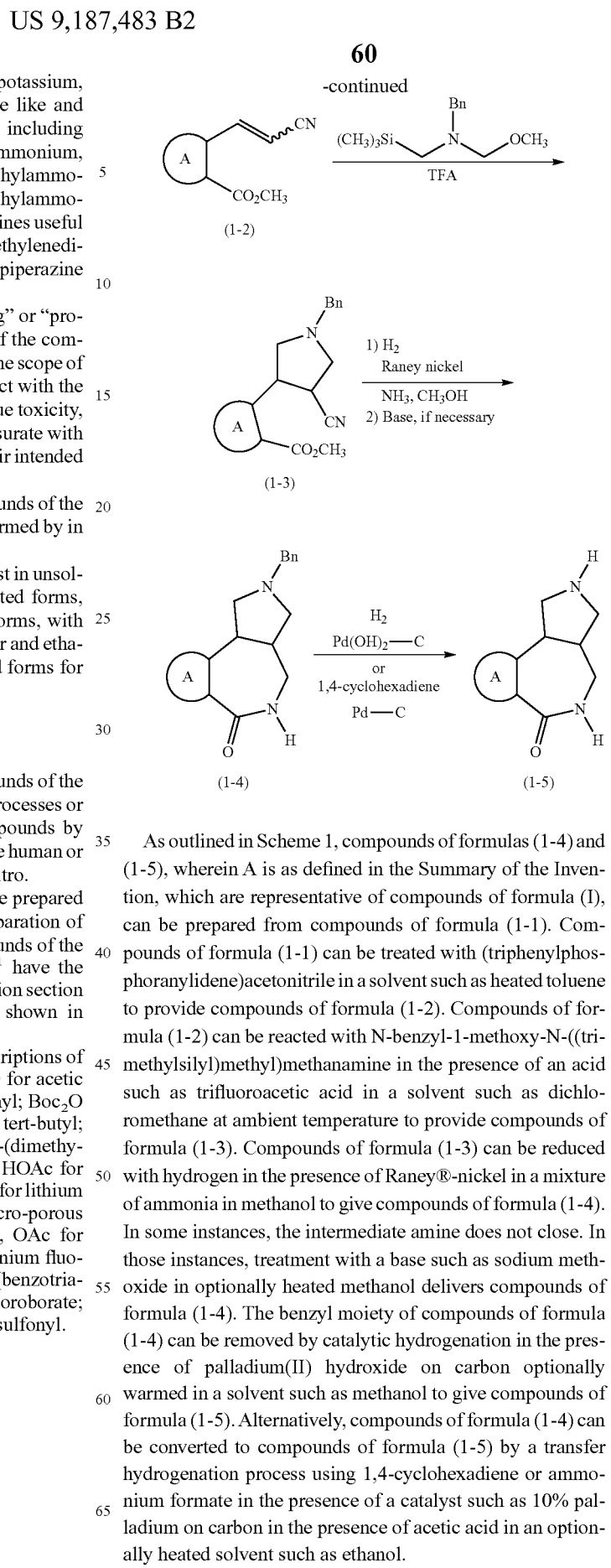

As outlined in Scheme 1, compounds of formulas (1-4) and (1-5), wherein A is as defined in the Summary of the Invention, which are representative of compounds of formula (I), can be prepared from compounds of formula (1-1). Compounds of formula (1-1) can be treated with (triphenylphosphoranylidene)acetonitrile in a solvent such as heated toluene to provide compounds of formula (1-2). Compounds of formula (1-2) can be reacted with N-benzyl-1-methoxy-N-((trimethylsilyl)methyl)methanamine in the presence of an acid such as trifluoroacetic acid in a solvent such as dichloromethane at ambient temperature to provide compounds of formula (1-3). Compounds of formula (1-3) can be reduced with hydrogen in the presence of Raney®-nickel in a mixture of ammonia in methanol to give compounds of formula (1-4). In some instances, the intermediate amine does not close. In those instances, treatment with a base such as sodium methoxide in optionally heated methanol delivers compounds of formula (1-4). The benzyl moiety of compounds of formula (1-4) can be removed by catalytic hydrogenation in the presence of palladium(II) hydroxide on carbon optionally warmed in a solvent such as methanol to give compounds of formula (1-5). Alternatively, compounds of formula (1-4) can be converted to compounds of formula (1-5) by a transfer hydrogenation process using 1,4-cyclohexadiene or ammonium formate in the presence of a catalyst such as 10% palladium on carbon in the presence of acetic acid in an optionally heated solvent such as ethanol.

Scheme 2

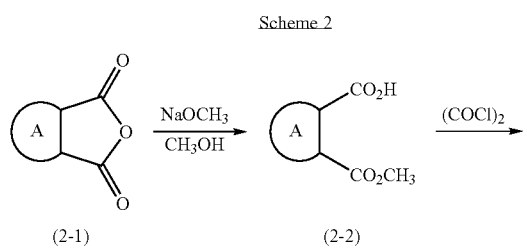

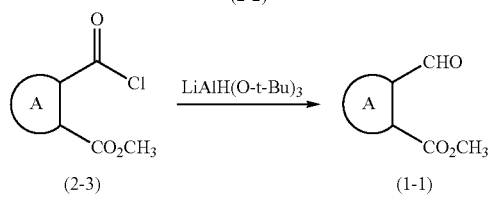

As outlined in Scheme 2, compounds of formula (1-1), wherein A is as defined in the Summary of the Invention can be prepared from compounds of formula (2-1). Accordingly, anhydrides of formula (2-1) can be treated with an alkoxide, such as sodium methoxide, in methanol at or near ambient temperature to give after acidification compounds of formula (2-2). Compounds of formula (2-2) are converted to the corresponding acid chloride (2-3) with treatment with oxalyl chloride or thionyl chloride in a solvent such as dichloromethane and a catalytic amount of N,N-dimethylformamide. Then the acid chloride moiety can be selectively reduced with an agent such as lithium tri-t-butoxyaluminum hydride in a solvent such as diglyme initially at −70° C. followed by gradual warming to room temperature to give compounds of formula (1-1). Compounds of formula (1-1) can be used as described in Scheme 1.

Scheme 3

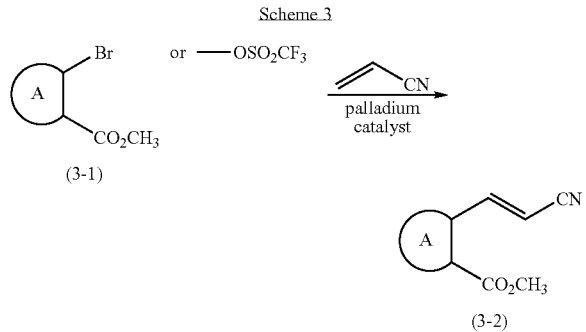

As outlined in Scheme 3, compounds of formula (3-2), wherein A is as defined in the Summary of the Invention can be prepared from compounds of formula (3-1). Compounds of formula (3-1) can be reacted with acrylonitrile in the presence of a catalyst such as palladium(II) acetate, a ligand such as tri(o-tolyl)phosphine, and a base such as sodium acetate in a solvent such as N,N-dimethylformamide heated to 120-135° C. over a period of 15 to 60 hours to give compounds of formula (3-2). Alternative conditions to produce compounds of formula (3-2) from (3-1) include reacting with compounds of formula (3-1) with acrylonitrile in the presence of a catalyst such as tris(dibenzylideneacetone)dipalladium(0), a ligand such as tri-tert-butylphosphine or tri-tert-butylphosphonium tetrafluoroborate, and a base such as N,N-dicyclohexylmethylamine in a solvent such as 1,4-dioxane heated from 40 to 80° C. for 1 to 5 hours under nitrogen. Iodine or trifluoromethanesulfonate groups can be substituted for the bromine in compounds of formula (3-1). Compounds of formula (3-2) can be used in Scheme 1 for compounds of formula (1-2).

Scheme 4

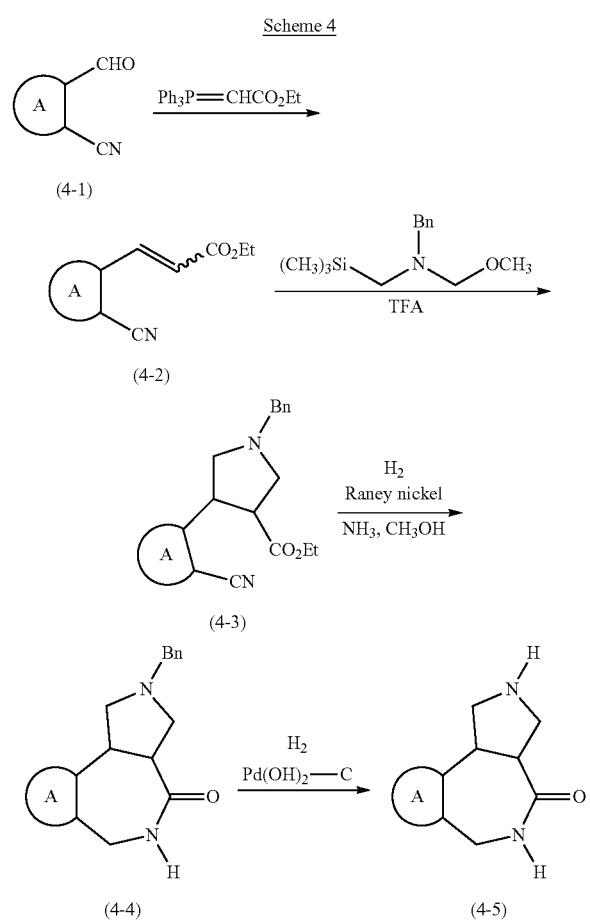

As outlined in Scheme 4, compounds of formulas (4-4) and (4-5), wherein A is as defined in the Summary of the Invention, which are representative of compounds of formula (I), can be prepared from compounds of formula (4-1). Compounds of formula (4-1) can be treated with (carboethoxymethylene)triphenylphosphorane in a solvent such as heated toluene to provide compounds of formula (4-2). Compounds of formula (4-2) can be reacted with N-benzyl-1-methoxy-N-((trimethylsilyl)methyl)methanamine in the presence of an acid such as trifluoroacetic acid in a solvent such as dichloromethane at ambient temperature to provide compounds of formula (4-3). Compounds of formula (4-3) can be reduced with hydrogen in the presence of Raney®-nickel in a mixture of ammonia in methanol to give compounds of formula (4-4). The benzyl moiety of compounds of formula (4-4) can be removed by catalytic hydrogenation in the presence of palladium(II) hydroxide on carbon optionally warmed in a solvent such as methanol to give compounds of formula (4-5).

Scheme 5

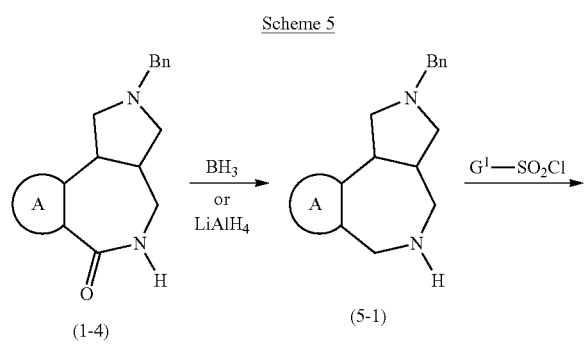

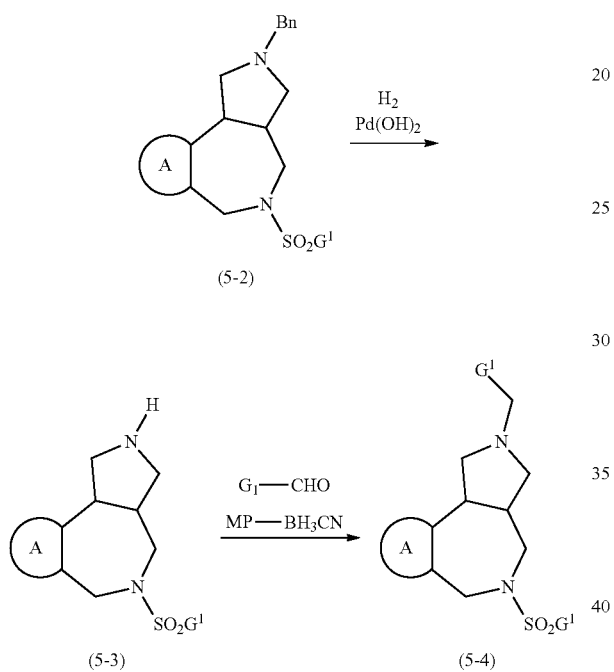

As outlined in Scheme 5, compounds of formulas (5-1), (5-2), (5-3) and (5-4), wherein A and $G^1$ are as defined in the Summary of the Invention, which are representative of compounds of formula (I), can be prepared from compounds of formula (1-4). Compounds of formula (1-4) can be treated with borane tetrahydrofuran complex in heated tetrahydrofuran to provide compounds of formula (5-1). Alternatively, compounds of formula (1-4) can be treated with lithium aluminum hydride initially at −78° C. followed by warming to room temperature in tetrahydrofuran to give compounds of formula (5-1). Compounds of formula (5-1) can be reacted with sulfonyl chlorides of formula $G^1$-$SO_2Cl$ in the presence of a base such as pyridine in a solvent such as dichloromethane over 8 to 24 hours at room temperature to give compounds of formula (5-2). Alternatively, compounds of formula (5-1) can be reacted with sulfonyl chlorides of formula $G^1$-$SO_2Cl$ in the presence of a base such as triethylamine in a solvent mixture such as dichloromethane and N,N-dimethylformamide over 8 to 24 hours at room temperature to give compounds of formula (5-2). Then the benzyl group of compounds of formula (5-2) can be removed by reduction with hydrogen (30 psi) in the presence of a catalyst such as palladium hydroxide in a solvent such as trifluoroethanol over 24 to 48 hours at room temperature to give compounds of formula (5-3). Compounds of formula (5-3) can subsequently be reductively aminated to give compounds of formula (5-4) by reacting with aldehydes of formula $G^1$-CHO in the presence of macro-porous cyanoborohydride resin or sodium cyanoborohydride in the presence of acetic acid in a solvent such as methanol or ethanol at room temperature over 8 to 24 hours.

Scheme 6

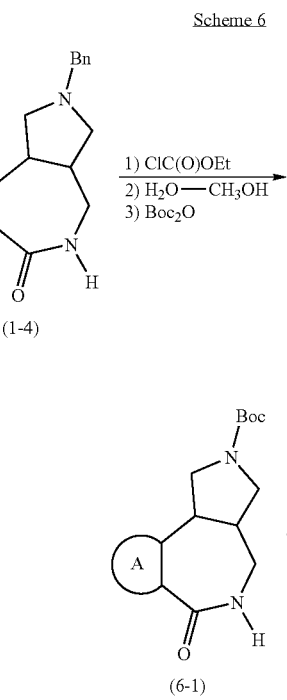

As outlined in Scheme 6, compounds of formula (1-5), wherein A is as defined in the Summary of the Invention, which are representative of compounds of formula (I) can be prepared in an alternative method from compounds of formula (1-4). Compounds of formula (1-4) can be treated in a first step with 1-chloroethylchloroformate in dichloroethane at 80° C. for 8 to 24 hours. In a second step, reaction with a heated mixture of water and methanol over 2 to 8 hours hydrolyzes the intermediate ethyl carbamate. The tert-butoxy carbonyl group is introduced in a third step by reaction with di-tert-butyl dicarbonate in a solvent such as dichloromethane in the presence of a base such as triethylamine to give compounds of formula (6-1). Compounds of formula (6-1) can then be treated with an acid such as trifluoroacetic acid or hydrochloric acid in a solvent such as dioxane or dichloromethane at room temperature for 4 to 36 hours to give compounds of formula (1-5).

Scheme 7

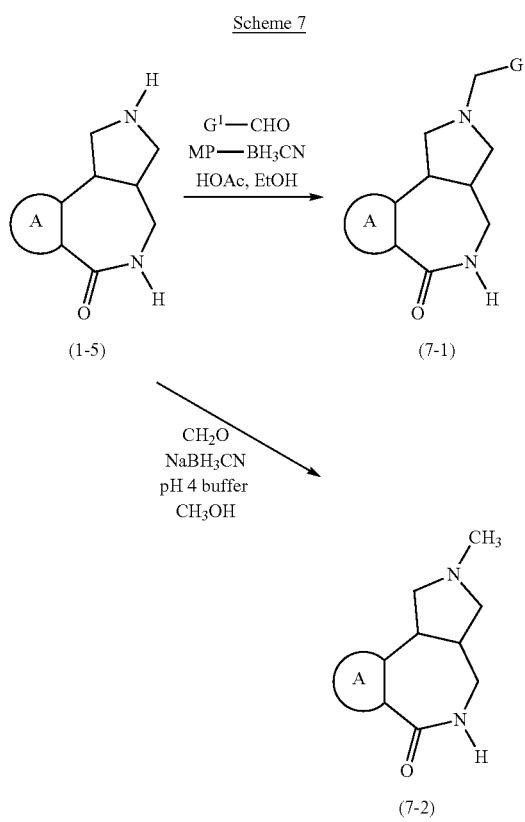

Scheme 8

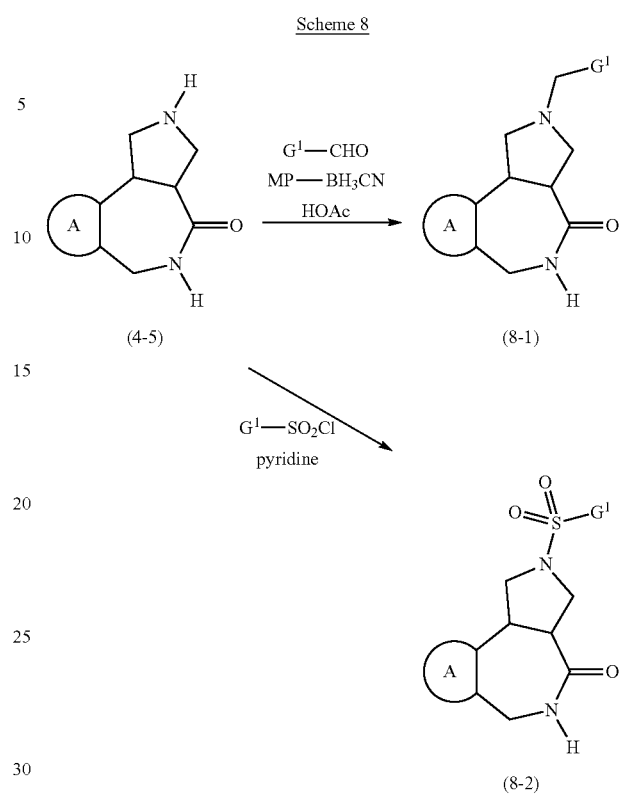

As outlined in Scheme 7, compounds of formula (7-1) and (7-2), wherein A and G¹ are as defined in the Summary of the Invention, which are representative of compounds of formula (I) can be prepared from compounds of formula (1-5). Compounds of formula (1-5) can be reacted with an aldehyde of formula G¹-CHO in the presence of macro-porous cyanoborohydride resin and acetic acid in a solvent such as ethanol heated to or near 65° C. for 4 to 24 hours to give compounds of formula (7-1). Formaldehyde can substitute for G¹-CHO to prepare compounds of formula (7-2). Alternatively, compounds of formula (1-5) can be reacted with formaldehyde in the presence of sodium cyanoborohydride in methanolic acetate buffer to give compounds of formula (7-2).

As outlined in Scheme 8, compounds of formula (8-1) and (8-2), wherein A and G¹ are as defined in the Summary of the Invention, which are representative of compounds of formula (I) can be prepared from compounds of formula (4-5). Compounds of formula (4-5) can be reacted with an aldehyde of formula G¹-CHO in the presence of macro-porous cyanoborohydride resin and acetic acid in a solvent such as ethanol to give compounds of formula (8-1). Formaldehyde can also be used in this reductive amination procedure to give the methylamine analog corresponding to compounds of formula (8-1). Compounds of formula (4-5) can also be reacted with sulfonyl chlorides of formula G¹-SO₂Cl in the presence of pyridine in dichloromethane at room temperature for 8-24 hours to give compounds of formula (8-2).

Scheme 9

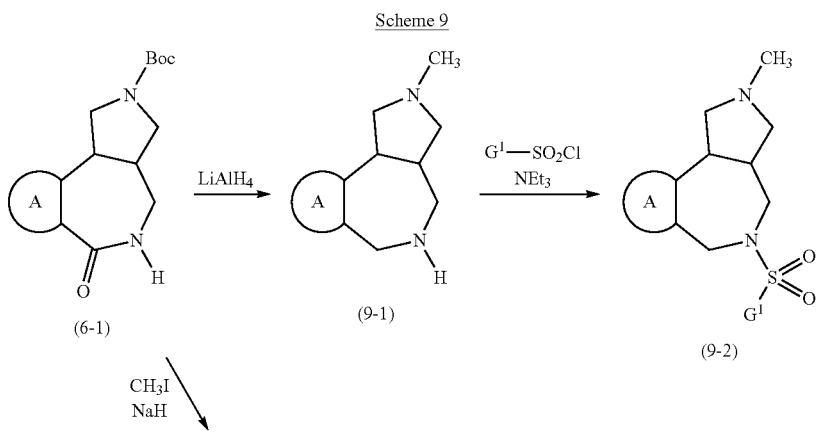

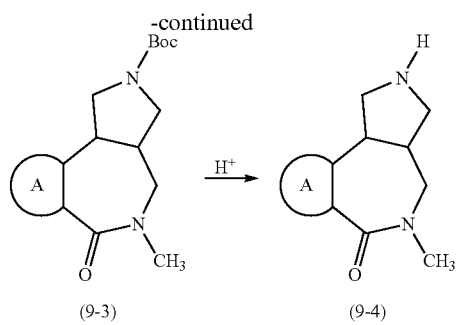

As outlined in Scheme 9, compounds of formula (9-2), wherein A and $G^1$ are as defined in the Summary of the Invention, which are representative of compounds of formula (I) can be prepared from compounds of formula (6-1). Compounds of formula (6-1) can be reacted with lithium aluminum hydride in a solvent such as tetrahydrofuran at room temperature over 12 to 36 hours to give compounds of formula (9-1). Compounds of formula (9-1) can then be reacted with sulfonyl chlorides of formula $G^1$-$SO_2Cl$ and a base such as triethylamine or pyridine in dichloromethane at room temperature to furnish compounds of formula (9-2). Compounds of formula (6-1) can be treated with a base such as sodium hydride in a solvent such as N,N-dimethylformamide followed by iodomethane to give compounds of formula (9-3). Compounds of formula (9-3) can be treated with hydrochloric acid in dioxane or trifluoroacetic acid in dichloromethane to provide compounds of formula (9-4).

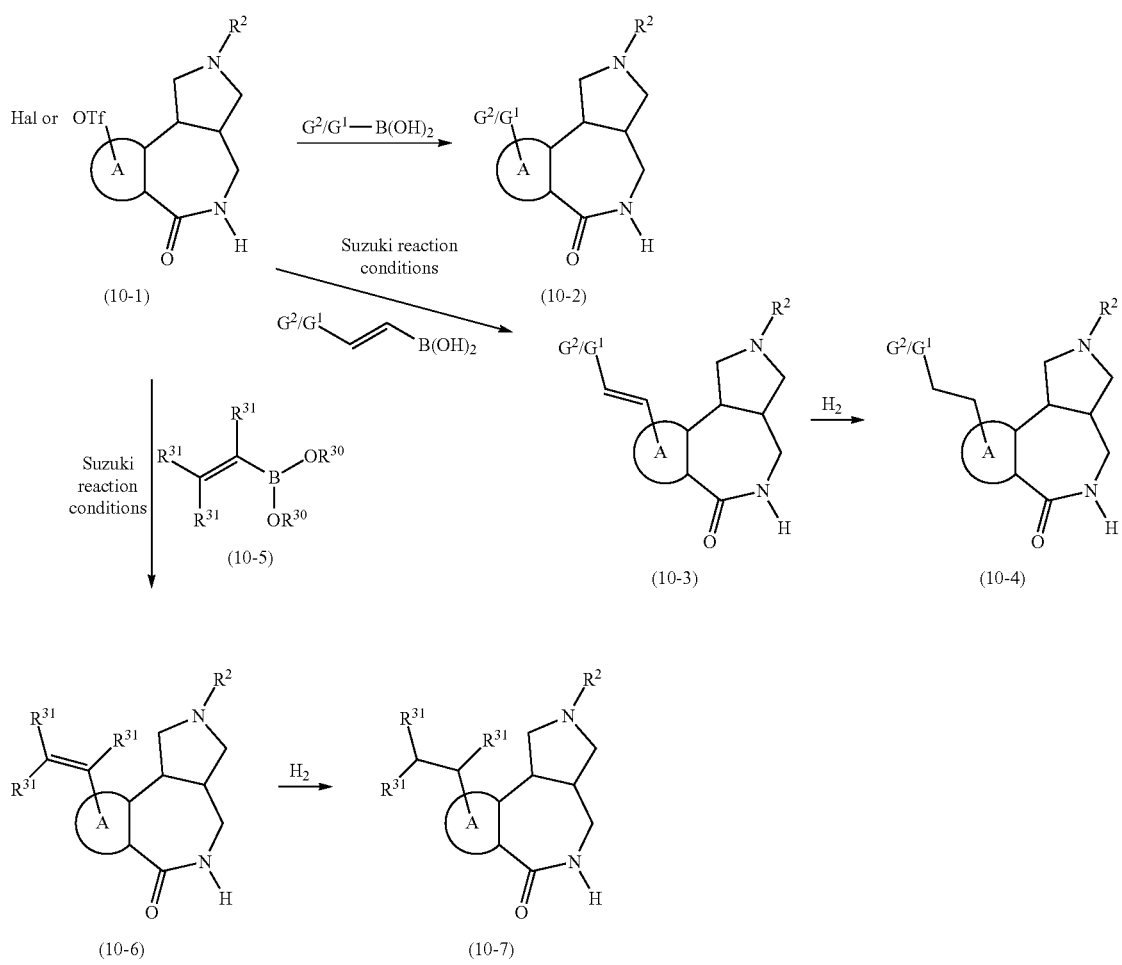

As outlined in Scheme 10, compounds of formula (10-2), (10-3), and (10-4), wherein A, $G^1$, $G^2$, and $R^2$ are as defined in the Summary of the Invention except $R^2$ is other than hydrogen, which are representative of compounds of formula (I) can be prepared from compounds of formula (10-1). Compounds of formula (10-1), wherein Hal is chlorine, bromine, or iodine and OTf is trifluoromethanesulfonate can be reacted with a boronic acid of formula $G^2/G^1$-B(OH)$_2$ or the corresponding boronate under Suzuki reaction conditions to give compounds of formula (10-2). Suzuki reaction conditions include one or more bases such as cesium carbonate, potassium carbonate or 1,8-diazabicyclo[5.4.0]undec-7-ene, a catalyst such as palladium(II) acetate, a ligand such as tri-tert-butylphosphine or 2-dicyclohexylphosphino-2',6'-dimethoxybiphenyl in a solvent such as N,N-dimethylformamide or dimethoxyethane heated either conventionally or in a microwave reactor at or near 150° C. for 30 to 70 minutes. An alternative set of Suzuki reaction conditions include a base such as potassium carbonate, a solid-supported palladium catalyst such as FC-1007, in a solvent such as ethanol heated in a microwave reactor to 150° C. for 30 to 60 minutes. Similarly, compounds of formula (10-1) can be transformed to compounds of formula (10-3) using the Suzuki reaction conditions previously described except a styryl-boronic acid or boronate is used. Compounds of formula (10-3) can be reduced with hydrogen (30 psi) in the presence of a catalyst such as 5% palladium on carbon in a solvent such as methanol at room temperature to furnish compounds of formula (10-4). Compounds of formula (10-1) can also be reacted with compounds of formula (10-5), wherein each $R^{30}$ is hydrogen, alkyl, or together with the oxygen atoms and adjacent boron atom to which they are attached form a dioxaborolane or a dioxaborinane and each $R^{31}$ is selected from hydrogen, alkyl, or haloalkyl or two $R^{31}$ groups taken together with the carbon atoms to which they are attached form a substituted or unsubstituted cycloalkyl or heterocycle, under Suzuki reaction conditions to give compounds of formula (10-6). Compounds of formula (10-6) can be reduced with hydrogen and an appropriate catalyst to give compounds of formula (10-7).

As outlined in Scheme 11, compounds of formula (7-2), wherein A is as defined in the Summary of the Invention, which are representative of compounds of formula (I) can alternatively be prepared from compounds of formula (3-2). Compounds of formula (3-2) can be reacted with 2-(methylamino)acetic acid in the presence of paraformaldehyde in heated toluene over one to four hours to provide compounds of formula (11-1). Alternatively, compounds of formula (3-2) can be reacted with 1-methoxy-N-methyl-N-((trimethylsilyl)methyl)methanamine in the presence of an acid such as trifluoroacetic acid to give compounds of formula (11-1). Compounds of formula (11-1) can be treated with the conditions described in Scheme 1 to provide compounds of formula (7-2).

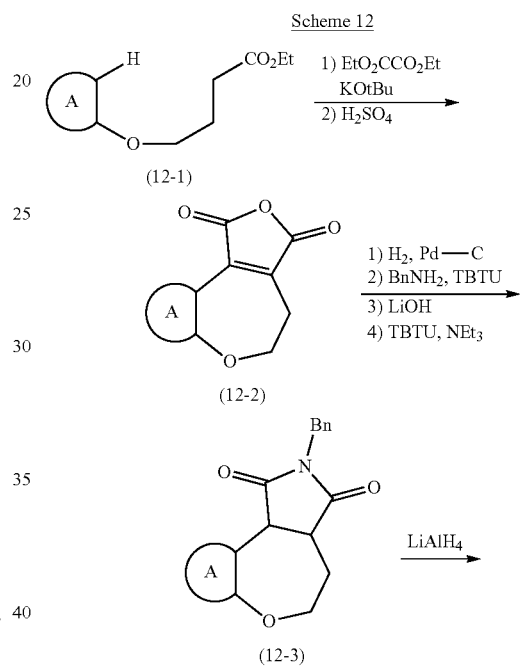

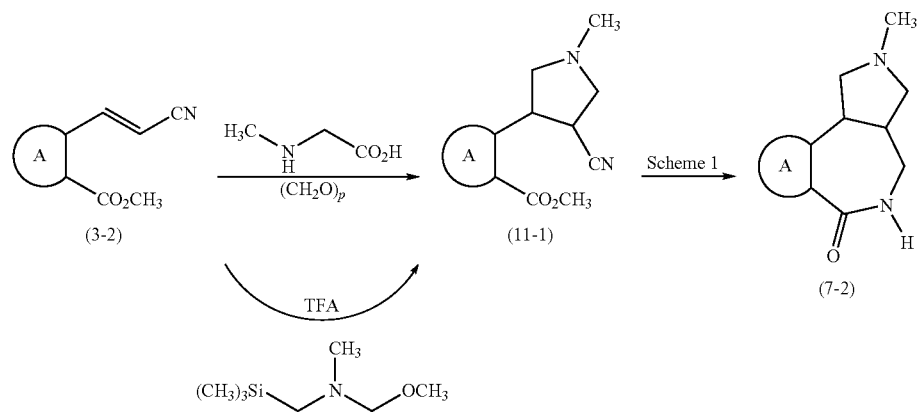

-continued

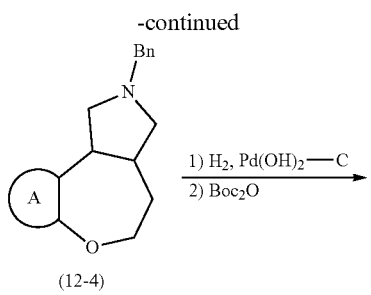
(12-4)

1) H₂, Pd(OH)₂—C
2) Boc₂O

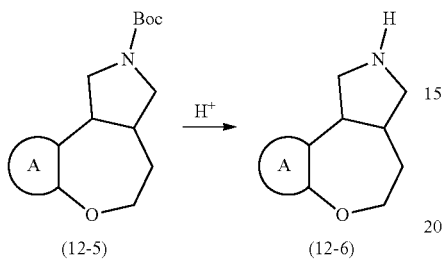
(12-5)      (12-6)

H⁺

As outlined in Scheme 12, compounds of formula (12-4) and (12-6), wherein A is as defined in the Summary of the Invention, which are representative of compounds of formula (I) can be prepared from compounds of formula (12-1). Compounds of formula (12-1) can be reacted first with diethyl oxalate in the presence of a base such as potassium tert-butoxide at approximately 0° C. in tetrahydrofuran. Then the intermediate is treated with concentrated sulfuric acid at 0° C. to supply compounds of formula (12-2). Compounds of formula (12-2) are treated in a four-step sequence to give compounds of formula (12-3). First compounds of formula (12-2) are treated with hydrogen (30 psi) in the presence of 5% palladium on carbon in heated methanol. Following workup, the material is taken into N,N-dimethylformamide and treated with benzyl amine in the presence of triethylamine and O-(benzotriazol-1-yl)-N,N,N',N'-tetramethyluronium tetrafluoroborate. Again after workup, the material is treated with lithium hydroxide in a solvent mixture such as methanol and water for 2 to 6 hours. Lastly, the material is taken into heated N,N-dimethylformamide and treated with O-(benzotriazol-1-yl)-N,N,N'N',N'-tetramethyluronium tetrafluoroborate in the presence of triethylamine to give compounds of formula (12-3). Compounds of formula (12-3) can be reduced with lithium aluminum hydride over 8 to 24 hours in tetrahydrofuran to give compounds of formula (12-4). Compounds of formula (12-4) can be reduced with hydrogen (30 psi) in the presence of palladium hydroxide on carbon in a solvent such as heated trifluoroethanol. Subsequent treatment with di-tert-butyl dicarbonate in dichloromethane provides compounds of formula (12-5). Compounds of formula (12-5) can be treated with hydrochloric acid in dioxane or trifluoroacetic acid in dichloromethane at room temperature to provide compounds of formula (12-6).

Scheme 13

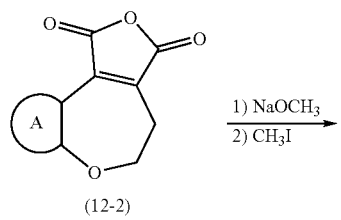
(12-2)

1) NaOCH₃
2) CH₃I

-continued

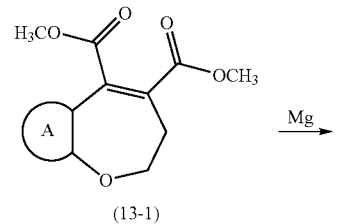
(13-1)

Mg

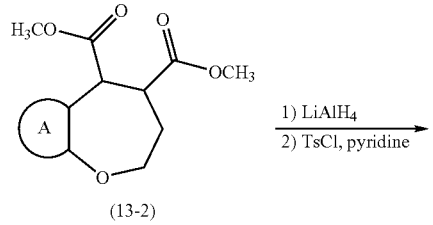
(13-2)

1) LiAlH₄
2) TsCl, pyridine

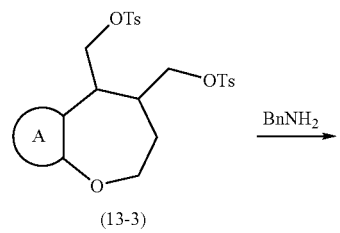
(13-3)

BnNH₂

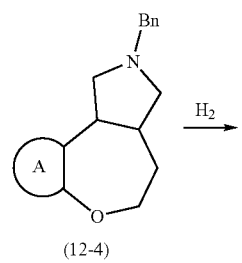
(12-4)

H₂

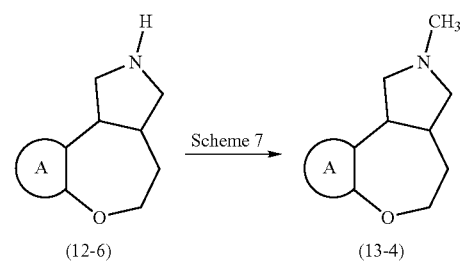
(12-6)      (13-4)

Scheme 7

As outlined in Scheme 13, compounds of formula (12-4), (12-6), and (13-4), wherein A is as defined in the Summary of the Invention, which are representative of compounds of formula (I) can be prepared from compounds of formula (12-2). Compounds of formula (12-2) can be treated sequentially with sodium methoxide in methanol and then with iodomethane in N,N-dimethylformamide to deliver compounds of formula (13-1). Compounds of formula (13-1) can be reduced in the presence of magnesium turnings in methanol to give compounds of formula (13-2). The ester moieties in compounds of formula (13-2) can be reduced with lithium aluminum hydride and the intermediate alcohols sulfonylated with p-toluenesulfonyl chloride in the presence of pyridine to give compounds of formula (13-3). Compounds of formula (13-3) can be treated with benzyl amine in the presence of a base such as triethylamine in optionally heated N,N-dimethylformamide to give compounds of formula (12-4). Compounds of formula (12-4) can be treated with hydrogen in the presence of a catalyst such as palladium hydroxide on carbon to give compounds of formula (12-6). Compounds of formula (12-6) can be alkylated as described in Scheme 7 to give compounds of formula (13-4).

Scheme 14

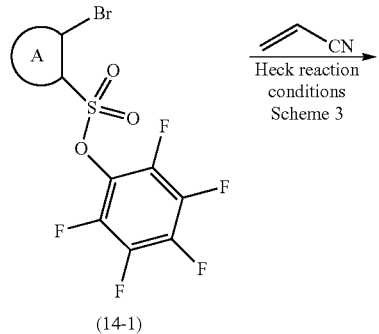

(14-1)

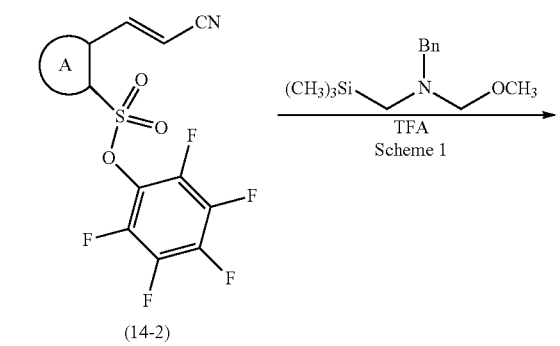

(14-2)

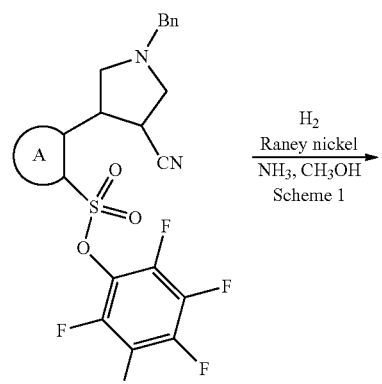

(14-3)

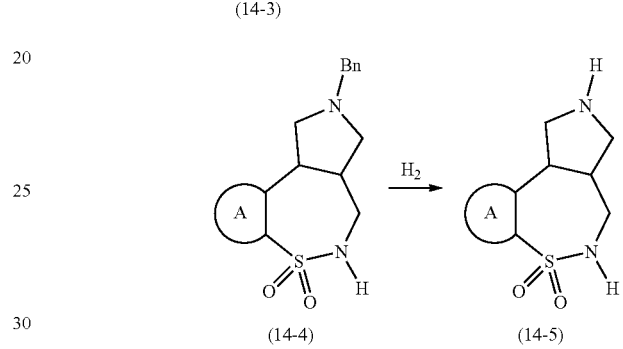

(14-4)     (14-5)

As outlined in Scheme 14, compounds of formula (14-4) and (14-5), wherein A is as defined in the Summary of the Invention, which are representative of compounds of formula (I) can be prepared from compounds of formula (14-1). Compounds of formula (14-1) can be treated with acrylonitrile under Heck reaction conditions described in Scheme 3 to supply compounds of formula (14-2). Compounds of formula (14-2) can then be treated with N-benzyl-1-methoxy-N-((trimethylsilyl)methyl)methanamine as described in Scheme 1 to give compounds of formula (14-3). The nitrile moiety of compounds of formula (14-3) can be reduced with hydrogen in the presence of Raney® nickel as described in Scheme 1 to give sulfonamides of formula (14-4). The benzyl group of compounds of formula (14-4) can be removed to supply compounds of formula (14-5) using the benzyl group removal conditions described in Scheme 1.

Scheme 15

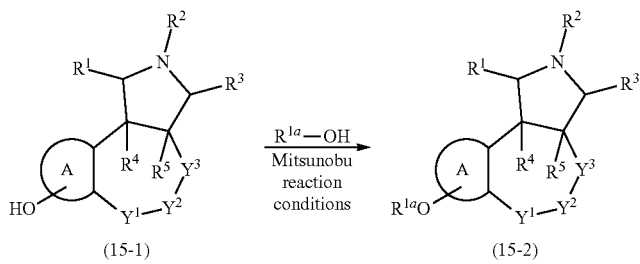

(15-1)     (15-2)

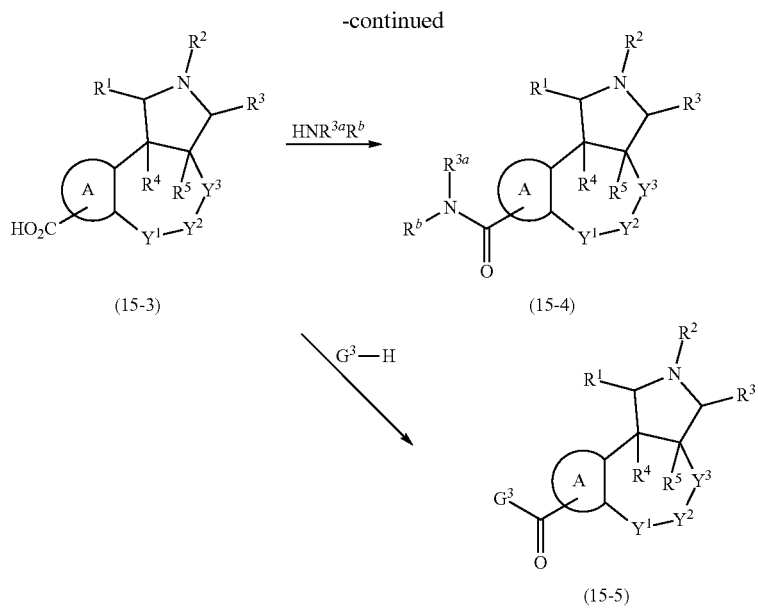

(15-3) (15-4) (15-5)

As described in Scheme 15, compounds of formula (15-2), wherein $R^1$, $R^2$, $R^3$, $R^4$, $R^5$, $R^{1a}$, A, $Y^1$, $Y^2$, and $Y^3$ are as defined in the Summary of the Invention, which are representative of compounds of formula (I) can be prepared from compounds of formula (15-1). Compounds of formula (15-1) can be treated with an alcohol, $R^{1a}$—OH, in the presence of an azodicarboxylate such as di-tert-butyl azodicarboxylate (DBAD) and triphenylphosphine, which may be optionally polymer supported, in a solvent such as tetrahydrofuran to give compounds of formula (15-2).

Also as described in Scheme 15, compounds of formula (15-4) and formula (15-5), wherein $R^1$, $R^2$, $R^3$, $R^4$, $R^5$, $R^b$, $R^{1a}$, A, $G^3$, $Y^1$, $Y^2$, and $Y^3$ are as defined in the Summary of the Invention, which are representative of compounds of formula (I) can be prepared from compounds of formula (15-3). Compounds of formula (15-3) can be coupled with an amine, $HNR^{3a}R^b$, or nitrogen containing heterocycle, $G^3$-H, under amide bond forming conditions to supply compounds of formula (15-4) and formula (15-5), respectively. Examples of conditions known to generate amides from a mixture of a carboxylic acid and an amine or nitrogen containing heterocycle include but are not limited to adding a coupling reagent such as but not limited to N-(3-dimethylaminopropyl)-N'-ethylcarbodiimide hydrochloride (EDCI, EDAC), 1,3-dicyclohexylcarbodiimide (DCC), bis(2-oxo-3-oxazolidinyl)phosphinic chloride (BOPCI), O-(7-azabenzotriazol-1-yl)-N,N,N',N'-tetramethyluronium hexafluorophosphate (HATU), 2-(1H-benzo[d][1,2,3]triazol-1-yl)-1,1,3,3-tetramethylisouronium tetrafluoroborate (TBTU). The coupling reagents may be added as a solid, a solution or as the reagent bound to a solid support resin. In addition to the coupling reagents, auxiliary-coupling reagents may facilitate the coupling reaction. Auxiliary coupling reagents that are often used in the coupling reactions include but are not limited to 4-dimethylaminopyridine (DMAP), 1-hydroxy-7-azabenzotriazole (HOAT) and 1-hydroxybenzotriazole (HOBT). The coupling reaction may be carried out in the presence of a base such as triethylamine or diisopropylethylamine. The coupling reaction may be carried out in solvents such as but not limited to tetrahydrofuran, N,N,-dimethylformamide, pyridine and ethyl acetate or a combination thereof. The reaction may be conducted at ambient or elevated temperatures.

Alternatively compounds of formula (15-4) and formula (15-5) can be produced from compounds of formula (15-3) by initially converting (15-3) to the corresponding acid chloride. The acid chloride can be typically prepared by suspending the carboxylic acid (15-3) in a solvent such as dichloromethane and then adding oxalyl chloride and a catalytic amount of N,N,-dimethylformamide. The solvent may be removed by evaporation, and the acid chloride redissolved in a solvent such as tetrahydrofuran or pyridine. Addition of an amine, $HNR^{3a}R^b$, or nitrogen containing heterocycle, $G^3$-H, in the presence of Hunig's base will furnish compounds of formula (15-4), or formula (15-5), respectively. The reaction may be conducted at ambient or elevated temperatures over a period ranging from several hours to several days.

Scheme 16

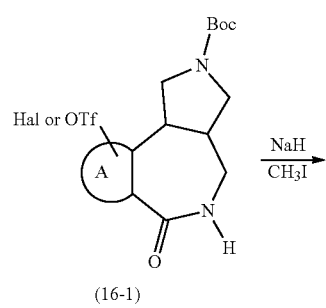

(16-1)

Scheme 17

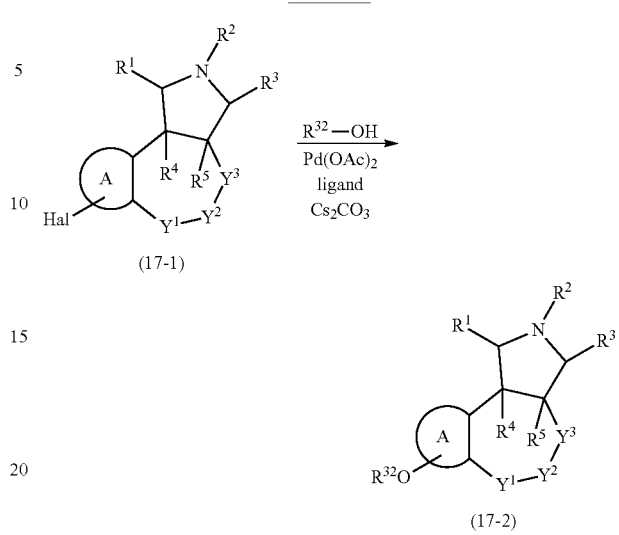

As described in Scheme 17, compounds of formula (17-2); wherein $R^1$, $R^2$, $R^3$, $R^4$, $R^5$, A, $Y^1$, $Y^2$, and $Y^3$ are as defined in the Summary of the Invention and $R^{32}$ is alkyl, $G^1$, and m are as defined in the Summary of the Invention; which are representative of compounds of formula (I) can be prepared from compounds of formula (17-1). Compounds of formula (17-1) wherein Hal is chlorine, bromine or iodine, can be treated with alcohols or phenols, $R^{32}$—OH, in the presence of palladium(II) acetate, a ligand such as 2-di-tert-butylphosphino-3,4,5,6-tetramethyl-2',4',6'-triisopropyl-1,1'-biphenyl, a base such as cesium carbonate, and a heated solvent such as toluene under an inert atmosphere to give compounds of formula (17-2). Compounds of formula (17-2) are representative of compounds of formula (I).

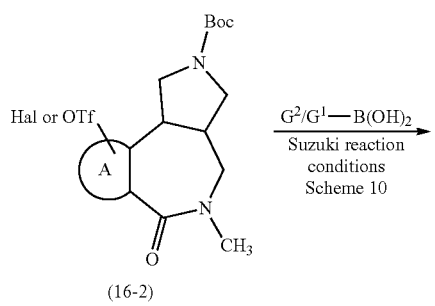

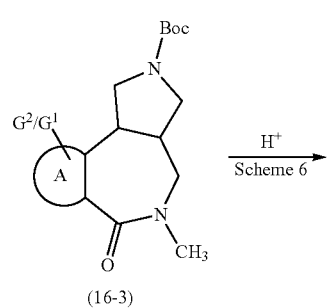

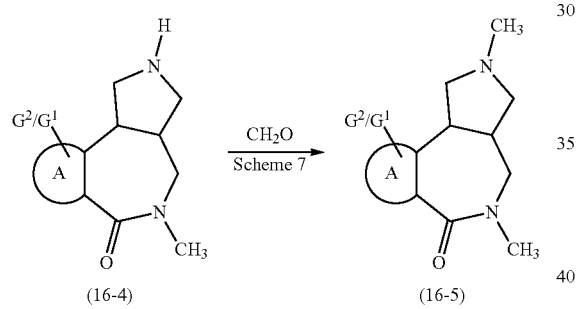

As described in Scheme 16, compounds of formula (16-4) and formula (16-5), wherein A, $G^1$ and $G^2$ are as defined in the Summary of the Invention, which are representative of compounds of formula (I) can be prepared from compounds of formula (16-1). Compounds of formula (16-1), wherein Hal is chlorine, bromine, or iodine and OTf is trifluoromethanesulfonate, can be treated with iodomethane in the presence of sodium hydride in a solvent such as N,N-dimethylformamide to give compounds of formula (16-2). Compounds of formula (16-2) can be reacted with boronic acids, $G^1$-B(OH)$_2$, $G^2$-B(OH)$_2$, or the corresponding boronates, or dioxaborolanes under Suzuki reaction conditions as described in Scheme 10 to give compounds of formula (16-3). The tert-butoxycarbonyl group in compounds of formula (16-3) can be removed under acidic conditions as described in Scheme 6 to furnish compounds of formula (16-4). The pyrrolidine nitrogen of compounds of formula (16-4) can be reductively alkylated as described in Scheme 7 to deliver compounds of formula (16-5).

Scheme 18

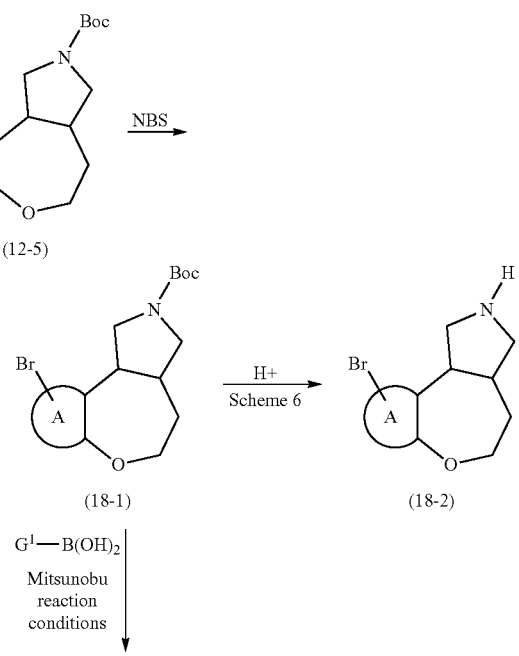

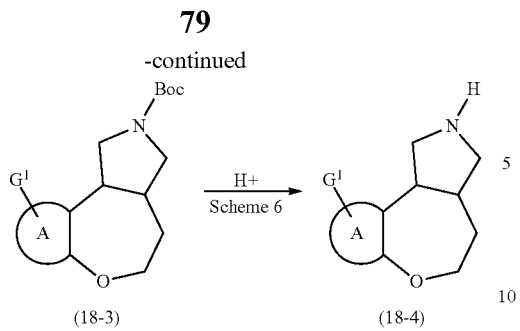

(18-3)  (18-4)

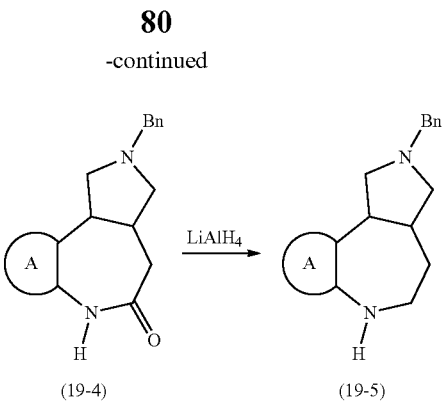

(19-4)  (19-5)

As described in Scheme 18, compounds of formula (18-2) and formula (18-4); wherein A and $G^1$ are as defined in the Summary of the Invention, which are representative of compounds of formula (I) can be prepared from compounds of formula (12-5). Compounds of formula (12-5) can be treated with N-bromosuccinimide (NBS) in heated N,N-dimethylformamide to supply compounds of formula (18-1). Compounds of formula (18-1) can be treated under acidic conditions described in Scheme 6 to give compounds of formula (18-2). Compounds of formula (18-1) can be reacted with boronic acids, $G^1$-B(OH)$_2$, or the corresponding boronates or dioxaborolanes under Suzuki reaction conditions as described in Scheme 10 to give compounds of formula (18-3). The heating of the Suzuki reaction may either be conventional or achieved through microwave irradiation. Compounds of formula (18-3) can be treated under acidic conditions described in Scheme 6 to give compounds of formula (18-4). Compounds of formula (18-2) and formula (18-4) are representative of compounds of formula (I).

As depicted in Scheme 19, compounds of formula (19-4) and formula (19-5), wherein A is as defined in the Summary of the Invention, which are representative of compounds of formula (I) can be prepared from compounds of formula (19-1). Compounds of formula (19-1) can be treated with methoxylcarbonylmethylenetriphenylphosphorane in optionally heated toluene to give compounds of formula (19-2). Compounds of formula (19-2) can be reacted with N-benzyl-1-methoxy-N-((trimethylsilyl)methyl)methanamine as described in Scheme 1 to give compounds of formula (19-3). Treatment of compounds of (19-3) with hydrogen in the presence of Raney® nickel reduces the nitro group to the corresponding amine Cyclization is achieved by subsequent treatment with a base such as sodium methoxide in optionally heated methanol go give compounds of formula (19-4). Compounds of formula (19-4) can be reduced with a reagent such as lithium aluminum hydride to give compounds of formula (19-5).

Scheme 19

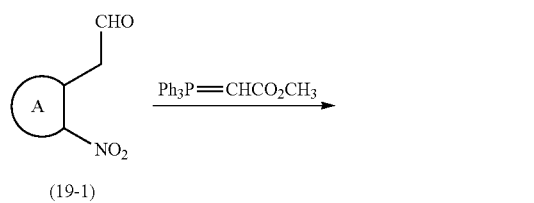

(19-1)

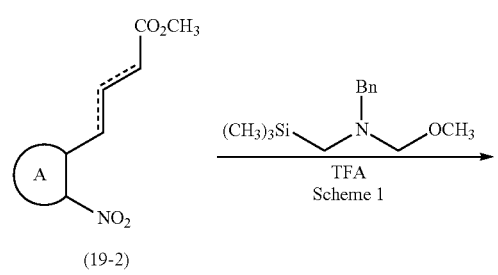

(19-2)

(19-3)

Scheme 20

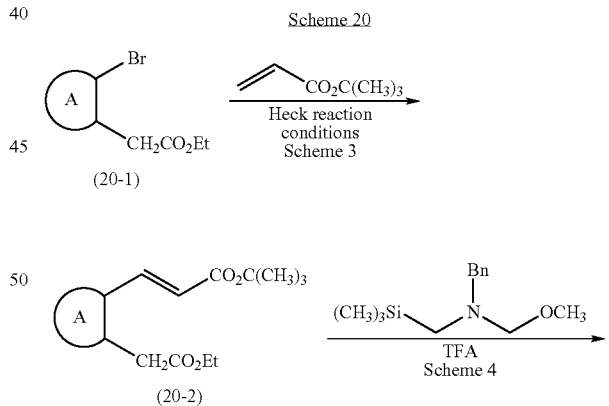

(20-1)

(20-2)

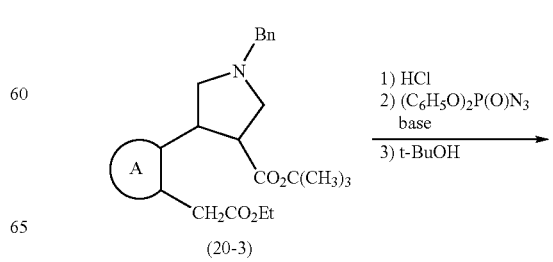

(20-3)

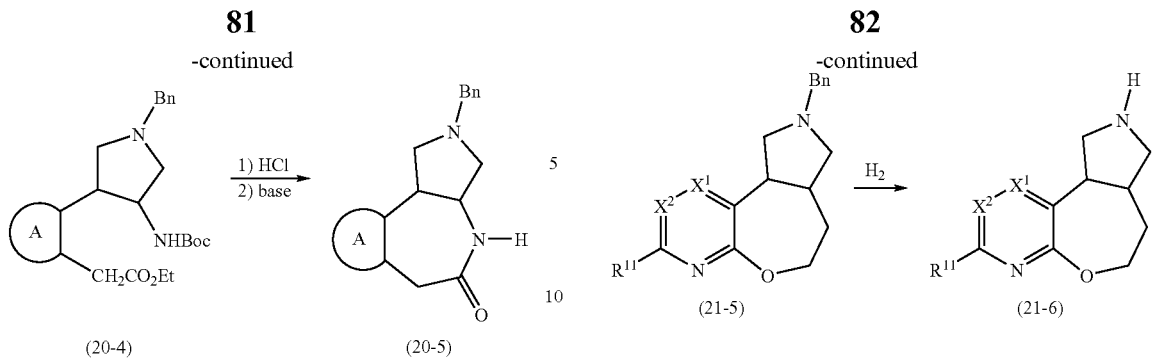

As depicted in Scheme 20, compounds of formula (20-5), wherein A is as defined in the Summary of the Invention, which are representative of compounds of formula (I) can be prepared from compounds of formula (20-1). Compounds of formula (20-1) can be treated with t-butyl acrylate under Heck reaction conditions as described in Scheme 3 to produce compounds of formula (20-2). Compounds of formula (20-2) can be reacted with N-benzyl-1-methoxy-N-((trimethylsilyl)methyl)methanamine as described in Scheme 4 to give compounds of formula (20-3). Compounds of formula (20-3) can be treated with acid such as hydrochloric acid or trifluoroacetic acid to selectively cleave the t-butyl ester. Treatment of the revealed carboxylic acid with diphenylphosphoryl azide in the presence of a base such as triethylamine produces the corresponding acyl azide. Treatment of the acyl azide with t-butanol in heated toluene gives carbamates of formula (20-4). Removal of the t-butoxycarbonyl group under acid conditions similar to those used to cleave the t-butyl ester followed by treatment with a base such as sodium methoxide in methanol gives cyclized compounds of formula (20-5).

As shown in Scheme 21, compounds of formula (21-5) and formula (21-6), wherein $R^{11}$, $X^1$ and $X^2$ are as defined in the Summary of the Invention, which are representative of compounds of formula (I) can be prepared from compounds of formula (21-1). Compounds of formula (21-1) can be treated with nitromethane in the presence of ethylamine hydrochloride and sodium hydroxide in ethanol. Subsequent treatment with acetic anhydride in the presence of 4-(dimethylamino)pyridine and triethylamine gives compounds of formula (21-2). Compounds of formula (21-2) can be reacted with 4-(tert-butyldimethylsilyloxy)butanal in the presence of a base such as piperidine gives compounds of formula (21-3). Compounds of formula (21-3) can be treated with zinc in the presence of acetic acid to reduce the nitro group concomitant with cyclization to the aldehyde group. Reduction of the intermediate pyrrolidinium with sodium cyanoborohydride delivers the pyrrolidine moiety. Reductive alkylation with benzaldehyde in the presence of sodium cyanoborohydride provides compounds of formula (21-4). Treatment of compounds of formula (21-4) with tetrabutylammonium fluoride removes the silyloxy protecting group. Treatment of the revealed alcohol functionality with a base such as potassium t-butoxide gives cyclization to compounds of formula (21-5). Exposure of compounds of formula (21-5) to hydrogen and a catalyst such as palladium hydroxide gives compounds of formula (21-6).

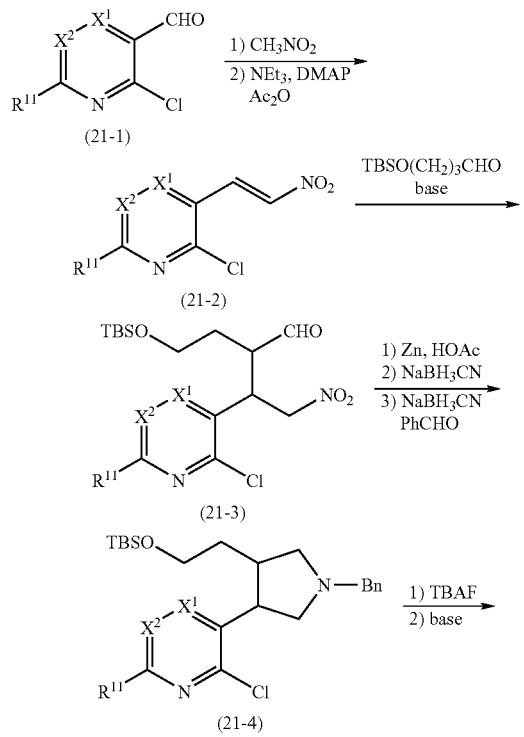

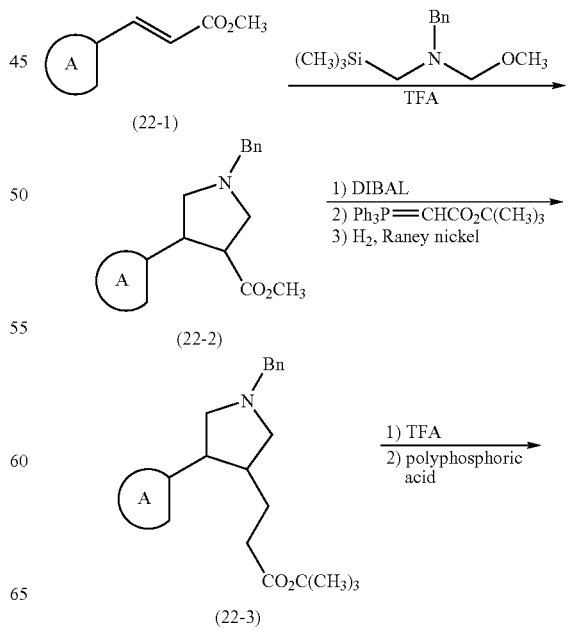

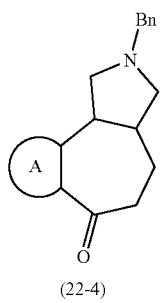

(22-4)

As shown in Scheme 22, compounds of formula (22-4), wherein A is as defined in the Summary of the Invention, which are representative of compounds of formula (I) can be prepared from compounds of formula (22-1). Compounds of formula (22-1) can be treated with N-benzyl-1-methoxy-N-((trimethylsilyl)methyl)methanamine as described in Scheme 4 to give compounds of formula (22-2). Compounds of formula (22-2) can be treated first with diisobutylaluminum hydride in toluene to give the corresponding aldehyde. The aldehyde can then be reacted with t-butoxycarbonylmethylenetriphenylphosphorane in heated toluene. The resultant unsaturated ester can then be hydrogenated in the presence of Raney® nickel to give compounds of formula (22-3). Compounds of formula (22-3) can then be reacted with an acid such as trifluoroacetic acid in methylene chloride or hydrochloric acid in dioxane to cleave the t-butyl ester an reveal the corresponding carboxylic acid. The carboxylic acid can then be treated with heated polyphosphoric acid to induce cyclization to compounds of formula (22-4).

As shown in Scheme 23, compounds of formula (23-2) and formula (23-4), wherein A is as defined in the Summary of the Invention, which are representative of compounds of formula (I) can be prepared from compounds of formula (22-4). Compounds of formula (22-4) can be hydrogenated in the presence of a catalyst such as palladium hydroxide on carbon resulting in reduction of the carbonyl to the corresponding methylene and alcohol moieties. Treatment with di-tert-butyl dicarbonate gives compounds of formulas (23-1) and (23-3). Compounds of formula (23-1) and formula (23-3) can then be reacted with an acid such as trifluoroacetic acid in methylene chloride or hydrochloric acid in dioxane to remove the t-butoxycarbonyl protecting group to give compounds of formula (23-2) and formula (23-4), respectively.

Scheme 24

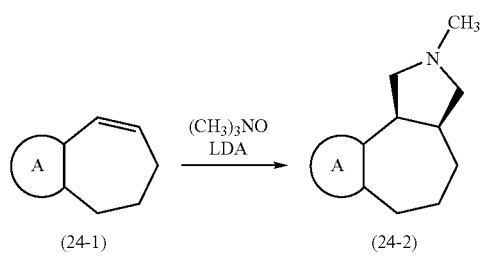

(24-1)　　　　　　　　(24-2)

As shown in Scheme 24, compounds of formula (24-2), wherein A is as defined in the Summary of the Invention, which are representative of compounds of formula (I), can be prepared form compounds of formula (24-1). Compounds of formula (24-1) can be treated with trimethylamine oxide in the presence of lithium diisopropyl amide (LDA) initially at −78° C. followed by warming and continued reaction at ambient temperature to give compounds of formula (24-2).

Scheme 23

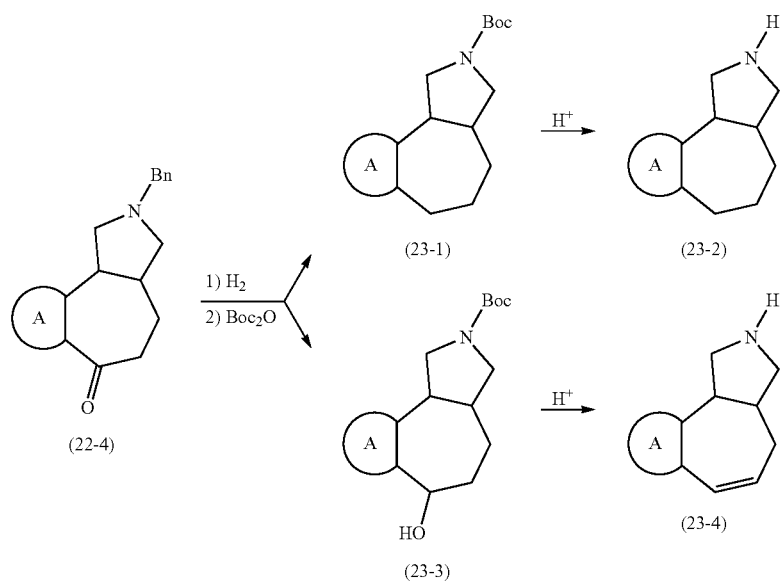

Scheme 25

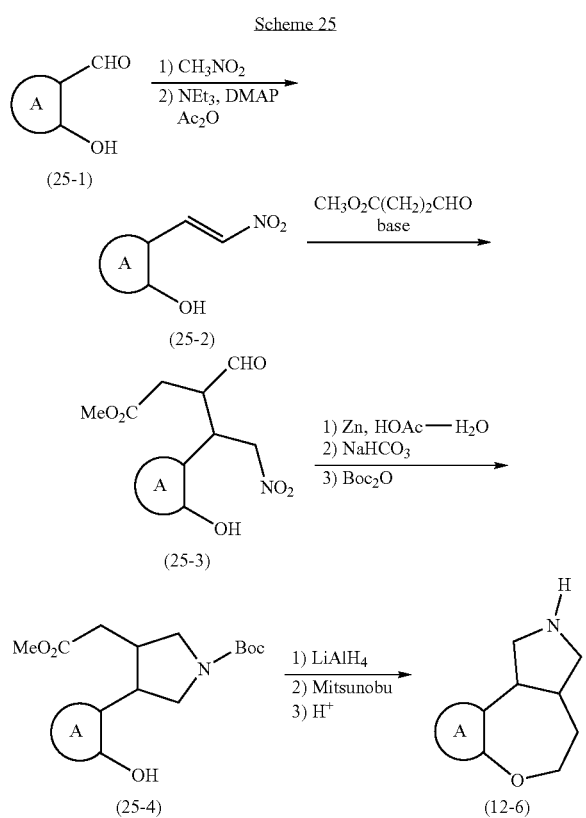

As shown in Scheme 25, compounds of formula (12-6), which are representative of compounds of formula (I) wherein A is as described in the Summary of the Invention, can also be prepared from compounds of formula (25-1). Compounds of formula (25-1) can be treated with nitromethane in the presence of ethylamine hydrochloride and sodium hydroxide in ethanol. Subsequent treatment with acetic anhydride in the presence of 4-(dimethylamino)pyridine and triethylamine gives compounds of formula (25-2). Compounds of formula (25-2) can be reacted with methyl 4-oxobutanoate in the presence of a base such as piperidine gives compounds of formula (25-3). The nitro group of compounds of formula (25-3) can be reduced with zinc in the presence of acetic acid and water followed by cyclization and reduction of the intermediate iminium to give a pyrrolidine. After adjusting the pH to 8 with a base such as sodium bicarbonate, treatment with di-tert-butyl dicarbonate gives compounds of formula (25-4). The ester group of compounds of formula (25-4) can be reduced with lithium aluminum hydride to give the corresponding alcohol. Cyclization to the benzoxepinopyrrole is achieved under Mitsunobu reaction conditions. Removal of the tert-butoxy carbonyl group under acidic conditions delivers compounds of formula (12-6).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g., by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protective Groups in Organic Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. Examples

The compounds and processes of the present invention will be better understood by reference to the following Examples, which are intended as an illustration of and not a limitation upon the scope of the application.

Abbreviations:

AA for ammonium acetate; APCI for atmospheric pressure chemical ionization; aq for aqueous; DCI for desorption chemical ionization; DMSO for dimethyl sulfoxide; eq for equivalent(s); ESI for electrospray ionization; HPLC for high performance liquid chromatography; LC/MS for liquid chromatography/mass spectrometry; PS for polymer supported; psi for pounds per square inch; TFA for trifluoroacetic acid; TLC for thin layer chromatography.

Analytical HPLC (LC/MS) Procedure:

Analytical LC/MS was performed on a Finnigan Navigator mass spectrometer and Agilent 1100 HPLC system running Xcalibur 1.2, Open-Access 1.3, and custom login software.

The mass spectrometer was operated under positive APCI ionization conditions. The HPLC system comprised an Agilent Quaternary pump, degasser, column compartment, autosampler and diode-array detector, with a Sedere Sedex 75 evaporative light-scattering detector. The column used was a Phenomenex® Luna® Combi-HTS C8(2) 5 nm 100 Å (2.1× 30 mm)

Trifluoroacetic acid (TFA) method: A gradient of 10-100% acetonitrile (A) and 0.1% trifluoroacetic acid in water (B) was used, at a flow rate of 2.0 mL/minute (0-0.1 minutes 10% A, 0.1-2.6 minutes 10-100% A, 2.6-2.9 minutes 100% A, 2.9-3.0 minutes 100-10% A. 0.5 minute post-run delay).

Ammonium acetate (AA) method: A gradient of 10-100% acetonitrile (A) and 10 mM ammonium acetate in water (B) was used, at a flow rate of 2.0 mL/minute (0-0.1 minute 10% A, 0.1-2.6 minutes 10-100% A, 2.6-2.9 minutes 100% A, 2.9-3.0 minutes 100-10% A. 0.5 minute post-run delay).

Preparative HPLC Procedure:

Unless otherwise noted, compounds purified by HPLC used the following protocol. Samples were purified by preparative HPLC on a Phenomenex Luna C8(2) 5 μm 100 Å AXIA column (30 mm×75 mm) A gradient of acetonitrile (A) and 0.1% trifluoroacetic acid in water (B) was used, at a flow rate of 50 mL/minute (0-0.5 minutes 10% A, 0.5-7.0 minutes linear gradient 10-95% A, 7.0-10.0 minutes 95% A, 10.0-12.0 minutes linear gradient 95-10% A). Samples were injected in 1.5 mL of dimethyl sulfoxide:methanol (1:1). With specified samples, ammonium acetate was used instead of trifluoroacetic acid. A custom purification system was used, consisting of the following modules: Waters LC4000 preparative pump; Waters 996 diode-array detector; Waters 717+ autosampler; Waters SAT/IN module, Alltech Varex III evaporative light-scattering detector; Gilson 506C interface box; and two Gilson FC204 fraction collectors. The system was controlled using Waters Millennium32 software, automated using an Abbott developed Visual Basic application for fraction collector control and fraction tracking. Fractions were collected based upon UV signal threshold and selected fractions subsequently analyzed by flow injection analysis mass spectrometry using positive APCI ionization on a Finnigan LCQ using 70:30 methanol:10 mM NH$_4$OH(aqueous) at a flow rate of 0.8 mL/minute. Loop-injection mass spectra were acquired using a Finnigan LCQ running LCQ Navigator 1.2 software and a Gilson 215 liquid handler for fraction injection controlled by an Abbott developed Visual Basic application.

Example 1

Trans-2-benzyl-1,2,3,3a,4,5-hexahydrobenzo[c]pyrrolo[3,4-e]azepin-6(10bH)-one

Example 1A

Methyl 2-(2-cyanovinyl)benzoate

Methyl 2-formylbenzoate (10 g, 60.9 mmol) was dissolved in toluene (200 mL). (Triphenylphosphoranylidene)acetonitrile (20.19 g, 67.0 mmol) was then added to the mixture. The reaction was heated at 110° C. for 20 hours, then cooled to room temperature, concentrated under vacuum and the residue was triturated with ether (2×). The ether solution was passed though a plug of silica gel to provide Example 1A (mixture of E and Z isomers). The mixture of E and Z isomers was used directly for the next step. MS (DCI+) m/z 205.0 [M+NH$_3$]$^+$.

Example 1B

Trans-methyl 2-(1-benzyl-4-cyanopyrrolidin-3-yl)benzoate

In a 50 mL round bottom flask were combined methyl 2-(2-cyanovinyl)benzoate (Example 1A, 11.03 g, 58.9 mmol) trifluoroacetic acid (0.045 mL, 0.589 mmol) and dichloromethane (100 mL). N-Benzyl-1-methoxy-N-((trimethylsilyl)methyl)methanamine (64.8 mmol) was added as a solution in dichloromethane (100 mL) dropwise over 15 minutes while stirring under argon. The reaction was stirred at room temperature for 20 hours, then quenched with aqueous sodium bicarbonate and extracted with dichloromethane. The organic washes were combined and washed with brine, dried over Na$_2$SO$_4$, filtered, and the solvent was removed in vacuo to provide the crude product. The mixture of isomers was added to a silica gel column and was eluted with ethyl acetate/hexanes (gradient 0-20%, 40 minutes) to provide the title compound as the faster eluting (less polar) isomer. $^1$H NMR (500 MHz, CDCl$_3$) δ ppm 2.82 (dd, 1H, J=9.09 Hz, J=7.81 Hz), 2.88 (dd, 1H, J=9.74 Hz, J=4.27 Hz), 2.99-3.03 (m, 1H), 3.05-3.09 (m, 1H), 3.29 (t, 1H, J=8.37 Hz), 3.71 (m, 2H), 3.94 (s, 3H), 4.51 (ddd, 1H, J=8.29 Hz, J=6.36 Hz, J=4.35 Hz), 7.25-7.40 (m, 6H), 7.50 (dt, 1H, J=7.65 Hz, J=1.45 Hz), 7.62 (d, 1H, J=7.24 Hz), 7.81 (dd, 1H, J=7.89 Hz, J=1.29 Hz); MS (DCI+) m/z 321.2 [M+H]$^+$.

Example 1C

Trans-2-benzyl-1,2,3,3a,4,5-hexahydrobenzo[c]pyrrolo[3,4-e]azepin-6(10bH)-one

Example 1B (9.25 g, 30.2 mmol) and 100 mL of a 7 M NH$_3$/methanol solution were added to Raney®-nickel (water-wet, 19 g) in a pressure bottle and stirred at room temperature for 18 hours under hydrogen at 40 psi. After the HPLC indicated reaction was complete, the solution was filtered through a nylon membrane and was concentrated in vacuo to provide the title compound. The crude material was triturated with ethyl acetate (3×50 mL). The resulting solid was collected by filtering through a Buchner funnel and rinsed with ethyl acetate. $^1$H NMR (500 MHz, pyridine-d$_5$) δ ppm 2.23-2.27 (m, 1H), 2.69 (d, 2H, J=8.54 Hz), 3.00 (dd, 1H, J=10.53 Hz, J=9.00 Hz), 3.13 (dd, 1H, J=8.54 Hz, J=6.41 Hz), 3.20-3.25 (m, 1H), 3.30-3.35 (m, 1H), 3.45-3.50 (m, 1H), 3.69-3.72 (m, 1H), 7.08 (d, 1H, J=7.32 Hz), 7.32-7.38 (m, 2H), 7.40-7.45 (m, 3H), 7.53 (d, 1H, J=7.32 Hz), 8.40 (dd, 1H, J=7.48 Hz, J=1.07 Hz), 8.77 (br s, 1H); MS (DCI+) m/z 293.2 [M+H]$^+$.

Example 2

Trans-1,2,3,3a,4,5-hexahydrobenzo[c]pyrrolo[3,4-e]azepin-6(10bH)-one

A solution of Example 1 (10.91 g, 37.3 mmol) in 200 mL of methanol was added to 20% Pd(OH)$_2$/carbon (water wet, 1.1 g) in a pressure bottle and stirred at 50° C. for 32 hours under hydrogen (30 psi). When the HPLC indicated the reaction was complete, the solution was cooled, was filtered through a nylon membrane and was concentrated in vacuo to provide the title compound. $^1$H NMR (500 MHz, pyridine-d$_5$) δ ppm 2.10-2.17 (m, 1H), 2.91 (t, 1H, J=10.07 Hz), 3.12-3.40 (m, 6H), 7.16 (d, 1H, J=7.32 Hz), 7.38 (t, 1H, J=7.02 Hz), 7.42 (dt, 1H, J=7.40 Hz, J=1.37 Hz), 8.25 (dd, 1H, J=7.48 Hz, J=1.07 Hz), 8.80 (br s, 1H); MS (DCI+) m/z 203.0 [M+H]$^+$.

Example 3

Cis-2-benzyl-1,2,3,3a,4,5-hexahydrobenzo[c]pyrrolo[3,4-e]azepin-6(10bH)-one

Example 3A

Methyl cis-2-(1-benzyl-4-cyanopyrrolidin-3-yl)benzoate

The title compound was prepared according to the procedure outlined in Example 1B as the slower eluting (more polar) isomer. $^1$H NMR (500 MHz, CDCl$_3$) δ ppm 2.87 (dd, 2H, J=9.5 Hz, J=7.73 Hz), 2.97-3.01 (m, 2H), 3.04-3.08 (m, 2H), 3.88 (s, 3H), 4.45 (m, 1H), 7.25-7.40 (m, 6H), 7.55 (dt, 1H, J=7.65 Hz, J=1.29 Hz), 7.70 (d, 1H, J=7.89 Hz), 7.91 (dd, 1H, J=7.89 Hz, J=1.13 Hz); MS (DCI+) m/z 321.2 [M+H]$^+$.

Example 3B

Cis-2-benzyl-1,2,3,3a,4,5-hexahydrobenzo[c]pyrrolo[3,4-e]azepin-6(10bH)-one

Example 3A (7 g, 21.85 mmol) and 100 mL of a 7 M NH$_3$/methanol solution were added to Raney®-nickel (water wet, 14 g) in a pressure bottle and stirred at 50° C. for 16 hours under hydrogen (50 psi). After the HPLC indicated the reaction was complete, the solution was cooled, filtered through a nylon membrane and concentrated in vacuo to provide the title compound. $^1$H NMR (500 MHz, pyridine-d$_5$) δ ppm 2.59 (t, 1H, J=9.51 Hz), 2.65-2.67 (m, 1H), 2.73-2.81 (m, 1H), 2.93-2.99 (m, 2H), 3.15-3.25 (m, 2H), 3.54 (s, 2H), 3.59-3.66 (m, 1H), 7.23-7.43 (m, 8H), 8.15-8.18 (m, 1H), 9.12 (t, 1H, J=5.83 Hz); MS (DCI+) m/z 293.2 [M+H]$^+$.

Example 4

Cis-1,2,3,3a,4,5-hexahydrobenzo[c]pyrrolo[3,4-e]azepin-6(10bH)-one

Example 3 (12.3 g, 42.1 mmol) dissolved in methanol (150 mL) was added to 20% Pd(OH)$_2$/carbon (water wet, 2.46 g) in a pressure bottle and stirred at room temperature for 22 hours under hydrogen (30 psi). When the HPLC indicated the reaction was complete, the mixture was filtered through a nylon membrane and was concentrated in vacuo to provide the title compound. $^1$H NMR (500 MHz, pyridine-d$_5$) δ ppm 3.10-3.15 (m, 1H), 3.17-3.26 (m, 1H), 3.58 (t, 1H, J=3.58 Hz), 3.88-4.00 (m, 2H), 4.11-4.20 (m, 2H), 7.31 (br s, 1H), 7.40 (dt, 2H, J=3.97 Hz), 8.03-8.05 (m, 1H), 9.40 (t, 1H, J=5.95 Hz); MS (DCI+) m/z 203.0 [M+H]$^+$.

Example 5

Trans-2-benzyl-1,2,3,3a,5,6-hexahydrobenzo[c]pyrrolo[3,4-e]azepin-4(10bH)-one

Example 5A (E)-Ethyl 3-(2-cyanophenyl)acrylate

2-Formylbenzonitrile (5 g, 38.1 mmol) was added to a round bottom flask, equipped with a stir bar, and dissolved in toluene (50 mL). (Carbethoxymethylene)triphenylphosphorane (14.6 g, 41.9 mmol) was then added to the mixture. The reaction was heated at 110° C. for 20 hours. The solution was concentrated under vacuum, and the residue was redissolved in dichloromethane. The solution was passed though a plug of silica (dichloromethane eluent) to provide the title compound. $^1$H NMR (300 MHz, CDCl$_3$) δ ppm 1.37 (t, 3H, J=7.12 Hz), 4.30 (q, 2H, J=7.12 Hz), 6.61 (d, 1H, J=15.94 Hz), 7.47 (dt, 1H, J=7.71 Hz, J=1.19 Hz), 7.62 (dt, 1H, J=7.80 Hz, J=1.36 Hz), 7.7-7.75 (m, 2H), 7.97 (d, 1H, J=15.94 Hz); MS (DCI+) m/z 218.9 [M+NH$_3$]$^+$.

Example 5B

Trans-ethyl 1-benzyl-4-(2-cyanophenyl)pyrrolidine-3-carboxylate

Example 5A (12.12 g, 60.3 mmol) was combined with trifluoroacetic acid (4.6 mL, 0.603 mmol) and dichloromethane (300 mL). N-Benzyl-1-methoxy-N-((trimethylsilyl)methyl)methanamine (15.74 g, 66.3 mmol) was added as a solution in dichloromethane (6 mL) dropwise over 1 hour via an addition funnel while stirring under argon. The reaction was stirred at room temperature for 20 hours then quenched with aqueous sodium bicarbonate solution and extracted with dichloromethane. The organic washes were combined and washed with brine, dried over Na$_2$SO$_4$, filtered, and the solvent was removed in vacuo to provide the title compound. $^1$H NMR (300 MHz, CDCl$_3$) δ ppm 1.24 (t, 3H, J=7.12 Hz), 2.85 (m, 2H), 3.00 (t, 1H, J=8.48 Hz), 3.06-313 (m, 1H), 3.20 (t, 1H, J=8.48 Hz), 3.69 (d, 2H), 4.02-4.08 (m, 1H), 4.15 (dq, 2H, J=7.12 Hz, J=2.3 Hz), 7.25-7.40 (m, 6H), 7.55-7.70 (m, 3H); MS (DCI+) m/z 335.2 [M+H]$^+$.

Example 5C

Trans-2-benzyl-1,2,3,3a,5,6-hexahydrobenzo[c]pyrrolo[3,4-e]azepin-4(10bH)-one

Example 5B (20.14 g, 60.2 mmol) and 200 mL of a 7 M NH$_3$/methanol solution were added to Raney®-nickel (water wet, 40 g) in a pressure bottle and stirred at room temperature for 16 hours under hydrogen (60 psi). After the HPLC indicated reaction was complete, the solution was filtered through a nylon membrane and was concentrated in vacuo to provide the title compound. $^1$H NMR (500 MHz, pyridine-d$_5$) δ ppm 2.68 (t, 1H, J=9.31 Hz), 2.84 (t, 1H, J=9.15 Hz), 3.53 (t, 1H, J=8.24 Hz), 3.59-3.64 (m, 1H), 3.72-3.82 (m, 3H), 3.97 (dd, 1H, J=9.31 Hz, J=6.87 Hz), 4.28 (dd, 1H, J=16.78 Hz, J=6.71 Hz), 4.93 (d, 1H, J=18.00 Hz) 7.00 (d, 1H, J=7.63 Hz), 7.11-7.12 (m, 1H), 7.16-7.24 (m, 5H), 7.31 (t, 1H, J=7.48 Hz), 7.40 (t, 1H, J=7.48 Hz), 7.54 (d, 1H, J=6.31 Hz); MS (DCI+) m/z 293.2 [M+H]$^+$.

Example 6

Trans-1,2,3,3a,5,6-hexahydrobenzo[c]pyrrolo[3,4-e]azepin-4(10bH)-one

Example 5 (6.74 g, 20.05 mmol) dissolved in methanol (80 mL) was added to 20% Pd(OH)$_2$/carbon (water wet, 1.2 g) in a pressure bottle and stirred at room temperature for 30 hours under hydrogen (30 psi). When the HPLC indicated the reaction was complete, the mixture was cooled, was filtered through a nylon membrane and was concentrated in vacuo to provide the title compound. $^1$H NMR (500 MHz, pyridine-d$_5$) δ ppm 3.07 (t, 1H, J=10.07 Hz), 3.45-3.62 (m, 3H), 3.89 (dd, 1H, J=10.22 Hz, J=6.87 Hz), 4.07 (dd, 1H, J=10.68 Hz, J=7.93 Hz), 4.26 (dd, 1H, J=16.78 Hz, J=7.02 Hz), 4.96 (dd, 1H, J=16.94 Hz, J=3.51 Hz), 7.12-7.27 (m, 4H), 8.82 (br s, 1H); MS (DCI+) m/z 203.0 [M+H]$^+$.

Example 7

Trans-2-benzyl-1,2,3,3a,4,5,6,10b-octahydrobenzo[c]pyrrolo[3,4-e]azepine

To a 1 M solution of borane tetrahydrofuran complex (46.1 mL, 46.1 mmol) in tetrahydrofuran (10 mL) was added Example 5 (3.37 g, 11.53 mmol) at room temperature. The mixture was refluxed for 3 hours under nitrogen. Methanol (6 mL) was added carefully and the mixture was refluxed for 1 hour. 2 M HCl (10 mL) was added and the mixture was heated at 80° C. overnight. The reaction mixture was evaporated and the residue diluted with $H_2O$, basified with $K_2CO_3$ (pH 10), and extracted with dichloromethane (2×). The organics were combined and washed with brine, dried over $Mg_2SO_4$, and evaporated to give the crude product. The crude product was purified by reverse phase HPLC to afford the title compound. $^1$H NMR (500 MHz, pyridine-$d_5$) δ ppm 2.63-2.71 (m, 1H), 3.03-3.07 (m, 1H), 3.15 (t, 1H, J=10.37 Hz), 3.45 (t, 1H, J=10.22 Hz), 3.65 (dd, 1H, J=9.31 Hz, J=6.26 Hz), 3.72 (t, 1H, J=12.51 Hz), 3.98-4.04 (m, 2H), 4.07-4.10 (m, 1H), 4.19-4.21 (m, 1H), 4.61-4.64 (m, 1H), 4.70-4.73 (m, 1H), 7.11 (d, 1H, J=7.63 Hz), 7.18 (t, 1H, J=7.32 Hz), 7.28-7.33 (m, 2H), 7.38 (t, 1H, J=7.32 Hz), 7.42 (t, 2H, J=7.32 Hz), 7.64 (d, 2H, J=7.32 Hz); MS (DCI+) m/z 279.2 [M+H]$^+$.

Example 8

Trans-2-benzyl-5-(3-fluorophenylsulfonyl)-1,2,3,3a,4,5,6,10b-octahydrobenzo[c]pyrrolo[3,4-e]azepine Example 7 (106.5 mg, 0.383 mmol) was added to a vial and dissolved in a 1:1 mixture of pyridine and dichloromethane (2 mL). 3-Fluorobenzene-1-sulfonyl chloride (56 μL, 0.421 mmol) was added to the reaction, and the mixture was vortexed overnight at room temperature. The solvent was concentrated to dryness and the residue was redissolved in 1:1 methanol/dimethyl sulfoxide and purified by reverse phase HPLC to provide the title compound as the trifluoroacetic acid salt. $^1$H NMR (300 MHz, pyridine-$d_5$) δ ppm 2.10-2.19 (m, 1H), 2.80 (d, 1H, J=8.54 Hz), 3.06 (t, 1H, J=9.92H), 3.16 (t, 1H, J=12.21 Hz), 3.44-3.47 (m, 1H), 3.60-3.65 (m, 1H), 3.84 (d, 1H, J=12.84 Hz), 4.01 (d, 1H, J=12.82 Hz), 4.23-4.26 (m, 2H), 4.98 (d, 1H, J=15.26 Hz), 6.98 (d, 1H, J=8.24 Hz), 7.2-7.6 (m, 10H), 7.77 (d, 1H, J=8.24 Hz), 7.81 (dt, 1H, J=8.31 Hz, J=2.10 Hz); MS (DCI+) m/z 437.2 [M+H]$^+$.

Example 9

Trans-2-benzyl-5-(2,3-dichlorophenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 2,3-dichlorobenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-$d_6$/$D_2O$) δ ppm 2.03-2.11 (m, 1H), 2.67 (t, 1H, J=9.92 Hz), 2.91 (t, 1H, J=9.76H), 3.17-3.21 (m, 2H), 3.26 (dd, 1H, J=13.27 Hz, J=11.44 Hz), 3.47-3.52 (m, 1H), 3.63 (d, 1H, J=12.82 Hz), 3.85 (dd, 1H, J=13.43 Hz, J=2.75 Hz), 4.50-4.53 (m, 1H), 4.59-4.62 (m, 1H), 7.09 (d, 1H, J=7.63 Hz), 7.24-7.2.8 (m, 2H), 7.32-7.37 (m, 4H), 7.57 (t, 1H, J=8.09 Hz), 7.93 (dd, 1H, J=8.09 Hz, J=1.37 Hz), 7.99 (dd, 1H, J=7.93 Hz, J=1.53 Hz); MS (DCI+) m/z 487.1 [M+H]$^+$.

Example 10

Trans-2-benzyl-5-(2,5-dichlorophenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 2,5-dichlorobenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-$d_6$/$D_2O$) δ ppm 2.00-2.10 (m, 1H), 2.55-2.59 (m, 1H), 2.65-2.73 (m, 1H), 2.89-2.96 (m, 1H), 3.25 (dd, 1H, J=13.43 Hz, J=11.6 Hz), 3.47-3.53 (m, 1H), 3.65 (d, 1H, J=12.51 Hz), 3.81 (d, 1H, J=12.82 Hz), 3.90 (dd, 1H, J=12.82 Hz, J=2.75 Hz), 4.36-4.39 (m, 2H), 4.52 (d, 1H, J=15.56 Hz), 4.66 (d, 1H, J=15.56 Hz), 7.07 (d, 1H, J=7.32 Hz), 7.16-7.19 (m, 1H), 7.22-7.37 (m, 7H), 7.68-7.72 (m, 2H), 7.92 (d, 1H, J=2.14 Hz); MS (DCI+) m/z 487.1 [M+H]$^+$.

Example 11

Trans-2-benzyl-5-(2-bromophenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 2-bromobenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-$d_6$/$D_2O$) δ ppm 2.05-2.13 (m, 1H), 2.66 (t, 1H, J=10.07 Hz), 2.90 (t, 1H, J=9.76H), 3.18-3.26 (m, 2H), 3.50 (td, 1H, J=10.37 Hz, J=6.1 Hz), 3.63 (d, 1H, J=13.12 Hz), 3.75-3.85 (m, 3H), 4.50 (d, 1H, J=15.87 Hz), 4.62-4.65 (m, 2H), 7.08 (d, 1H, J=7.93 Hz), 7.15-7.19 (m, 2H), 7.23-7.28 (m, 2H), 7.32-7.37 (m, 4H), 7.53-7.60 (m, 2H), 7.86 (dd, 1H, J=7.63 Hz, J=1.53 Hz), 8.00 (dd, 1H, J=7.63 Hz, J=1.83 Hz); MS (DCI+) m/z 497.1 [M+H]$^+$.

Example 12

Trans-2-benzyl-5-(3-bromophenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 3-bromobenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-$d_6$/$D_2O$) δ ppm 1.85 (br, 1H), 2.61 (br, 1H), 2.75 (br, 1H), 2.93 (br, 1H), 3.09 (t, 1H, J=12.21 Hz), 3.25 (br, 1H), 3.42 (br, 1H), 3.87 (br, 2H), 3.98 (d, 1H, J=13.43 Hz), 4.32 (d, 1H, J=15.26 Hz), 4.68 (d, 1H, J=15.26 Hz), 7.02 (d, 1H, J=6.71 Hz), 7.21-7.41 (m, 8H), 7.49 (t, 1H, J=7.93 Hz), 7.74-7.77 (m, 2H), 7.82 (d, 1H, J=7.02 Hz); MS (DCI+) m/z 497.1 [M+H]$^+$.

Example 13

Trans-2-benzyl-5-(naphthalen-1-ylsulfonyl)-1,2,3,3a, 4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and naphthalene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-d$_6$/D$_2$O) δ ppm 2.02-2.12 (m, 1H), 2.57-2.64 (m, 1H), 2.79 (br, 1H), 3.02 (br, 1H), 3.18-3.33 (m, 2H), 3.46-3.52 (m, 1H), 4.49 (d, 1H, J=15.56 Hz), 4.71 (d, 1H, J=15.56 Hz), 7.05 (d, 1H, J=7.05 Hz), 7.17-7.41 (m, 8H), 7.64-7.70 (m, 3H), 8.07-8.12 (m, 2H), 8.24 (d, 1H, J=8.54 Hz), 8.44-8.47 (m, 1H); MS (DCI+) m/z 469.2 [M+H]$^+$.

Example 14

Trans-2-benzyl-5-(3-chloro-4-fluorophenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 3-chloro-4-fluorobenzene-1-sulfonyl chloride (0.296 mmol). The vial was sealed and shaken overnight at room temperature. The solvent was evaporated in vacuum and the residue was dissolved in dichloromethane (2 mL). This solution was washed consecutively with water and aqueous sodium bicarbonate solution, and then purified by preparative thin layer chromatography to provide the title compound. $^1$H NMR (500 MHz, DMSO-d$_6$/D$_2$O) δ ppm 1.86 (br, 1H), 2.60 (br, 1H), 2.76 (br, 1H), 2.95 (br, 1H), 3.09 (t, 1H, J=12.21 Hz), 3.18 (s, 1H), 3.23 (br, 1H), 3.42 (br, 1H), 3.86 (br, 1H), 3.98 (d, 1H, J=12.82 Hz), 4.32 (d, 2H, J=15.56 Hz), 4.68 (d, 1H, J=15.26 Hz), 7.02 (d, 1H, J=7.32 Hz), 7.21-7.39 (m, 8H), 7.55 (t, 1H, J=8.07 Hz), 7.76-7.79 (m, 1H), 7.82 (dd, 1H, J=6.87 Hz, J=2.29 Hz); MS (DCI+) m/z 471.2 [M+H]$^+$.

Example 15

Trans-2-benzyl-5-(2,5-dimethoxyphenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 2,5-dimethoxybenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-d$_6$/D$_2$O) δ ppm 2.12 (br, 1H), 2.73 (br, 1H), 3.02 (t, 1H, J=11.90), 3.41 (br, 1H), 3.51 (br, 1H), 3.77 (s, 3H), 3.81-4.1 (m, 6H), 4.31 (d, 1H, J=15.56 Hz), 4.63 (d, 1H, J=15.87 Hz), 7.07 (d, 1H, J=7.07 Hz), 7.16-7.22 (m, 4H), 7.24-7.27 (m, 2H), 7.33-7.44 (m, 5H); MS (DCI+) m/z 479.2 [M+H]$^+$.

Example 16

Trans-2-benzyl-5-(3-(trifluoromethyl)phenylsulfonyl)-1,2,3,3a,4,5,6,10b-octahydrobenzo[c]pyrrolo[3,4-e]azepine To an 8 mL vial were added Example 7 (75 mg, 0.269 mmol), dichloromethane (1.2 mL), dry pyridine (1.2 mL) and 3-(trifluoromethyl)benzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-d$_6$/D$_2$O) δ ppm 1.77 (br, 1H), 2.69 (br, 1H), 2.84 (br, 1H), 3.12-3.19 (m, 3H), 3.39 (br, 1H), 3.64 (br, 1H), 3.80 (br, 1H), 4.02 (d, 1H, J=11.60 Hz), 4.39 (d, 1H, J=15.56), 4.72 (d, 1H, J=15.26 Hz), 6.98 (d, 1H, J=7.32 Hz), 7.17-7.23 (m, 2H), 7.27-7.31 (m, 2H), 7.34-7.38 (m, 4H), 7.76 (t, 1H, J=7.78 Hz), 7.84 (s, 1H), 7.98 (d, 1H, J=7.93 Hz), 8.03 (d, 1H, J=7.63); MS (DCI+) m/z 487.2 [M+H]$^+$.

Example 17

Trans-2-benzyl-5-(2,5-dimethylphenylsulfonyl)-1,2,3,3a,4,5,6,1013-octahydrobenzo[c]pyrrolo[3,4-e]azepine To an 8 mL vial was added Example 7 (75 mg, 0.269 mmol), dichloromethane (1.2 mL), dry pyridine (1.2 mL) and 2,5-dimethylbenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-d$_6$/D$_2$O) δ ppm 2.27 (br, 1H), 2.33 (s, 3H), 2.42 (t, 3H), 2.90 (br, 1H), 3.29 (br, 2H), 3.83 (d, 1H, J=12.21 Hz), 4.23 (br d, 2H), 4.44 (d, 1H, J=15.56 Hz), 4.61 (d, 1H, J=15.56 Hz), 7.10 (s, 1H, J=7.32 Hz), 7.18-7.20 (m, 1H), 7.24 (t, 1H, J=7.32 Hz), 7.29-7.32 (m, 2H), 7.35-7.37 (m, 1H), 7.40-7.46 (m, 3H), 7.49-7.52 (m, 2H), 7.57 (s, 1H); MS (DCI+) m/z 447.2 [M+H]$^+$.

Example 18

Trans-2-benzyl-5-(3-methoxyphenylsulfonyl)-1,2,3,3a,4,5,6,10b-octahydrobenzo[e]pyrrolo[3,4-e]azepine To an 8 mL vial was added Example 7 (75 mg, 0.269 mmol), dichloromethane (1.2 mL), dry pyridine (1.2 mL) and 3-methoxybenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-d$_6$/D$_2$O) δ ppm 1.91 (br, 1H), 2.63 (br, 1H), 2.81 (br, 1H), 2.98-3.02 (m, 2H), 3.16 (s, 1H), 3.28 (br, 1H), 3.42 (br, 1H), 3.76 (s, 3H), 3.85-3.98 (m, 2H), 4.26 (d, 1H, J=15.26 Hz), 4.66 (d, 1H, J=15.26 Hz), 7.03 (d, 1H, J=7.32 Hz), 7.13 (s, 1H), 7.18-7.41 (m, 10H), 7.47 (t, 1H, J=7.93 Hz); MS (DCI+) m/z 449.2 [M+H]+.

Example 19

Trans-2-benzyl-5-(2-dichlorophenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 2-chlorobenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-$d_6$/D$_2$O) δ ppm 2.15 (br, 1H), 2.68 (br, 1H), 3.05-3.24 (m, 2H), 3.37 (br, 1H), 3.55 (br, 1H), 3.77-4.05 (m, 3H), 4.47 (d, 1H, J=15.56 Hz), 4.63 (d, 1H, J=15.87 Hz), 7.09 (d, 1H, J=7.63 Hz), 7.13-7.21 (m, 2H), 7.25-7.28 (m, 2H), 7.31-7.42 (m, 5H), 7.55 (ddd, 1H, J=8.16 Hz, J=6.22 Hz, J=1.98 Hz), 7.64-7.69 (m, 2H), 7.98-7.99 (m, 1H); MS (DCI+) m/z 453.2 [M+H]+.

Example 20

Trans-2-benzyl-5-(3-chlorophenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 3-chlorobenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-$d_6$/D$_2$O) δ ppm 1.83 (br, 1H), 2.55 (br, 1H), 2.70 (br, 1H), 2.88 (br, 1H), 3.08 (t, 1H, J=12.51 Hz), 3.19 (br, 1H), 3.66 (br, 1H), 3.82 (br, 1H), 3.96 (d, 1H, J=13.73 Hz), 4.32 (d, 1H, J=15.26 Hz), 4.67 (d, 1H, J=14.95 Hz), 7.02 (d, 1H, J=87.02 Hz), 7.20-7.31 (m, 4H), 7.56 (t, 1H, J=7.93 Hz), 7.63-7.65 (m, 1H), 7.69 (dt, 1H, J=7.86 Hz, J=1.37 Hz); MS (DCI+) m/z 453.2 [M+H]+.

Example 21

Trans-2-benzyl-5-(2-cyanophenylsulfonyl)-1,2,3,3a,4,5,6,10b-octahydrobenzo[c]pyrrolo[3,4-e]azepine To an 8 mL vial was added Example 7 (75 mg, 0.269 mmol), dichloromethane (1.2 mL), dry pyridine (1.2 mL) and 2-cyanobenzene-1-sulfonyl chloride (0.296 mmol). The vial was sealed and shaken overnight at room temperature. The solvent was evaporated in vacuum and the residue was dissolved in dichloromethane (2 mL) and washed consecutively with water and aqueous sodium bicarbonate solution, and then purified by preparative thin layer chromatography to provide the title compound. $^1$H NMR (500 MHz, DMSO-$d_6$/D$_2$O) δ ppm 1.97-2.07 (m, 1H), 2.66-2.73 (m, 1H), 2.86-2.94 (m, 1H), 3.16-3.22 (m, 1H), 3.45-3.50 (m, 1H), 3.64 (d, 1H, J=11.90 Hz), 3.80 (d, 1H, J=13.12 Hz), 3.97 (dd, 1H, J=13.43 Hz, J=3.05 Hz), 4.49 (d, 1H, J=15.56 Hz), 4.68 (d, 1H, J=15.56 Hz), 7.05 (d, 1H, J=7.05 Hz), 7.16-7.29 (m, 4H), 7.33-7.37 (m, 4H), 7.81 (dt, 1H, J=7.55 Hz, J=1.07 Hz), 7.81 (dt, 1H, J=7.70 Hz, J=1.37 Hz), 8.02 (dd, 1H, J=7.93 Hz, J=0.92 Hz), 8.07 (dd, 1H, J=7.48 Hz, J=1.07 Hz); MS (DCI+) m/z 444.2 [M+H]+.

Example 22

Trans-2-(3,5-dimethylbenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 3,5-dimethylbenzaldehyde (23 mg, 0.2 mmol) dissolved in ethanol (0.9 mL). Then a solution of acetic acid (60 mg, 1.0 mmol) dissolved in ethanol (0.4 mL) was added, followed by the addition of macroporous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/D$_2$O) δ ppm 2.27-2.33 (s, 6H), 2.72-2.89 (m, 1H), 3.13-3.23 (m, 1H), 3.47-3.55 (m, 1H), 3.61-3.73 (m, 1H), 3.85-4.04 (m, 3H), 4.13-4.24 (m, 1H), 4.70-4.85 (m, 2H), 7.11-7.18 (m, 1H), 7.28-7.32 (m, 2H), 7.37-7.44 (s, 2H), 7.66-7.71 (s, 1H), 8.03-8.10 (m, 1H); MS (ESI+) 321 [M+H]+.

Example 23

Trans-2-(2,5-dimethylbenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 2,5-dimethylbenzaldehyde (27 mg, 0.2 mmol) dissolved in ethanol (0.9 mL). Then a solution of acetic acid (60 mg, 1.0 mmol) dissolved in ethanol (0.4 mL) was added, followed by the addition of macroporous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/D$_2$O) δ ppm 2.28-2.35 (s, 3H), 2.46-2.51 (s, 3H), 2.68-2.81 (m, 1H), 3.15-3.27 (m, 1H), 3.47-3.55 (m, 1H), 3.61-3.67 (m, 1H), 3.78-4.02 (m, 3H), 4.10-4.22 (m, 1H), 4.67-4.76 (m, 2H), 7.15-7.22 (m, 2H), 7.36-7.49 (m, 2H), 7.62-7.71 (m, 2H), 8.03-8.13 (m, 1H); MS (ESI+) 321 [M+H]+.

Example 24

Trans-2-(2,4-dimethylbenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 2,4-dimethylbenzaldehyde (27 mg, 0.2 mmol) dissolved in ethanol (0.9 mL). Then a solution of acetic acid (60 mg, 1.0 mmol) dissolved in ethanol (0.4 mL) was added, followed by the addition of macroporous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/D$_2$O) δ ppm 2.23-2.26 (s, 3H), 2.47-2.53 (s, 3H), 2.72-2.83 (m, 1H), 3.16-3.28 (m, 1H), 3.49-3.57 (m, 1H), 3.61-3.67 (m, 1H), 3.81-4.00 (m, 3H), 4.11-4.23 (m, 1H), 4.70-4.77 (m, 2H), 7.06-7.11 (m, 1H), 7.18-7.23 (m, 1H), 7.37-7.50 (m, 2H), 7.66-7.69 (m, 1H), 7.71-7.76 (m, 1H), 8.03-8.14 (m, 1H); MS (ESI+) 321 [M+H]$^+$.

Example 25

Trans-2-(3,4-dimethylbenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 3,4-dimethylbenzaldehyde (27 mg, 0.2 mmol) dissolved in ethanol (0.9 mL). Then a solution of acetic acid (60 mg, 1.0 mmol) dissolved in ethanol (0.4 mL) was added, followed by the addition of macroporous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/D$_2$O) δ ppm 2.12-2.20 (m, 6H), 2.69-2.78 (m, 1H), 3.14-3.23 (m, 1H), 3.47-3.55 (m, 1H), 3.61-3.65 (m, 1H), 3.81-3.97 (m, 3H), 4.07-4.16 (m, 1H), 4.68-4.77 (m, 2H), 7.13-7.21 (m, 2H), 7.37-7.44 (m, 2H), 7.55-7.63 (m, 2H), 8.02-8.11 (m, 1H); MS (ESI+) 321 [M+H]$^+$.

Example 26

Trans-2-(3-methylbenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 3-methylbenzaldehyde (24 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/D$_2$O) δ ppm 2.26-2.33 (s, 3H), 2.67-2.80 (m, 1H), 3.13-3.24 (m, 1H), 3.46-3.53 (m, 1H), 3.60-3.64 (m, 1H), 3.80-3.97 (m, 3H), 4.06-4.16 (m, 1H), 4.72-4.77 (m, 2H), 7.10-7.16 (m, 1H), 7.20-7.25 (m, 1H), 7.32-7.46 (m, 3H), 7.59-7.66 (m, 2H), 8.04-8.10 (m, 1H); MS (ESI+) 307 [M+H]$^+$.

Example 27

Trans-2-(2,3-dimethylbenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 2,3-dimethylbenzaldehyde (27 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/D$_2$O) δ ppm 2.13-2.18 (s, 3H), 2.35-2.40 (s, 3H), 2.70-2.82 (m, 1H), 3.17-3.25 (m, 1H), 3.48-3.56 (m, 1H), 3.60-3.66 (m, 1H), 3.79-4.01 (m, 3H), 4.08-4.23 (m, 1H), 4.75-4.81 (m, 2H), 7.17-7.27 (m, 3H), 7.36-7.49 (m, 2H), 7.68-7.71 (m, 1H), 8.04-8.13 (m, 1H); MS (ESI+) 321 [M+H]$^+$.

Example 28

Trans-2-(3-methoxybenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 3-methoxybenzaldehyde (27 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/D$_2$O) δ ppm 2.73-2.86 (m, 1H), 3.14-3.22 (m, 1H), 3.46-3.55 (m, 1H), 3.60-3.67 (m, 1H), 3.82-3.85 (m, 3H), 3.85-3.91 (m, 2H), 3.91-3.99 (m, 1H), 4.10-4.23 (m, 1H), 4.77-4.85 (m, 2H), 7.04-7.10 (m, 1H), 7.11-7.16 (m, 1H), 7.37-7.49 (m, 4H), 7.52-7.57 (m, 1H), 8.02-8.08 (m, 1H); MS (ESI+) 323 [M+H]$^+$.

Example 29

Trans-2-(2-methoxybenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 2-methoxybenzaldehyde (27 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/D$_2$O) δ ppm 2.69-2.82 (m, 1H), 3.12-3.22 (m, 1H), 3.48-3.57 (m, 1H), 3.63-3.71 (m, 1H), 3.82-3.88 (m, 3H), 3.88-4.02 (m, 3H), 4.15-4.24 (m, 1H), 4.70-4.82 (m, 2H), 6.99-7.10 (m, 2H), 7.12-7.20 (m, 1H), 7.37-7.53 (m, 3H), 7.76-7.86 (m, 1H), 7.98-8.11 (m, 1H); MS (ESI+) 323 [M+H]$^+$.

Example 30

Trans-2-(3,5-dichlorobenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 3,5-dichlorobenzaldehyde (35 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.37-2.46 (m, 1H), 3.03-3.20 (m, 2H), 3.22-3.30 (m, 1H), 3.35-3.50 (m, 3H), 3.51-3.57 (m, 1H), 4.05-4.26 (m, 2H), 7.08-7.14 (m, 1H), 7.36-7.50 (m, 3H), 7.61-7.65 (m, 2H), 8.16-8.22 (m, 1H); MS (ESI+) 361 [M+H]$^+$.

Example 31

Trans-2-(2,5-dichlorobenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 2,5-dichlorobenzaldehyde (35 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.23-2.48 (m, 1H), 2.91-3.04 (m, 2H), 3.22-3.42 (m, 4H), 3.41-3.53 (m, 1H), 4.02-4.10 (m, 2H), 7.07-7.17 (m, 1H), 7.37-7.53 (m, 4H), 7.78-7.83 (m, 1H), 8.20-8.27 (m, 1H); MS (ESI+) 361 [M+H]$^+$.

Example 32

Trans-2-(3-chlorobenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 3-chlorobenzaldehyde (28 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.57-2.68 (m, 1H), 3.18-3.29 (m, 1H), 3.37-3.50 (m, 2H), 3.53-3.58 (m, 1H), 3.71-3.82 (m, 2H), 3.85-3.92 (m, 1H), 4.48-4.60 (m, 2H), 7.10-7.17 (m, 1H), 7.35-7.48 (m, 4H), 7.70-7.74 (m, 1H), 7.83-7.90 (m, 1H), 8.08-8.16 (m, 1H); MS (ESI+) 327 [M+H]$^+$.

Example 33

Trans-2-(2-chlorobenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 2-chlorobenzaldehyde (28 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.49-2.58 (m, 1H), 3.22-3.36 (m, 2H), 3.40-3.52 (m, 2H), 3.62-3.82 (m, 3H), 4.38-4.55 (m, 2H), 7.13-7.21 (m, 1H), 7.35-7.55 (m, 5H), 7.86-7.94 (m, 1H), 8.12-8.25 (m, 1H); MS (ESI+) 321 [M+H]$^+$.

Example 34

Trans-2-(3-fluorobenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 3-fluorobenzaldehyde (25 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.54-2.65 (m, 1H), 3.17-3.25 (m, 1H), 3.34-3.56 (m, 3H), 3.68-3.78 (m, 2H), 3.81-3.88 (m, 1H), 4.51-4.61 (m, 2H), 7.10-7.22 (m, 2H), 7.36-7.51 (m, 3H), 7.57-7.65 (m, 2H), 8.11-8.16 (m, 1H); MS (ESI+) 311 [M+H]$^+$.

Example 35

Trans-2-(2-fluorobenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 2-fluorobenzaldehyde (25 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.53-2.62 (m, 1H), 3.17-3.27 (m, 1H), 3.35-3.50 (m, 2H), 3.53-3.59 (m, 1H), 3.68-3.78 (m, 2H), 3.81-3.90 (m, 1H), 4.49-4.60 (m, 2H), 7.10-7.18 (m, 1H), 7.18-7.27 (m, 2H), 7.36-7.50 (m, 3H), 7.81-7.91 (m, 1H), 8.11-8.19 (m, 1H); MS (ESI+) 311 [M+H]$^+$.

Example 36

3-((Trans-6-oxo-1,3a,4,5,6,10b-hexahydrobenzo[c]pyrrolo[3,4-e]azepin-2(3H)-yl)methyl)benzonitrile Example 2 (36 mg, 0.2 mmol) was dissolved in ethanol (0.4 mL) followed by the addition of 3-formylbenzonitrile (26 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.53-2.62 (m, 1H), 3.20-3.34 (m, 2H), 3.41-3.49 (m, 2H), 3.63-3.81 (m, 3H), 4.39-4.61 (m, 2H), 7.12-7.20 (m, 1H), 7.38-7.49 (m, 2H), 7.56-7.61 (m, 1H), 7.69-7.74 (m, 1H), 7.99-8.05 (m, 1H), 8.07-8.12 (m, 1H), 8.13-8.16 (m, 1H); MS (ESI+) 318 [M+H]$^+$.

Example 37

Trans-2-(2,5-dimethoxybenzyl)-1,2,3,3a,4,5-hexahydrobenzo[c]pyrrolo[3,4-c]azepin-6(10bH)-one Example 2 (36 mg, 0.2 mmol) was dissolved in ethanol (0.4 mL) followed by the addition of 2,5-dimethoxybenzaldehyde (33 mg, 0.2 mmol) dissolved in ethanol (0.9 mL). Then a solution of acetic acid (60 mg, 1.0 mmol) dissolved in ethanol (0.4 mL) was added followed by the addition of macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.70-2.83 (m, 1H), 3.13-3.21 (m, 1H), 3.46-3.56 (m, 1H), 3.62-3.71 (m, 1H), 3.80-3.85 (m, 6H), 3.85-4.05 (m, 3H), 4.16-4.27 (m, 1H), 4.74-4.81 (m, 2H), 6.99-7.06 (m, 1H), 7.10-7.20 (m, 2H), 7.36-7.46 (m, 2H), 7.52-7.58 (m, 1H), 8.02-8.10 (m, 1H); MS (ESI+) 353 [M+H]$^+$.

Example 38

Trans-2-(3,5-dimethoxybenzyl)-1,2,3,3a,4,5-hexahydrobenzo[c]pyrrolo[3,4-e]azepin-6(10bH)-one Example 2 (36 mg, 0.2 mmol) was dissolved in ethanol (0.4 mL) followed by the addition of 3,5-dimethoxybenzaldehyde (33 mg, 0.2 mmol) dissolved in ethanol (0.9 mL). Then a solution of acetic acid (60 mg, 1.0 mmol) dissolved in ethanol (0.4 mL) was added followed by the addition macro-porous cyanoborohydride resin (253 mg, 3 equivalents; substitution 2.15 mmoles/g). The resulting mixture was shaken overnight at 65° C. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.69-2.83 (m, 1H), 3.15-3.28 (m, 1H), 3.47-3.65 (m, 2H), 3.82-3.86 (m, 2H), 3.86-3.89 (m, 6H), 3.91-3.97 (m, 1H), 4.06-4.19 (m, 1H), 4.65-4.82 (m, 2H), 6.72-6.77 (m, 1H), 7.16-7.18 (m, 1H), 7.27-7.31 (m, 2H), 7.37-7.50 (m, 2H), 8.02-8.14 (m, 1H); MS (ESI+) 353 [M+H]$^+$.

Example 39

Trans-2-(2,3-dichlorophenylsulfonyl)-1,2,3,3a,5,6-hexahydrobenzo[c]pyrrolo[3,4-e]azepin-4(10bH)-one To an 8 mL vial was added Example 6 (75 mg, 0.371 mmol), dichloromethane (1.2 mL), dry pyridine (1.2 mL) and 2,3-dichlorobenzene-1-sulfonyl chloride (0.408 mmol). The vial was sealed and shaken overnight at room temperature. The solvent was evaporated under vacuum. Water (1.5 mL) was added to the residue dropwise, and then the mixture was shaken vigorously. The precipitate was filtered and washed with a 2:1 mixture of water/methanol to provide the title compound. $^1$H NMR (500 MHz, DMSO-$d_6$/$D_2O$) δ ppm 3.31 (dd, 1H, J=10.68 Hz, J=9.15 Hz), 347-3.54 (m, 1H), 3.63 (t, 1H, J=8.85 Hz), 3.89 (dt, 1H, J=12.89 Hz, J=8.96 Hz), 3.98 (d, 1H, J=16.78 Hz), 4.39 (dd, 1H, J=8.85 Hz, J=7.63 Hz), 4.85 (d, 1H, J=16.78 Hz), 7.16-7.22 (m, 1H), 7.60 (t, 1H, J=8.09 Hz), 7.96 (dd, 1H, J=8.09 Hz, J=1.37 Hz), 8.03 (dd, 1H, J=7.93 Hz, J=1.53 Hz); MS (DCI+) m/z 411.1 [M+H]$^+$.

Example 40

Cis-2-(3,5-dichlorobenzyl)-1,2,3,3a,4,5-hexahydrobenzo[c]pyrrolo[3,4-e]azepin-6(10bH)-one Example 4 (39 mg, 0.2 mmol) was dissolved in dichloromethane/methanol (1:1 solution) (0.7 mL) followed by the addition of 3,5-dichlorobenzaldehyde (42 mg, 0.24 mmol) dissolved in dichloromethane/methanol (1:1 solution) (1.2 mL). Then a solution of acetic acid (60 mg, 1.0 mmol) dissolved in dichloromethane/methanol (1:1 solution) (0.7 mL) was added. The mixture was shaken and macro-porous cyanoborohydride resin (239 mg, 3 equivalents; substitution 2.44 mmoles/g) was added and the resulting mixture was shaken overnight at room temperature. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.59-2.68 (m, 1H), 2.88-3.00 (m, 2H), 3.03-3.10 (m, 1H), 3.11-3.19 (m, 2H), 3.33-3.52 (m, 1H), 3.66-3.82 (m, 3H), 7.25-7.28 (m, 1H), 7.34-7.37 (m, 1H), 7.37-7.41 (m, 2H), 7.43-7.52 (m, 2H), 8.05-8.14 (m, 1H); MS (ESI+) m/z 361 [M+H]$^+$.

Example 41

Cis-2-(3-chlorobenzyl)-1,2,3,3a,4,5-hexahydrobenzo[c]pyrrolo[3,4-e]azepin-6(10bH)-one Example 4 (39 mg, 0.2 mmol) was dissolved in dichloromethane/methanol (1:1 solution) (0.7 mL) followed by the addition of 3-chlorobenzaldehyde (34 mg, 0.24 mmol) dissolved in dichloromethane/methanol (1:1 solution) (1.2 mL). Then a solution of acetic acid (60 mg, 1.0 mmol) dissolved in dichloromethane/methanol (1:1 solution) (0.7 mL) was added. The mixture was shaken and macro-porous cyanoborohydride resin (239 mg, 3 equivalents; substitution 2.44 mmoles/g) was added and the resulting mixture was shaken overnight at room temperature. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.68-2.76 (m, 1H), 2.91-3.10 (m, 2H), 3.11-3.24 (m, 3H), 3.44-3.59 (m, 1H), 3.77-3.90 (m, 3H), 7.25-7.28 (m, 1H), 7.33-7.36 (m, 2H), 7.37-7.42 (m, 1H), 7.42-7.49 (m, 2H), 7.52-7.57 (m, 1H), 8.03-8.15 (m, 1H); MS (ESI+) m/z 327 [M+H]$^+$.

Example 42

Cis-2-(3-fluorobenzyl)-1,2,3,3a,4,5-hexahydrobenzo[c]pyrrolo[3,4-e]azepin-6(10bH)-one Example 4 (39 mg, 0.2 mmol) was dissolved in dichloromethane/methanol (1:1 solution) (0.7 mL) followed by the addition of 3-fluorobenzaldehyde (30 mg, 0.24 mmol) dissolved in dichloromethane/methanol (1:1 solution) (1.2 mL). Then a solution of acetic acid (60 mg, 1.0 mmol) dissolved in dichloromethane/methanol (1:1 solution) (0.7 mL) was added. The mixture was shaken and then macro-porous cyanoborohydride resin (239, 3 equivalents; substitution 2.44 mmoles/g) was added and the resulting mixture was shaken overnight at room temperature. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.71-2.85 (m, 1H), 2.95-3.06 (m, 1H), 3.07-3.29 (m, 4H), 3.55-3.63 (m, 1H), 3.73-4.01 (m, 3H), 7.04-7.16 (m, 1H), 7.27-7.29 (m, 2H), 7.33-7.40 (m, 2H), 7.43-7.50 (m, 2H), 8.05-8.14 (m, 1H); MS (ESI+) m/z 311 [M+H]$^+$.

Example 43

Cis-2-(naphthalen-1-ylmethyl)-1,2,3,3a,4,5-hexahydrobenzo[c]pyrrolo[3,4-e]azepin-6(10bH)-one Example 4 (39 mg, 0.2 mmol) was dissolved in dichloromethane/methanol (1:1 solution) (0.7 mL) followed by the addition of 1-naphthaldehyde (37 mg, 0.24 mmol) dissolved in dichloromethane/methanol (1:1 solution) (1.2 mL). Then a solution of acetic acid (60 mg, 1.0 mmol) dissolved in dichloromethane/methanol (1:1 solution) (0.7 mL) was added. The mixture was shaken and then macro-porous cyanoborohydride resin (239, 3 equivalents; substitution 2.44 mmoles/g) was added and the resulting mixture was shaken overnight at room temperature. The reaction was filtered, checked by LC/MS and concentrated to dryness. The residues were dissolved in 1:1 dimethyl sulfoxide/methanol and purified by reverse phase HPLC to provide the title compound as the trifluoroacetic acid salt. $^1$H NMR (500 MHz, pyridine-$d_5$/$D_2O$) δ ppm 2.76-3.02 (m, 2H), 3.10-3.28 (m, 4H), 3.59-3.68 (m, 1H), 3.70-3.80 (m, 1H), 4.20-4.49 (m, 2H), 7.16-7.25 (m, 1H), 7.37-7.65 (m, 6H), 7.84-8.00 (m, 2H), 8.05-8.13 (m, 1H), 8.40-8.52 (m, 1H); MS (ESI+) m/z 343 [M+H]$^+$.

Example 44

(3aR,10bS)-1,2,3,3a,4,5-Hexahydrobenzo[c]pyrrolo[3,4-e]azepin-6(10bH)-one

Example 1 was resolved into pure enantiomers using supercritical fluid chromatography: ChiralPak® OD-H 21×250 mm SN 711141 column eluted with methanol/supercritical $CO_2$ and the pure enantiomer (200 mg, 0.68 mmol) was dissolved in trifluoroethanol (20 mL) in a 50 mL pressure bottle. 20% Pd(OH)$_2$/carbon (wet, 40.0 mg, 0.285 mmol) was added and the mixture was stirred for 2 hours under a hydrogen atmosphere (30 psi) and 50° C. The mixture was filtered through a nylon membrane and the filtrate was concentrated and dissolved in 1 mL of $CH_2Cl_2$. Di-tert-butyl dicarbonate (218 mg, 1 mmol) was added. The mixture was purified by silica gel column chromatography eluting with 50% ethyl acetate/hexanes and the pure (3aS,10bS)-tert-butyl 6-oxo-1,3a,4,5,6,10b-hexahydrobenzo[e]pyrrolo[3,4-c]azepine-2 (3H)-carboxylate was treated with 1 mL 4 N HCl in dioxane. The mixture was stirred at room temperature for 4 hours and concentrated to afford the title compound as the hydrochloride salt. $^1$H NMR (400 MHz, DMSO-$d_6$) δ ppm 9.32 (s, 2H), 8.06 (m, 1H), 7.65 (dd, J=1.6, 7.6 Hz, 1H), 7.51 (dt, J=1.2, 7.6 Hz, 1H), 7.41 (t, J=7.6 Hz, 1H), 7.26 (d, J=7.6 Hz, 1H), 3.62 (m, 1H), 3.53 (m, 1H). 3.43 (m, 1H), 3.23 (m, 1H), 3.17 (m, 1H), 3.05 (m, 1H), 2.96 (m, 1H), and 2.45 (m, 1H); MS (ESI+) m/z 203 [M+H]$^+$.

Example 45

Trans-2-benzyl-8-chloro-1,2,3,3a,4,5-hexahydrobenzo[c]pyrrolo[3,4-e]azepin-6(10bH)-one Example 45A (E)-Methyl 5-chloro-2-(2-cyanovinyl)benzoate To an N,N-dimethylformamide solution (100 mL) of methyl 2-bromo-5-chlorobenzoate (25, 100 mmol) was added palladium(II) acetate (480 mg, 2.1 mmol) tri(o-tolyl) phosphine (1.2 g, 3.9 mmol), acrylonitrile (6 g, 113 mmol), and anhydrous sodium acetate (10 g, 122 mmol). The mixture was heated at 120° C. Additional palladium(II) acetate (224 mg, 1 mmol) and tri(o-tolyl)phosphine (600 mg, 2 mmol) were added, after 36 hours. The mixture was heated at 120° C. for 24 hours. N,N-Dimethylformamide was removed in vacuo and the remaining mixture was quenched with 1 N HCl$_{(aq)}$ and extracted with ethyl acetate. The ethyl acetate extracts were concentrated and the residue was dissolved in 1:1 dichloromethane:methanol (50 mL). (Trimethylsilyl)diazomethane (30 mL, 2 N in diethyl ether, 60 mmol) was added dropwise. After stirring overnight, the mixture was quenched with acetic acid, concentrated under reduced pressure and purified by silica gel column chromatography eluting with 2:1 hexanes:ethyl acetate to afford the title compound (2:1 E/Z isomers). $^1$H NMR (E isomer, Example 45A, 300 MHz, DMSO-$d_6$) δ ppm 8.08 (d, J=16.2 Hz, 1H), 7.91 (d, J=2.1 HZ, 1H), 7.84 (d, J=8.7 HZ, 1H), 7.78 (dd, J=2.1, 8.4 Hz, 1H), 6.45 (d, J=16.5 Hz, 1H), and 3.88 (s, 3H).

Example 45B

Trans-methyl 2-(1-benzyl-4-cyanopyrrolidin-3-yl)-5-chlorobenzoate

To Example 45A (3.7 g, 16.7 mmol) in dichloromethane (30 mL) was added trifluoroacetic acid (10 mg). N-Benzyl-1-methoxy-N-((trimethylsilyl)methyl)methanamine (4.0 g, 16.7 mmol) was added dropwise. More of this reagent (2 g, 8.4 mmol) was added after 4 hours, and the mixture was allowed to stir overnight. The mixture was concentrated and purified by silica gel column chromatography eluting with 3:1 hexanes:ethyl acetate to afford the title compound. $^1$H NMR (300 MHz, DMSO-$d_6$) δ ppm 7.71 (m, 3H), 7.34 (m, 4H), 7.27 (m, 1H), 4.25 (q, J=6.0 Hz, 1H), 3.86 (s, 3H), 3.69 (s, 2H), 3.36 (m, 1H), 3.16 (t, J=9.0 Hz, 1H), 3.00 (t, J=9.3 Hz, 1H), 2.78 (dd, J=6.3, 9.3 Hz, 1H), and 2.59 (dd, J=5.7, 9.6 Hz, 1H).

Example 45C

Trans-2-benzyl-8-chloro-1,2,3,3a,4,5-hexahydrobenzo[c]pyrrolo[3,4-e]azepin-6(10bH)-one To Example 45B in 7 M NH$_3$-methanol (56.4 mL) was added to Raney®-nickel (water wet, 14.0 g, 239 mmol) that had been washed once with methanol, and the mixture was stirred in a 250 mL stainless steel pressure bottle under 30 psi of hydrogen at room temperature for 60 minutes. The Raney®-nickel was filtered off, the filtrate was concentrated and the residue was triturated in ethyl acetate to afford the title compound. ¹H NMR (500 MHz, DMSO-d$_6$) δ ppm 8.05 (s, 1H), 7.77 (d, J=2.5 Hz, 1H), 7.48 (dd, J=2.5, 8.5 Hz, 1H), 7.33 (m, 4H), 7.25 (t, J=7.0, 1H), 7.17 (d, J=8.5 Hz, 1H), 3.79 (d, J=13.5 Hz, 1H), 3.70 (d, J=13.0 Hz, 1H), 3.19 (m, 2H), 3.15 (m, 1H), 3.05 (m, 1H), 2.97 (t, J=9.5 Hz, 1H), 2.72 (t, J=8.5 Hz, 1H), 2.60 (t, J=8.5 Hz, 1H), and 2.19 (m, 1H); MS (ESI+) m/z 327 [M+H]⁺.

Example 46

Trans-8-chloro-1,2,3,3a,4,5-hexahydrobenzo[c]pyrrolo[3,4-c]azepin-6(10bH)-one

Example 46A

Trans-tert-butyl 8-chloro-6-oxo-1,3a,4,5,6,10b-hexahydrobenzo[c]pyrrolo[3,4-c]azepine-2(3H)-carboxylate To a slurry of Example 45 (1.5 g, 4.6 mmol) in dichloroethane (10 mL) was added 1-chloroethylchloroformate (1.1 g, 8 mmol) at room temperature. This mixture was heated at 80° C. for 16 hours. Methanol (10 mL) and H$_2$O (0.3 mL) were added, and the mixture was heated at 80° C. for 4 hours and then the mixture was concentrated. The residue was dissolved in 5 mL of CH$_2$Cl$_2$ and triethylamine was added to pH10. Di-tert-butyl dicarbonate (1.6 g, 7.3 mmol) was added. After 1 hour, the mixture was concentrated and purified by silica gel column chromatography eluting with 1:2 hexanes:ethyl acetate to afford the title compound. ¹H NMR (300 MHz, DMSO-d$_6$) δ ppm 8.16 (m, 1H), 7.59 (d, J=2.4 Hz, 1H), 7.52 (dt, J=2.4, 8.4 Hz, 1H), 7.28 (dd, J=4.2, 8.4 Hz, 1H), 3.71 (dd, J=6.9, 9.6 Hz, 1H), 3.62 (t, J=11.7 Hz, 1H), 3.50 (t, J=7.5 Hz, 1H), 3.05 (m, 4H), and 2.21 (m, 1H); MS (ESI+) m/z 337 [M+H]⁺.

Example 46B

Trans-8-chloro-1,2,3,3a,4,5-hexahydrobenzo[c]pyrrolo[3,4-e]azepin-6(10bH)-one hydrochloride Example 46A (190 mg, 0.56 mmol) was treated with 4 N HCl in dioxane (3 mL, 12 mmol) in additional dioxane (6 mL). The mixture was allowed to stir for 24 hours and concentrated to afford the title compound as the hydrochloride salt (solvated with 1 equivalent of dioxane). ¹H NMR (500 MHz, DMSO-d$_6$) δ ppm 9.40 (s, 1H), 9.35 (s, 1H), 8.25 (m, 1H), 7.63 (d, J=2.0 Hz, 1H), 7.58 (dd, J=2.0, 8.0 Hz, 1H), 7.31 (d, J=8.5 Hz, 1H), 3.62 (m, 1H), 3.51 (m, 1H), 3.43 (m, 1H), 3.20 (m, 1H), 3.16 (m, 1H), 3.09 (m, 1H), 2.94 (m, 1H), and 2.25 (m, 1H); MS (ESI+) m/z 237 [M+H]⁺.

Example 47

(3aR,10bS)-1,2,3,3a,4,5-Hexahydrobenzo[e]pyrrolo[3,4-c]azepin-6(10bH)-one

Example 46A was resolved into pure enantiomers using supercritical fluid chromatography: ChiralPak® OD-H 21×250 mm SN 711141 column eluting with methanol/supercritical CO$_2$ and the pure enantiomer (190 mg, 0.56 mmol) was treated with HCl (4 N in dioxane). The mixture was stirred at room temperature for 24 hours and the precipitates were collected to afford the title compound as the hydrochloride salt (solvated with 1 equivalent of dioxane). ¹H NMR (500 MHz, DMSO-d$_6$) δ ppm 9.40 (s, 1H), 9.35 (s, 1H), 8.25 (m, 1H), 7.63 (d, J=2.0 Hz, 1H), 7.58 (dd, J=2.0, 8.0 Hz, 1H), 7.31 (d, J=8.5 Hz, 1H), 3.62 (m, 1H), 3.51 (m, 1H), 3.43 (m, 1H), 3.20 (m, 1H), 3.16 (m, 1H), 3.09 (m, 1H), 2.94 (m, 1H), and 2.25 (m, 1H); MS (ESI+) m/z 237 [M+H]⁺.

Example 48

Trans-2-benzyl-10-chloro-1,2,3,3a,4,5-hexahydrobenzo[c]pyrrolo[3,4-c]azepin-6(10bH)-one Example 48A (E)-Methyl 3-chloro-2-(2-cyanovinyl)benzoate To 4-chloroisobenzofuran-1,3-dione (1.82 g, 10 mmol) in tetrahydrofuran (20 mL) was added lithium tri-tert-butoxyaluminum hydride (0.5 M, 20 mL, 10 mmol, diglyme) at –20° C. The mixture was stirred at room temperature overnight. (Triphenylphosphoranylidene)acetonitrile (3.0 g, 10 mmol) was added, and the resultant mixture was heated at 120° C. for 16 hours. 2 N Sodium hydroxide$_{(aq)}$ was added and the mixture was extracted with ethyl acetate (2×). HCl$_{(aq)}$ (1 M) was added to the aqueous layer to pH3, and the mixture was extracted with ethyl acetate. The organic extracts was dried and concentrated. The residue was dissolved in 20 mL of 1:1 CH$_2$Cl$_2$:methanol followed by the addition of (trimethylsilyl)diazomethane (4 mL, 2 N in diethyl ether, 8 mmol). The mixture was stirred for 1 hour and quenched with acetic acid. The mixture was concentrated and purified by silica gel column chromatography eluting with 2:1 hexanes:ethyl acetate to afford the title compound. ¹H NMR (500 MHz, DMSO-d$_6$) δ ppm 7.85 (dd, J=1.0, 7.5 Hz, 1H), 7.81 (dd, J=1.0, 8.0 Hz, 1H), 6.04 (d, J=17 Hz, 1H), and 3.84 (s, 3H).

Example 48B

Trans-2-benzyl-10-chloro-1,2,3,3a,4,5-hexahydrobenzo[c]pyrrolo[3,4-c]azepin-6(10bH)-one The title compound was prepared according to the procedure outlined in Examples 45B and 45C substituting Example 48A for Example 45A. ¹H NMR (500 MHz, DMSO-d$_6$) δ ppm 8.24 (t, J=5.0 Hz, 1H), 7.50 (dd, J=1.5, 7.5 Hz, 1H), 7.48 (dd, J=1.0, 8.0 Hz, 1H), 7.33 (m, 5H), 7.24 (m, 1H), 3.86 (d, J=13.5 Hz, 1H), 3.73 (d, J=13.0 Hz, 1H), 3.58 (dd, J=8.5, 11.5 Hz, 1H), 3.28 (m, 1H), 3.16 (m, 1H), 2.97 (dd, J=6.5, 14.5 Hz, 1H), 2.89 (dt, J=15.0, 6.0 Hz, 1H), 2.65 (d, J=9.5 Hz, 2H), and 2.38 (m, 1H); MS (ESI+) m/z 327 [M+H]⁺.

Example 49

Trans-7-chloro-1,2,3,3a,4,5-hexahydrobenzo[c]pyrrolo[3,4-c]azepin-6(10bH)-one

The title compound was prepared as the hydrochloride salt according to the procedure outlined in Example 46 substituting Example 48 for Example 45. ¹H NMR (500 MHz, DMSO-d$_6$) δ ppm 9.55 (s, 1H), 9.40 (s, 1H), 8.35 (t, J=5.5 Hz, 1H), 7.55 (dd, J=1.5, 8.0 Hz, 1H), 7.52 (dd, J=1.0, 7.5 Hz, 1H), 7.41 (t, J=8.0 Hz, 1H), 4.00 (m, 1H), 3.80 (m, 1H), 3.38 (m, 1H), 3.14 (m, 2H), 2.92 (m, 2H), and 2.48 (m, 1H); MS (ESI+) m/z 237 [M+H]⁺.

Example 50

Trans-7-chloro-1,2,3,3a,4,5-hexahydrobenzo[c]pyrrolo[3,4-c]azepin-6(10bH)-one

The title compound was prepared as the hydrochloride salt according to the procedure outlined in Example 45 and Example 46 substituting methyl 2-bromo-6-chlorobenzoate for methyl 2-bromo-5-chlorobenzoate. $^1$H NMR (500 MHz, DMSO-$d_6$) δ ppm 9.42 (s, 1H), 9.34 (s, 1H), 8.42 (t, J=6.5 Hz, 1H), 7.48 (m, 2H), 7.26 (dd, J=2.0, 6.5 Hz, 1H), 3.62 (m, 31H), 3.50 (m, 1H), 3.43 (m, 1H), 3.15 (m, 1H), 3.04 (m, 1H), 3.00 (m, 1H), 2.95 (m, 1H), and 2.15 (m, 1H); MS (ESI+) m/z 237 [M+H]$^+$.

Example 51

Trans-2-benzyl-9-chloro-1,2,3,3a,4,5-hexahydrobenzo[c]pyrrolo[3,4-c]azepin-6(10bH)-one The title compound was prepared according to the procedure outlined in Example 45 substituting methyl 2-bromo-4-chlorobenzoate for methyl 2-bromo-5-chlorobenzoate. $^1$H NMR (500 MHz, DMSO-$d_6$) δ ppm 8.05 (t, J=4.0 Hz, 1H), 7.81 (d, J=8.0 Hz, 1H), 7.35 (m, 5H), 7.25 (dt, J=7.0, 2.0 Hz, 1H), 7.17 (d, J=2.0 Hz, 1H), 3.79 (d, J=13 Hz, 1H), 3.70 (d, J=13.5 Hz, 1H), 3.23 (m, 1H), 3.16 (m, 2H), 3.05 (m, 1H), 2.99 (t, J=10 Hz, 1H), 2.72 (t, J=9.0 Hz, 1H), 2.60 (t, J=9.0 Hz, 1H), and 2.21 (m, 1H); MS (ESI+) m/z 327 [M+H]$^+$.

Example 52

Trans-9-chloro-1,2,3,3a,4,5-hexahydrobenzo[c]pyrrolo[3,4-c]azepin-6(10bH)-one

The title compound was prepared as the hydrochloride salt according to the procedure outlined in Example 46 substituting Example 51 for Example 45. $^1$H NMR (500 MHz, DMSO-$d_6$) δ ppm 9.34 (s, 1H), 9.27 (s, 1H), 8.18 (m, 1H), 7.65 (d, J=8.5 Hz, 1H), 7.48 (dd, J=2.0, 8.5 Hz, 1H), 7.37 (d, J=1.5 Hz, 1H), 3.60 (m, 1H), 3.55 (m, 2H), 3.22 (m, 1H), 3.14 (m, 1H), 3.05 (m, 1H), 2.94 (m, 1H), and 2.29 (m, 1H); MS (ESI+) m/z 237 [M+H]$^+$.

Example 53

Trans-8-chloro-2-methyl-1,2,3,3a,4,5-hexahydrobenzo[c]pyrrolo[3,4-c]azepin-6(10bH)-one To Example 46 (27 mg, 0.1 mmol) was added formaldehyde (8 mg, 37% in $H_2O$, 0.1 mmol) in pH4 methanol acetate buffer (0.5 mL, 1 M), then sodium cyanoborohydride (6.2 mg, 0.1 mmol) was added. The mixture was quenched with 2 M NaOH$_{(aq)}$ after 3 hours and extracted with ethyl acetate. The crude material was purified by silica gel column chromatography eluting with ethyl acetate to afford the titled compound. $^1$H NMR (500 MHz, DMSO-$d_6$) δ ppm 8.12 (s, 1H), 7.81 (d, J=2.0 Hz, 1H), 7.49 (dd, J=2.5, 8.0 Hz, 1H), 7.18 (d, J=8.0 Hz, 1H), 3.26 (m, 1H), 3.20 (m, 1H), 3.11 (m, 1H), 3.08 (m, 1H), 2.84 (dd, J=9.0, 10.5 Hz, 1H), 2.62 (m, 2H), and 2.18 (m, 1H); MS (ESI+) m/z 251 [M+H]$^+$.

Example 53 (Alternative Preparation)

Trans-8-chloro-2-methyl-1,2,3,3a,4,5-hexahydrobenzo[c]pyrrolo[3,4-c]azepin-6(10bH)-one Example 45A (Alternative Preparation)

(E)-Methyl 5-chloro-2-(2-cyanovinyl)benzoate

To a vessel under inert atmosphere was charged tris(dibenzylideneacetone)dipalladium(0) (14.3 g), tri-tert-butylphosphonium tetrafluoroborate (9.1 g), and degassed dioxane (1.1 L). A separate flask was charged with methyl 2-bromo-5-chlorobenzoate (420 g), degassed dioxane (420 mL), N,N-dicyclohexylmethylamine (378 g), and acrylonitrile (98 g). Then the flask containing acrylonitrile was degassed by bubbling for 1 hour with argon. A portion (approximately 15%) of the acrylonitrile containing solution was added to the palladium containing vessel, and then the mixture was warmed to 60° C. The remainder of the acrylonitrile solution was added over 1 hour, maintaining the temperature at 60° C. After 1.5 hours, the reaction mixture was cooled to ambient temperature, filtered through a pad of diatomaceous earth, and then concentrated under vacuum to a solid. The solid was dissolved in ethyl acetate (4 L) and treated with activated carbon (30 g). After removal of the carbon by filtration, the solution was extracted twice with 1 N HCl, water, then twice with saturated brine. After evaporation of the solvent, the residue was crystallized by addition of ethyl acetate (2.4 L), warming to 45° C., and then cooling to −5° C. Heptane (1.2 L) was added over 1 hour, and then the product was recovered by filtration, washed with heptane/ethyl acetate (2:1 ratio, 500 mL) and dried under vacuum at 40° C. (140 g). NMR data identical to Example 45A.

Example 53 (Alternate Preparation)

Trans-8-chloro-2-methyl-1,2,3,3a,4,5-hexahydrobenzo[c]pyrrolo[3,4-c]azepin-6(10bH)-one To a vessel containing Example 45A (128 g), 2-methyltetrahydrofuran (1.1 kg) and trifluoroacetic acid (3.2 g) was added 1-methoxy-N-methyl-N-((trimethylsilyl)methyl)methanamine (178 g) over approximately 2.5 hours. Ethyl acetate (650 mL) was added and the mixture was extracted twice with 9% aqueous sodium bicarbonate (1 L) and then 25% brine (0.8 L). The organic layer was concentrated under vacuum and the residue was dissolved in ethyl acetate (1 L) and then filtered to remove inorganic salts. The product was isolated by concentration of the filtrate under vacuum, replacing the volume with isopropanol (500 mL). The slurry was cooled to 0° C., filtered and washed with cold isopropanol. The solid was dried under vacuum at 50° C. to yield trans-methyl 5-chloro-2-(4-cyano-1-methylpyrrolidin-3-yl)benzoate (154 g).

To a 2 gallon Parr vessel was charged Raney®-nickel (77 g, Grace 2800 (water decanted)) and 7 M ammonia in methanol (3 L) and trans-methyl 5-chloro-2-(4-cyano-1-methylpyrrolidin-3-yl)benzoate (152.7 g). The reactor was sealed, purged with nitrogen, then purged with hydrogen and pressurized to 30 psi with hydrogen. After 2 hours, the reaction mixture was filtered through a polypropylene cartridge and rinsed with methanol (1 L). The solvent was removed under vacuum to provide the title compound (crude) used as is in Example 199.

Example 54

Trans-5-(3-fluorophenylsulfonyl)-1,2,3,3a,4,5,6,10b-octahydrobenzo[c]pyrrolo[3,4-e]azepine Example 54A Trans-2-benzyl-(3-fluorophenylsulfonyl)-1,2,3,3a,4,5,6,10b-octahydrobenzo[e]pyrrolo[3,4-e]azepine To a solution of Example 7 (397 mg, 1.43 mmol) in a 1:1 solution of N,N-dimethylformamide:dichloromethane (20 mL) was added triethylamine (506 mg, 5.0 mmol) followed by 3-fluorobenzenesulfonyl chloride (311 mg, 1.6 mmol).

The reaction was stirred at ambient temperature for 18 hours. The reaction mixture was partitioned between ethyl acetate and water. The aqueous portion was extracted with additional ethyl acetate and the combined organic extracts were washed with brine and dried ($Na_2SO_4$). The organic solution was concentrated and the residue purified via flash chromatography on a silica gel column (3:1 ethyl acetate:hexane) to afford the title compound. $^1$H NMR (300 MHz, DMSO-$d_6$) δ ppm 1.75-1.90 (m, 1H) 2.52-2.63 (m, 2H) 2.75-2.86 (m, 1H) 3.04 (d, J=13.09 Hz, 1H) 3.09-3.17 (m, 1H) 3.41 (td, J=10.31, 5.95 Hz, 1H) 3.57 (d, J=13.09 Hz, 1H) 3.77 (d, J=13.09 Hz, 1H) 3.95 (dd, J=13.09, 3.17 Hz, 1H) 4.31 (d, J=15.07 Hz, 1H) 4.64 (d, J=15.47 Hz, 1H) 6.97-7.07 (m, 1H) 7.18-7.33 (m, 8H) 7.46-7.60 (m, 4H); MS (DCI+) m/z 437.2 [M+H]$^+$.

Example 54B

Trans-5-(3-fluorophenylsulfonyl)-1,2,3,3a,4,5,6,10b-octahyrobenzo[c]pyrrolo[3,4-e]azepine A solution of Example 54A (3.39 g, 7.77 mmol) in a 4:1 solution of 2,2,2-trifluoroethanol:tetrahydrofuran (50 mL) was placed in a pressure bottle and wet 20% palladium hydroxide (Degussa type, 747 mg) was added and the bottle capped. The reaction was stirred for 32 hours under hydrogen at 30 psi at ambient temperature. The mixture was filtered through a nylon membrane and concentrated. The residue was purified via flash chromatography on a silica gel column (95:5 dichloromethane: 2 M ammonia solution in methanol) to afford the title compound. $^1$H NMR (300 MHz, DMSO-$d_6$) δ ppm 1.61-1.76 (m, 1H) 2.97-3.10 (m, 4H) 3.18-3.28 (m, 3H) 4.02 (dd, J=13.22, 2.71 Hz, 1H) 4.25 (d, J=15.26 Hz, 1H) 4.67 (d, J=15.26 Hz, 1H) 7.00-7.08 (m, 1H) 7.16-7.30 (m, 3H) 7.45-7.61 (m, 4H); MS (DCI+) m/z 347.1 [M+H]$^+$.

Example 55

Trans-2-benzyl-8-fluoro-1,2,3,3a,4,5-hexahydrobenzo[c]pyrrolo[3,4-e]azepin-6(10bH)-one Example 55A Methyl-2-bromo-5-fluorobenzoate To a solution of 2-bromo-5-fluorobenzoic acid (7.92 g, 36.2 mmol) in N,N-dimethylformamide (75 mL) was added potassium carbonate (6.91 g, 50.0 mmol) as a solid in one portion at room temperature. The mixture was stirred for 5 minutes and iodomethane (6.39 g, 45.0 mmol) was added in one portion. The mixture was stirred at ambient temperature for 22 hours. The reaction mixture was partitioned between ethyl acetate and water. The aqueous portion was extracted with additional ethyl acetate (3×) and the combined organic extracts were washed successively with 10% potassium carbonate solution, water and brine. The organic portion was dried ($Na_2SO_4$) and concentrated to afford the title compound. $^1$H NMR (300 MHz, DMSO-$d_6$) δ ppm 3.87 (s, 3H) 7.41 (td, J=8.56, 3.22 Hz, 1H) 7.65 (dd, J=8.99, 3.22 Hz, 1H) 7.81 (dd, J=9.16, 5.09 Hz, 1H); MS (+DCI/$NH_3$) m/z 250.0 [M+$NH_4$]$^+$.

Example 55B (E)-Methyl 2-(2-cyanovinyl)-5-fluorobenzoate

A mixture of the product from Example 55A (8.25 g, 35.6 mmol), sodium acetate (3.28 g, 40.0 mmol), and acrylonitrile (2.39 g, 45.0 mmol) in N,N-dimethylformamide (65 mL) was treated with a solution of palladium(II) acetate (112 mg, 0.50 mmol) and tri(o-tolyl)phosphine (609 mg, 2.0 mmol) in N,N-dimethylformamide (5 mL) under nitrogen. The reaction was heated at 135° C. for 24 hours and then cooled to ambient temperature and partitioned between ethyl acetate and water. The aqueous portion was extracted with additional ethyl acetate (3×) and the combined organic extracts were washed with water (2×) and brine (1×) and dried ($Na_2SO_4$). The organic solution was concentrated and the residue purified via flash chromatography on a silica gel column (15:85 ethyl acetate:hexane) to afford the title compound as approximately a 4:1 mixture with the corresponding Z isomer. $^1$H NMR (300 MHz, DMSO-$d_6$) δ ppm 3.88 (s, 3H) 6.40 (d, J=16.61 Hz, 1H) 7.59 (td, J=8.39, 2.54 Hz, 1H) 7.65-7.72 (m, 1H) 7.78-7.91 (m, 2H); MS (+DCI/$NH_3$) m/z 223.0 [M+$NH_4$]$^+$.

Example 55C

Methyl 2-trans(1-benzyl-4-cyanopyrrolidin-3-yl)-5-fluorobenzoate

A solution of the product from Example 55B (2.05 g, 10.0 mmol) and one drop or trifluoroacetic acid in dichloromethane (50 mL) was treated with a solution of N-benzyl-1-methoxy-N-((trimethylsilyl)methyl)-methanamine (2.61 g, 11.0 mmol) in dichloromethane (25 mL) added dropwise over 30 minutes under nitrogen at ambient temperature. The reaction was stirred for 20 hours and then quenched with saturated sodium bicarbonate solution (25 mL). The layers were separated and the aqueous portion was extracted with additional dichloromethane. The combined organic extracts were washed with brine and dried ($Na_2SO_4$). The organic solution was concentrated and the residue purified via flash chromatography on a silica gel column (1:9 ethyl acetate: hexane) to afford the title compound and the corresponding cis isomer. Trans isomer $^1$H NMR (300 MHz, DMSO-$d_6$) δ ppm 2.60 (dd, J=9.72, 5.75 Hz, 1H) 2.80 (dd, J=9.12, 6.35 Hz, 1H) 2.97-3.05 (m, 1H) 3.16 (t, J=8.72 Hz, 1H) 3.32-3.42 (m, 2H) 3.69 (s, 2H) 3.86 (s, 3H) 4.21-4.30 (m, 1H) 7.22-7.32 (m, 1H) 7.35 (d, J=4.36 Hz, 4H) 7.45-7.54 (m, 2H) 7.72 (dd, J=8.73, 5.55 Hz, 1H); MS (DCI+) m/z 339.2 [M+H]$^+$. Cis isomer $^1$H NMR (300 MHz, DMSO-$d_6$) δ ppm 2.75 (dd, J=9.72, 7.73 Hz, 1H) 2.81-2.88 (m, 1H) 2.96 (dt, J=9.62, 2.92 Hz, 2H) 3.70 (s, 2H) 3.78-3.84 (m, 1H) 3.85 (s, 3H) 4.21 (ddd, J=9.82, 7.63, 5.16 Hz, 1H) 7.25-7.37 (m, 3H) 7.37-7.40 (m, 2H) 7.46-7.58 (m, 2H) 7.77 (dd, J=8.72, 5.55 Hz, 1H).

Example 55D

Trans-2-benzyl-8-fluoro-1,2,3,3a,4,5-hexahydrobenzo[c]pyrrolo[3,4-c]azepin-6(10bH)-one To a solution of Example 55C (370 mg, 1.09 mmol) in 7 M ammonia in methanol (10 mL) was added wet Raney®-nickel (1.85 g) in a 50 mL pressure bottle. The bottle was capped and the reaction stirred under a hydrogen atmosphere at 30 psi at ambient temperature for 20 hours. The mixture was filtered through a nylon membrane and concentrated. The residue was purified via flash chromatography on a silica gel column (98:2 dichloromethane:2 N ammonia in methanol) to afford the title compound. $^1$H NMR (300 MHz, DMSO-$d_6$) δ ppm 2.04 (td, J=7.24, 3.37 Hz, 1H) 2.69 (t, J=10.11 Hz, 1H) 2.98-3.03 (m, 1H) 3.05-3.15 (m, 3H) 3.25 (dd, J=9.52, 6.35

Hz, 2H) 7.19-7.34 (m, 2H) 7.45 (dd, J=9.91, 2.78 Hz, 1H) 8.14 (s, 1H); MS (DCI+) m/z 311.2 [M+H]+.

Example 56

Trans-2-benzyl-8,9-dichloro-1,2,3,3a,4,5-hexahydrobenzo[c]pyrrolo[3,4-e]azepin-6(10bH)-one

Example 56A 4,5-Dichloro-2-(methoxycarbonyl)benzoic acid

To methanol (200 mL) was added sodium hydride (2.72 g, 60% dispersion, 68.0 mmol) portionwise under nitrogen at ambient temperature. To the solution was then added a solution of 4,5-dichlorophthalic anhydride (5.90 g, 27.2 mmol) in methanol (50 mL) dropwise under nitrogen at room temperature. The reaction was stirred for one hour and then concentrated to remove the methanol. The residue was taken up in aqueous 10% potassium carbonate solution and extracted with ethyl acetate (2×). The aqueous portion was acidified to pH 2 with 10% hydrochloric acid and extracted with ethyl acetate (3×), dried ($Na_2SO_4$) and concentrated to afford the title compound. $^1$H NMR (300 MHz, DMSO-$d_6$) δ ppm 3.81 (s, 3H) 7.94-8.01 (m, 2H) 13.60-13.70 (br, 1H); MS (+DCI/$NH_3$) m/z 266.0 [M+$NH_4$]+.

Example 56B

Methyl 4,5-dichloro-2-(chlorocarbonyl)benzoate

To a mixture of Example 56A (5.5 g, 22.2 mmol) and oxalyl chloride (3.17 g, 25.0 mmol) in dichloromethane (50 mL) was added one drop of N,N-dimethylformamide. The reaction was stirred at ambient temperature for 4 hours and concentrated to afford the title compound. $^1$H NMR (300 MHz, DMSO-$d_6$) δ ppm 3.81 (s, 3H) 7.97 (s, 1H) 8.01 (s, 1H); MS (+DCI/$NH_3$) m/z 266.0 [M+$NH_4$—$H_2O$]+.

Example 56C

Methyl 4,5-dichloro-2-formylbenzoate

A solution of Example 56B (5.7 g, 21.4 mmol) in diglyme (50 mL) was treated dropwise with a solution of lithium tri-t-butoxyaluminum hydride (44 mL of a 0.5 M solution in diglyme, 22.0 mmol) at −70° C. under nitrogen. After the addition was completed, the reaction was allowed to warm to room temperature and then most of the solvent was removed under vacuum. The residue was partitioned between ethyl acetate and 10% hydrochloric acid. The aqueous portion was extracted with additional ethyl acetate (2×) and the combined organic extracts were washed with brine and dried ($Na_2SO_4$). The organic solution was concentrated and the residue purified via flash chromatography on a silica gel column (5:95 ethyl acetate:hexane) to afford the title compound. $^1$H NMR (300 MHz, DMSO-$d_6$) δ ppm 3.91 (s, 3H) 8.04 (s, 1H) 8.14 (s, 1H) 10.32 (s, 1H); MS (DCI+) m/z 232.9 [M+H]+.

Example 56D (E)-Methyl 4,5-dichloro-2-(2-cyanovinyl)benzoate

A mixture of the product from Example 56C (2.0 g, 8.6 mmol) and (triphenylphosphoranylidene)acetonitrile (2.87 g, 9.5 mmol) in toluene (30 mL) was refluxed for 24 hours. The reaction was cooled to room temperature and filtered through a short plug of silica gel eluting with diethyl ether to remove the triphenyl phosphine oxide. The filtrate was concentrated and the residue was purified via flash chromatography on a silica gel:column (5:95 ethyl acetate:hexane) to afford the title compound and the corresponding Z isomer. $^1$H NMR (300 MHz, DMSO-$d_6$) δ ppm 3.88 (s, 3H) 6.55 (d, J=16.27 Hz, 1H) 8.05 (d, J=16.95 Hz, 1H) 8.09 (s, 1H) 8.13 (s, 1H); MS (DCI+) m/z 273.0 [M+H]+.

Example 56E

Methyl 2-trans-(1-benzyl-4-cyanopyrrolidin-3-yl)-4,5 dichlorobenzoate

The title compound was prepared according to the procedure outlined in Example 55C substituting Example 56D for Example 55B. $^1$H NMR (300 MHz, DMSO-$d_6$) δ ppm 2.63-2.77 (m, 2H) 2.93 (dd, J=9.83, 7.80 Hz, 1H) 3.24 (t, J=8.82 Hz, 1H) 3.38-3.47 (m, 1H) 3.63-3.76 (m, 2H) 3.86 (s, 3H) 4.26 (ddd, J=7.88, 5.51, 5.26 Hz, 1H) 7.24-7.33 (m, 1H) 7.33-7.37 (m, 4H) 7.95 (d, J=6.44 Hz, 2H); MS (DCI+) m/z 389.2 [M+H]+.

Example 56F

Trans-2-benzyl-8,9-dichloro-1,2,3,3a,4,5-hexahydrobenzo[c]pyrrolo[3,4-e]azepin-6(10bH)-one The title compound was prepared according to the procedure outlined in Example 55D substituting Example 56E for Example 55C. $^1$H NMR (300 MHz, DMSO-$d_6$) δ ppm 2.15-2.30 (m, 1H) 2.59 (t, J=8.53 Hz, 1H) 2.72 (t, J=8.92 Hz, 1H) 2.91-3.01 (m, 1H) 3.08 (ddd, J=13.88, 6.74, 4.36 Hz, 1H) 3.15-3.29 (m, 3H) 3.66-3.82 (m, 2H) 7.22-7.31 (m, 1H) 7.32-7.38 (m, 5H) 7.97 (s, 1H) 8.18 (t, J=3.57 Hz, 1H); MS (DCI+) m/z 361.2 [M+H]+.

Example 57

Trans-8-fluoro-1,2,3,3a,4,5-hexahydrobenzo[c]pyrrolo[3,4-e]azepin-6(10bH)-one

The title compound was prepared according to the procedure outlined in Example 54B substituting Example 55D for Example 54A. $^1$H NMR (300 MHz, DMSO-$d_6$) δ ppm 1.99-2.14 (m, 1H) 2.73 (t, J=10.17 Hz, 1H) 2.97-3.12 (m, 4H) 3.19-3.33 (m, 3H) 7.19-7.34 (m, 2H) 7.38-7.47 (m, 1H) 8.15 (t, J=4.58 Hz, 1H); MS (DCI+) m/z 221.0 [M+H]+.

Example 58

Trans-2-benzyl-7-fluoro-1,2,3,3a,4,5-hexahydrobenzo[c]pyrrolo[3,4-c]azepin-6(10bH)-one

Example 58A

3-Fluoro-2-(methoxycarbonyl)benzoic acid

To methanol (175 mL) was added sodium hydride (3.36 g, 60% dispersion, 84.0 mmol) portionwise at ambient temperature under nitrogen. To the solution was added a solution of 3-fluorophthalic anhydride (5.56 g, 33.5 mmol) in methanol (50 mL) dropwise under nitrogen at room temperature. The reaction was then worked-up as described for Example 56A to afford the title compound. The NMR data showed the product to be contaminated with 20% of the 6-fluoro isomer.

The material was used without further purification in the next step. $^1$H NMR (300 MHz, DMSO-$d_6$) δ ppm 3.79-3.84 (two s, 3H) 7.53-7.69 (m, 2H) 7.76 (ddd, J=15.60, 7.29, 1.53 Hz, 1H) 13.56 (s, 1H); MS (+DCI/NH$_3$) m/z 216.0 [M+NH$_4$]$^+$.

Example 58B

Methyl-2-(chlorocarbonyl)-6-fluorobenzoate

The title compound was prepared according to the procedure outlined in Example 56B substituting Example 58A for Example 56A. $^1$H NMR (300 MHz, DMSO-$d_6$) δ ppm 3.82-3.85 (two s, 3H) 7.57-7.69 (m, 2H) 7.76 (ddd, J=15.17, 7.21, 1.70 Hz, 1H); MS (+DCI/NH$_3$) m/z 216.0 [M+NH$_4$—H$_2$O]$^+$.

Example 58C

Methyl 2-fluoro-6-formylbenzoate

The title compound was prepared according to the procedure outlined in Example 56C substituting Example 58B for Example 56B. The crude reaction mixture was purified via flash chromatography on a silica gel column (5:95 ethyl acetate:hexane) to afford the pure single isomer. $^1$H NMR (300 MHz, DMSO-$d_6$) δ ppm 3.89 (s, 3H) 7.66-7.75 (m, 1H) 7.78-7.91 (m, 2H) 10.04 (d, J=2.03 Hz, 1H); MS (+DCI/NH$_3$) m/z 200.0 [M+NH$_4$]$^+$.

Example 58D (E)-Methyl 2-(2-cyanovinyl)-6-fluorobenzoate

The title compound was prepared according to the procedure outlined in Example 56D substituting Example 58C for Example 56C. The crude product was purified via flash chromatography on a silica gel column (7:93 ethyl acetate:hexane) to afford the product as a mixture of E and Z isomers (approximate ratio E/Z:5.5/1. $^1$H NMR (300 MHz, DMSO-$d_6$) δ ppm 3.87-3.94 (m, 3H) 6.54 (d, J=16.27 Hz, 1H) 7.44-7.53 (m, 1H) 7.57-7.72 (m, 3H); MS (+DCI/NH$_3$) m/z 223.0 [M+NH$_4$]$^+$.

Example 58E

Methyl 2-trans-(1-benzyl-4-cyanopyrrolidin-3-yl)-6-fluorobenzoate

The title compound was prepared according to the procedure outlined in Example 55C substituting Example 58D for Example 55B. The crude product was purified via flash chromatography on a silica gel column (15:85 ethyl acetate:hexane) to afford both trans and cis isomers in a ratio of 5/1. trans isomer $^1$H NMR (300 MHz, DMSO-$d_6$) δ ppm 2.62 (dd, J=9.49, 6.10 Hz, 1H) 2.80 (dd, J=9.16, 6.44 Hz, 1H) 2.96-3.03 (m, 1H) 3.13 (t, J=8.65 Hz, 1H) 3.33-3.42 (m, 1H) 3.56-3.65 (m, 1H) 3.69 (d, J=2.37 Hz, 2H) 3.89 (s, 3H) 7.23-7.31 (m, 2H) 7.33-7.36 (m, 4H) 7.44-7.48 (m, 1H) 7.59 (td, J=8.14, 6.10 Hz, 1H); MS (DCI+) m/z 339.2 [M+H]$^+$.

Example 58F

Cis-methyl 2-(1-benzyl-4-cyanopyrrolidin-3-yl)-6-fluorobenzoate

The title compound was prepared according to the procedure outlined in Example 58E. Cis isomer $^1$H NMR (501 MHz, DMSO-$d_6$) δ ppm 2.77-2.86 (m, 2H) 2.92 (td, J=9.66, 4.38 Hz, 2H) 3.64-3.72 (m, 4H) 3.87 (s, 3H) 7.21-7.28 (m, 2H) 7.31-7.36 (m, 4H) 7.49 (d, J=7.82 Hz, 1H) 7.54-7.60 (m, 1H); MS (DCI+) m/z 339.2 [M+H]$^+$.

Example 58G

Trans-2-benzyl-7-fluoro-1,2,3,3a,4,5-hexahydrobenzo[c]pyrrolo[3,4-c]azepin-6(10bH)-one The title compound was prepared according to the procedure outlined in Example 55D substituting Example 58E for Example 55C. In this instance, the lactam ring did not close. The reaction mixture was concentrated and the residue treated with a 5% solution of sodium methoxide in methanol at 65° C. for 3 hours. The reaction mixture was concentrated and the residue purified via flash chromatography on a silica gel column (97.5:2.5 dichloromethane: 2 N ammonia/methanol). $^1$H NMR (300 MHz, DMSO-$d_6$) δ ppm 2.05-2.19 (m, 1H) 2.58-2.68 (m, 1H) 2.79 (t, J=8.33 Hz, 1H) 2.95-3.11 (m, 4H) 3.14-3.23 (m, 1H) 3.75-3.88 (m, 2H) 7.02 (d, J=7.93 Hz, 1H) 7.11-7.18 (m, 1H) 7.24 (td, J=6.15, 2.38 Hz, 1H) 7.30-7.38 (m, 4H) 7.44 (td, J=8.03, 5.75 Hz, 1H) 8.25 (s, 1H); MS (DCI+) m/z 311.1 [M+H]$^+$.

Example 59

Cis-2-benzyl-7-fluoro-1,2,3,3a,4,5-hexahydrobenzo[c]pyrrolo[3,4-e]azepin-6(10bH)-one The title compound was prepared according to the procedure outlined in Example 55D substituting Example 58F for Example 55C. In this instance, the lactam ring did not close. The reaction mixture was concentrated and the residue treated with a 5% solution of sodium methoxide in methanol at room temperature for 1 hour. The reaction mixture was concentrated and the residue purified via flash chromatography on a silica gel column (97.5:2.5 dichloromethane:2 N ammonia/methanol). $^1$H NMR (300 MHz, DMSO-$d_6$) δ ppm 2.16-2.30 (m, 1H) 2.46 (s, 2H) 2.67-2.74 (m, 1H) 2.81 (s, 1H) 2.88-3.04 (m, 1H) 3.11 (t, J=8.82 Hz, 1H) 3.52-3.67 (m, 3H) 7.13-7.21 (m, 2H) 7.22-7.29 (m, 1H) 7.32 (d, J=4.41 Hz, 4H) 7.36-7.45 (m, 1H) 8.38 (t, J=5.93 Hz, 1H); MS (DCI+) m/z 311.2 [M+H]$^+$.

Example 60

Trans-7-fluoro-1,2,3,3a,4,5-hexahydrobenzo[c]pyrrolo[3,4-e]azepin-6(10bH)-one

The title compound was prepared according to the procedure outlined in Example 54B substituting Example 58 for Example 54A. $^1$H NMR (501 MHz, DMSO-$d_6$) δ ppm 2.01 (ddd, J=7.77, 4.18, 3.98 Hz, 1H) 2.71-2.79 (m, 1H) 2.88-2.96 (m, 1H) 3.00-3.08 (m, 4H) 3.21-3.28 (m, 2H) 7.04 (d, J=7.56 Hz, 1H) 7.14-7.21 (m, 1H) 7.47 (td, J=7.93, 5.71 Hz, 1H) 8.29 (t, J=5.55 Hz, 1H); MS (DCI+) m/z 221.0 [M+H]$^+$.

Example 61

(3aS,10bS)-2-Benzyl-8-fluoro-1,2,3,3a,4,5-hexahydrobenzo[c]pyrrolo[3,4-e]azepin-6(10bH)-one Example 55 was subjected to a chiral resolution using supercritical fluid chromatography (SFC). Chiral preparative SFC purification was carried out using a modified Berger Instruments MultigramII™ system. A manual version of the Berger system was integrated with a Gilson 232 autosampler for sample injection and a Cavro MiniPrep™ pipettor customized for fraction collection at atmospheric pressure (Olson, J.; Pan, J.; Hochlowski, J.; Searle, P.; Blanchard, D. *JALA* 2002, 7, 69-74). Custom designed collection shoes allowed collection into 18×150 mm tubes and a methanol wash system allows washing of shoes between fractions to maximize recovery and avoid cross-contamination of fractions. The column used was a ChiralPak® AS (Chiral Technologies Inc., West Chester, Pa.), 10 μm (21.2 mm i.d.×250 mm) A gradient of 10-30% methanol with 0.1% diethylamine and carbon dioxide was used, at a flow rate of 40 mL/minute, outlet pressure of 100 bar, and oven temperature of 35° C. The sample was injected as a solution in 1.5 mL of methanol. The preparative SFC system was controlled using SFC ProNTo™ software (version 1.5.305.15 Berger Instruments, Inc.) and custom software for autosampler and fraction collector control. Fractions were collected based upon UV signal threshold. The resulting product was subjected to an additional purification via flash chromatography on a silica gel column (97:3 dichloromethane: 2 N ammonia/methanol) to give the title compound. $^1$H NMR (300 MHz, DMSO-$d_6$) δ ppm 2.18 (dd, J=6.35, 3.97 Hz, 1H) 2.60 (t, J=8.72 Hz, 1H) 2.73 (t, J=8.72 Hz, 1H) 2.97-3.11 (m, 2H) 3.13-3.26 (m, 3H) 3.67-3.74 (m, 1H) 3.77-3.84 (m, 1H) 7.15-7.20 (m, 1H) 7.22-7.37 (m, 6H) 7.55 (dd, J=9.91, 2.78 Hz, 1H) 8.10 (s, 1H); MS (DCI+) m/z 311.2 [M+H]$^+$.

Example 62

Trans-7-fluoro-1,2,3,3a,4,5-hexahydrobenzo[c]pyrrolo[3,4-c]azepin-6(10bH)-one

The title compound was prepared according to the procedure outlined in Example 54B substituting Example 58 for Example 54A. The isolated product did not require further purification. $^1$H NMR (300 MHz, DMSO-$d_6$) δ ppm 2.04 (td, J=7.24, 3.37 Hz, 1H) 2.69 (t, J=10.11 Hz, 1H) 2.98-3.03 (m, 1H) 3.05-3.15 (m, 3H) 3.25 (dd, J=9.52, 6.35 Hz, 2H) 7.19-7.34 (m, 2H) 7.45 (dd, J=9.91, 2.78 Hz, 1H) 8.14 (s, 1H); MS (DCI+) m/z 221.1 [M+H]$^+$.

Example 63

Trans-2-benzyl-9-fluoro-1,2,3,3a,4,5-hexahydrobenzo[c]pyrrolo[3,4-e]azepin-6(10bH)-one The title compound was prepared according to the procedure outlined in Example 55 substituting methyl 2-bromo-4-fluorobenzoic acid for 2-bromo-5-fluorobenzoic acid. $^1$H NMR (300 MHz, DMSO-$d_6$) δ ppm 2.14-2.28 (m, 1H) 2.59 (t, J=8.65 Hz, 1H) 2.73 (t, J=8.65 Hz, 1H) 2.96-3.09 (m, 2H) 3.12-3.28 (m, 3H) 3.67-3.83 (m, 2H) 6.97 (dd, J=10.00, 2.54 Hz, 1H) 7.13 (td, J=8.56, 2.54 Hz, 1H) 7.21-7.28 (m, 1H) 7.30-7.38 (m, 4H) 7.85 (dd, J=8.82, 6.10 Hz, 1H) 7.98 (t, J=3.90 Hz, 1H); MS (DCI+) m/z 311.2 [M+H]$^+$.

Example 64

Trans-9-fluoro-1,2,3,3a,4,5-hexahydrobenzo[c]pyrrolo[3,4-e]azepin-6(10bH)-one

The title compound was prepared according to the procedure outlined in Example 54B substituting Example 63 for Example 54A. Preparative HPLC was used to obtain the title compound as the trifluoroacetic acid salt. $^1$H NMR (300 MHz, DMSO-$d_6$) δ ppm 2.05 (td, J=6.95, 3.39 Hz, 1H) 2.67 (t, J=9.83 Hz, 1H) 2.95-3.11 (m, 5H) 3.13-3.21 (m, 2H) 6.99 (dd, J=10.00, 2.54 Hz, 1H) 7.14 (td, J=8.65, 2.71 Hz, 1H) 7.75 (dd, J=8.48, 6.10 Hz, 1H) 8.02 (s, 1H); MS (DCI+) m/z 221.1 [M+NH$_4$]$^+$.

Example 65

Trans-2-benzyl-10-fluoro-1,2,3,3a,4,5-hexahydrobenzo[c]pyrrolo[3,4-e]azepin-6(10bH)-one The title compound was prepared from 2-bromo-3-fluorobenzoic acid utilizing the same sequence of steps outlined for the preparation of Example 55. $^1$H NMR (300 MHz, DMSO-$d_6$) δ ppm 2.33 (s, 1H) 2.57-2.72 (m, 2H) 3.01-3.06 (m, 2H) 3.12-3.23 (m, 2H) 3.25-3.29 (m, 1H) 3.68-3.77 (m, 1H) 3.79-3.87 (m, 1H) 7.21-7.38 (m, 7H) 7.51 (dd, J=7.46, 1.36 Hz, 1H) 8.14 (t, J=4.75 Hz, 1H); MS (DCI+) m/z 311.2 [M+H]$^+$.

Example 66

Cis-2-benzyl-10-fluoro-1,2,3,3a,4,5-hexahydrobenzo[c]pyrrolo[3,4-e]azepin-6(10bH)-one The title compound was prepared from 2-bromo-3-fluorobenzoic acid utilizing the sequence of steps outlined for the preparation of Examples 55A, 55B, 58E, and 58F. $^1$H NMR (300 MHz, DMSO-$d_6$) δ ppm 2.13 (dd, J=10.91, 8.53 Hz, 1H) 2.74-2.82 (m, 1H) 2.84-2.94 (m, 2H) 3.01 2.45-2.55 (m, 2H) (ddd, J=14.67, 5.55, 2.38 Hz, 1H) 3.12 (t, J=8.72 Hz, 1H) 3.53-3.67 (m, 2H) 3.94 (td, J=10.91, 7.14 Hz, 1H) 7.28-7.35 (m, 6H) 7.41-7.44 (m, 1H) 8.31 (t, J=6.15 Hz, 1H); MS (DCI+) m/z 311.3 [M+H]$^+$.

Example 67

Trans-10-fluoro-1,2,3,3a,4,5-hexahydrobenzo[c]pyrrolo[3,4-e]azepin-6(10bH)-one

The title compound was prepared according to the procedure outlined in Example 54B substituting Example 65 for Example 54A. The product was recrystallized from ethanol. $^1$H NMR (300 MHz, DMSO-$d_6$) δ ppm 2.37-2.48 (m, 1H) 2.87 (t, J=11.50 Hz, 1H) 3.03-3.17 (m, 4H) 3.58 (td, J=11.50, 4.36 Hz, 1H) 3.77 (dd, J=10.31, 6.35 Hz, 1H) 7.33-7.48 (m, 3H) 8.19-8.32 (m, 1H) 9.15 (s, 1H); MS (DCI+) m/z 221.1 [M+H]$^+$.

Example 68

Trans-methyl-3-((6-oxo-1,3a,4,5,6,10b-hexahydrobenzo[c]pyrrolo[3,4-c]azepin-2(3H)-yl)methyl)benzoate To a 50 mL round bottom flask were added Example 2 (80 mg, 0.396 mmol), methyl 3-formylbenzoate (64.9 mg, 0.396 mmol), acetic acid (119 mg, 1.978 mmol), macro-porous cyanoborohydride (0.55 g, 1.18 mmol 2.15 mmol/g) and ethanol (3 mL). The reaction mixture was heated at 65° C. for 5 hours, and the reaction was complete as indicated by LC/MS. The reaction mixture was cooled, filtered, washed with ethanol, and concentrated. The crude material was purified by preparative HPLC under neutral condition to afford the title compound. $^1$H NMR (300 MHz, DMSO-$d_6$) δ ppm 7.96 (m, 2H), 7.89-7.81 (m, 1H), 7.76 (dd, J=1.4, 7.7, 1H), 7.64 (d, J=7.7, 1H), 7.49 (t, J=7.6, 1H), 7.42 (td, J=1.5, 7.5, 1H), 7.31 (t, J=7.0, 1H), 7.15 (d, J=7.5, 1H), 3.97-3.73 (m, 4H), 3.29-2.98 (m, 5H), 2.75 (t, J=8.7, 1H), 2.62 (t, J=8.9, 1H), 2.22 (dd, J=8.8, 15.8, 1H); MS (APCI+) m/z 351.0 [M+H]⁺.

Example 69

Trans-2-methyl-1,2,3,3a,4,5-hexahydrobenzo[c]pyrrolo[3,4-e]azepin-6(10bH)-one

The title compound was prepared according to the procedure outlined in Example 68 substituting formaldehyde for methyl 3-formylbenzoate. ¹H NMR (300 MHz, DMSO-d₆) δ ppm 7.98 (s, 1H), 7.84-7.77 (m, 1H), 7.43 (dt, J=3.8, 7.5, 1H), 7.31 (t, J=7.2, 1H), 7.16 (d, J=7.6, 1H), 3.29-2.98 (m, 1H), 2.98-2.87 (m, 5H), 2.64 (dd, J=3.1, 8.3, 1H), 2.39 (s, 3H), 2.16 (m, 1H); MS (APCI+) m/z 216.9 [M+H]⁺.

Example 70

Trans-2-(5-chloro-2-fluorobenzyl)-1,2,3,3a,4,5-hexahydrobenzo[c]pyrrolo[3,4-e]azepin-6(10bH)-one The title compound was prepared according to the procedure outlined in Example 68 substituting 5-chloro-2-fluorobenzaldehyde for methyl 3-formylbenzoate. ¹H NMR (300 MHz, DMSO) δ ppm 8.04-7.95 (m, 1H), 7.75 (dd, J=1.4, 7.7, 1H), 7.54 (dd, J=2.7, 6.3, 1H), 7.48-7.12 (m, 5H), 3.90-3.73 (m, 2H), 3.31-2.98 (m, 5H), 2.78 (t, J=8.6, 1H), 2.66 (t, J=8.9, 1H), 2.21 (t, J=12.2, 1H); MS (APCI+) m/z 344.9 [M+H]⁺.

Example 71

Trans-2-methyl-5-(phenylsulfonyl)-1,2,3,3a,4,5,6,10b-octahydrobenzo[c]pyrrolo[3,4-e]azepine

Example 71A

Trans-tert-butyl 6-oxo-1,3a,4,5,6,10b-hexahydrobenzo[c]pyrrolo[3,4-e]azepine-2(3H)-carboxylate To a suspension of Example 2 (2 g, 9.89 mmol) in dichloromethane (49.4 mL) was added triethylamine (2.76 mL, 19.78 mmol) and di-tert-butyl dicarbonate (2.76 mL, 11.87 mmol) and the mixture was stirred at room temperature for 2 hours. The reaction was quenched with water and extracted twice with dichloromethane. The organic layers were washed once with water, dried over Na₂SO₄ and the solvent was evaporated to afford the title compound. ¹H NMR (500 MHz, DMSO-d₆) δ ppm 8.02 (s, 1H), 7.61 (dd, J=1.1, 7.6, 1H), 7.52-7.44 (m, 1H), 7.36 (t, J=7.5, 1H), 7.31-7.18 (m, 1H), 3.70 (dt, J=7.7, 15.3, 1H), 3.62 (dd, J=8.9, 20.0, 1H), 3.50 (t, J=8.5, 1H), 3.26-3.09 (m, 1H), 3.09-2.93 (m, 3H), 2.25-2.11 (m, 1H), 1.42-1.45 (br d, 9H); MS (ESI−) m/z 301.0 [M−H]⁻.

Example 71B

Trans-2-methyl-1,2,3,3a,4,5,6,10b-octahydrobenzo[c]pyrrolo[3,4-e]azepine

To a solution of Example 71A (2.62 g, 8.66 mmol) in tetrahydrofuran (87 mL) was added lithium aluminum hydride in tetrahydrofuran (13.00 mL, 26.0 mmol) in small portions, and the mixture was stirred at room temperature for 24 hours. Water was added carefully and the product was extracted once with dichloromethane, dried over Na₂SO₄ and concentrated to afford the title compound. ¹H NMR (500 MHz, pyridine-d₅) δ ppm 7.31 (d, J=7.4, 1H), 7.20-7.17 (m, 2H), 7.13 (d, J=7.7, 1H), 4.58 (dd, J=14.5, 48.4, 2H), 4.01-3.90 (m, 2H), 3.71-3.57 (m, 2H), 3.40 (t, J=10.4, 1H), 3.19-3.05 (m, 2H), 2.71 (s, 3H), 2.66-2.52 (m, 1H); MS (ESI+) m/z 203.0 [M+H]⁺.

Example 71C

Trans-2-methyl-5-(phenylsulfonyl)-1,2,3,3a,4,5,6,10b-octahydrobenzo[c]pyrrolo[3,4-e]azepine To a solution of Example 71B (0.11 g, 0.544 mmol) in dichloromethane (1.088 mL) was added triethylamine (0.114 mL, 0.816 mmol) and benzenesulfonyl chloride (0.087 mL, 0.680 mmol). The solution was stirred for 10 minutes at room temperature and then the solvent was evaporated. The crude material was purified by reverse phase HPLC to afford the title compound as the trifluoroacetic acid salt. ¹H NMR (400 MHz, DMSO) δ ppm 7.80-7.70 (m, 2H), 7.69-7.59 (m, 1H), 7.58-7.48 (m, 2H), 7.34-7.20 (m, 3H), 7.11-6.97 (m, 1H), 4.69 (d, J=15.5, 1H), 4.25 (d, J=15.5, 1H), 4.05 (dd, J=3.9, 13.2, 1H), 3.96-3.80 (m, 1H), 3.80-3.49 (m, 3H), 3.14-3.05 (m, 1H), 2.93 (s, 3H), 2.30 (brs, 1H); MS (ESI+) m/z 342.9 [M+H]⁺.

Example 72

Cis-2-methyl-5-(phenylsulfonyl)-1,2,3,3a,4,5,6,10b-octahydrobenzo[c]pyrrolo[3,4-e]azepine The title compound was prepared as the trifluoroacetic acid salt according to the procedure outlined in Example 71 substituting Example 4 for Example 2. ¹H NMR (400 MHz, DMSO) δ ppm 7.85-7.73 (m, 2H), 7.64 (t, J=7.4, 1H), 7.56 (t, J=7.5, 2H), 7.28 (t, J=7.6, 1H), 7.21-7.03 (m, 3H), 4.60 (d, J=14.4, 1H), 4.39 (d, J=14.5, 1H), 4.05-3.76 (m, 2H), 3.73-3.55 (m, 1H), 3.50 (d, J=12.1, 1H), 2.91 (s, 5H), 2.83-2.60 (m, 3H); MS (ESI+) m/z 342.9 [M+H]⁺.

Example 73

Trans-5-(3-fluorophenylsulfonyl)-2-(4-methoxybenzyl)-1,2,3,3a,4,5,6,10b-octahydrobenzo[e]pyrrolo[3,4-e]azepine A 20 mL scintillation vial was charged with Example 54 (30 mg, 0.0866 mmol, 1.0 equivalent) dissolved in 1.0 mL of methanol, 4-methoxybenzaldehyde (10.41 mg, 0.104 mmol, 1.20 equivalents), and acetic acid (24.79 μL, 0.433 mmol, 5.0 equivalents). The vial was stirred at room temperature for one hour. Macro-porous cyanoborohydride resin (38.66 mg, 2.24 mmol/g) was then added; the vial was capped and stirred overnight at room temperature. The mixture was then filtered, concentrated, and re-dissolved in 1.4 mL of dimethyl sulfoxide/methanol (1:1 v/v). The crude material was purified using reverse phase HPLC to afford the title compound as the trifluoroacetic acid salt. ¹H NMR (500 MHz, pyridine-d₅) δ ppm 2.25-2.35 (m, 1H) 3.07 (t, 1H) 3.20 (t, 1H) 3.31 (t, 1H) 3.40 (t, 1H) 3.72-3.76 (m, 4H) 3.77-3.84 (m, 1H) 4.15 (d, 1H) 4.31 (ddd, 3H) 4.97 (d, 1H) 7.03 (d, 3H) 7.23 (d, 2H) 7.35 (ddd, 1H) 7.44-7.48 (m, 1H) 7.52-7.57 (m, 1H) 7.64-7.65 (m, 1H) 7.79 (t, 2H); MS (ESI+) m/z 467.1 [M+H]⁺.

Example 74

Trans-2-(4-fluorobenzyl)-5-(3-fluorophenylsulfonyl)-1,2,3,3a,4,5,6,10b-octahydrobenzo[c]pyrrolo[3,4-e]azepine A 20 mL scintillation vial was charged with Example 54 (30 mg, 0.0866 mmol, 1.0 equivalent) dissolved in 1.0 mL of methanol, 4-fluorobenzaldehyde (12.90 mg, 0.104 mmol, 1.20 equivalents), and acetic acid (24.79 µL, 0.433 mmol, 5.0 equivalents). The vial was stirred at room temperature for one hour. Macro-porous cyanoborohydride resin (38.66 mg, 2.24 mmol/g) was then added; the vial was capped and stirred overnight at room temperature. The mixture was then filtered, concentrated, and re-dissolved in 1.4 mL of dimethyl sulfoxide/methanol (1:1 v/v). The crude material was purified using reverse phase HPLC to afford the title compound as the trifluoroacetic acid salt. ¹H NMR (500 MHz, pyridine-d₅) δ ppm 2.18-2.29 (m, 1H) 2.98 (tt, 2H) 3.23-3.30 (m, 2H) 3.60 (q, 1H) 3.69-3.76 (m, 1H) 4.03 (d, 1H) 4.17 (d, 1H) 4.27-4.34 (m, 2H) 4.98 (d, 1H) 7.02 (dd, 1H) 7.21 (t, 2H) 7.24-7.25 (m, 2H) 7.37 (ddd, 1H) 7.47 (dd, 1H) 7.53-7.59 (m, 1H) 7.66 (d, 2H) 7.80 (t, 2H); MS (ESI+) m/z 455.1 [M+H]⁺.

Example 75

Trans-8-(4-fluorophenyl)-2-methyl-1,2,3,3a,4,5-hexahydrobenzo[c]pyrrolo[3,4-c]azepin-6(10bH)-one To a microwave vial was added a mixture of Example 53 (750 mg, 2.99 mmol), 4-fluorophenylboronic acid (1674 mg, 11.97 mmol), Cs₂CO₃ (1170 mg, 3.59 mmol) and N,N-dimethylformamide (6.5 mL). Then tri-tert-butylphosphine (0.179 mL, 0.179 mmol, 1.0 M in toluene), palladium(II) acetate (20.15 mg, 0.09 mmol) and 1,8-diazabicyclo[5.4.0]undec-7-ene (0.067 mL, 0.449 mmol) subsequently were added under nitrogen. The vial was sealed, and this mixture was then irradiated in a Biotage Initiator™ 2.0 microwave instrument for 50 minutes at 150° C. Reaction completion was monitored by LC/MS. Another batch was done at same scale. After the reactions were cooled to room temperature, the two reaction mixtures were combined and diluted with ethyl acetate and then filtered through a pad of diatomaceous earth. The filtrate was washed with saturated brine (2×), and the combined aqueous phases were extracted with ethyl acetate. The combined organic layers were dried over Na₂SO₄, then concentrated, and purified by flash column chromatography with methanol in dichloromethane (0-20%, 0.5% triethylamine) A solid was obtained, which was purified again by crystallization from ethyl acetate to provide the title compound. ¹H NMR (300 MHz, DMSO-d₆) δ ppm 8.07 (d, J=2.1, 1H), 8.03 (s, 1H), 7.74-7.66 (m, 3H), 7.34-7.22 (m, 3H), 3.34-3.21 (m, 2H), 3.19-3.04 (m, 2H), 2.93 (dd, J=8.9, 10.3, 1H), 2.71-2.59 (m, 2H), 2.39 (s, 3H), 2.30-2.14 (m, 1H); MS (ESI+) m/z 310.9 [M+H]⁺.

Example 76

Trans-8-(3-fluorophenyl)-2-methyl-1,2,3,3a,4,5-hexahydrobenzo[c]pyrrolo[3,4-c]azepin-6(10bH)-one The title compound was prepared in a similar procedure as described in Example 75 substituting 3-fluorophenylboronic acid for 4-fluorophenylboronic acid. ¹H NMR (300 MHz, DMSO-d₆) δ ppm 8.11 (d, J=2.1, 1H), 8.05 (s, 1H), 7.77 (dd, J=2.2, 8.0, 1H), 7.50 (td, J=2.5, 5.9, 3H), 7.26 (d, J=8.1, 1H), 7.21 (td, J=3.2, 5.9, 1H), 3.42-3.20 (m, 2H), 3.19-3.05 (m, 2H), 2.97-2.87 (m, 1H), 2.67-2.61 (m, 2H), 2.38 (s, 3H), 2.30-2.15 (m, 1H); MS (ESI+) m/z 310.9 [M+H]⁺.

Example 77

Trans-8-(2-fluorophenyl)-2-methyl-1,2,3,3a,4,5-hexahydrobenzo[c]pyrrolo[3,4-c]azepin-6(10bH)-one The title compound was prepared in a similar procedure as described in Example 75 substituting 2-fluorophenylboronic acid for 4-fluorophenylboronic acid. ¹H NMR (300 MHz, DMSO-d₆) δ ppm 8.02 (d, J=1.7, 2H), 7.62 (d, J=8.0, 1H), 7.53 (dd, J=6.9, 8.9, 1H), 7.47-7.39 (m, 1H), 7.31 (dt, J=5.7, 14.9, 3H), 3.39-3.23 (m, 2H), 3.20-3.06 (m, 2H), 2.97-2.88 (m, 1H), 2.68-2.61 (m, 2H), 2.38 (s, 3H), 2.26 (s, 1H); MS (ESI+) m/z 311.0 [M+H]⁺.

Example 78

Trans-8-(3,4-difluorophenyl)-2-methyl-1,2,3,3a,4,5-hexahydrobenzo[c]pyrrolo[3,4-c]azepin-6(10bH)-one The title compound was prepared in a similar procedure as described in Example 75 substituting 3,4-difluorophenylboronic acid for 4-fluorophenylboronic acid. ¹H NMR (300 MHz, DMSO-d₆) δ ppm 8.08 (t, J=5.0, 2H), 7.81-7.70 (m, 2H), 7.52 (dd, J=4.6, 9.7, 2H), 7.26 (d, J=8.1, 1H), 3.32-3.21 (m, 3H), 3.19-3.03 (m, 2H), 2.97-2.86 (m, 1H), 2.68-2.59 (m, 2H), 2.38 (s, 3H), 2.30-2.13 (m, 1H); MS (ESI+) m/z 328.9 [M+H]⁺.

Example 79

Trans-2-methyl-8-(4-(trifluoromethyl)phenyl)-1,2,3,3a,4,5-hexahydrobenzo[c]pyrrolo[3,4-c]azepin-6(10bH)-one The title compound was prepared in a similar procedure as described in Example 75 substituting 4-(trifluoromethyl)phenylboronic acid for 4-fluorophenylboronic acid. ¹H NMR (300 MHz, DMSO-d₆) δ ppm 8.17 (d, J=2.1, 1H), 8.07 (s, 1H), 7.85 (dt, J=5.3, 10.9, 5H), 7.31 (d, J=8.0, 1H), 3.37-3.23 (m, 2H), 3.20-3.06 (m, 2H), 2.99-2.88 (m, 1H), 2.69-2.62 (m, 2H), 2.39 (s, 3H), 2.22 (s, 1H); MS (ESI+) m/z 361.1 [M+H]⁺.

Example 80

Trans-2-methyl-8-(naphthalen-2-yl)-1,2,3,3a,4,5-hexahydrobenzo[c]pyrrolo[3,4-c]azepin-6(10bH)-one The title compound was prepared in a similar procedure as described in Example 75 substituting naphthalen-2-ylboronic acid for 4-fluorophenylboronic acid. ¹H NMR (300 MHz, DMSO-d₆) δ ppm 8.26 (d, J=2.1, 1H), 8.23 (s, 1H), 8.02 (d, J=8.2, 3H), 7.98-7.82 (m, 3H), 7.58-7.50 (m, 2H), 7.31 (d, J=8.0, 1H), 3.29 (dd, J=6.8, 10.2, 3H), 3.16 (dd, J=8.5, 13.5, 2H), 3.01-2.92 (m, 1H), 2.67 (dd, J=3.2, 8.3, 1H), 2.40 (s, 3H), 2.27 (s, 1H); MS (ESI+) m/z 343.0 [M+H]⁺.

Example 81

Trans-2-methyl-8-m-tolyl-1,2,3,3a,4,5-hexahydrobenzo[c]pyrrolo[3,4-c]azepin-6(10bH)-one The title compound was prepared in a similar procedure as described in Example 75 substituting m-tolylboronic acid for 4-fluorophenylboronic acid. $^1$H NMR (300 MHz, DMSO-$d_6$) δ ppm 8.08 (d, J=2.1, 1H), 8.03 (s, 1H), 7.71 (dd, J=2.1, 7.9, 1H), 7.50-7.41 (m, 2H), 7.35 (t, J=7.5, 1H), 7.24 (d, J=8.0, 1H), 7.19 (d, J=7.3, 1H), 3.34-3.21 (m, 2H), 3.19-3.05 (m, 2H), 2.97-2.87 (m, 1H), 2.68-2.61 (m, 2H), 2.38 (s, 6H), 2.25 (dd, J=9.5, 17.0, 1H); MS (ESI+) m/z 307.0 [M+H]$^+$.

Example 82

Trans-2-methyl-8-p-tolyl-1,2,3,3a,4,5-hexahydrobenzo[c]pyrrolo[3,4-c]azepin-6(10bH)-one The title compound was prepared in a similar procedure as described in Example 75 substituting p-tolylboronic acid for 4-fluorophenylboronic acid. $^1$H NMR (300 MHz, DMSO-$d_6$) δ ppm 8.07 (d, J=2.1, 1H), 8.02 (s, 1H), 7.70 (dd, J=2.1, 8.0, 1H), 7.55 (d, J=8.1, 2H), 7.25 (dd, J=8.0, 14.2, 3H), 3.26 (dd, J=9.7, 16.0, 2H), 3.10 (ddd, J=6.5, 9.5, 13.7, 2H), 2.97-2.88 (m, 1H), 2.67-2.61 (m, 2H), 2.38 (s, 3H), 2.34 (s, 3H), 2.30-2.18 (m, 1H); MS (ESI+) m/z 307.0 [M+H]$^+$.

Example 83

Trans-2-methyl-8-(4-(methylsulfonyl)phenyl)-1,2,3,3a,4,5-hexahydrobenzo[c]pyrrolo[3,4-c]azepin-6(10bH)-one The title compound was prepared in a similar procedure as described in Example 75 substituting 4-(methylsulfonyl)phenylboronic acid for 4-fluorophenylboronic acid. Additionally, the title compound was purified by preparative HPLC. $^1$H NMR (300 MHz, DMSO-$d_6$) δ ppm 10.04 (d, J=44.5, 1H), 8.19 (t, J=4.7, 1H), 8.00 (q, J=8.7, 6H), 7.37 (dd, J=8.0, 18.7, 1H), 4.03 (s, 1H), 3.76 (s, 1H), 3.70-3.45 (m, 1H), 3.26 (s, 4H), 3.18 (d, J=4.8, 2H), 3.00 (s, 3H), 2.65 (d, J=20.0, 1H), 2.32 (d, J=12.7, 1H); MS (ESI+) m/z 371.0 [M+H]$^+$.

Example 84

Trans-2-methyl-8-(3-(methylsulfonyl)phenyl)-1,2,3,3a,4,5-hexahydrobenzo[c]pyrrolo[3,4-c]azepin-6(10bH)-one The title compound was prepared in a similar procedure as described in Example 75 substituting 3-(methylsulfonyl)phenylboronic acid for 4-fluorophenylboronic acid. $^1$H NMR (300 MHz, DMSO-$d_6$) δ ppm 8.19 (d, J=2.1, 1H), 8.15 (t, J=1.7, 1H), 8.09 (s, 1H), 8.06-8.01 (m, 1H), 7.96-7.89 (m, 1H), 7.84 (dd, J=2.1, 8.0, 1H), 7.76 (t, J=7.8, 1H), 7.31 (d, J=8.0, 1H), 3.30 (m, 3H), 3.26 (d, J=3.1, 2H), 3.20-3.06 (m, 2H), 2.98-2.89 (m, 1H), 2.65 (dd, J=2.0, 8.2, 2H), 2.39 (s, 3H), 2.23 (dd, J=7.3, 17.7, 1H); MS (ESI+) m/z 371.0 [M+H]$^+$.

Example 85

Trans-2-methyl-8-styryl-1,2,3,3a,4,5-hexahydrobenzo[c]pyrrolo[3,4-c]azepin-6(10bH)-one The title compound was prepared in a similar procedure as described in Example 75 substituting (E)-styrylboronic acid for 4-fluorophenylboronic acid. $^1$H NMR (300 MHz, DMSO-$d_6$) δ ppm 8.04 (d, J=1.9, 1H), 8.00 (s, 1H), 7.70-7.59 (m, 3H), 7.42-7.32 (m, 2H), 7.31-7.23 (m, 3H), 7.17 (d, J=8.0, 1H), 3.30-3.19 (m, 2H), 3.15-3.03 (m, 3H), 2.95-2.86 (m, 1H), 2.63 (dd, J=3.0, 8.3, 2H), 2.36 (d, J=8.8, 3H), 2.25-2.12 (m, 1H); MS (ESI+) m/z 319.0 [M+H]$^+$.

Example 86

Trans-2-methyl-8-phenyl-1,2,3,3a,4,5-hexahydrobenzo[c]pyrrolo[3,4-c]azepin-6(10bH)-one To a microwave vial were added Example 53 (40 mg, 0.16 mmol), phenylboronic acid (42.8 mg, 0.35 mmol), $K_2CO_3$ (2 M aqueous solution, 0.25 mL), FC-1007 (Johnson Matthey polymer supported Pd catalyst, 44.4 mg, 0.36 mmol/g) and ethanol (1 mL). The vial was sealed, and this mixture was then irradiated in a Biotage Initiator™ 2.0 microwave instrument for 40 minutes at 150° C. Reaction completion was monitored by LC/MS. After the reaction was cooled to room temperature, the reaction mixture was filtered through a pad of diatomaceous earth, and washed with ethyl acetate. The filtrate was concentrated and purified by preparative HPLC to provide the title compound. $^1$H NMR (300 MHz, DMSO-$d_6$) δ ppm 8.09 (d, J=2.1, 1H), 8.02 (s, 1H), 7.73 (dd, J=2.1, 7.9, 1H), 7.68-7.62 (m, 2H), 7.47 (t, J=7.4, 2H), 7.38 (d, J=7.4, 1H), 7.25 (d, J=8.0, 1H), 3.28 (dd, J=8.5, 18.8, 2H), 3.18-3.04 (m, 2H), 2.97-2.88 (m, 1H), 2.68-2.62 (m, 2H), 2.38 (s, 3H), 2.24 (dd, J=9.6, 16.7, 1H); MS (ESI+) m/z 292.9 [M+H]$^+$.

Example 87

Trans-2-methyl-8-phenethyl-1,2,3,3a,4,5-hexahydrobenzo[c]pyrrolo[3,4-c]azepin-6(10bH)-one To a 50 mL pressure bottle was added a mixture of Example 85 (31.8 mg, 0.100 mmol), 5% palladium on carbon, wet (7.95 mg, 0.075 mmol) and methanol (10 mL). This was stirred for 5 hours under an atmosphere of hydrogen (30 psi) at room temperature. The reaction was complete as indicated by LC/MS. The mixture was filtered through a nylon membrane, concentrated, and purified by silica gel chromatography eluting with a gradient of methanol in dichloromethane (0-20%) to give the title compound. $^1$H NMR (300 MHz, DMSO-$d_6$) δ ppm 7.90 (t, J=3.6, 1H), 7.71 (d, J=1.9, 1H), 7.32-7.12 (m, 6H), 7.06 (d, J=7.8, 1H), 3.27-3.13 (m, 2H), 3.07 (dt, J=9.2, 18.4, 2H), 2.92-2.82 (m, 5H), 2.65-2.56 (m, 2H), 2.35 (d, J=3.9, 3H), 2.20-2.06 (m, 1H); MS (ESI+) m/z 321.0 [M+H]$^+$.

Example 88

Trans-methyl 2-methyl-6-oxo-1,2,3,3a,4,5,6,1013-octahydrobenzo[c]pyrrolo[3,4-c]azepine-8-carboxylate

Example 88A

Dimethyl 4-bromoisophthalate

To a solution of 4-bromoisophthalic acid (5.13 g, 20.94 mmol) in methanol (55 mL) at 0° C. was added thionyl chloride (6.09 mL, 84 mmol) dropwise. The reaction mixture was allowed to stir 24 hours at room temperature. Then the reaction mixture was concentrated. The resulting residue was taken up in ethyl acetate and washed with saturated $NaHCO_3$ ($aq$) solution. The organic layer was washed with brine, dried over Na$_2$SO$_4$, concentrated, and dried on house vacuum to provide the title compound. $^1$H NMR (300 MHz, DMSO-d$_6$) δ ppm 8.28 (d, J=2.0, 1H), 7.97 (dt, J=5.2, 16.5, 2H), 3.89 (s, 3H), 3.31 (s, 3H).

Example 88B

Dimethyl 4-(trans-4-cyano-1-methylpyrrolidin-3-yl) isophthalate

A microwave vial was charged with dimethyl 4-bromoisophthalate (Example 88A, 500 mg, 1.83 mmol), acrylonitrile (117 mg, 2.20 mmol), N,N-dicyclohexylmethylamine (429 mg, 2.20 mmol), tri-tert-butylphosphine (0.11 mL, 0.11 mmol, 1.0 M in toluene), tris(dibenzylideneacetone)dipalladium(0) (50.3 mg, 0.055 mmol), and 1,4-dioxane (1.4 mL) under nitrogen. The reaction mixture was heated to 80° C. in an oil bath for 4 hours. Reaction was complete as indicated by thin layer chromatography (40% ethyl acetate/hexane). The reaction mixture was cooled to room temperature and diluted with ethyl acetate. Filtration removed HBr salts. The filtrate was concentrated. The residue was triturated with ethyl acetate/hexane (1:6) to provide dimethyl 4-(2-cyanovinyl)isophthalate as a mixture of trans and cis isomers (ratio 5.5:1) which was used in next step without further purification.

A 100 mL round bottom flask was charged with dimethyl 4-(2-cyanovinyl)isophthalate (380 mg, 1.55 mmol), 2-(methylamino)acetic acid (276 mg, 3.1 mmol), paraformaldehyde (326 mg, 10.85 mmol) and toluene (5 mL). The reaction mixture was heated to 125° C. under nitrogen for 2 hours. Then the solution was transferred to another flask leaving the dark tar behind. 2-(Methylamino)acetic acid (276 mg, 3.1 mmol) and paraformaldehyde (326 mg, 10.85 mmol) were added. The reaction mixture was heated to 125° C. under nitrogen for another 2 hours. Then this was cooled and concentrated and partitioned between saturated NaHCO$_3$(aq.) and ethyl acetate. The organic layer was washed with brine, dried over Na$_2$SO$_4$, concentrated, and purified by flash column chromatography with 80-100% ethyl acetate/hexane to provide the title compound. $^1$H NMR (300 MHz, DMSO-d$_6$) δ ppm 8.30 (d, J=1.9, 1H), 8.13 (dd, J=2.0, 8.3, 1H), 7.81 (d, J=8.3, 1H), 4.43-4.33 (m, 1H), 3.89 (d, J=5.7, 3H), 3.36 (q, J=8.1, 1H), 3.30 (s, 3H), 3.20-3.10 (m, 1H), 3.02-2.92 (m, 1H), 2.75 (dd, J=6.4, 9.2, 1H), 2.62 (dd, J=5.5, 9.5, 1H), 2.34 (s, 3H); MS (ESI+) m/z 302.9 [M+H]$^+$.

Example 88C

Trans-methyl 2-methyl-6-oxo-1,2,3,3a,4,5,6,10b-octahydrobenzo[c]pyrrolo[3,4-c]azepine-8-carboxylate The title compound was prepared in a similar procedure as shown in Example 45C substituting Example 88B for Example 45B. $^1$H NMR (300 MHz, DMSO-d$_6$) δ 8.45 (d, J=1.9, 1H), 8.12 (s, 1H), 7.99 (dd, J=1.9, 8.0, 1H), 7.32 (d, J=8.0, 1H), 3.92-3.81 (m, 3H), 3.31-3.23 (m, 2H), 3.13 (ddd, J=4.4, 6.9, 9.8, 2H), 2.94-2.83 (m, 1H), 2.62 (d, J=8.2, 2H), 2.36 (s, 3H), 2.20 (td, J=7.6, 15.4, 1H); MS (ESI+) m/z 274.9 [M+H]$^+$.

Example 89

Trans-10-fluoro-2-methyl-1,2,3,3a,4,5-hexahydrobenzo[c]pyrrolo[3,4-c]azepin-6(10bH)-one The title compound was prepared according to the procedure outlined in Example 88 substituting 2-bromo-3-fluorobenzoic acid for 4-bromoisophthalic acid. $^1$H NMR (500 MHz, DMSO-d$_6$) δ ppm 8.14 (t, J=1.0 Hz, 1H), 7.55 (dd, J=1.0, 6.5 Hz, 1H), 7.33 (m, 1H), 7.28 (m, 1H), 3.22 (ddd, J=1.5, 6.5, 8.0 Hz, 1H), 3.13 (ddd, J=6.0, 10.5, 10.5 Hz, 1H), 3.08 (m, 1H), 3.03 (m, 2H), 2.62 (t, J=9.0 Hz, 1H), 2.58 (t, J=9.0 Hz, 1H), 2.37 (s, 3H), and 2.31 (m, 1H); MS (ESI+) m/z 235 [M+H]$^+$.

Example 90

Trans-9-fluoro-2-methyl-1,2,3,3a,4,5-hexahydrobenzo[c]pyrrolo[3,4-c]azepin-6(10bH)-one The title compound was prepared according to the procedure outlined in Example 88 substituting 2-bromo-4-fluorobenzoic acid for 4-bromoisophthalic acid. $^1$H NMR (300 MHz, DMSO-d$_6$) δ ppm 7.96 (t, J=0.9 Hz, 1H), 7.90 (dd, J=6.3, 8.7 Hz, 1H), 7.12 (dt, J=2.7, 8.7 Hz, 1H), 6.97 (dd, J=2.4, 9.9 Hz, 1H), 3.27 (m, 1H), 3.23 (m, 1H), 3.08 (m, 2H), 2.85 (dd, J=8.7, 10.2 Hz, 1H), 2.64 (t, J=9.0 Hz, 1H), 2.57 (t, J=9.0 Hz, 1H) 2.35 (s, 3H), and 2.20 (m, 1H); MS (ESI+) m/z 235 [M+H]$^+$.

Example 91

Trans-8-fluoro-2-methyl-1,2,3,3a,4,5-hexahydrobenzo[c]pyrrolo[3,4-c]azepin-6(10bH)-one The title compound was prepared according to the procedure outlined in Example 88 substituting 2-bromo-5-fluorobenzoic acid for 4-bromoisophthalic acid. $^1$H NMR (500 MHz, DMSO-d$_6$) δ ppm 8.10 (t, J=1.0 Hz, 1H), 7.59 (dd, J=3.0, 10.5 Hz, 1H), 7.27 (dt, J=3.0, 8.5 Hz, 1H), 7.18 (dd, J=5.5, 8.5 Hz, 1H), 3.25 (m, 1H), 3.19 (m, 1H), 3.12 (m, 1H), 3.09 (m, 1H), 2.84 (dd, J=9.0, 10.5 Hz, 1H), 2.61 (m, 2H), 2.37 (s, 3H), and 2.17 (m, 1H); MS (ESI+) m/z 235 [M+H]$^+$.

Example 92

Trans-7-fluoro-2-methyl-1,2,3,3a,4,5-hexahydrobenzo[c]pyrrolo[3,4-c]azepin-6(10bH)-one The title compound was prepared according to the procedure outlined in Example 88 substituting 2-bromo-6-fluorobenzoic acid for 4-bromoisophthalic acid. $^1$H NMR (500 MHz, DMSO-d$_6$) δ ppm 8.26 (t, J=1.0 Hz, 1H), 7.45 (m, 1H), 7.14 (t, J=9.5 Hz, 1H), 7.03 (d, J=7.5 Hz, 1H), 3.09 (m, 1H), 3.04 (m, 2H), 2.97 (m, 2H), 2.72 (t, J=8.5 Hz, 1H), 2.60 (t, J=9.0 Hz, 1H), 2.40 (s, 3H), and 2.10 (m, 1H); MS (ESI+) m/z 235 [M+H]$^+$.

Example 93

Trans-2-benzyl-2,3,3a,4,5,10b-hexahydro-1H-[1]benzoxepino[4,5-c]pyrrole

Example 93A 4,5-Dihydrobenzo[b]furo[3,4-d]oxepine-1,3-dione

To potassium tert-butoxide (1.35 g, 12 mmol) in tetrahydrofuran (30 mL) was added diethyl oxalate (2.2 g, 15 mmol) and ethyl 4-phenoxybutanoate (2.08 g, 10 mmol) in tetrahydrofuran (30 mL) at 0° C. dropwise. The mixture was allowed to stir overnight, concentrated, quenched with 1 N HCl$_{(aq)}$, extracted with ethyl acetate, and concentrated. A fraction of this material (308 mg, 1 mmol) was added to concentrated H₂SO₄ at 0° C. The mixture was stirred for 1.5 hours and was poured onto ice chips. The precipitate was collected to afford the title compound. ¹H NMR (300 MHz, DMSO-d₆) δ ppm 8.44 (dd, J=1.5, 8.1 Hz, 1H), 7.48 (t, J=8.1 Hz, 1H), 7.25 (t, J=7.8 Hz, 1H), 7.14 (d, J=8.4 Hz, 1H), 4.28 (t, J=5.1 Hz, 2H), and 3.02 (t, J=5.1 Hz, 2H).

Example 93B

Cis-N-benzyl-4,5-dihydrobenzo[b]pyro[3,4-d]oxepine-1,3-dione and

Example 93C

Trans-N-benzyl-4,5-dihydrobenzo[b]pyro[3,4-d]oxepine-1,3-dione

To Example 93A (3.1 g, 14 mmol) in methanol (60 mL) was added 5% palladium on carbon, wet (0.93 g, 8.7 mmol) in a 250 mL stainless steel pressure bottle, and the mixture was stirred for 16 hours under hydrogen (30 psi) at 50° C. The mixture was filtered through a nylon membrane and concentrated. This crude material was dissolved in N,N-dimethylformamide (30 mL) followed by the addition of benzyl amine (1.3 g, 12.5 mmol), triethylamine (1.5 g, 15 mmol), and O-(benzotriazol-1-yl)-N,N,N',N'-tetramethyluronium tetrafluoroborate (4 g, 12.5 mmol). The mixture was stirred at room temperature for 5 hours. Ethyl acetate was added, and the mixture was washed with water (3×) and concentrated. The crude was treated in 1 N lithium hydroxide in methanol:water (5:3, 20 mL) and was quenched with HCl$_{(aq)}$ (1 M) after 4 hours. The mixture was extracted with ethyl acetate and concentrated. The crude was dissolved in N,N-dimethylformamide (20 mL) followed by the addition of triethylamine (2 g, 20 mmol) and O-(benzotriazol-1-yl)-N,N,N',N'-tetramethyluronium tetrafluoroborate (4 g, 12.5 mmol). The mixture was heated. At 80° C. for 1 hour. Ethyl acetate was added, and the mixture was washed with water (3×). Column chromatography purification eluting with 30% ethyl acetate/hexane afforded the title compounds.

Example 93B: ¹H NMR (300 MHz, DMSO-d₆) δ ppm 7.27-7.38 (m, 7H), 7.19 (dt, J=1.2, 7.2 Hz, 1H), 7.02 (d, J=7.2 Hz, 1H), 4.68 (d, J=15.3 Hz, 1H), 4.63 (d, J=15.3 Hz, 1H), 4.23 (d, J=9.6 Hz, 1H), 3.80 (dd, J=3.0, 9.3 Hz, 2H), 3.42 (m, 1H), 1.94 (m, 1H), and 1.72 (m, 1H).

Example 93C: ¹H NMR (300 MHz, DMSO-d₆) δ ppm 7.68 (d, J=8.4 Hz, 1H), 7.20-7.37 (m, 6H), 7.11 (dt, J=1.2, 7.5 Hz, 1H), 7.05 (dd, J=1.5, 7.8 Hz, 1H), 4.67 (d, J=15.0 Hz, 1H), 4.62 (d, J=15.0 Hz, 1H), 4.51 (m, 2H), 3.58 (m, 1H), 2.94 (m, 1H), and 2.23 (m, 2H).

Example 93D

Trans-2-benzyl-2,3,3a,4,5,10b-hexahydro-1H-[1]benzoxepino[4,5-c]pyrrole

To Example 93C (200 mg, 0.65 mmol) in tetrahydrofuran (1.5 mL) was added lithium aluminum hydride (1.5 mL, 1 N in toluene, 1.5 mmol). The mixture was stirred at room temperature overnight and quenched with methanol and NaHCO₃$_{(aq)}$. Ethyl acetate was added, and the mixture was filtered through diatomaceous earth. The filtrate was concentrated and purified by flash chromatography eluting with 50% ethyl acetate/hexane to afford the title compound. ¹H NMR (500 MHz, DMSO-d₆) δ ppm 7.34 (m, 4H), 7.24 (m, 1H), 7.12 (t, J=7.5 Hz, 1H), 7.03 (t, J=7.0 Hz, 1H), 6.98 (t, J=7.5 Hz, 1H), 6.94 (d, J=8.0 Hz, 1H), 4.35 (dt, J=2.5, 12.5 Hz, 1H), 3.79 (d, J=13 Hz, 1H), 3.64 (d, J=13 Hz, 1H), 3.23 (d, J=10 Hz, 1H), 3.22 (m, 1H), 3.13 (dd, J=6.4, 8.5 Hz, 1H), 2.90 (dd, J=9.0, 10 Hz, 1H), 2.76 (t, J=9.5 Hz, 1H), 2.59 (dd, J=7.0, 9.0 Hz, 1H), 1.96 (m, 1H), and 1.84 (m, 2H); MS (ESI+) m/z 280 [M+H]⁺.

Example 94

Trans-2,3,3a,4,5,10b-hexahydro-1H-[1]benzoxepino[4,5-c]pyrrole

Example 94A tert-Butyl trans-1,3,3a,4,5,10b-hexahydro-2H-[1]benzoxepino[4,5-c]pyrrole-2-carboxylate To Example 93 (90 mg, 0.32 mmol) in trifluoroethanol (20 mL) was added 20% Pd(OH)₂-carbon, wet (18 mg, 0.13 mmol) in a 50 mL pressure bottle, and the mixture was stirred for 2 hours under hydrogen (30 psi) at 50° C. The mixture was filtered through a nylon membrane and concentrated. This crude material was dissolved in dichloromethane (3 mL) and di-tert-butyl dicarbonate (218 mg, 1 mmol) was added. The mixture was stirred at room temperature overnight and purified by flash chromatography eluting with 20% ethyl acetate/hexane to afford the title compound. ¹H NMR (300 MHz, DMSO-d₆) δ ppm 7.18 (m, 1H), 7.06 (m, 2H), 6.97 (d, J=7.5 Hz, 1H), 4.37 (dt, J=2.4, 12.3 Hz, 1H), 3.83 (dd, J=7.5, 10.2 Hz, 1H), 3.58 (m, 3H), 3.22 (m, 1H), 3.01 (q, J=10.2 Hz, 1H), 2.02 (m, 2H), 1.83 (m, 1H), and 1.42 (s, 9H).

Example 94B

Trans-2,3,3a,4,5,10b-hexahydro-1H-[1]benzoxepino[4,5-c]pyrrole hydrochloride

Example 94A (30 mg, 0.10 mmol) was treated with 4 N HCl in dioxane (1 mL). The mixture was stirred at room temperature for 2 hours, concentrated, and triturated in ethyl acetate to afford the title compound as the hydrochloride salt. ¹H NMR (500 MHz, DMSO-d₆) δ ppm 9.25 (s, 2H), 7.22 (dt, J=1.5, 6.5 Hz, 1H), 7.11 (t, J=6.0 Hz, 1H), 7.07 (d, J=7.0 Hz, 1H), 7.01 (d, J=7.0 Hz, 1H), 4.00 (dt, J=3.5, 12.5 Hz, 1H), 3.71 (dd, J=7.0, 11 Hz, 1H), 3.54 (m, 2H), 3.46 (t, J=11.5 Hz, 1H), 3.29 (m, 1H), 2.94 (t, J=11 Hz, 1H), 2.09 (d, J=7.0 Hz, 1H), 2.00 (m, 1H), and 1.80 (m, 1H); MS (ESI+) m/z 180 [M+H]⁺.

Example 95

Trans-9-chloro-2,3,3a,4,5,10b-hexahydro-1H-[1]benzoxepino[4,5-c]pyrrole

Example 94A (29 mg, 0.1 mmol) and N-chlorosuccinimide (27 mg, 0.2 mmol) were heated in N,N-dimethylformamide (0.3 mL) at 80° C. for 3 hours. The reaction mixture was diluted with ethyl acetate, washed with water (3×), and concentrated. The crude residue was stirred in 4 N HCl in dioxane (1 mL) for 2 hours, concentrated, and triturated in ethyl acetate to afford the title compound as the hydrochloride salt. ¹H NMR (500 MHz, DMSO-d₆) δ ppm 9.21 (s, 2H), 7.27 (dd, J=2.5, 8.5 Hz, 1H), 7.17 (d, J=2.0 Hz, 1H), 7.04 (d, J=8.5 Hz, 1H), 4.00 (dt, J=3.5, 12.0 Hz, 1H), 3.72 (dd, J=7.0, 11 Hz, 1H), 3.54 (m, 2H), 3.47 (t, J=11.5 Hz, 1H), 3.29 (m, 1H), 2.94 (t, J=11 Hz, 1H), 2.06 (m, 2H), and 1.82 (m, 1H); MS (ESI+) m/z 224 [M+H]$^+$.

Example 96

Cis-2,3,3a,4,5,1013-hexahydro-1H-[1]benzoxepino [4,5-c]pyrrole

The title compound was prepared as the hydrochloride salt according to the procedure outlined in Examples 94 substituting Example 93B for Example 93C. $^1$H NMR (500 MHz, DMSO-d$_6$) δ ppm 9.37 (s, 2H), 7.26 (m, 2H), 7.11 (dt, J=1.0, 7.5 Hz, 1H), 6.69 (dd, J=1.0, 7.0 Hz, 1H), 4.17 (dt, J=3.5, 12.0 Hz, 1H), 3.83 (ddd, J=4.0, 9.0, 12.5 Hz, 1H), 3.62 (q, J=8.5 Hz, 1H), 3.49 (dd, J=8.0, 11.5 Hz, 1H), 3.42 (dd, J=7.0, 11.5 Hz, 1H), 3.25 (t, 10.5 Hz, 1H), 2.96 (dd, J=7.0, 11.5 Hz, 1H), 2.68 (m, 1H), and 1.70 (m, 2H); MS (ESI+) m/z 180 [M+H]$^+$.

Example 97

Trans-2-benzyl-2,3,3a,4,5,11c-hexahydro-[1]benzothieno[2,3-c]pyrrolo[3,4-e]azepin-6(1H)-one

Example 97A

Methyl 3-bromobenzo[b]thiophene-2-carboxylate

The title compound was prepared as described in Example 55A substituting 3-bromobenzo[b]thiophene-2-carboxylic acid for 2-bromo-5-fluorobenzoic acid. $^1$H NMR (300 MHz, DMSO-d$_6$) δ ppm 3.92 (s, 3H) 7.59-7.69 (m, 2H) 7.93-8.00 (m, 1H) 8.14 (d, J=7.12 Hz, 1H).

Example 97B (E)-Methyl 3-(2-cyanovinyl)benzo[b]thiophene-2-carboxylate

In a flask under nitrogen was placed tris(dibenzylideneacetone)dipalladium(0) (313 mg, 0.34 mmol) in 25 mL of 1,4-dioxane followed by the product obtained from Example 97A (4.5 g, 16.7 mmol), N-methyldicyclohexylamine (3.91 g, 20.0 mmol), tri-tert-butylphosphine (0.68 mL of a 1.0 M solution in toluene, 0.68 mmol) and acrylonitrile (1.06 g, 20.0 mmol). The mixture was stirred and heated at 50° C. under nitrogen for 90 minutes and then cooled and diluted with 100 mL of ethyl acetate and stirred for 15 minutes. The mixture was filtered and the precipitate washed with 25 mL of ethyl acetate. The filtrate was concentrated and worked up as described in Example 55B to afford the title compound. $^1$H NMR (300 MHz, DMSO-d$_6$) δ ppm 3.92 (s, 3H) 6.55 (d, J=17.29 Hz, 1H) 7.54-7.66 (m, 2H) 8.13-8.25 (m, 3H).

Example 97C

Trans-2-benzyl-2,3,3a,4,5,11c-hexahydro[1]benzothieno[2,3-c]pyrrolo[3,4-e]azepin-6(1H)-one The title compound was prepared as described in Examples 45B and 45C from the product obtained in Example 97B. $^1$H NMR (300 MHz, DMSO-d$_6$) δ ppm 2.51-2.62 (m, 2H) 2.85-2.98 (m, 2H) 3.52 (d, J=7.80 Hz, 1H) 3.76-3.91 (m, 3H) 7.21-7.27 (m, 1H) 7.30-7.45 (m, 7H) 7.81-7.94 (m, 2H) 8.27 (dd, J=5.43, 2.37 Hz, 1H); MS (DCI$^+$) m/z 349.1 [M+H]$^+$.

Example 98

Trans-2-benzyl-8,10-dimethoxy-1,2,3,3a,4,5-hexahydrobenzo[c]pyrrolo[3,4-e]azepin-6(10bH)-one The title compound was prepared as outlined in Example 1 substituting methyl 2-formyl-3,5-dimethoxybenzoate for methyl 2-formylbenzoate. $^1$H NMR (300 MHz, DMSO-d$_6$) δ ppm 2.13-2.28 (m, 1H) 2.52-2.66 (m, 2H) 2.89-3.02 (m, 3H) 3.17 (dd, J=8.99, 5.93 Hz, 1H) 3.31-3.42 (m, 1H) 3.67-3.80 (m, 8H) 6.63 (d, J=2.37 Hz, 1H) 6.73 (d, J=2.71 Hz, 1H) 7.20-7.35 (m, 5H) 8.02 (t, J=5.43 Hz, 1H); MS (DCI$^+$) m/z 353.2 [M+H]$^+$.

Example 99

Trans-2,3,3a,4,5,11c-hexahydro[1]benzothieno[2,3-c]pyrrolo[3,4-e]azepin-6(1H)-one The product from Example 97 (315 mg, 0.90 mmol) was dissolved in 10 mL of ethanol under nitrogen and treated with acetic acid (162 mg, 2.70 mmol), 1,4 cyclohexadiene (361 mg, 4.50 mmol) and 10% palladium on carbon (300 mg). The mixture was stirred and heated at 51° C. for 16 hours. The reaction was cooled and filtered through a pad of diatomaceous earth, washed with ethanol (10 mL) and the filtrate concentrated. The residue was purified via flash chromatography on a silica gel column (95:5 dichloromethane: 2 M ammonia in methanol) to afford the title compound. $^1$H NMR (300 MHz, DMSO-d$_6$) δ ppm 2.39 (dd, J=10.85, 7.12 Hz, 1H) 2.63-2.77 (m, 3H) 3.08 (dd, J=9.49, 7.46 Hz, 2H) 4.07 (dd, J=9.66, 7.63 Hz, 1H) 7.35-7.47 (m, 3H) 7.92 (d, J=7.80 Hz, 3H) 8.28 (d, J=3.73 Hz, 1H); MS (DCI$^+$) m/z 259.1 [M+H]$^+$.

Example 100

Trans-8,10-dimethoxy-1,2,3,3a,4,5-hexahydrobenzo[c]pyrrolo[3,4-e]azepin-6(10bH)-one The title compound was prepared as outlined in Example 2 substituting the product obtained from Example 98 for the product from Example 1. $^1$H NMR (300 MHz, DMSO-d$_6$) δ ppm 2.00-2.14 (m, 1H) 2.56-2.65 (m, 1H) 2.71 (td, J=11.90, 5.95 Hz, 1H) 2.84-2.99 (m, 3H) 3.16-3.28 (m, 1H) 3.39-3.48 (m, 2H) 3.73 (s, 3H) 3.76 (s, 3H) 6.64 (d, J=2.38 Hz, 1H) 6.72 (d, J=2.78 Hz, 1H) 8.04 (t, J=5.35 Hz, 1H); MS (DCI$^+$) m/z 263.1 [M+H]$^+$.

Example 101

Trans-8-benzyl-6,6a,7,8,9,9a-hexahydropyrrolo[3,4-e]thieno[3,2-e]azepin-4(5H)-one The title compound was prepared as described in Example 97 substituting 2-bromo-3-thiophenecarboxylic acid for 3-bromobenzo[b]thiophene-2-carboxylic acid. $^1$H NMR (300 MHz, DMSO-d$_6$) δ ppm 2.20 (t, J=8.99 Hz, 1H) 2.25-2.33 (m, 1H) 2.76-2.85 (m, 1H) 2.87-3.01 (m, 2H) 3.03-3.15 (m, 2H) 3.55 (s, 2H) 3.65-3.76 (m, 1H) 7.18 (d, J=5.09 Hz, 1H) 7.22-7.35 (m, 6H) 7.95 (t, J=5.76 Hz, 1H); MS (DCI$^+$) m/z 299.1 [M+H]$^+$.

Example 102

Trans-2-benzyl-7-(trifluoromethoxy)-1,2,3,3a,4,5-hexahydrobenzo[c]pyrrolo[3,4-e]azepin-6(10bH)-one The title compound was prepared as described in Example 97 substituting 2-bromo-6-(trifluoromethoxy)benzoic acid for 3-bromobenzo[b]thiophene-2-carboxylic acid. $^1$H NMR (300 MHz, DMSO-d$_6$) δ ppm 2.13 (d, J=5.76 Hz, 1H) 2.60-2.69 (m, 1H) 2.79 (t, J=8.14 Hz, 1H) 2.92-3.01 (m, 2H) 3.02-3.12 (m, 2H) 3.16-3.26 (m, 1H) 3.76-3.89 (m, 2H) 7.21-7.27 (m, 2H) 7.30-7.38 (m, 5H) 7.49-7.59 (m, 1H) 8.32 (t, J=5.76 Hz, 1H); MS (DCI$^+$) m/z 377.2 [M+H]$^+$.

Example 103

Trans-7-(trifluoromethoxy)-1,2,3,3a,4,5-hexahydrobenzo[c]pyrrolo[3,4-e]azepin-6(10bH)-one The title compound was prepared as outlined in Example 2 substituting the product obtained from Example 102 for the product obtained from Example 1. $^1$H NMR (300 MHz, DMSO-d$_6$) δ ppm 1.92-2.06 (m, 1H) 2.73 (dd, J=11.53, 9.49 Hz, 1H) 2.88-3.04 (m, 5H) 3.19-3.25 (m, 2H) 7.25 (d, J=7.46 Hz, 1H) 7.34 (d, J=8.48 Hz, 1H) 7.56 (t, J=7.97 Hz, 1H) 8.35 (t, J=5.59 Hz, 1H); MS (DCI$^+$) m/z 287.1 [M+H]$^+$.

Example 104

Trans-6,6a,7,8,9,9a-hexahydropyrrolo[3,4-e]thieno[3,2-e]azepin-4(5H)-one

The title compound was prepared as described in Example 99 substituting the product obtained from Example 101 for the product obtained from Example 97. $^1$H NMR (300 MHz, DMSO-d$_6$) δ ppm 1.92-2.06 (m, 1H) 2.73 (dd, J=11.53, 9.49 Hz, 1H) 2.88-3.04 (m, 4H) 3.19-3.25 (m, 2H) 7.25 (d, J=7.46 Hz, 1H) 7.34 (d, J=8.48 Hz, 1H) 7.56 (t, J=7.97 Hz, 1H) 8.35 (t, J=5.59 Hz, 1H); MS (DCI$^+$) m/z 209.1 [M+H]$^+$.

Example 105

(3aS,10bS)-2-Benzyl-8,10-difluoro-1,2,3,3a,4,5-hexahydrobenzo[c]pyrrolo[3,4-e]azepin-6(10bH)-one The title compound was prepared as outlined in Example 97 substituting 2-bromo-3,5-difluorobenzoic acid for 3-bromobenzo[b]thiophene-2-carboxylic acid. The racemic mixture was subjected to a chiral purification using a Chiralpak® AS, 5 cm ID×50 cm column (mobile phase: hexanes/ethyl acetate/methanol/diethylamine 70:15:15:0.1, flow rate 75 mL/minute, column temperature 40° C., UV 230 nm detection), retention time 39 minutes, to obtain the titled compound. $^1$H NMR (300 MHz, DMSO-d$_6$) δ ppm 2.26-2.41 (m, 1H) 2.56-2.71 (m, 2H) 3.01-3.14 (m, 4H) 3.28 (s, 1H) 3.67-3.74 (m, 1H) 3.79-3.86 (m, 1H) 7.20-7.28 (m, 1H) 7.29-7.35 (m, 5H) 7.36-7.39 (m, 1H) 8.26 (t, J=4.75 Hz, 1H); MS (DCI$^+$) m/z 329.2 [M+H]$^+$.

Example 106

(3aR,10bS)-8,10-Difluoro-1,2,3,3a,4,5-hexahydrobenzo[c]pyrrolo[3,4-e]azepin-6(10bH)-one The title compound was prepared as described in Example 2 substituting the product obtained from Example 105 for the product obtained from Example 1. $^1$H NMR (300 MHz, DMSO-d$_6$) δ ppm 2.18 (dd, J=11.53, 3.39 Hz, 1H) 2.59-2.67 (m, 1H) 2.82 (ddd, J=11.61, 5.68, 5.43 Hz, 1H) 2.87-2.95 (m, 1H) 3.05 (t, J=4.75 Hz, 2H) 3.16-3.26 (m, 2H) 7.27-7.38 (m, 2H) 8.29 (s, 1H); MS (DCI$^+$) m/z 239.1 [M+H]$^+$.

Example 107

Trans-2-benzyl-8-fluoro-2,3,3a,4,5,10b-hexahydro-1H-[1]benzoxepino[4,5-c]pyrrole Example 107A Ethyl 4-(3-fluorophenoxy)butanoate A mixture of 3-fluorophenol (10.0 g, 89.2 mmol), ethyl-4-bromobutanoate (21.5 g, 110 mmol), potassium carbonate (17.3 g, 125 mmol) and 100 mL of N,N-dimethylformamide was stirred and heated at 100° C. under nitrogen for 16 hours. The reaction mixture was cooled and partitioned between ethyl acetate and water. The aqueous portion was separated and extracted with 2×50 mL of ethyl acetate. The combined organic extracts were washed with 3×50 mL of water and 1×50 mL of brine and dried over sodium sulfate. The organic solution was concentrated and the residue was purified via flash chromatography on a silica gel column (95:5 hexane:ethyl acetate) to afford the title compound. $^1$H NMR (300 MHz, DMSO-d$_6$) δ ppm 1.18 (t, J=7.12 Hz, 3H) 1.91-2.00 (m, 2H) 2.44 (t, J=7.29 Hz, 2H) 4.00 (t, J=6.44 Hz, 2H) 4.07 (q, J=7.12 Hz, 2H) 6.71-6.82 (m, 3H) 7.25-7.34 (m, 1H); MS (DCI$^+$) m/z 244.1 [M+NH$_4$]$^+$.

Example 107B

8-Fluoro-4,5-dihydrobenzo[b]furo[3,4-d]oxepine-1,3-dione

The title compound was prepared as outlined in Example 93A substituting the product from Example 107A for ethyl 4-phenoxybutanoate. $^1$H NMR (300 MHz, DMSO-d$_6$) δ ppm 3.02 (t, J=5.16 Hz, 2H) 4.32 (t, J=5.16 Hz, 2H) 7.05 (dd, J=10.11, 2.58 Hz, 1H) 7.16 (td, J=8.53, 2.78 Hz, 1H) 8.51 (dd, J=9.12 6.74 Hz, 1H).

Example 107C (Z)-Dimethyl 8-fluoro-2,3-dihydrobenzo[b]oxepine-4,5-dicarboxylate

To a suspension of the product from Example 107B (2.34 g, 10.0 mmol) in 20 mL of methanol was added sodium methoxide (594 mg, 11.0 mmol) in one portion at room temperature. The reaction was stirred at ambient temperature for 1 hour and then concentrated. The residue was taken up in 25 mL of N,N-dimethylformamide at room temperature and methyl iodide (2.28 g, 15.0 mmol) was added in one portion and stirring was continued for 2.5 hours. The reaction mixture was partitioned between 1 N aqueous hydrochloric acid and ethyl acetate. The aqueous portion was separated and extracted with 2×50 mL ethyl acetate. The combined organic extracts were washed with 2×50 mL of water and 1×50 mL with brine and dried over sodium sulfate. The organic solution was concentrated and the residue was purified by flash chromatography on a silica gel column (15:85 ethyl acetate:hexane) to afford the title compound $^1$H NMR (300 MHz, DMSO-d$_6$) δ ppm 2.70 (t, J=5.76 Hz, 2H) 3.74 (s, 3H) 4.48 (t, J=5.76 Hz, 2H) 6.99-7.09 (m, 2H) 7.26 (dd, J=8.82, 6.44 Hz, 1H); MS (DCI$^+$) m/z 298.1 (M+NH$_4$)$^+$.

Example 107D

Trans-dimethyl 8-fluoro-2,3,4,5-tetrahydrobenzo[b]oxepine-4,5-dicarboxylate

To an oven dried flask were placed magnesium turnings (1.46 g, 60.0 mmol) under nitrogen, and then a solution of the product from 107C (1.70 g, 6.1 mmol) in 50 mL of methanol was added in one portion at room temperature. The reaction was stirred at ambient temperature for 16 hours and then concentrated. The residue was partitioned between 2 N aqueous HCl solution and ethyl acetate. The aqueous portion was separated and extracted with 2×50 mL of ethyl acetate and the combined organic extracts were washed with 50 mL of a 10% aqueous sodium bicarbonate solution and 50 mL of brine and dried over sodium sulfate. The organic solution was concentrated and the residue was purified via flash chromatography on a silica gel column (9:1 hexane:ethyl acetate to afford the title compound. $^1$H NMR (300 MHz, DMSO-$d_6$) δ ppm 2.03-2.15 (m, 2H) 3.38 (q, J=5.55 Hz, 1H) 3.55 (s, 3H) 3.61 (s, 3H) 3.83-3.92 (m, 1H) 4.07-4.15 (m, 1H) 4.32 (d, J=5.55 Hz, 1H) 6.80 6.93 (m, 2H) 7.17 (dd, J=8.33, 6.74 Hz, 1H); MS (DCI$^+$) m/z 300.2 [M+NH$_4$]$^+$.

Example 107E (Trans-8-fluoro-2,3,4,5-tetrahydrobenzo[b]oxepine-4,5-diyl)dimethanol A solution of the product from Example 107D (695 mg, 2.46 mmol) in 10 mL of tetrahydrofuran was chilled to −70° C. under nitrogen and treated dropwise with lithium aluminum hydride (5.0 mL of a 1.0 M solution in tetrahydrofuran). After the addition was completed the reaction was allowed to warm to room temperature over 3 hours and then quenched with 5 mL of ethyl acetate followed by 15 mL of 2 N aqueous hydrochloric acid solution. The layers were separated and the aqueous portion was extracted with 4×10 mL of ethyl acetate and the combined organic extracts were dried over sodium sulfate. The organic solution was concentrated and the residue was purified via flash chromatography on a silica gel column (100%) ethyl acetate to afford the title compound. $^1$H NMR (300 MHz, DMSO-$d_6$) δ ppm 1.71 (dd, J=12.89, 2.03 Hz, 1H) 2.01-2.15 (m, 2H) 2.86 (td, J=7.71, 3.90 Hz, 1H) 3.16-3.29 (m, 2H) 3.52 (ddd J=10.51, 7.12, 5.43 Hz, 1H) 3.66-3.78 (m, 2H) 4.12 (dt, J=12.12, 4.11 Hz, 1H) 4.48 (t, J=5.09 Hz, 1H) 4.59 (t, J=5.43 Hz, 1H) 6.71 (dd, J=10.17, 2.71 Hz, 1H) 6.81 (td, J=8.31, 2.71 Hz, 1H) 7.12 (dd, J=8.48, 6.78 Hz, 1H); MS (DCI$^+$) m/z 226.1 [M+NH$_4$]$^+$.

Example 107F (Trans-8-fluoro-2,3,4,5-tetrahydrobenzo[b]oxepine-4,5-diyl)bis(methylene)bis(4-methylbenzenesulfonate To a solution of the product from Example 107E (410 mg, 1.81 mmol) in 10 mL of pyridine under nitrogen and chilled in an ice bath was added tosyl chloride (715 mg, 3.75 mmol) in one portion. Stirring was continued for 16 hours while warming to room temperature. The reaction was quenched with 10 mL of water and the aqueous portion was separated and extracted with 2×10 mL of ethyl acetate. The combined organic extracts were washed with 2×10 mL of water and 1×10 mL of brine and dried over sodium sulfate. The organic solution was concentrated and the residue was purified via flash chromatography on a silica gel column (3:7 ethyl acetate:hexane to afford the title compound. $^1$H NMR (300 MHz, DMSO-$d_6$) δ ppm 1.58 (d J=13.48 Hz, 1H) 1.85-1.95 (m, 1H) 2.30 (td, J=7.54, 3.17 Hz, 1H) 2.40 (s, 2H) 2.41 (s, 1H) 3.09 (td, J=7.54, 3.97 Hz, 1H) 3.40-3.51 (m, 1H) 3.83 (dd, J=7.54, 1.98 Hz, 2H) 3.97-4.06 (m, 1H) 4.10-4.19 (m, 1H) 4.31 (dd, J=9.52, 6.74 Hz, 1H) 6.62 (dd, J=9.91, 2.78 Hz, 1H) 6.75 (td, J=8.53, 2.78 Hz, 1H) 6.88-6.95 (m, 1H) 7.41 (dd J=17.25, 8.13 Hz, 4H) 7.58 (d, J=8.33 Hz, 2H) 7.71 (d, J=8.33 Hz, 2H).

Example 107G

Trans-2-benzyl-8-fluoro-2,3,3a,4,5,10b-hexahydro-1H-[1]benzoxepino[4,5-c]pyrrole A solution of the product obtained from Example 107F (570 mg, 1.07 mmol), benzylamine (375 mg, 3.50 mmol), triethylamine (465 mg, 4.60 mmol) and 5 mL of N,N-dimethylformamide was heated at 110° C. under nitrogen for 3 hours. The reaction was cooled and partitioned between 20 mL of water and 20 mL of ethyl acetate. The aqueous portion was separated and extracted with 2×10 mL of ethyl acetate and the combined organic extracts were washed with 2×10 mL of water and 1×10 mL of brine and dried over sodium sulfate. The organic solution was concentrated and the residue was purified via flash chromatography on a silica gel column (1:1 ethyl acetate:hexane) to afford the title compound. $^1$H NMR (300 MHz, DMSO-$d_6$) δ ppm 1.81-1.90 (m, 1H) 1.92-2.00 (m, 1H) 2.59 (dd, J=9.16, 7.12 Hz, 1H) 2.77 (t, J=8.82 Hz, 1H) 2.83-2.91 (m, 1H) 3.11-3.18 (m, 2H) 3.56-3.67 (m, 2H) 3.75-3.82 (m, 1H) 4.37 (dt, J=12.21, 3.73 Hz, 1H) 6.78-6.86 (m, 2H) 6.99-7.08 (m, 1H) 7.24 (ddd, J=6.95, 5.26, 2.37 Hz, 1H) 7.31-7.36 (m, 4H); MS (DCI$^+$) m/z 298.2 [M+H]$^+$.

Example 108

Trans-8-phenyl-2,3,3a,4,5,10b-hexahydro-1H-[1]benzoxepino[4,5-c]pyrrole

Example 108A

Trans-2-benzyl-8-phenyl-2,3,3a,4,5,10b-hexahydro-1H-[1]benzoxepino[4,5-c]pyrrole The title compound was prepared according to the procedure outlined in Example 107 substituting biphenyl-3-ol for 3-fluorophenol in Example 107A.

Example 108B

Trans-8-phenyl-2,3,3a,4,5,10b-hexahydro-1H-[1]benzoxepino[4,5-c]pyrrole

The title compound was prepared according to the procedure outlined in Example 2 substituting the product obtained from Example 108A for the product obtained from Example 1. $^1$H NMR (300 MHz, DMSO-$d_6$) δ ppm 1.78-1.93 (m, 2H) 2.04-2.13 (m, 1H) 2.74-2.88 (m, 1H) 3.16 (td, J=10.81, 6.94 Hz, 2H) 3.51-3.67 (m, 3H) 4.43 (dt, J=12.29, 3.37 Hz, 1H) 7.17 (d, J=7.93 Hz, 1H) 7.28 (d, J=1.98 Hz, 1H) 7.32-7.39 (m, 2H) 7.45 (t, J=7.34 Hz, 2H) 7.65 (s, 2H); MS (DCI$^+$) m/z 266.2 [M+H]$^+$.

Example 109

Trans-8-fluoro-2,3,3a,4,5,10b-hexahydro-1H-[1]benzoxepino[4,5-c]pyrrole

The title compound was prepared according to the procedure described in Example 2 substituting the product obtained from Example 107G for the product obtained from Example 1. $^1$H NMR (300 MHz, DMSO-$d_6$) δ ppm 1.67-1.83

(m, 2H) 1.96-2.09 (m, 1H) 2.61 (dd, J=10.31, 8.73 Hz, 1H) 2.83-2.96 (m, 1H) 3.06 (t, J=10.51 Hz, 1H) 3.17 (dd, J=10.71, 7.93 Hz, 1H) 3.51-3.66 (m, 2H) 4.38 (dt, J=12.20, 3.42 Hz, 1H) 6.84 (ddd, J=16.26, 9.12, 2.78 Hz, 2H) 7.02-7.14 (m, 1H); MS (DCI$^+$) m/z 208.1 [M+H]$^+$.

Example 110

Trans-2-methyl-7-(trifluoromethoxy)-1,2,3,3a,4,5-hexahydrobenzo[c]pyrrolo[3,4-e]azepin-6(10bH)-one

Example 110A

Methyl 2-((3S,4R)-4-cyano-1-methylpyrrolidin-3-yl)-6-(trifluoromethoxy)benzoate

The title compound was prepared according to the procedure outlined in Example 88B substituting (E)-methyl 2-(2-cyanovinyl)-6-(trifluoromethoxy)benzoate for dimethyl 4-(2-cyanovinyl)isophthalate.

Example 110B

Methyl 2-((3S,4S)-4-(aminomethyl)-1-methylpyrrolidin-3-yl)-6-(trifluoromethoxy)benzoate The title compound was prepared according to the procedure outlined in Example 45C substituting the product obtained from Example 110A for the product obtained from Example 45B. In this instance, the aminoester did not cyclize. $^1$H NMR (300 MHz, DMSO-d$_6$) δ ppm 1.42 (s, 1H) 2.10-2.21 (m, 1H) 2.32-2.48 (m, 4H) 2.55-2.63 (m, 1H) 2.73 (t, J=8.48 Hz, 1H) 2.79-2.87 (m, 3H) 3.87 (s, 3H) 7.28-7.36 (m, 1H) 7.55-7.64 (m, 3H); MS (DCI$^+$) m/z 333.2 [M+H]$^+$.

Example 110C

Trans-2-methyl-7-(trifluoromethoxy)-1,2,3,3a,4,5-hexahydrobenzo[c]pyrrolo[3,4-c]azepin-6(10bH)-one The product obtained from Example 110B (5.5 g) was dissolved in 25 mL of methanol and treated with 5 mL of 25 weight % sodium methoxide in methanol. The reaction was stirred and heated at 70° C. for 16 hours. The reaction was cooled and concentrated, and the residue was purified via flash chromatography on a silica gel column (95:5 dichloromethane:2 N ammonia in methanol) to afford the title compound. $^1$H NMR (300 MHz, DMSO-d$_6$) δ ppm 2.04-2.20 (m, 1H) 2.41 (s, 3H) 2.62 (dd, J=10.85 Hz, 8.82 Hz, 1H) 2.73 (t, J=8.31 Hz, 1H) 2.93-3.01 (m, 3H) 3.03-3.14 (m, 2H) 7.24 (d, J=7.80 Hz, 1H) 7.32 (d, J=8.14 Hz, 1H) 7.51-7.59 (m, 1H) 8.33 (t, J=5.76 Hz, 1H); MS (DCI$^+$) m/z 301.1 [M+H]$^+$.

Example 111

Trans-2,3,3a,4,5,10b-hexahydro-1H-pyrrolo[3,4-d][1,2]benzothiazepine 6,6-dioxide

Example 111A (E)-Perfluorophenyl 2-(2-cyanovinyl)benzenesulfonate

The title compound was prepared as described in Example 97B substituting pentafluorophenyl 2-bromobenzenesulfonate for the product obtained from Example 97A.

Example 111B

Perfluorophenyl 2-((3S,4R)-1-benzyl-4-cyanopyrrolidin-3-yl))benzenesulfonate

The title compound was prepared as described in Example 45B substituting the product obtained from Example 111A for the product obtained from Example 45A

Example 111C

Trans-2-benzyl-2,3,3a,4,5,10b-hexahydro-1H-pyrrolo[3,4-d][1,2]benzothiazepine 6,6-dioxide The title compound was prepared as described in Example 55D substituting the product obtained from Example 111B for the product obtained from Example 55C. The crude reaction product was treated with 1.1 equivalents of tetra-n-butylammonium chloride in tetrahydrofuran at ambient temperature for one hour and then partitioned between ethyl acetate and water. The organic portion was washed with water and brine and dried over sodium sulfate. The organic portion was concentrated and purified via flash chromatography on a silica gel column eluting with ethyl acetate/hexane (1:1) to afford the title compound.

Example 111D

Trans-2,3,3a,4,5,10b-hexahydro-1H-pyrrolo[3,4-d][1,2]benzothiazepine 6,6-dioxide The title compound was prepared as described in Example 54B substituting the product obtained from Example 111C for the product obtained from 54A. The crude product was purified via flash chromatography on a silica gel column (9:1 dichloromethane:2 M ammonia solution in methanol) to afford the title compound. $^1$H NMR (300 MHz, DMSO-d$_6$) δ ppm 1.76-1.91 (m, 1H) 2.58 (dd, J=11.36, 6.61 Hz, 1H) 3.03 (ddd, J=17.12, 10.51, 10.34 Hz, 2H) 3.17 (d, J=3.73 Hz, 2H) 3.52 (td, J=10.43, 5.93 Hz, 1H) 4.07 (d, J=5.09 Hz, 1H) 7.30-7.43 (m, 2H) 7.53 (td, J=7.63, 1.36 Hz, 2H) 7.89 (dd, J=7.63, 1.53 Hz, 1H); MS (+ESI) m/z 239.2 [M+H]$^+$.

Example 112

(3aR,10bR)-2-Methyl-7-(trifluoromethoxy)-1,2,3,3a,4,5-hexahydrobenzo[c]pyrrolo[3,4-e]azepin-6(10bH)-one The title compound was obtained by subjecting the product described in Example 110 to a chiral resolution as outlined in Example 61 (retention time 6.25 minutes). $^1$H NMR (300 MHz, DMSO-d$_6$) δ ppm 2.04-2.19 (m, 1H) 2.41 (s, 3H) 2.56-2.65 (m, 1H) 2.73 (t, J=8.31 Hz, 1H) 2.93-3.01 (m, 3H) 3.03-3.17 (m, 2H) 7.24 (d, J=7.80 Hz, 1H) 7.33 (d, J=8.14 Hz, 1H) 7.51-7.61 (m, 1H) 8.34 (t, J=5.59 Hz, 1H); MS (DCI$^+$) m/z 301.1 [M+H]$^+$.

Example 113

(3aS,10bS)-2-Methyl-7-(trifluoromethoxy)-1,2,3,3a,4,5-hexahydrobenzo[c]pyrrolo[3,4-e]azepin-6(10bH)-one The title compound was obtained by subjecting the product described in Example 110 to a chiral resolution as outlined in Example 61 (retention time 8.2 minutes). $^1$H NMR (300

MHz, DMSO-$d_6$) δ ppm 2.04-2.19 (m, 1H) 2.41 (s, 3H) 2.56-2.65 (m, 1H) 2.73 (t, J=8.31 Hz, 1H) 2.93-3.01 (m, 3H) 3.03-3.17 (m, 2H) 7.24 (d, J=7.80 Hz, 1H) 7.33 (d, J=8.14 Hz, 1H) 7.51-7.61 (m, 1H) 8.34 (t, J=5.59 Hz, 1H); MS (DCI$^+$) m/z 301.1 [M+H]$^+$.

Example 114

Trans-2-methyl-7-phenyl-1,2,3,3a,4,5-hexahydrobenzo[c]pyrrolo[3,4-e]azepin-6(10bH)-one Example 114A Methyl 2,6-dibromobenzoate The title compound was prepared as outlined in Example 55A substituting 2,6-dibromobenzoic acid for 2-bromo-5-fluorobenzoic acid. $^1$H NMR (300 MHz, DMSO-$d_6$) δ ppm 3.91 (s, 3H) 7.34-7.40 (m, 1H) 7.75 (d, J=8.14 Hz, 2H).

Example 114B

Methyl 3-bromobiphenyl-2-carboxylate

A mixture of the product from Example 114A (2.2 g, 7.5 mmol), phenylboronic acid (919 mg, 7.5 mmol), sodium carbonate (7.55 mL, 2 M aqueous solution, 15.1 mmol) tetrakis(triphenyphosphine)palladium(0) (261 mg, 0.23 mmol) and 50 mL of toluene were refluxed for 16 hours under nitrogen. The reaction was cooled and partitioned between 50 mL of water and 50 mL of ethyl acetate. The aqueous portion was separated and extracted with 2×25 mL of ethyl acetate and the combined organic extracts were washed with 2×25 mL of water and 1×25 mL of brine and dried over sodium sulfate. The organic solution was concentrated and the residue was purified via flash chromatography on a silica gel column (95:5 hexane:ethyl acetate) to afford the title compound. $^1$H NMR (300 MHz, DMSO-$d_6$) δ ppm 3.63 (s, 3H) 7.35-7.60 (m, 6H) 7.71-7.79 (m, 2H); MS (DCI$^+$) m/z 308.0 [M+NH$_4$]$^+$.

Example 114C (E)-Methyl 3-(2-cyanovinyl)biphenyl-2-carboxylate

The title compound was prepared as outlined in Example 97B substituting the product obtained from Example 114B for the product obtained from Example 97A. $^1$H NMR (300 MHz, DMSO-$d_6$) δ ppm 3.58 (s, 3H) 6.57 (d, J=16.62 Hz, 1H) 7.30-7.36 (m, 2H) 7.40-7.49 (m, 3H) 7.53-7.59 (m, 2H) 7.65 (t, J=7.80 Hz, 1H) 7.89 (d, J=7.12 Hz, 1H); MS (DCI$^+$) m/z 281.1 [M+NH$_4$]$^+$.

Example 114D

Methyl 3-(trans-cyano-1-methylpyrrolidin-3-yl)biphenyl-2-carboxylate

The title compound was prepared as outlined in Example 88B substituting the product obtained from Example 114C for dimethyl 4-bromoisophthalate. $^1$H NMR (300 MHz, DMSO-$d_6$) δ ppm 2.33 (s, 3H) 2.59 (dd, J=9.49, 6.10 Hz, 1H) 2.80 (dd, J=9.49, 6.10 Hz, 1H) 2.93-3.01 (m, 1H) 3.04-3.12 (m, 1H) 3.35-3.42 (m, 1H) 3.49-3.56 (m, 1H) 3.58 (s, 3H) 7.30-7.47 (m, 6H) 7.55-7.61 (m, 2H); MS (DCI$^+$) m/z 321.2 [M+H]$^+$.

Example 114E

Trans-2-methyl-7-phenyl-1,2,3,3a,4,5-hexahydrobenzo[c]pyrrolo[3,4-e]azepin-6(10bH)-one The title compound was prepared from the product obtained in Example 114D utilizing the procedures described in Example 110B followed by that outlined in Example 110C. $^1$H NMR (300 MHz, DMSO-$d_6$) 2.10-2.24 (m, 1H) 2.45 (s, 3H) 2.64-2.73 (m, 1H) 2.80 (t, J=8.33 Hz, 1H) 2.98-3.12 (m, 3H) 3.14-3.27 (m, 2H) 7.17 (d, J=7.54 Hz, 1H) 7.28-7.41 (m, 6H) 7.45 (t, J=7.54 Hz, 1H) 8.20 (t, J=5.95 Hz, 1H); MS (DCI$^+$) m/z 293.1 [M+H]$^+$.

Example 115

(3aS,10bS)-8-(4-Fluorophenyl)-2-methyl-1,2,3,3a,4,5-hexahydrobenzo[c]pyrrolo[3,4-e]azepin-6(10bH)-one Example 75 was resolved into pure enantiomers using supercritical fluid chromatography (ChiralPak® AS, 21×250 mm, 5 nm, 10-50% methanol with 0.1% diethyl amine-CO$_2$ gradient over 20 minutes, at 40 mL/minute, retention time=10.2 minutes) to afford the title compound. $^1$H NMR (300 MHz, DMSO-$d_6$) δ ppm 8.07 (d, J=2.1, 1H), 8.03 (s, 1H), 7.74-7.66 (m, 3H), 7.34-7.22 (m, 3H), 3.34-3.21 (m, 2H), 3.19-3.04 (m, 2H), 2.93 (dd, J=8.9, 10.3, 1H), 2.71-2.59 (m, 2H), 2.39 (s, 3H), 2.30-2.14 (m, 1H); MS (ESI+) m/z 310.9 [M+H]$^+$.

Example 116

(3aR,10bR)-8-(4-Fluorophenyl)-2-methyl-1,2,3,3a,4,5-hexahydrobenzo[c]pyrrolo[3,4-c]azepin-6(10bH)-one Example 75 was resolved into pure enantiomers using supercritical fluid chromatography (ChiralPak® AS, 21×250 mm, 5 μm, 10-50% methanol with 0.1% diethyl amine-CO$_2$ gradient over 20 minutes, at 40 mL/minute, retention time=15.8 minutes) to afford the title compound. $^1$H NMR (300 MHz, DMSO-$d_6$) δ ppm 8.07 (d, J=2.1, 1H), 8.03 (s, 1H), 7.74-7.66 (m, 3H), 7.34-7.22 (m, 3H), 3.34-3.21 (m, 2H), 3.19-3.04 (m, 2H), 2.93 (dd, J=8.9, 10.3, 1H), 2.71-2.59 (m, 2H), 2.39 (s, 3H), 2.30-2.14 (m, 1H); MS (ESI+) m/z 310.9 [M+H]$^+$.

Example 117

Trans-2-benzyl-8-hydroxy-1,2,3,3a,4,5-hexahydrobenzo[c]pyrrolo[3,4-c]azepin-6(10bH)-one Example 117A Trans-2-benzyl-8-methoxy-1,2,3,3a,4,5-hexahydrobenzo[c]pyrrolo[3,4-c]azepin-6(10bH)-one The title compound was prepared according to the procedure outlined in Examples 45A-C substituting methyl 2-bromo-5-methoxybenzoate for methyl 2-bromo-5-chlorobenzoate in Example 45A. (10:1 Trans/Cis isomers).

Example 117B

Trans-2-benzyl-8-hydroxy-1,2,3,3a,4,5-hexahydrobenzo[c]pyrrolo[3,4-c]azepin-6(10bH)-one To Example 117A (2.66 g, 8.25 mmol) was added BBr$_3$ (1.0 M in dichloromethane, 10.73 mL, 10.73 mmol) at −78°

C. dropwise. This was stirred at −78° C. for 3 hours. Then, the reaction mixture was stirred at room temperature overnight. Since TLC (dichloromethane/methanol (9:1)) still shows starting material, this was cooled down to −78° C. again, more BBr$_3$ (1.0 M in dichloromethane, 5.5 mL) was added to the reaction mixture. This was stirred at −78° C. for 2 hours, then warmed and stirred at room temperature for 2 hours when the reaction was complete as indicated by TLC. The reaction was quenched with saturated NaHCO$_3$ solution until pH=6-7, and the phases were separated. The organic phase was then washed with brine, dried over Na$_2$SO$_4$ and concentrated. The residue was purified with flash column with 10-20% methanol in dichloromethane (with 0.5% triethylamine added) to afford the title compound. The combined H$_2$O phases were concentrated and then extracted with 10% methanol/dichloromethane to provide a second batch of the title compound. $^1$H NMR (300 MHz, DMSO-d$_6$) δ ppm 9.42 (s, 1H), 7.85-7.87 (m, 1H), 7.25-7.36 (m, 5H), 7.19 (d, J=2.5, 1H), 6.93 (d, J=8.3, 1H), 6.80 (dd, J=8.3, 2.7, 1H), 3.89-3.68 (m, 2H), 3.22-2.94 (m, 5H), 2.63 (m, 2H), 2.12-2.16 (m, 1H); MS (ESI+) m/z 308.9 [M+H]$^+$.

Example 118

Trans-2-benzyl-8-((R)-1-phenylpropan-2-yloxy)-1,2,3,3a,4,5-hexahydrobenzo[c]pyrrolo[3,4-c]azepin-6(10bH)-one To Example 117 (60 mg, 0.195 mmol) was added (S)-1-phenylpropan-2-ol (34.4 mg, 0.253 mmol), di-tert-butyl azodicarboxylate (DBAD, 67.2 mg, 0.292 mmol), PS-triphenylphosphine (134 mg, 0.428 mmol, 3.2 mmol/g) and 2 mL of dry tetrahydrofuran. The reaction mixture was stirred at room temperature overnight. The reaction was complete as indicated by LC/MS. The reaction mixture was filtered through a phase separator (Biotage) followed by a methanol washed. The filtrate was concentrated and purified by flash column with (0-20%) methanol in dichloromethane to afford the title compound. $^1$H NMR (500 MHz, DMSO-d$_6$) δ ppm 7.95 (m, 1H), 7.38-7.16 (m, 11H), 6.98 (dt, J=8.5, 5.0, 2H), 4.65 (dt, J=12.5, 6.3, 1H), 3.84-3.66 (m, 2H), 3.21-3.07 (m, 3H), 2.99 (m, 3H), 2.89-2.80 (m, 1H), 2.71 (t, J=8.7, 1H), 2.59 (t, J=8.9, 1H), 2.14 (m, 1H), 1.25-1.17 (m, 3H); MS (ESI+) m/z 427.3 [M+H]$^+$.

Example 119

Trans-2-benzyl-8-(3-fluorophenethoxy)-1,2,3,3a,4,5-hexahydrobenzo[c]pyrrolo[3,4-c]azepin-6(10bH)-one The title compound was prepared according to the procedure outlined in Examples 118 substituting 2-(3-fluorophenyl)ethanol for (S)-1-phenylpropan-2-ol. $^1$H NMR (500 MHz, DMSO-d$_6$) δ ppm 8.00-7.93 (m, 1H), 7.38-7.29 (m, 6H), 7.24 (t, J=6.8, 1H), 7.18 (dd, J=11.8, 4.7, 2H), 7.08-6.96 (m, 3H), 4.26-4.16 (m, 2H), 3.85-3.67 (m, 2H), 3.21-3.10 (m, 3H), 3.08-2.94 (m, 4H), 2.72 (t, J=8.5, 1H), 2.60 (t, J=8.9, 1H), 2.18-2.08 (m, 1H); MS (ESI+) m/z 431.5 [M+H]$^+$.

Example 120

Trans-2-benzyl-8-((S)-1-phenylpropan-2-yloxy)-1,2,3,3a,4,5-hexahydrobenzo[c]pyrrolo[3,4-c]azepin-6(10bH)-one The title compound was prepared according to the procedure outlined in Example 118 substituting (R)-1-phenylpropan-2-ol for (S)-1-phenylpropan-2-ol. The crude material was purified by reverse phase HPLC to afford the title compound as the trifluoroacetic acid salt $^1$H NMR (500 MHz, DMSO-d$_6$) δ ppm 10.60 (d, J=71.4, 1H), 8.06 (s, 1H), 7.59 (s, 2H), 7.48 (d, J=5.9, 3H), 7.28-7.26 (dd, J=5.1, 3.3, 4H), 7.25-7.00 (m, 4H), 4.73-4.68 (m, 1H), 4.52 (m, 2H), 3.86-3.50 (m, 4H), 3.25-2.91 (m, 4H), 2.86 (dt, J=13.6, 5.7, 1H), 2.19 (s, 1H), 1.23 (dd, J=6.0, 2.3, 3H); MS (ESI+) m/z 427.4 [M+H]$^+$.

Example 121

Trans-2-benzyl-8-phenethoxy-1,2,3,3a,4,5-hexahydrobenzo[c]pyrrolo[3,4-c]azepin-6(10bH)-one The title compound was prepared according to the procedure outlined in Example 118 substituting 2-phenylethanol for (S)-1-phenylpropan-2-ol. The crude material was purified by reverse phase HPLC to afford the title compound as the trifluoroacetic acid salt $^1$H NMR (500 MHz, DMSO-d$_6$) δ ppm 10.26 (d, J=56.9, 1H), 8.06 (m, 1H), 7.60-7.57 (t, J=6.6, 2H), 7.49 (t, J=5.9, 3H), 7.31 (dd, J=8.7, 5.3, 4H), 7.24-7.20 (m, 2H), 7.15 (m, 1H), 7.06 (dt, J=8.5, 5.8, 1H), 4.53 (dd, J=20.8, 3.6, 2H), 4.23-4.20 (m, 2H), 3.83-3.59 (m, 2H), 3.58-3.46 (m, 1H), 3.18-3.08 (m, 3H), 3.03 (dd, J=13.8, 7.1, 3H), 2.61 2.11 (m, 1H); MS (ESI+) m/z 413.5 [M+H]$^+$.

Example 122

Trans-2-methyl-8-(piperidine-1-carbonyl)-1,2,3,3a,4,5-hexahydrobenzo[c]pyrrolo[3,4-c]azepin-6(10bH)-one Example 122A Trans-2-methyl-6-oxo-1,2,3,3a,4,5,6,10b-octahydrobenzo[c]pyrrolo[3,4-c]azepine-8-carboxylic acid To Example 88 (2.115 g, 7.71 mmol) in a solution of methanol/water (10 mL/5 mL) was added LiOH monohydrate (0.324 g, 7.71 mmol). The resultant mixture was stirred at room temperature overnight. The reaction was complete as indicated by analytical LC/MS (TFA method). This was concentrated to remove methanol and then neutralized with 1 N HCl to pH=4-5. The mixture was concentrated to afford the title compound which was used in next step without further purification.

Example 122B

Trans-2-methyl-8-(piperidine-1-carbonyl)-1,2,3,3a,4,5-hexahydrobenzo[c]pyrrolo[3,4-c]azepin-6(10bH)-one A 20 mL vial were charged with Example 122A (100 mg, 0.384 mmol), 2-(1H-benzo[d][1,2,3]triazol-1-yl)-1,1,3,3-tetramethylisouronium tetrafluoroborate (185 mg, 0.576 mmol), triethylamine (117 mg, 1.153 mmol), piperidine (39.3 mg, 0.461 mmol) and 1.5 mL of N,N-dimethylformamide. The reaction was stirred at room temperature overnight. The reaction was complete as indicated by analytical LC/MS (TFA method). The reaction mixture was filtered and first purified by reverse phase HPLC, and then purified again by silica gel flash column chromatography with 10-20% methanol in dichloromethane to afford the title compound. $^1$H NMR (500 MHz, DMSO-d$_6$) δ ppm 10.26 (d, J=66.5, 1H), 8.17 (t, J=4.9, 1H), 7.63 (s, 1H), 7.53 (d, J=7.8, 1H), 7.26 (m, 1H), 4.01 (s, 1H), 3.82-3.46 (m, 4H), 3.14 (d, J=25.9, 3H), 2.95 (d, J=25.5, 4H), 2.64 (m, 1H), 2.34 (m, 1H), 1.56 (dd, J=57.6, 25.7, 7H). MS (ESI+) m/z 328.6 [M+H]$^+$.

Example 123

Trans-8-phenethoxy-1,2,3,3a,4,5-hexahydrobenzo[c]pyrrolo[3,4-c]azepin-6(10bH)-one Example 121 (146.4 mg, 0.355 mmol) dissolved in trifluoroethanol (10 mL) was added to 20% Pd(OH)$_2$/carbon (water wet, 29.3 mg, 0.208 mmol) in a 50 mL pressure bottle and stirred for 2 hours under a hydrogen atmosphere (30 psi) and 50° C. Then the mixture was cooled and filtered through a nylon membrane. The obtained solution was concentrated, and the residue was triturated with dichloromethane to give the title compound. $^1$H NMR (300 MHz, DMSO-d$_6$) δ ppm 8.88 (d, J=31.0, 2H), 8.07 (dd, J=6.3, 3.9, 1H), 7.44-6.94 (m, 8H), 4.22 (td, J=6.7, 1.5, 2H), 3.59 (m, 1H), 3.56-3.36 (m, 2H), 3.21-2.99 (m, 5H), 2.88 (s, 1H), 2.29-2.10 (m, 1H); MS (ESI+) m/z 323.5 [M+H]$^+$.

Example 124

Trans-8-(3-fluorophenethoxy)-1,2,3,3a,4,5-hexahydrobenzo[c]pyrrolo[3,4-c]azepin-6(10bH)-one The title compound was prepared according to the procedure outlined in Example 123 substituting Example 119 for Example 121. $^1$H NMR (500 MHz, DMSO-d$_6$) δ ppm 9.03-8.91 (m, 2H), 8.09-8.07 (m, 1H), 7.38-7.31 (m, 1H), 7.22-7.13 (m, 4H), 7.10-7.01 (m, 2H), 4.30-4.18 (m, 2H), 3.65-3.57 (m, 1H), 3.55-3.38 (m, 3H), 3.19-3.09 (m, 2H), 3.06 (t, J=6.6, 3H), 2.25-2.13 (m, 1H); MS (ESI+) m/z 341.6 [M+H]$^+$.

Example 125

Trans-N,2-dimethyl-6-oxo-1,2,3,3a,4,5,6,10b-octahydrobenzo[c]pyrrolo[3,4-c]azepine-8-carboxamide The title compound was prepared according to the procedure outlined in Examples 122 substituting methanamine for piperidine. $^1$H NMR (400 MHz, DMSO-d$_6$) δ ppm 8.63-8.56 (m, 1H), 8.22-8.14 (m, 2H), 7.96 (dd, J=7.9, 2.0, 1H), 7.30 (d, J=8.0, 1H), 3.62 (d, J=8.2, 4H), 3.27-2.96 (m, 3H), 2.82 (s, 3H), 2.79 (d, J=4.5, 3H), 2.42 (m, 1H); MS (ESI-0 m/z 291.3 [M+NH4]$^+$.

Example 126

Trans-2-methyl-6-oxo-N-phenethyl-1,2,3,3a,4,5,6,10b-octahydrobenzo[c]pyrrolo[3,4-c]azepine-8-carboxamide The title compound was prepared according to the procedure outlined in Example 122 substituting 2-phenylethanamine for piperidine. $^1$H NMR (400 MHz, DMSO-d$_6$) δ ppm 8.73 (t, J=5.6, 1H), 8.22-8.16 (m, 2H), 7.96 (dd, J=7.9, 2.0, 1H), 7.32-7.26 (m, 3H), 7.27-7.16 (m, 3H), 3.69 (m, 2H), 3.54 (m, 3H), 3.19-3.02 (m, 4H), 2.94-2.81 (m, 5H), 2.44 (m, 1H); MS (ESI+) m/z 364.9 [M+H]$^+$.

Example 127

Trans-2-methyl-6-oxo-N-(3-(trifluoromethyl)phenethyl)-1,2,3,3a,4,5,6,10b-octahydrobenzo[e]pyrrolo[3,4-c]azepine-8-carboxamide The title compound was prepared according to the procedure outlined in Example 122 substituting 2-(3-(trifluoromethyl)phenyl)ethanamine for piperidine. $^1$H NMR (400 MHz, DMSO-d$_6$) δ ppm 8.77-8.70 (m, 1H), 8.22-8.14 (m, 2H), 7.96-7.90 (m, 1H), 7.62-7.48 (m, 4H), 7.33-7.26 (m, 1H), 3.68-3.59 (m, 1H), 3.53 (dt, J=6.6, 5.3, 3H), 3.21-3.10 (m, 4H), 3.00-2.93 (m, 3H), 2.87-2.79 (m, 3H), 2.47-2.37 (m, 1H); MS (ESI+) m/z 432.7 [M+H]$^+$.

Example 128

Trans-2-methyl-6-oxo-N-phenyl-1,2,3,3a,4,5,6,10b-octahydrobenzo[c]pyrrolo[3,4-c]azepine-8-carboxamide The title compound was prepared according to the procedure outlined in Example 122 substituting aniline for piperidine. $^1$H NMR (400 MHz, DMSO-d$_6$) δ ppm 10.37 (s, 1H), 8.40 (s, 1H), 8.21-8.14 (m, 1H), 8.06 (dd, J=8.0, 1.9, 1H), 7.78 (t, J=7.5, 2H), 7.35 (t, J=8.0, 3H), 7.11 (t, J=7.4, 1H), 3.46-3.30 (m, 4H), 3.27-3.10 (m, 3H), 2.81 (t, J=9.3, 1H), 2.56 (s, 3H), 2.32 (dd, J=15.3, 9.2, 1H); MS (ESI+) m/z 336.8 [M+H]$^+$.

Example 129

Trans-methyl 2-benzyl-6-oxo-1,2,3,3a,4,5,6,10b-octahydrobenzo[c]pyrrolo[3,4-c]azepine-8-carboxylate The title compound was prepared using the procedures described in Examples 55B-55D substituting dimethyl 4-bromoisophthalate for methyl-2-bromo-5-fluorobenzoate in Example 55B. $^1$H NMR (300 MHz, DMSO-d$_6$) δ ppm 8.40 (bs, 1H), 8.12 (bs, 1H), 8.02-7.94 (m, 1H), 7.38-7.22 (m, 6H), 3.88-3.81 (m, 3H), 3.71 (d, J=13.2, 2H), 3.29-2.96 (m, 5H), 2.79-2.52 (m, 2H), 2.41-2.13 (m, 1H). MS (ESI+) m/z 351.8 [M+H]$^+$.

Example 130

Cis-2-benzyl-8-methoxy-1,2,3,3a,4,5-hexahydrobenzo[c]pyrrolo[3,4-c]azepin-6(10bH)-one The title compound was prepared according to the procedure outlined in Examples 45A-C substituting methyl 2-bromo-5-methoxybenzoate for methyl 2-bromo-5-chlorobenzoate in Example 45A (10:1 trans/cis isomers). The title compound was separated from the corresponding trans isomer by flash chromatography on silica gel (1-15% methanol/dichloromethane). $^1$H NMR (500 MHz, DMSO-d$_6$) δ ppm 8.19 (t, J=6.1, 1H), 7.31 (d, J=4.4, 4H), 7.25-7.20 (m, 2H), 7.10 (d, J=2.8, 1H), 6.97 (dd, J=8.4, 2.9, 1H), 3.76 (s, 3H), 3.64-3.53 (m, 2H), 3.49 (td, J=10.6, 7.3, 1H), 3.07 (dd, J=9.5, 7.7, 1H), 2.99 (ddd, J=14.4, 5.5, 2.7, 1H), 2.87 (t, J=7.8, 1H), 2.82-2.67 (m, 2H), 2.48-2.42 (m, 1H), 2.15 (m, 1H); MS (ESI+) m/z 323.2 [M+H]$^+$.

Example 131

Trans-8-(4-methoxyphenyl)-2-methyl-1,2,3,3a,4,5-hexahydrobenzo[c]pyrrolo[3,4-c]azepin-6(10bH)-one The title compound was prepared according to the procedure outlined in Example 75 substituting 4-methoxyphenylboronic acid for 4-fluorophenylboronic acid. $^1$H NMR (300 MHz, DMSO-$d_6$) δ ppm 8.02 (m, 2H), 7.69 (dd, J=8.0, 2.1, 1H), 7.63-7.57 (m, 2H), 7.22 (d, J=8.1, 1H), 7.07-7.00 (m, 2H), 3.80 (s, 3H), 3.26-3.02 (m, 5H), 2.94-2.67 (m, 5H), 2.25 (d, J=9.2, 1H); MS (ESI+) m/z 323.2 [M+H]$^+$.

Example 132

Trans-2-methyl-8-(3-(trifluoromethoxy)phenyl)-1,2,3,3a,4,5-hexahydrobenzo[c]pyrrolo[3,4-c]azepin-6(10bH)-one The title compound was prepared according to the procedure outlined in Example 75 substituting 3-(trifluoromethoxy)phenylboronic acid for 4-fluorophenylboronic acid. $^1$H NMR (300 MHz, DMSO-$d_6$) δ ppm 8.09 (m, 2H), 7.81 (dd, J=8.0, 2.1, 1H), 7.73 (d, J=8.1, 1H), 7.62 (dd, J=10.5, 5.3, 2H), 7.43-7.36 (m, 1H), 7.29 (d, J=8.0, 1H), 3.29-3.08 (m, 5H), 2.90 (m, 4H), 2.75 (dd, J=13.4, 5.4, 1H), 2.27 (m, 1H); MS (ESI+) m/z 377.2 [M+H]$^+$.

Example 133

Trans-8-(3-methoxyphenyl)-2-methyl-1,2,3,3a,4,5-hexahydrobenzo[c]pyrrolo[3,4-c]azepin-6(10bH)-one The title compound was prepared according to the procedure outlined in Example 75 substituting 3-methoxyphenylboronic acid for 4-fluorophenylboronic acid. $^1$H NMR (300 MHz, DMSO-$d_6$) δ ppm 8.05 (dd, J=7.3, 2.9, 2H), 7.74 (dd, J=8.0, 2.1, 1H), 7.39 (t, J=7.9, 1H), 7.28-7.14 (m, 3H), 6.95 (dd, J=7.9, 2.3, 1H), 3.82 (s, 3H), 3.36-2.96 (m, 4H), 2.70 (m, 4H), 2.44 (s, 3H), 2.26 (m, 1H); MS (ESI+) m/z 323.2 [M+H]$^+$.

Example 134

Trans-8-(3-isobutoxyphenyl)-2-methyl-1,2,3,3a,4,5-hexahydrobenzo[c]pyrrolo[3,4-c]azepin-6(10bH)-one The title compound was prepared according to the procedure outlined in Example 75 substituting 3-isobutoxyphenylboronic acid for 4-fluorophenylboronic acid. $^1$H NMR (300 MHz, DMSO-$d_6$) δ ppm 8.05 (d, J=2.0, 2H), 7.74 (dd, J=8.0, 2.1, 1H), 7.37 (t, J=7.9, 1H), 7.22 (dd, J=12.6, 8.0, 2H), 7.18-7.13 (m, 1H), 6.94 (dd, J=7.9, 2.3, 1H), 3.82 (d, J=6.5, 2H), 3.37-3.19 (m, 6H), 3.18-3.00 (m, 3H), 2.87-2.67 (m, 4H), 2.47 (s, 3H), 2.33-2.20 (m, 1H), 2.02 (dq, J=13.1, 6.5, 1H). MS (ESI+) m/z 365.3 [M+H]$^+$.

Example 135

Cis-8-methoxy-1,2,3,3a,4,5-hexahydrobenzo[c]pyrrolo[3,4-c]azepin-6(10bH)-one

The title compound was prepared according to the procedure outlined in Example 123 substituting Example 130 for Example 121. $^1$H NMR (500 MHz, DMSO-$d_6$) δ ppm 8.15 (t, J=3.5, 1H), 7.19 (d, J=8.4, 1H), 7.10 (dd, J=11.2, 1.9, 1H), 7.01-6.96 (m, 1H), 3.76 (s, 3H), 3.24-3.15 (m, 3H), 3.06-2.97 (m, 2H), 2.89-2.81 (m, 1H), 2.80-2.75 (m, 1H), 2.65-2.56 (m, 1H), 2.41 (t, J=10.6, 1H); MS (ESI+) m/z 233.1 [M+H]$^+$.

Example 136

Trans-2-benzyl-8-(1,3,4-oxadiazol-2-yl)-1,2,3,3a,4,5-hexahydrobenzo[c]pyrrolo[3,4-c]azepin-6(10bH)-one

Example 136A

Trans-2-benzyl-6-oxo-1,2,3,3a,4,5,6,10b-octahydrobenzo[c]pyrrolo[3,4-c]azepine-8-carboxylic acid The title compound was prepared according to the procedure outlined in Example 122A substituting Example 129 for Example 88.

Example 136B

Trans-2-benzyl-6-oxo-1,2,3,3a,4,5,6,10b-octahydrobenzo[c]pyrrolo[3,4-c]azepine-8-carbohydrazide To Example 136A (300 mg, 0.892 mmol) in dichloroethane (3 mL) was added thionyl chloride (1.3 mL, 18 mmol). The reaction mixture was heated to reflux for 6 hours at which time, analytical LC/MS (TFA method) showed the reaction was complete. The reaction mixture was cooled and concentrated. The residue obtained was added to 3 mL of dichloroethane, and then the mixture was cooled down to 0° C. Hydrazine (0.28 mL, 8.92 mmol) was and added, and the resultant mixture was stirred at 0° C. for 15 minutes, and then at room temperature for 3 hours at which time LC/MS showed the reaction was complete. The reaction mixture was filtered followed with a dichloromethane wash. The filtrate was concentrated and the residue was dissolved in ethyl acetate. The mixture was washed with water and separated. The ethyl acetate layer was concentrated to afford a first batch of the title compound. The aqueous phase was concentrated, and the residue was dissolved in dichloromethane/ethyl acetate (volume ratio 1:1) and filtered. The filtrate was concentrated to give a second batch of the title compound.

Example 136C

Trans-2-benzyl-8-(1,3,4-oxadiazol-2-yl)-1,2,3,3a,4,5-hexahydrobenzo[c]pyrrolo[3,4-c]azepin-6(10bH)-one To Example 136B (114.7 mg, 0.327 mmol) was added triethyl orthoformate (3 mL, 18 mmol) and 1.25 mg of p-toluenesulfonic acid monohydrate (0.655 μmol). The mixture was heated up to 120° C. for 6 hours. TLC (dichloromethane/methanol (9:1) with 0.5% triethylamine) showed the reaction was complete. The reaction mixture was cooled and then concentrated. Purification by silica gel flash column chromatography with 0-10% methanol in dichloromethane (0.5% triethylamine) to afford the title compound. $^1$H NMR (500 MHz, DMSO-$d_6$) δ ppm 9.36 (s, 1H), 8.44 (d, J=1.9, 1H), 8.19 (t, J=3.7, 1H), 8.06 (dd, J=8.0, 1.9, 1H), 7.42-7.31 (m, 5H), 7.26 (t, J=6.9, 1H), 3.77 (ddd, J=45.5, 13.2, 6.1, 2H), 3.26 (ddd, J=14.0, 6.6, 3.3, 1H), 3.21 (dd, J=8.6, 6.5, 1H), 3.17 (s, 1H), 3.12 (ddd, J=13.8, 6.5, 4.7, 1H), 3.06-3.00 (m, 1H), 2.75 (t, J=8.8, 1H), 2.63 (t, J=8.6, 1H), 2.29-2.22 (m, 1H); MS (ESI+) m/z 361.2 [M+H]+.

Example 137

Trans-8-(2-methoxyphenyl)-2-methyl-1,2,3,3a,4,5-hexahydrobenzo[c]pyrrolo[3,4-c]azepin-6(10bH)-one The title compound was prepared according to the procedure outlined in Example 75 substituting 2-methoxyphenylboronic acid for 4-fluorophenylboronic acid. $^1$H NMR (500 MHz, DMSO-d$_6$) δ ppm 8.05 (m, 1H), 7.84 (d, J=1.8, 1H), 7.59 (dd, J=7.9, 1.9, 1H), 7.40-7.34 (m, 1H), 7.33-7.27 (m, 1H), 7.22 (d, J=8.0, 1H), 7.14 (d, J=7.9, 1H), 7.04 (t, J=7.4, 1H), 3.77 (d, J=3.7, 3H), 3.26-3.10 (m, 6H), 2.94 (m, 1H), 2.70 (s, 3H), 2.38 (m, 1H); MS (ESI+) m/z 323.2 [M+H]+.

Example 138

Trans-8-(4-isopropylphenyl)-2-methyl-1,2,3,3a,4,5-hexahydrobenzo[c]pyrrolo[3,4-c]azepin-6(10bH)-one The title compound was prepared according to the procedure outlined in Example 75 substituting 4-isopropylphenylboronic acid for 4-fluorophenylboronic acid. $^1$H NMR (500 MHz, DMSO-d$_6$) δ ppm 8.06 (m, 1H), 8.03 (d, J=2.0, 1H), 7.73 (dd, J=8.0, 2.1, 1H), 7.61-7.56 (m, 2H), 7.35 (d, J=8.2, 2H), 7.25 (d, J=8.0, 1H), 3.37-3.20 (m, 5H), 3.20-3.09 (m, 4H), 2.97-2.86 (m, 4H), 2.78 (t, J=9.2, 1H), 2.54 (s, 3H), 2.34-2.25 (m, 1H); MS (ESI+) m/z 335.3 [M+H]+.

Example 139

Trans-8-(4-ethylphenyl)-2-methyl-1,2,3,3a,4,5-hexahydrobenzo[c]pyrrolo[3,4-c]azepin-6(10bH)-one The title compound was prepared according to the procedure outlined in Example 75 substituting 4-ethylphenylboronic acid for 4-fluorophenylboronic acid. $^1$H NMR (500 MHz, DMSO-d$_6$) δ ppm 8.06 (m, 1H), 8.03 (d, J=2.1, 1H), 7.73 (dd, J=8.0, 2.1, 1H), 7.58 (d, J=8.2, 2H), 7.31 (d, J=8.2, 2H), 7.25 (d, J=8.0, 1H), 3.37-3.21 (m, 3H), 3.19-3.08 (m, 4H), 2.94-2.84 (m, 4H), 2.77 (t, J=9.1, 1H), 2.53 (s, 3H), 2.29 (dd, J=20.4, 11.0, 1H); MS (ESI+) m/z 321.2 [M+H]+.

Example 140

Trans-2-methyl-8-(4-(trifluoromethoxy)phenyl)-1,2,3,3a,4,5-hexahydrobenzo[c]pyrrolo[3,4-c]azepin-6(10bH)-one The title compound was prepared according to the procedure outlined in Example 75 substituting 4-(trifluoromethoxy)phenylboronic acid for 4-fluorophenylboronic acid. $^1$H NMR (500 MHz, DMSO-d$_6$) δ ppm 8.08 (m, 1H), 7.81-7.78 (m, 2H), 7.78-7.75 (m, 1H), 7.46 (d, J=8.2, 2H), 7.28 (d, J=8.0, 1H), 3.37-3.21 (m, 1H), 3.16-3.09 (m, 2H), 3.08-3.02 (m, 1H), 2.80 (dt, J=11.8, 8.0, 3H), 2.75-2.68 (m, 1H), 2.47 (s, 3H), 2.31-2.23 (m, 1H); MS (ESI+) m/z 377.2 [M+H]+.

Example 141

Trans-8-amino-2-benzyl-1,2,3,3a,4,5-hexahydrobenzo[c]pyrrolo[3,4-c]azepin-6(10bH)-one The title compound was prepared according to the procedure outlined in Examples 45A-C substituting methyl 2-bromo-5-nitrobenzoate for methyl 2-bromo-5-chlorobenzoate in Example 45A (7:1 trans/cis isomers). The title compound was separated from the corresponding cis isomer by flash chromatography on silica gel eluting with 0-7% methanol in dichloromethane containing 0.5% triethylamine $^1$H NMR (300 MHz, DMSO-d$_6$) δ ppm 7.74 (m, 1H), 7.37-7.29 (m, 4H), 7.28-7.20 (m, 1H), 7.02 (d, J=2.5, 1H), 6.77 (d, J=8.2, 1H), 6.59 (dd, J=8.1, 2.5, 1H), 5.04 (s, 2H), 3.75 (dd, J=30.4, 13.3, 2H), 3.20-2.89 (m, 5H), 2.76-2.66 (m, 1H), 2.58 (t, J=9.0, 1H), 2.16-2.00 (m, 1H). MS (ESI+) m/z 308.4 [M+H]+.

Example 142

Cis-8-amino-2-benzyl-1,2,3,3a,4,5-hexahydrobenzo[c]pyrrolo[3,4-c]azepin-6(10bH)-one The title compound was prepared according to the procedure outlined in Examples 45A-C substituting methyl 2-bromo-5-nitrobenzoate for methyl 2-bromo-5-chlorobenzoate in Example 45A (7:1 trans/cis isomers). The title compound was separated from the corresponding trans isomer by flash chromatography on silica gel eluting with 0-7% methanol in dichloromethane containing 0.5% triethylamine $^1$H NMR (300 MHz, DMSO-d$_6$) δ ppm 7.96 (t, J=6.0, 1H), 7.31 (m, 4H), 7.28-7.18 (m, 1H), 6.90 (d, J=8.2, 1H), 6.83 (d, J=2.5, 1H), 6.56 (dd, J=8.1, 2.5, 1H), 5.12 (s, 2H), 3.56 (m, 2H), 3.12-2.93 (m, 3H), 2.73 (m, 4H), 2.09 (m, 1H); MS (ESI+) m/z 308.4 [M+H]+.

Example 143

Trans-2-methyl-8-(pyridin-3-yl)-1,2,3,3a,4,5-hexahydrobenzo[c]pyrrolo[3,4-c]azepin-6(10bH)-one The title compound was prepared according to the procedure outlined in Example 75 substituting pyridin-3-ylboronic acid for 4-fluorophenylboronic acid. $^1$H NMR (400 MHz, DMSO-d$_6$) δ ppm 10.33 (d, J=59.8, 1H), 9.05 (d, J=2.0, 1H), 8.71 (dd, J=5.1, 1.4, 1H), 8.38 (d, J=8.0, 1H), 8.22 (t, J=4.8, 1H), 8.04 (dd, J=14.3, 2.0, 1H), 8.00-7.92 (m, 1H), 7.72 (dd, J=8.0, 5.0, 1H), 7.39 (dd, J=25.5, 8.0, 1H), 3.80-3.59 (m, 2H), 3.58-3.31 (m, 2H), 3.28-3.08 (m, 2H), 3.06-2.91 (m, 2H), 2.66 (d, J=7.1, 1H), 2.41-2.30 (m, 1H), 1.64 (d, J=10.2, 1H); MS (ESI+) m/z 294.6 [M+H]+.

Example 144

Trans-8-amino-1,2,3,3a,4,5-hexahydrobenzo[c]pyrrolo[3,4-c]azepin-6(10bH)-one

The title compound was prepared according to the procedure outlined in Example 123 substituting Example 141 for Example 121. $^1$H NMR (300 MHz, DMSO-d$_6$) δ ppm 7.82 (t, J=4.8, 1H), 6.90 (d, J=2.4, 1H), 6.84 (d, J=8.2, 1H), 6.63 (dd, J=8.2, 2.5, 1H), 5.14 (s, 2H), 3.36-3.10 (m, 4H), 3.04 (dd, J=11.5, 6.3, 2H), 2.92 (td, J=11.8, 6.6, 1H), 2.81-2.71 (m, 1H), 2.01 (m, 1H); MS (ESI+) m/z 218.3 [M+H]+.

Example 145

Cis-8-amino-1,2,3,3a,4,5-hexahydrobenzo[c]pyrrolo[3,4-c]azepin-6(10bH)-one

The title compound was prepared according to the procedure outlined in Example 123 substituting Example 142 for Example 121. $^1$H NMR (500 MHz, DMSO-$d_6$) δ ppm 7.95 (t, J=6.0, 1H), 6.92 (d, J=8.1, 1H), 6.84 (t, J=9.0, 1H), 6.60 (dd, J=8.1, 2.5, 1H), 5.18 (s, 2H), 3.18 (m, 5H), 3.01 (ddd, J=14.4, 5.5, 3.0, 1H), 2.94 (dd, J=11.7, 6.7, 1H), 2.82-2.75 (m, 1H), 2.62 (m, 1H); MS (ESI+) m/z 218.6 [M+H]$^+$.

Example 146

Trans-8-(3-fluorobenzyloxy)-1,2,3,3a,4,5-hexahydrobenzo[c]pyrrolo[3,4-c]azepin-6(10bH)-one To Example 227F (80 mg, 0.251 mmol) was added 3-fluorobenzyl alcohol (41.2 mg, 0.327 mmol), di-tert-butyl azodicarboxylate (DBAD, 87 mg, 0.377 mmol), PS-triphenylphosphine (173 mg, 0.553 mmol, 3.2 mmol/g) and 2 mL of dry tetrahydrofuran. The reaction mixture was stirred at room temperature overnight. The reaction was complete as indicated by LC/MS (TFA method). The reaction mixture was filtered followed by a methanol wash. The filtrate was concentrated, and to the residue was added 0.3 mL of 1,4-dioxane and 0.4 mL of 4 M HCl in dioxane. The reaction mixture was stirred at room temperature for 3 hours and LC/MS indicated complete reaction at that time. The reaction mixture was concentrated, and the crude was purified by reverse phase HPLC to afford the title compound as the trifluoroacetic acid salt. $^1$H NMR (500 MHz, DMSO-$d_6$) δ ppm 9.02 (m, 2H), 8.14-8.08 (m, 1H), 7.48-7.41 (m, 1H), 7.32-7.25 (m, 3H), 7.22-7.13 (m, 3H), 5.19 (s, 2H), 3.49-3.39 (m, 3H), 3.22-3.12 (m, 2H), 3.10-3.03 (m, 1H), 2.99-2.89 (m, 1H), 2.27-2.16 (m, 1H); MS (ESI+) m/z 327.5 [M+H]$^+$.

Example 147

Trans-8-(2-fluorobenzyloxy)-1,2,3,3a,4,5-hexahydrobenzo[c]pyrrolo[3,4-c]azepin-6(10bH)-one The title compound was prepared according to the procedure outlined in Example 146 substituting 2-fluorobenzyl alcohol for 3-fluorobenzyl alcohol. $^1$H NMR (400 MHz, DMSO-$d_6$) δ ppm 8.99 (d, J=46.0, 2H), 8.10 (dd, J=6.6, 3.8, 1H), 7.56 (td, J=7.5, 1.6, 1H), 7.47-7.39 (m, 1H), 7.30-7.13 (m, 5H), 5.18 (s, 2H), 3.59-3.37 (m, 3H), 3.22-3.02 (m, 3H), 2.94 (dt, J=17.7, 9.6, 1H), 2.21 (m, 1H); MS (ESI+) m/z 327.5 [M+H]$^+$.

Example 148

Trans-8-(2-(trifluoromethyl)benzyloxy)-1,2,3,3a,4,5-hexahydrobenzo[c]pyrrolo[3,4-c]azepin-6(10bH)-one The title compound was prepared according to the procedure outlined in Example 146 substituting 2-(trifluoromethyl)benzyl alcohol for 3-fluorobenzyl alcohol. $^1$H NMR (400 MHz, DMSO-$d_6$) δ ppm 8.96 (d, J=45.9, 2H), 8.11 (dd, J=6.4, 3.9, 1H), 7.84-7.69 (m, 3H), 7.60 (t, J=7.5, 1H), 7.27 (d, J=2.7, 1H), 7.21 (d, J=8.5, 1H), 7.14 (dd, J=8.5, 2.7, 1H), 5.28 (s, 2H), 3.67-3.56 (m, 2H), 3.22-3.02 (m, 2H), 2.93 (t, J=12.2, 1H), 2.30-2.15 (m, 1H); MS (ESI+) m/z 377.4 [M+H]$^+$.

Example 149

Trans-8-((S)-1-phenylpropan-2-yloxy)-1,2,3,3a,4,5-hexahydrobenzo[c]pyrrolo[3,4-c]azepin-6(10bH)-one The title compound was prepared according to the procedure outlined in Example 123 substituting Example 120 for Example 121. $^1$H NMR (500 MHz, DMSO-$d_6$) δ ppm 8.10-7.90 (m, 1H), 7.30-7.27 (m, 4H), 7.22-7.16 (m, 2H), 7.07 (d, J=8.1, 1H), 6.99 (dd, J=8.4, 2.6, 1H), 4.73-4.63 (m, 1H), 3.30-3.21 (m, 2H), 3.21-3.14 (m, 1H), 3.10-3.01 (m, 3H), 3.01-2.90 (m, 2H), 2.90-2.81 (m, 1H), 2.77-2.67 (m, 1H), 2.09-1.96 (m, 1H), 1.22 (dd, J=6.0, 2.8, 3H); MS (ESI+) m/z 337.4 [M+H]$^+$.

Example 150

Trans-84(R)-1-phenylethoxy)-1,2,3,3a,4,5-hexahydrobenzo[c]pyrrolo[3,4-c]azepin-6(10bH)-one The title compound was prepared according to the procedure outlined in Example 146 substituting (S)-(−)-1-phenylethanol for 3-fluorobenzyl alcohol. The crude material was purified by reverse phase HPLC to afford the title compound as the trifluoroacetic acid salt. $^1$H NMR (400 MHz, DMSO-$d_6$) δ ppm 8.97 (d, J=48.5, 2H), 8.04 (m, 1H), 7.41 (m, 2H), 7.38-7.31 (m, 2H), 7.29-7.22 (m, 1H), 7.16 (t, J=2.4, 1H), 7.09 (dd, J=8.5, 3.6, 1H), 7.07-6.99 (m, 1H), 5.60-5.48 (m, 1H), 3.64-3.52 (m, 1H), 3.51-3.35 (m, 2H), 3.16-2.85 (m, 4H), 2.25-2.09 (m, 1H), 1.54 (dt, J=17.9, 8.9, 3H); MS (ESI+) m/z 323.5 [M+H]$^+$.

Example 151

Trans-9-benzyl-7,7a,8,9,10,10a-hexahydropyrido[2,3-e]pyrrolo[3,4-c]azepin-5(6H)-one The title compound was prepared according to the procedure outlined in Examples 154A-C substituting methyl 2-bromonicotinate for methyl 3-bromopicolinate as starting material. $^1$H NMR (400 MHz, DMSO-$d_6$) δ ppm 8.52 (dd, J=4.7, 1.7, 1H), 8.27 (dd, J=7.9, 1.7, 1H), 8.13 (s, 1H), 7.39-7.21 (m, 6H), 3.70 (dd, J=30.6, 13.0, 2H), 3.47 (dd, J=17.2, 9.0, 1H), 3.41-3.35 (m, 2H), 3.17 (ddd, J=13.0, 9.6, 3.1, 1H), 3.08-3.01 (m, 1H), 2.80 (t, J=8.6, 1H), 2.55 (d, J=8.1, 1H), 2.29 (dd, J=14.2, 8.4, 1H); MS (ESI+) m/z 294.4 [M+H]$^+$.

Example 152

Trans-2-benzyl-1,2,3,3a,4,5-hexahydropyrido[3,4-e]pyrrolo[3,4-c]azepin-6(10bH)-one The title compound was prepared according to the procedure outlined in Examples 154A-C substituting methyl 3-bromoisonicotinate for methyl 3-bromopicolinate as starting material. $^1$H NMR (300 MHz, DMSO-$d_6$) δ ppm 8.56 (d, J=5.0, 1H), 8.40 (s, 1H), 8.25 (t, J=1.2, 1H), 7.78 (d, J=5.0, 1H), 7.40-7.21 (m, 5H), 3.75 (dd, J=38.8, 13.2, 2H), 3.25-3.10 (m, 4H), 3.08-2.96 (m, 1H), 2.77-2.61 (m, 1H), 2.64 (dd, J=33.9, 9.0, 1H), 2.30-2.20 (m, 1H); MS (ESI+) m/z 294.6 [M+H]$^+$.

Example 153

Trans-7,7a,8,9,10,10a-hexahydropyrido[2,3-e]pyrrolo[3,4-c]azepin-5(6H)-one

The title compound was prepared according to the procedure outlined in Examples 157 substituting Example 151 for Example 154. ¹H NMR (400 MHz, DMSO-d₆) δ ppm 8.62 (dd, J=4.9, 1.7, 1H), 8.27 (m, 1H), 8.15 (dd, J=7.8, 1.7, 1H), 7.47 (dd, J=7.8, 4.8, 2H), 3.77 (t, J=11.3, 1H), 3.67 (dd, J=11.0, 7.0, 1H), 3.62-3.49 (m, 3H), 3.25 (dd, J=8.7, 4.4, 1H), 3.03 (t, J=11.3, 1H), 2.43 (m, 1H); MS (ESI+) m/z 204.0 [M+H]⁺.

Example 154

Trans-2-benzyl-1,2,3,3a,4,5-hexahydropyrido[3,2-e] pyrrolo[3,4-c]azepin-6(10bH)-one Example 154A (E)-Methyl 3-(2-cyanovinyl)picolinate A microwave vial were charged with methyl 3-bromopicolinate (2.84 g, 13.15 mmol), acrylonitrile (0.907 g, 17.09 mmol), N,N-dicyclohexylmethylamine (3.08 g, 15.78 mmol), tri-tert-butylphosphine (0.789 mL, 0.789 mmol, 1 M in toluene), tris(dibenzylideneacetone)dipalladium (0) (0.361 g, 0.394 mmol) and 10 mL of 1,4-dioxane under nitrogen. The reaction mixture was capped and heated to 80° C. in an oil bath for 20 hours. The reaction mixture was diluted with ethyl acetate and filtered. The filtrate was concentrated, and the residue was triturated with ethyl acetate to give the title compound as a solid as the first batch. ¹H NMR analysis showed only the trans isomer. The mother liquor was concentrated, and the residue was purified by silica gel flash column chromatography eluting with 20-50% ethyl acetate in hexane to give a second batch of the title compound. ¹H NMR analysis showed indicated only trans product. ¹H NMR (300 MHz, DMSO-d₆) δ ppm 8.70 (dd, J=4.6, 1.6, 1H), 8.27 (dd, J=8.1, 1.6, 1H), 8.04-7.94 (m, 1H), 7.71 (dd, J=8.1, 4.6, 1H), 6.53 (d, J=16.5, 1H), 3.91 (s, 3H).

Example 154B

Trans-methyl 3-(1-benzyl-4-cyanopyrrolidin-3-yl)picolinate

Example 154A (1.26 g, 6.70 mmol), trifluoroacetic acid (5.16 µL, 0.067 mmol) and dichloromethane (15 mL) were combined. N-Benzyl-1-methoxy-N-((trimethylsilyl)methyl) methanamine (2.06 mL, 8.03 mmol) was added dropwise. The reaction was stirred at room temperature overnight, and LC/MS showed the reaction to be done. The reaction mixture was concentrated and purified by silica gel flash column chromatography with 20-50% ethyl acetate in hexane to provide the title compound.

Example 154C

Trans-2-benzyl-1,2,3,3a,4,5-hexahydropyrido[3,2-e] pyrrolo[3,4-c]azepin-6(10bH)-on Example 154B (1.35 g, 4.20 mmol) and 7 M ammonia-methanol (7.50 mL) were added to Raney®-nickel, water wet, A-7000 (6.75 g, 115 mmol) in a 50 mL pressure bottle. The reaction mixture was stirred for 16 hours under hydrogen (30 psi) at room temperature. HPLC indicated no start material. The mixture was filtered through a nylon membrane and concentrated. The residue was triturated with ethyl acetate/hexane to provide the title compound. ¹H NMR (400 MHz, DMSO-d₆) δ ppm 8.53 (dd, J=4.7, 1.5, 1H), 8.25-8.18 (m, 1H), 7.65-7.60 (m, 1H), 7.41 (dd, J=7.6, 4.5, 1H), 7.38-7.29 (m, 4H), 7.24 (ddd, J=8.5, 3.6, 1.8, 1H), 3.80 (dd, J=30.8, 13.4, 2H), 3.19-3.12 (m, 2H), 3.10-3.01 (m, 3H), 2.79 (t, J=8.3, 1H), 2.64 (dd, J=16.8, 6.8, 1H), 2.21-2.12 (m, 1H); MS (ESI+) m/z 294.2 [M+H]⁺.

Example 155

Trans-8-((S)-phenylethoxy)-1,2,3,3a,4,5-hexahydrobenzo[c]pyrrolo[3,4-c]azepin-6(10bH)-one The title compound was prepared according to the procedure outlined in Examples 146 and substituting (R)-(+)-1-phenylethanol for 3-fluorobenzyl alcohol. ¹H NMR (400 MHz, DMSO-d₆) δ ppm 9.00-8.76 (m, 2H), 8.08-7.99 (m, 1H), 7.43-7.38 (m, 2H), 7.38-7.31 (m, 2H), 7.29-7.22 (m, 1H), 7.16 (dd, J=5.0, 2.6, 1H), 7.09 (dd, J=8.6, 3.3, 1H), 7.04 (m, 2), 3.62-3.52 (m, 2), 3.17-2.95 (m, 4H), 2.96-2.83 (m, 1H), 2.23-2.10 (m, 1H), 1.59-1.51 (m, 3H); MS (ESI+) m/z 323.7 [M+H]⁺.

Example 156

Trans-8-((R)-1-phenylpropan-2-yloxy)-1,2,3,3a,4,5-hexahydrobenzo[c]pyrrolo[3,4-c]azepin-6(10bH)-one The title compound was prepared according to the procedure outlined in Examples 146 and substituting (S)-(-)-1-phenylpropan-2-ol for 3-fluorobenzyl alcohol. ¹H NMR (400 MHz, DMSO-d₆) δ ppm 9.03 (d, J=47.2, 2H), 8.12-8.04 (m, 1H), 7.33-7.26 (m, 4H), 7.25-7.17 (m, 1H), 7.17-7.10 (m, 2H), 7.08-7.00 (m, 1H), 4.71 (tt, J=12.4, 6.0, 2H), 3.66-3.56 (m, 1H), 3.56-3.36 (m, 2H), 3.20-3.01 (m, 3H), 3.02-2.80 (m, 3H), 2.27-2.04 (m, 1H), 1.23 (dd, J=6.0, 2.0, 3H); MS (ESI+) m/z 337.5 [M+H]⁺.

Example 157

Trans-1,2,3,3a,4,5-hexahydropyrido[3,2-e]pyrrolo[3,4-c]azepin-6(10bH)-one

Example 154 (690 mg, 2.352 mmol) and trifluoroethanol (10 mL) were added to 20% Pd(OH)₂—C, wet (138 mg, 0.983 mmol) in a 50 mL pressure bottle and stirred under hydrogen (30 psi) at 50° C. The reaction was monitored by HPLC until the reaction was judged complete by the absence of starting material. The mixture was filtered through a nylon membrane and concentrated to give the title compound. ¹H NMR (500 MHz, DMSO-d₆) δ ppm 8.56-8.51 (m, 1H), 8.25 (m, 1H), 7.68 (d, 1H), 7.43 (m, 1H), 3.22-3.02 (m, 5H), 3.02-2.90 (m. 2H), 2.70 (t, J=10.2, 1H), 2.01 (m, 1H); MS (ESI+) m/z 204.2 [M+H]⁺.

Example 158

(3aS,10bS)-8-(4-Methoxyphenyl)-2-methyl-1,2,3,3a,4,5-hexahydrobenzo[c]pyrrolo[3,4-c]azepin-6(10bH)-one Example 158A Trans-8-(4-methoxyphenyl)-2-methyl-1,2,3,3a,4,5-hexahydrobenzo[c]pyrrolo[3,4-c]azepin-6(10bH)-one The title compound was prepared according to the procedure outlined in Example 75, substituting 4-methoxyphenylboronic acid for 4-fluorophenylboronic acid.

Example 158B (3aS,10bS)-8-(4-Methoxyphenyl)-2-methyl-1,2,3,3a,
4,5-hexahydrobenzo[c]pyrrolo[3,4-c]azepin-6
(10bH)-one Example 158A was resolved into pure enantiomers using supercritical fluid chromatography (ChiralPak® AS, 21×250 mm, 5 nm, 10-30% methanol with 0.1% diethyl amine-$CO_2$ gradient over 20 minutes, at 40 mL/minute, retention time=12.05 minutes) to afford the title compound. $^1$H NMR (400 MHz, DMSO-$d_6$) δ ppm 8.04 (d, J=2.1, 1H), 8.01 (m, 1H), 7.67 (dd, J=8.0, 2.1, 1H), 7.63-7.56 (m, 2H), 7.21 (d, J=8.0, 1H), 7.03 (d, J=8.8, 2H), 3.80 (s, 3H), 3.31-3.21 (m, 3H), 3.17-3.06 (m, 2H), 2.95-2.88 (m, 1H), 2.68-2.60 (m, 2H), 2.38 (s, 3H), 2.27-2.15 (m, 1H); MS (ESI+) m/z 323.2 [M+H]$^+$.

Example 159

(3aR,10bR)-8-(4-Methoxyphenyl)-2-methyl-1,2,3,
3a,4,5-hexahydrobenzo[c]pyrrolo[3,4-c]azepin-6
(10bH)-one Example 158A was resolved into pure enantiomers using supercritical fluid chromatography (ChiralPak® AS, 21×250 mm, 5 nm, 10-30% methanol with 0.1% diethyl amine-$CO_2$ gradient over 20 minutes, at 40 mL/minute, retention time=16.87 minutes) to afford the title compound. $^1$H NMR (400 MHz, DMSO-$d_6$) δ ppm 8.04 (d, J=2.2, 1H), 8.04-7.99 (m, 1H), 7.67 (dd, J=7.9, 2.2, 1H), 7.62-7.56 (m, 2H), 7.21 (d, J=8.0, 1H), 7.06-7.00 (m, 2H), 3.80 (s, 3H), 3.30-3.20 (m, 3H), 3.21-3.04 (m, 2H), 2.91 (dd, J=10.4, 8.7, 1H), 2.67-2.60 (m, 2H), 2.38 (s, 3H), 2.28-2.14 (m, 1H); MS (ESI+) m/z 323.2 [M+H]$^+$.

Example 160

(3aS,10bS)-8-(3-Methoxyphenyl)-2-methyl-1,2,3,3a,
4,5-hexahydrobenzo[c]pyrrolo[3,4-c]azepin-6
(10bH)-one

Example 160A

Trans-8-(3-methoxyphenyl)-2-methyl-1,2,3,3a,4,5-
hexahydrobenzo[c]pyrrolo[3,4-c]azepin-6(10bH)-
one The title compound was prepared according to the procedure outlined in Example 75, substituting 3-methoxyphenylboronic acid for 4-fluorophenylboronic acid.

Example 160B (3aS,10bS)-8-(3-Methoxyphenyl)-2-methyl-1,2,3,3a,
4,5-hexahydrobenzo[c]pyrrolo[3,4-c]azepin-6
(10bH)-one Example 160A was resolved into pure enantiomers using supercritical fluid chromatography (ChiralPak® AS, 21×250 mm, 5 nm, 10-30% methanol with 0.1% diethyl amine-$CO_2$ gradient over 20 minutes, at 40 mL/minute, retention time=14.0 minutes) to afford the title compound. $^1$H NMR (400 MHz, DMSO-$d_6$) δ ppm 8.08 (d, J=2.1, 1H), 8.07-8.02 (m, 1H), 7.73 (dd, J=7.9, 2.1, 1H), 7.39 (t, J=7.9, 1H), 7.23 (dd, J=12.3, 7.9, 1H), 7.16 (d, J=2.4, 1H), 6.95 (dd, J=8.2, 2.5, 1H), 3.83 (s, 3H), 3.35-3.23 (m, 3H), 3.18-3.05 (m, 2H), 2.96-2.88 (m, 1H), 2.67-2.61 (m, 1H), 2.38 (s, 3H), 2.37-2.15 (m, 1H); MS (ESI+) m/z 323.2 [M+H]$^+$.

Example 161

(3aR,10bR)-8-(3-Methoxyphenyl)-2-methyl-1,2,3,
3a,4,5-hexahydrobenzo[c]pyrrolo[3,4-c]azepin-6
(10bH)-one Example 160A was resolved into pure enantiomers using supercritical fluid chromatography (ChiralPak® AS, 21×250 mm, 5 nm, 10-30% methanol with 0.1% diethyl amine-$CO_2$ gradient over 20 minutes, at 40 mL/minute, retention time=16.5 minutes) to afford the title compound. $^1$H NMR (500 MHz, DMSO-$d_6$) δ ppm 8.08 (d, J=2.1, 1H), 8.04 (t, J=3.7, 1H), 7.73 (dd, J=7.9, 2.1, 1H), 7.39 (t, J=7.9, 1H), 7.23 (dd, J=15.4, 8.2, 1H), 7.18-7.14 (m, 1H), 6.98-6.92 (m, 1H), 3.82 (s, 3H), 3.32-3.23 (m, 3H), 3.17-3.07 (m, 2H), 2.92 (dd, J=10.3, 8.9, 1H), 2.68-2.60 (m, 1H), 2.38 (s, 3H), 2.27-2.18 (m, 1H); MS (ESI+) m/z 323.2 [M+H]$^+$.

Example 162

(3aS,10bS)-8,10-Difluoro-2-methyl-1,2,3,3a,4,5-
hexahydrobenzo[c]pyrrolo[3,4-c]azepin-6(10bH)-
one The title compound was prepared according to the procedure outlined in Example 68 substituting formaldehyde for methyl 3-formylbenzoate and substituting Example 106 for Example 2. $^1$H NMR (400 MHz, DMSO-$d_6$) δ ppm 8.28 (s, 1H), 7.43-7.31 (m, 2H), 3.29-3.21 (m, 1H), 3.18-2.96 (m, 4H), 2.61 (dd, J=8.7, 2.7, 2H), 2.37 (s, 3H), 2.36-2.27 (m, 1H); MS (ESI+) m/z 253.2 [M+H]$^+$.

Example 163

(3aR,10bS)-8-Fluoro-2,5-dimethyl-1,2,3,3a,4,5-
hexahydrobenzo[c]pyrrolo[3,4-c]azepin-6(10bH)-
one The title compound was prepared according to the procedure outlined in Example 68 substituting formaldehyde for methyl 3-formylbenzoate and substituting (3aR,10bS)-8-fluoro-5-methyl-1,2,3,3a,4,5-hexahydrobenzo[c]pyrrolo[3,4-e]azepin-6(10bH)-one hydrochloride (Example 225B) for Example 2. $^1$H NMR (400 MHz, DMSO-$d_6$) δ ppm 7.46 (dt, J=16.6, 8.3, 1H), 7.27 (td, J=8.5, 2.8, 1H), 7.18 (dd, J=8.5, 5.6, 1H), 3.36 (ddd, J=19.2, 14.5, 5.7, 3H), 3.15-2.92 (m, 5H), 2.71 (dt, J=25.9, 9.0, 2H), 2.41 (d, J=6.1, 3H), 2.24-2.07 (m, 1H); MS (ESI+) m/z 249.1 [M+H]$^+$.

Example 164

Trans-8-(2-fluorobenzyloxy)-2-methyl-1,2,3,3a,4,5-
hexahydrobenzo[c]pyrrolo[3,4-c]azepin-6(10bH)-
one

Example 164A

Trans-8-methoxy-2-methyl-1,2,3,3a,4,5-hexahydrobenzo[c]pyrrolo[3,4-c]azepin-6(10bH)-one The title compound was prepared according to the procedure outlined in Example 88B and Example 88C substituting methyl 2-bromo-5-methoxybenzoate for dimethyl 4-bromoisophthalate.

Example 164B

Trans-8-hydroxy-2-methyl-1,2,3,3a,4,5-hexahydrobenzo[c]pyrrolo[3,4-c]azepin-6(10bH)-one The title compound was prepared according to the procedure outlined in Example 117B substituting Example 164A for Example 117A.

Example 164C

Trans-8-(2-fluorobenzyloxy)-2-methyl-1,2,3,3a,4,5-hexahydrobenzo[c]pyrrolo[3,4-c]azepin-6(10bH)-one The title compound was prepared according to the procedure outlined in Example 118 substituting 2-fluorobenzyl alcohol for (5)-1-phenylpropan-2-ol and substituting Example 164B for Example 117. $^1$H NMR (500 MHz, DMSO-$d_6$) δ ppm 8.14 (dd, J=6.8, 3.9, 1H), 7.56 (td, J=7.6, 1.5, 1H), 7.47-7.40 (m, 1H), 7.29-7.21 (m, 4H), 7.19-7.15 (m, 1H), 5.22-5.15 (m, 2H), 4.27 (dd, J=11.1, 7.7, 1H), 3.82 (dt, J=23.9, 12.4, 2H), 3.64 (td, J=12.6, 7.6, 1H), 3.49-3.41 (m, 1H), 3.29 (s, 3H), 3.21-3.13 (m, 1H), 3.09 (ddd, J=15.2, 7.2, 3.9, 1H), 2.87-2.74 (m, 1H); MS (ESI+) m/z 341.4 [M+H]$^+$.

Example 165

Trans-8-sec-butoxy-1,2,3,3a,4,5-hexahydrobenzo[c]pyrrolo[3,4-c]azepin-6(10bH)-one The title compound was prepared according to the procedure outlined in Example 146 substituting 2-butanol for 3-fluorobenzyl alcohol. $^1$H NMR (300 MHz, DMSO-$d_6$) δ ppm 8.90 (d, J=32.7, 2H), 8.10-8.01 (m, 1H), 7.15 (dd, J=5.5, 2.9, 2H), 7.04 (dd, J=8.4, 2.5, 1H), 4.49-4.34 (m, 1H), 3.69-3.55 (m, 1H), 3.58-3.36 (m, 2H), 3.23-3.01 (m, 3H), 2.93 (dt, J=17.2, 9.3, 1H), 2.31-2.13 (m, 1H), 1.74-1.50 (m, 2H), 1.22 (dt, J=6.0, 3.0, 3H), 0.92 (td, J=7.3, 1.0, 3H); MS (ESI+) m/z 275.1 [M+H]$^+$.

Example 166

Trans-8-isobutoxy-1,2,3,3a,4,5-hexahydrobenzo[c]pyrrolo[3,4-c]azepin-6(10bH)-one The title compound was prepared according to the procedure outlined in Example 146 substituting 2-methylpropan-1-ol for 3-fluorobenzyl alcohol. $^1$H NMR (300 MHz, DMSO-$d_6$) δ ppm 8.90 (d, J=32.5, 2H), 8.12-8.02 (m, 1H), 7.16 (dd, J=5.4, 2.7, 2H), 7.06 (dd, J=8.4, 2.7, 1H), 3.78 (m, 1H), 3.52-3.38 (m, 4H), 3.21-3.02 (m, 3H), 3.00-2.85 (m, 1H), 2.22 (m, 1H), 2.09-1.91 (m, 1H), 0.99 (s, 3H), 0.97 (s, 3H); MS (ESI+) m/z 275.1 [M+H]$^+$.

Example 167

Trans-8-(cyclohexylmethoxy)-1,2,3,3a,4,5-hexahydrobenzo[c]pyrrolo[3,4-c]azepin-6(10bH)-one The title compound was prepared according to the procedure outlined in Example 146 substituting cyclohexyl methanol for 3-fluorobenzyl alcohol. $^1$H NMR (300 MHz, DMSO-$d_6$) δ ppm 8.85 (d, J=34.0, 2H), 8.12-8.02 (m, 1H), 7.15 (dd, J=5.5, 2.8, 2H), 7.05 (dd, J=8.5, 2.6, 1H), 3.80 (d, J=6.0, 2H), 3.66-3.54 (m, 1H), 3.22-3.03 (m, 3H), 2.92 (s, 1H), 2.28-2.12 (m, 2H), 1.75 (dd, J=26.1, 12.0, 6H), 1.10-1.20 (m, 6H); MS (ESI+) m/z 315.2 [M+H]$^+$.

Example 168

Trans-8-(2,6-difluorobenzyloxy)-1,2,3,3a,4,5-hexahydrobenzo[c]pyrrolo[3,4-c]azepin-6(10bH)-one The title compound was prepared according to the procedure outlined in Example 146 substituting (2,6-difluorophenyl)methanol for 3-fluorobenzyl alcohol. $^1$H NMR (400 MHz, DMSO-$d_6$) δ ppm 8.96 (d, J=44.8, 2H), 8.16-8.05 (m, 1H), 7.61-7.49 (m, 1H), 7.46-7.34 (m, 1H), 7.29 (d, J=2.6, 1H), 7.26-7.14 (m, 3H), 7.11-7.02 (m, 1H), 5.15 (s, 2H), 4.50 (s, 1H), 3.68-3.58 (m, 1H), 3.11 (m, 3H), 2.93 (m, 1H), 2.22 (m, 1H); MS (ESI+) m/z 345.1 [M+H]$^+$.

Example 169

Trans-8-(isopentyloxy)-1,2,3,3a,4,5-hexahydrobenzo[c]pyrrolo[3,4-c]azepin-6(10bH)-one The title compound was prepared according to the procedure outlined in Example 146 substituting 3-methylbutan-1-ol for 3-fluorobenzyl alcohol. $^1$H NMR (300 MHz, DMSO-$d_6$) δ ppm 8.85 (d, J=34.0, 2H), 8.15-7.98 (m, 1H), 7.15 (dd, J=5.5, 2.8, 2H), 7.05 (dd, J=8.5, 2.6, 1H), 3.80 (d, J=6.0, 2H), 3.69-3.55 (m, 2H), 3.23-3.01 (m, 3H), 2.92 (m, 1H), 2.29-2.11 (m, 1H), 1.75 (dd, J=26.1, 12.0, 5H), 1.17 (m, 5H); MS (ESI+) m/z 289.2 [M+H]$^+$.

Example 170

Trans-8-sec-butoxy-2-methyl-1,2,3,3a,4,5-hexahydrobenzo[c]pyrrolo[3,4-c]azepin-6(10bH)-one The title compound was prepared according to the procedure outlined in Example 118 substituting butan-2-ol for (S)-1-phenylpropan-2-ol and substituting Example 164B for Example 117. $^1$H NMR (400 MHz, DMSO-$d_6$) δ ppm 10.33 (d, J=54.9, 1H), 8.06 (t, J=4.7, 1H), 7.27-6.95 (m, 3H), 4.40 (dt, J=11.9, 6.0, 1H), 3.94 (dd, J=14.4, 8.4, 1H), 3.81-3.69 (m, 1H), 3.44-3.01 (m, 4H), 3.02-2.81 (m, 4H), 2.32-2.16 (m, 1H), 1.73-1.53 (m, 2H), 1.22 (dd, J=6.0, 1.8, 3H), 0.92 (td, J=7.4, 1.4, 3H); MS (ESI+) m/z 289.2 [M+H]$^+$.

Example 171

Trans-8-(isopentyloxy)-2-methyl-1,2,3,3a,4,5-hexahydrobenzo[c]pyrrolo[3,4-c]azepin-6(10bH)-one The title compound was prepared according to the procedure outlined in Example 118 substituting 3-methylbutan-1-ol for (5)-1-phenylpropan-2-ol and substituting Example 164B for Example 117. $^1$H NMR (400 MHz, DMSO-$d_6$) δ ppm 10.33-10.07 (m, 1H), 8.14-8.01 (m, 1H), 7.25-7.00 (m, 3H), 4.07-3.90 (m, 3H), 3.81-3.70 (m, 1H), 3.40-2.81 (m, 8H), 2.30-2.16 (m, 1H), 1.84-1.72 (m, 1H), 1.66-1.57 (m, 2H), 0.93 (d, J=6.6, 6H); MS (ESI+) m/z 303.2 [M+H]$^+$.

Example 172

Trans-8-isobutoxy-2-methyl-1,2,3,3a,4,5-hexahydrobenzo[c]pyrrolo[3,4-c]azepin-6(10bH)-one The title compound was prepared according to the procedure outlined in Example 118 substituting 2-methylpropan- 1-ol for (5)-1-phenylpropan-2-ol and substituting Example 164B for Example 117. $^1$H NMR (400 MHz, DMSO-d$_6$) δ ppm 10.05 (d, J=42.4, 1H), 8.07 (s, 1H), 7.13 (ddd, J=28.6, 12.3, 7.0, 3H), 3.96 (s, 1H), 3.77 (d, J=6.5, 3H), 3.30-2.81 (m, 7H), 2.22 (s, 1H), 2.01 (dt, J=13.1, 6.5, 2H), 0.98 (d, J=6.7, 6H); MS (ESI+) m/z 289.2 [M+H]$^+$.

Example 173

Trans-8-(2-methoxyphenethoxy)-1,2,3,3a,4,5-hexahydrobenzo[c]pyrrolo[3,4-c]azepin-6(10bH)-one The title compound was prepared according to the procedure outlined in Example 146 substituting 2-(2-methoxyphenyl)ethanol for 3-fluorobenzyl alcohol. $^1$H NMR (400 MHz, DMSO-d$_6$) δ ppm 8.91 (d, J=47.2, 2H), 8.14-8.05 (m, 1H), 7.28-7.11 (m, 4H), 7.07 (dd, J=8.4, 2.7, 1H), 6.99 (d, J=8.0, 1H), 6.95-6.81 (m, 2H), 4.20-4.11 (m, 2H), 3.82 (s, 3H), 3.60 (m, 1H), 3.56-3.38 (m, 2H), 3.21-2.85 (m, 4H), 2.71 (t, J=7.3, 1H), 2.20 (d, J=6.1, 1H); MS (ESI+) m/z 353.2 [M+H]$^+$.

Example 174

Trans-8-(3-methoxyphenethoxy)-1,2,3,3a,4,5-hexahydrobenzo[c]pyrrolo[3,4-c]azepin-6(10bH)-one The title compound was prepared according to the procedure outlined in Example 146 substituting 2-(3-methoxyphenyl)ethanol for 3-fluorobenzyl alcohol. $^1$H NMR (400 MHz, DMSO-d$_6$) δ ppm 8.94 (d, J=42.2, 2H), 8.08 (dd, J=6.5, 3.8, 1H), 7.27-7.19 (m, 1H), 7.20 (m, 2H), 7.07 (dd, J=8.4, 2.7, 1H), 6.89 (t, J=4.1, 2H), 6.83-6.76 (m, 1H), 4.27-4.16 (m, 2H), 3.74 (s, 3H), 3.66-3.42 (m, 5H), 3.20-3.04 (m, 3H), 3.01 (t, J=6.7, 2H), 2.93 (s, 1H), 2.19 (dd, J=12.3, 5.7, 1H); MS (ESI+) m/z 353.2 [M+H]$^+$.

Example 175

Trans-8-(4-methoxyphenethoxy)-1,2,3,3a,4,5-hexahydrobenzo[c]pyrrolo[3,4-c]azepin-6(10bH)-one The title compound was prepared according to the procedure outlined in Example 146 substituting 2-(4-methoxyphenyl)ethanol for 3-fluorobenzyl alcohol. $^1$H NMR (400 MHz, DMSO-d$_6$) δ ppm 8.87 (sb, 1H), 8.08 (m, 1H), 7.23 (d, J=8.6, 2H), 7.16 (dd, J=5.5, 2.8, 2H), 7.06 (dd, J=8.5, 2.7, 1H), 6.87 (d, J=8.6, 2H), 4.16 (dd, J=9.9, 6.7, 2H), 3.71 (d, J=5.4, 3H), 3.67-3.39 (m, 3H), 3.21-3.01 (m, 3H), 3.01-2.88 (m, 3H), 2.18 (s, 1H); MS (ESI+) m/z 353.2 [M+H]$^+$.

Example 176

Trans-8-(cyclohexylmethoxy)-2-methyl-1,2,3,3a,4,5-hexahydrobenzo[c]pyrrolo[3,4-c]azepin-6(10bH)-one The title compound was prepared according to the procedure outlined in Example 118 substituting cyclohexylmethanol for (5)-1-phenylpropan-2-ol and substituting Example 164B for Example 117. $^1$H NMR (400 MHz, DMSO-d$_6$) δ ppm 10.10 (d, J=43.9, 1H), 8.06 (m, 1H), 7.26-7.00 (m, 3H), 4.02-3.90 (m, 1H), 3.84-3.70 (m, 2H), 3.41-3.00 (m, 3H), 2.94 (dd, J=22.5, 17.4, 4H), 2.21 (s, 1H), 1.85-1.59 (m, 5H), 1.33-0.95 (m, 5H); MS (ESI+) m/z 329.2 [M+H]$^+$.

Example 177

Trans-8-(pyridin-4-yl)-1,2,3,3a,4,5-hexahydrobenzo[c]pyrrolo[3,4-c]azepin-6(10bH)-one The title compound was prepared according to the procedure outlined in Example 227I substituting pyridin-4-ylboronic acid for 3-(methylsulfonyl)phenylboronic acid. $^1$H NMR (400 MHz, DMSO-d$_6$) δ ppm 9.58 (d, J=21.0, 2H), 8.91 (d, J=6.5, 2H), 8.32 (d, J=5.8, 3H), 8.20 (d, J=2.0, 1H), 8.14 (dd, J=8.0, 2.1, 1H), 7.53 (d, J=8.1, 1H), 3.40-3.20 (m, 4H), 3.18-2.89 (m, 3H), 2.33 (dd, J=16.7, 9.6, 1H); MS (ESI+) m/z 280.2 [M+H]$^+$.

Example 178

Trans-8-(2-methoxypyrimidin-5-yl)-1,2,3,3a,4,5-hexahydrobenzo[c]pyrrolo[3,4-c]azepin-6(10bH)-one The title compound was prepared according to the procedure outlined in Example 227I substituting 2-methoxypyrimidin-5-ylboronic acid for 3-(methylsulfonyl)phenylboronic acid. $^1$H NMR (400 MHz, DMSO-d$_6$) δ ppm 9.38 (s, 2H), 8.97 (s, 1H), 8.78 (s, 1H), 8.35-8.13 (m, 1H), 8.02-7.76 (m, 2H), 7.38 (dd, J=21.2, 8.0, 1H), 3.59-3.38 (m, 6H), 3.31-2.91 (m, 4H), 2.36-2.20 (m, 1H); MS (ESI+) m/z 311.2 [M+H]$^+$.

Example 179

(3aR,10bS)-8-(2-Fluorobenzyloxy)-1,2,3,3a,4,5-hexahydrobenzo[c]pyrrolo[3,4-c]azepin-6(10bH)-one Example 179A (3aS,10bS)-tert-Butyl 8-(2-fluorobenzyloxy)-6-oxo-1,3a,4,5,6,10b-hexahydrobenzo[e]pyrrolo[3,4-c]azepine-2(3H)-carboxylate The title compound was prepared according to the procedure outlined in Example 146 and substituting 2-fluorobenzyl alcohol for 3-fluorobenzyl alcohol and the acidic deprotection step was not performed.

Example 179B (3aR,10bS)-8-(2-Fluorobenzyloxy)-1,2,3,3a,4,5-hexahydrobenzo[c]pyrrolo[3,4-c]azepin-6(10bH)-one Example 179A was resolved into pure enantiomers using supercritical fluid chromatography (ChiralPak® AS, 21×250 mm, 5 μm, 10-30% methanol with 0.1% diethyl amine-CO$_2$ gradient over 20 minutes, at 40 mL/minute, retention time=14.1 minutes) and the pure enantiomer (140 mg, 0.328 mmol) was treated with 3 mL of HCl (4 N in dioxane). The mixture was stirred at room temperature for 2 hours, concentrated, and triturated with hexane:ethyl acetate (1:4) to afford the title compound as the hydrochloride salt. $^1$H NMR (400 MHz, DMSO-d$_6$) δ ppm 9.42 (s, 2H), 8.12 (m, 1H), 7.56 (t, J=7.6, 1H), 7.43 (dt, J=7.3, 3.7, 1H), 7.34-7.12 (m, 5H), 5.27-5.11 (m, 2H), 3.67-3.43 (m, 2H), 3.25-3.02 (m, 3H), 2.92 (dd, J=14.8, 9.2, 1H), 2.20 (dt, J=11.9, 6.3, 1H); MS (ESI+) m/z 327.1 [M+H]$^+$.

Example 180

(3aR,10bS)-8-(2-Fluorobenzyloxy)-1,2,3,3a,4,5-hexahydrobenzo[c]pyrrolo[3,4-c]azepin-6(10bH)-one Example 179A was resolved into pure enantiomers using supercritical fluid chromatography (ChiralPak® AS, 21×250 mm, 5 μm, 10-30% methanol with 0.1% diethyl amine-CO$_2$ gradient over 20 minutes, at 40 mL/minute, retention time=16.2 minutes) and the pure enantiomer (150 mg, 0.352 mmol) was treated with 3 mL of HCl (4 N in dioxane). The mixture was stirred at room temperature for 2 hours, concentrated, and triturated with hexane:ethyl acetate (1:4) to afford the title compound as the hydrochloride salt. $^1$H NMR (400 MHz, DMSO-d$_6$) δ ppm 9.34-9.25 (m, 2H), 8.14-8.08 (m, 1H), 7.56 (td, J=7.5, 1.8, 1H), 7.48-7.39 (m, 1H), 7.30-7.13 (m, 5H), 5.17 (bs, 2H), 3.65-3.55 (m, 2H), 3.21-3.01 (m, 3H), 3.00-2.87 (m, 1H), 2.27-2.11 (m, 1H); MS (ESI+) m/z 327.1 [M+H]$^+$.

Example 181

(3aR,10bS)-8-((R)-1-Phenylpropan-2-yloxy)-1,2,3,3a,4,5-hexahydrobenzo[c]pyrrolo[3,4-c]azepin-6(10bH)-one Example 181A (3aS,10bS)-tert-Butyl 6-oxo-8-((R)-1-phenylpropan-2-yloxy)-1,3a,4,5,6,10b-hexahydrobenzo[e]pyrrolo[3,4-c]azepine-2(3H)-carboxylate The title compound was prepared according to the procedure outlined in Example 146 substituting (S)-1-phenylpropan-2-ol for 3-fluorobenzyl alcohol and the acidic deprotection step was not performed.

Example 181B (3aR,10bS)-8-((R)-1-Phenylpropan-2-yloxy)-1,2,3,3a,4,5-hexahydrobenzo[c]pyrrolo[3,4-c]azepin-6(10bH)-one Example 181A was resolved into pure enantiomers using supercritical fluid chromatography (ChiralPak® AS, 21×250 mm, 5 μm, 10-30% methanol with 0.1% diethyl amine-CO$_2$ gradient over 20 minutes, at 40 mL/minute, retention time=9.2 minutes), and the pure enantiomer (140 mg, 0.321 mmol) was treated with 3 mL of HCl (4 N in dioxane). The mixture was stirred at room temperature for 2 hours, concentrated, and triturated with hexane:ethyl acetate (1:4) to afford the title compound as the hydrochloride salt. $^1$H NMR (400 MHz, DMSO-d$_6$) δ ppm 9.30-9.15 (m, 2H), 8.11-8.04 (m, 1H), 7.33-7.26 (m, 4H), 7.27-7.10 (m, 3H), 7.04 (dd, J=8.4, 2.7, 1H), 4.76-4.66 (m, 1H), 3.62-3.54 (m, 1H), 3.50-3.36 (m, 3H), 3.20-2.82 (m, 5H), 2.41-2.11 (m, 1H), 1.23 (d, J=5.9, 3H); MS (ESI+) m/z 337.2 [M+H]$^+$.

Example 182

(3aS,10bR)-8-((R)-1-Phenylpropan-2-yloxy)-1,2,3,3a,4,5-hexahydrobenzo[c]pyrrolo[3,4-c]azepin-6(10bH)-one Example 181A was resolved into pure enantiomers using supercritical fluid chromatography (ChiralPak® AS, 21×250 mm, 5 μm, 10-30% methanol with 0.1% diethyl amine-CO$_2$ gradient over 20 minutes, at 40 mL/minute, retention time=12.2 minutes), and the pure enantiomer (150 mg, 0.344 mmol) was treated with 3 mL of HCl (4 N in dioxane).

The mixture was stirred at room temperature for 2 hours, concentrated, and triturated with hexane:ethyl acetate (1:4) to afford the title compound as the hydrochloride salt. $^1$H NMR (400 MHz, DMSO-d$_6$) δ ppm 9.28-9.08 (m, 2H), 8.08 (dd, J=6.6, 3.9, 1H), 7.31-7.26 (m, 4H), 7.25-7.16 (m, 1H), 7.18-7.11 (m, 2H), 7.04 (dd, J=8.4, 2.7, 1H), 4.76-4.64 (m, 1H), 3.58 (dd, J=10.5, 6.5, 1H), 3.50-3.35 (m, 3H), 3.19-2.81 (m, 4H), 2.90 (d, J=11.3, 1H), 2.35-1.97 (m, 1H), 1.23 (d, J=6.0, 3H); MS (ESI+) m/z 337.2 [M+H]$^+$.

Example 183

Trans-8-(2-methoxyphenethoxy)-2-methyl-1,2,3,3a,4,5-hexahydrobenzo[c]pyrrolo[3,4-c]azepin-6(10bH)-one The title compound was prepared according to the procedure outlined in Example 118 substituting 2-(2-methoxyphenyl)ethanol for (5)-1-phenylpropan-2-ol and substituting Example 164B for Example 117. $^1$H NMR (400 MHz, DMSO-d$_6$) δ ppm 10.06 (d, J=44.9, 1H), 8.07 (m, 1H), 7.30-7.18 (m, 3H), 7.17-7.05 (m, 2H), 6.99 (d, J=8.0, 1H), 6.89 (dd, J=7.3, 6.5, 1H), 4.22-4.10 (m, 2H), 3.95 (dd, J=9.5, 4.8, 1H), 3.82 (s, 3H), 3.75 (dd, J=10.8, 6.1, 1H), 3.40-3.09 (m, 4H), 3.09-2.83 (m, 6H), 2.20 (d, J=6.5, 1H); MS (ESI+) m/z 397.3 [M+H]$^+$.

Example 184

Trans-8-(thiophen-3-yl)-1,2,3,3a,4,5-hexahydrobenzo[c]pyrrolo[3,4-c]azepin-6(10bH)-one The title compound was prepared according to the procedure outlined in Example 227H and Example 227I substituting thiophen-3-ylboronic acid for 3-(methylsulfonyl)phenylboronic acid The crude material was purified by reverse phase HPLC to afford the title compound as the trifluoroacetic acid salt. $^1$H NMR (400 MHz, DMSO-d$_6$) δ ppm 9.02 (d, J=51.8, 2H), 8.16 (dd, J=6.5, 3.8, 1H), 8.00-7.92 (m, 2H), 7.86 (dd, J=8.0, 2.0, 1H), 7.67 (dd, J=5.0, 2.9, 1H), 7.59 (dd, J=5.1, 1.4, 1H), 7.31 (d, J=8.0, 1H), 3.59-3.42 (m, 2H), 3.16 (m, 4H), 2.98 (dd, J=15.9, 9.2, 1H), 2.34-2.21 (m, 1H); MS (ESI+) m/z 285.1 [M+H]$^+$.

Example 185

Trans-2-methyl-8-(3-(1,1,1-trifluoro-2-hydroxypropan-2-yl)phenyl)-1,2,3,3a,4,5-hexahydrobenzo[c]pyrrolo[3,4-c]azepin-6(10bH)-one

Example 185A

Trans-8-(3-acetylphenyl)-2-methyl-1,2,3,3a,4,5-hexahydrobenzo[c]pyrrolo[3,4-c]azepin-6(10bH)-one The title compound was prepared according to the procedure outlined in Example 75 substituting 3-acetylphenylboronic acid for 4-fluorophenylboronic acid.

Example 185B

Trans-2-methyl-8-(3-(1,1,1-trifluoro-2-hydroxypropan-2-yl)phenyl)-1,2,3,3a,4,5-hexahydrobenzo[c]pyrrolo[3,4-c]azepin-6(10bH)-one To Example 185A (60 mg, 0.179 mmol) and 1.44 mL of 0.5 M (in tetrahydrofuran) (trifluoromethyl)trimethylsilane was added 0.197 mL of 1.0 M tetrabutylammonium fluoride in tetrahydrofuran at 0° C. The reaction mixture was then warmed to room temperature and stirred overnight. LC/MS showed incomplete conversion. More (trifluoromethyl)trimethylsilane (0.72 mL, 0.5 M in tetrahydrofuran) and tetrabutylammonium fluoride (0.19 mL, 1.0 M in tetrahydrofuran) were added at 0° C., and then the reaction mixture was stirred another day at room temperature. The reaction mixture was diluted with saturated aqueous $Na_2CO_3$ solution and extracted with dichloromethane (3×). The combined organic layer was washed with brine, dried over $Na_2SO_4$, and concentrated. The crude material was purified by reverse phase HPLC to afford the title compound as the trifluoroacetic acid salt. $^1$H NMR (400 MHz, DMSO-$d_6$) δ ppm 10.11 (d, J=50.9, 1H), 8.17 (m, 1H), 7.99-7.77 (m, 3H), 7.68 (d, J=7.5, 1H), 7.60 (d, J=7.9, 1H), 7.52 (t, J=7.7, 1H), 7.44-7.28 (m, 1H), 6.72 (s, 1H), 4.03 (m, 1H), 3.69 (m, 2H), 3.39-3.28 (m, 3H), 3.18 (d, J=6.8, 2H), 2.98 (dd, J=17.5, 12.4, 2H), 2.67-2.32 (m, 1H), 1.75 (s, 3H); MS (ESI+) m/z 405.1 [M+H]$^+$.

Example 186

Trans-8-(3-(2-hydroxypropan-2-yl)phenyl)-2-methyl-1,2,3,3a,4,5-hexahydrobenzo[c]pyrrolo[3,4-c]azepin-6(10bH)-one To a cooled (−10° C.) and stirred Example 185A (83.5 mg, 0.25 mmol) in dry tetrahydrofuran (0.7 mL) was added dropwise methylmagnesium bromide (0.54 mL, 1.4 M in toluene/tetrahydrofuran). The reaction mixture was then slowly warmed up to room temperature and stirred overnight. The reaction was quenched with saturated aqueous ammonium chloride solution and extracted with ethyl acetate. The organic layer was washed with brine, dried over $Na_2SO_4$, and concentrated. The crude material was purified by reverse phase HPLC to afford the title compound as the trifluoroacetic acid salt. $^1$H NMR (400 MHz, DMSO-$d_6$) δ ppm 10.27-10.05 (m, 1H), 8.19-8.11 (m, 1H), 7.93 (dd, J=15.5, 2.0, 1H), 7.85-7.76 (m, 2H), 7.53-7.44 (m, 2H), 7.41 (t, J=7.5, 1H), 7.37-7.25 (m, 1H), 4.07-3.95 (m, 1H), 3.83-3.48 (m, 2H), 3.42-3.26 (m, 5H), 3.23-2.90 (m, 3H), 2.56-2.27 (m, 1H), 1.48 (s, 6H); MS (ESI+) m/z 351.3 [M+H]$^+$.

Example 187

Trans-8-(3-acetylphenyl)-5-methyl-1,2,3,3a,4,5-hexahydrobenzo[c]pyrrolo[3,4-c]azepin-6(10bH)-one

Example 187A

Trans-tert-butyl 5-methyl-6-oxo-8-(trifluoromethylsulfonyloxy)-1,3a,4,5,6,10b-hexahydrobenzo[e]pyrrolo[3,4-c]azepine-2(3H)-carboxylate To Example 227G (500 mg, 1.11 mmol) and iodomethane (354 mg, 2.493 mmol) in 5 mL of N,N-dimethylformamide was added NaH (101 mg, 2.53 mmol, 60% in mineral oil) at room temperature. The resultant mixture was stirred for 30 minutes, and then the reaction was quenched with saturated aqueous ammonium chloride solution. The mixture was extracted with ethyl acetate (2×). The combined organic layers were concentrated and purified by silica gel flash chromatography eluting with ethyl acetate (50-80%) in hexane to afford the title compound.

Example 187B

Trans-tert-butyl 8-(3-acetylphenyl)-5-methyl-6-oxo-1,3a,4,5,6,10b-hexahydrobenzo[e]pyrrolo[3,4-c]azepine-2(3H)-carboxylate The title compound was prepared according to the procedure outlined in Example 227H substituting 3-acetylphenylboronic acid for 3-(methylsulfonyl)phenylboronic acid and substituting Example 187A for Example 227G.

Example 187C

Trans-8-(3-acetylphenyl)-5-methyl-1,2,3,3a,4,5-hexahydrobenzo[c]pyrrolo[3,4-c]azepin-6(10bH)-one The title compound was prepared as the hydrochloride salt according to the procedure outlined in Example 46B substituting Example 187B for Example 46A. $^1$H NMR (400 MHz, DMSO-$d_6$) δ ppm 9.24 (d, J=61.6, 2H), 8.19 (d, J=1.6, 1H), 7.97 (t, J=7.3, 2H), 7.93 (d, J=2.0, 1H), 7.88 (dd, J=7.9, 2.0, 1H), 7.65 (t, J=7.8, 1H), 7.39 (d, J=8.0, 1H), 3.62 (d, J=39.0, 2H), 3.44 (dt, J=15.5, 11.1, 3H), 3.28-3.06 (m, 5H), 2.67 (s, 3H), 2.29 (dd, J=16.2, 9.8, 1H); MS (ESI+) m/z 335.2 [M+H]$^+$.

Example 188

Trans-8-methoxy-5-methyl-1,2,3,3a,4,5-hexahydrobenzo[c]pyrrolo[3,4-c]azepin-6(10bH)-one

Example 188A

Trans-tert-butyl 8-methoxy-5-methyl-6-oxo-1,3a,4,5,6,10b-hexahydrobenzo[e]pyrrolo[3,4-e]azepine-2(3H)-carboxylate The title compound was prepared as a by-product according to the procedure outlined in Example 187A.

Example 188B

Trans-8-methoxy-5-methyl-1,2,3,3a,4,5-hexahydrobenzo[c]pyrrolo[3,4-c]azepin-6(10bH)-one The title compound was prepared as the hydrochloride salt according to the procedure outlined in Example 46B substituting Example 188A for Example 46A. $^1$H NMR (400 MHz, DMSO-$d_6$) δ ppm 9.53-9.23 (m, 2H), 7.20-7.10 (m, 2H), 7.09-7.02 (m, 1H), 3.77 (s, 3H), 3.63-3.54 (m, 1H), 3.54-3.37 (m, 3H), 3.09 (s, 3H), 3.02-3.07 (m, 2H), 2.22-2.09 (m, 2H); MS (ESI+) m/z 247.1 [M+H]$^+$.

Example 189

Trans-8-(3-(2-hydroxyethyl)phenyl)-5-methyl-1,2,3,3a,4,5-hexahydrobenzo[c]pyrrolo[3,4-c]azepin-6(10bH)-one

Example 189A

Trans-tert-butyl 8-(3-(2-hydroxyethyl)phenyl)-5-methyl-6-oxo-1,3a,4,5,6,10b-hexahydrobenzo[e]pyrrolo[3,4-e]azepine-2(3H)-carboxylate The title compound was prepared according to the procedure outlined in Example 227H substituting 3-(2-hydroxyethyl)phenylboronic acid for 3-(methylsulfonyl)phenylboronic acid and substituting Example 187A for Example 227G.

Example 189B

Trans-8-(3-(2-hydroxyethyl)phenyl)-5-methyl-1,2,3,3a,4,5-hexahydrobenzo[c]pyrrolo[3,4-c]azepin-6(10bH)-one 6(10bH)-one The title compound was prepared as the hydrochloride salt according to the procedure outlined in Example 46B substituting Example 189A for Example 46A. $^1$H NMR (400 MHz, DMSO-$d_6$) δ ppm 9.24-9.10 (m, 2H), 7.86-7.82 (m, 1H), 7.81-7.76 (m, 1H), 7.55-7.46 (m, 2H), 7.42-7.32 (m, 2H), 7.28-7.21 (m, 1H), 4.71-4.62 (m, 1H), 3.71-3.63 (m, 3H), 3.62-3.52 (m, 3H), 3.54-3.36 (m, 3H), 3.24-3.06 (m, 3H), 2.85-2.77 (m, 2H), 2.34-2.20 (m, 1H); MS (ESI+) m/z 337.2 [M+H]$^+$.

Example 190

Trans-8-methoxy-2,5-dimethyl-1,2,3,3a,4,5-hexahydrobenzo[c]pyrrolo[3,4-c]azepin-6(10bH)-one The title compound was prepared according to the procedure outlined in Example 53 substituting Example 188 for Example 46. $^1$H NMR (400 MHz, DMSO-$d_6$) δ ppm 10.39-10.17 (m, 1H), 7.17-7.02 (m, 3H), 3.78 (s, 5H), 3.58-3.41 (m, 4H), 3.41-3.26 (m, 3H), 3.10 (d, J=7.0, 6H), 2.97 (dd, J=8.3, 4.8, 3H), 2.48-2.12 (m, 1H); MS (ESI+) m/z 261.1 [M+H]$^+$.

Example 191

Trans-8-(3-acetylphenyl)-2,5-dimethyl-1,2,3,3a,4,5-hexahydrobenzo[c]pyrrolo[3,4-c]azepin-6(10bH)-one The title compound was prepared according to the procedure outlined in Example 53 substituting Example 187 for Example 46. The crude material was purified by reverse phase HPLC to afford the title compound as the trifluoroacetic acid salt $^1$H NMR (400 MHz, DMSO-$d_6$) δ ppm 10.25 (d, J=55.7, 1H), 8.20 (s, 1H), 8.03-7.85 (m, 4H), 7.65 (t, J=7.8, 1H), 7.34 (dd, J=18.5, 8.0, 1H), 4.11-3.97 (m, 3H), 3.87-3.77 (m, 1H), 3.72-3.19 (m, 3H), 3.15 (d, J=6.7, 3H), 3.11-2.95 (m, 4H), 2.67 (s, 3H), 2.37-2.23 (m, 1H); MS (ESI+) m/z 349.2 [M+H]$^+$.

Example 192

Trans-8-(3-(2-hydroxyethyl)phenyl)-2,5-dimethyl-1,2,3,3a,4,5-hexahydrobenzo[c]pyrrolo[3,4-c]azepin-6(10bH)-one The title compound was prepared according to the procedure outlined in Example 53 substituting Example 189 for Example 46. The crude material was purified by reverse phase HPLC to afford the title compound as the trifluoroacetic acid salt $^1$H NMR (400 MHz, DMSO-$d_6$) δ ppm 10.30-10.08 (m, 1H), 7.92-7.75 (m, 2H), 7.65-7.47 (m, 2H), 7.47-7.35 (m, 1H), 7.37-7.22 (m, 2H), 4.06-3.99 (m, 1H), 3.74-3.23 (m, 6H), 3.17-3.11 (m, 5H), 3.00 (dd, J=8.9, 4.8, 3H), 2.80 (t, J=6.8, 2H), 2.48-2.22 (m, 1H); MS (ESI+) m/z 351.2 [M+H]$^+$.

Example 193

Trans-8-(3-(1-hydroxyethyl)phenyl)-2,5-dimethyl-1,2,3,3a,4,5-hexahydrobenzo[c]pyrrolo[3,4-c]azepin-6(10bH)-one The title compound was prepared according to the procedure outlined in Example 238 substituting Example 191 for Example 237. $^1$H NMR (500 MHz, DMSO-$d_6$) δ ppm 7.95 (d, J=2.0, 1H), 7.71 (dd, J=7.9, 2.0, 1H), 7.63 (s, 1H), 7.53-7.47 (m, 1H), 7.41 (t, J=7.6, 1H), 7.34 (d, J=7.6, 1H), 7.25 (d, J=8.0, 1H), 5.23 (d, J=3.1, 1H), 4.86-4.75 (m, 1H), 3.49-3.39 (m, 4H), 3.21-3.04 (m, 2H), 2.76 (dt, J=18.4, 8.9, 2H), 2.44 (s, 3H), 2.28-2.15 (m, 1H), 1.37 (d, J=6.4, 3H); MS (ESI+) m/z 351.2 [M+H]$^+$.

Example 194

Trans-8-(3-(2-hydroxypropan-2-yl)phenyl)-2,5-dimethyl-1,2,3,3a,4,5-hexahydrobenzo[c]pyrrolo[3,4-c]azepin-6(10bH)-one The title compound was prepared according to the procedure outlined in Example 186 substituting Example 191 for Example 185A. $^1$H NMR (400 MHz, DMSO-$d_6$) δ ppm 7.95 (d, J=2.0, 1H), 7.75 (d, J=1.7, 1H), 7.71 (dd, J=7.9, 2.0, 1H), 7.46 (dd, J=11.4, 4.6, 2H), 7.40 (d, J=7.6, 1H), 7.25 (d, J=8.0, 1H), 5.09 (s, 1H), 3.52-3.38 (m, 2H), 3.22-3.05 (m, 6H), 2.78 (dt, J=18.4, 8.9, 2H), 2.46 (s, 3H), 2.22 (s, 1H), 1.47 (s, 6H); MS (ESI+) m/z 365.3 [M+H]$^+$.

Example 195

Trans-8-(benzo[c][1,2,5]oxadiazol-5-yl)-2-methyl-1,2,3,3a,4,5-hexahydrobenzo[c]pyrrolo[3,4-c]azepin-6(10bH)-one

Example 195A

Trans-2-methyl-6-oxo-1,2,3,3a,4,5,6,10b-octahydrobenzo[c]pyrrolo[3,4-c]azepin-8-yl trifluoromethanesulfonate To a slurry of Example 164B (850 mg, 3.66 mmol) in 10 mL of dichloromethane was added triethylamine (459 mg, 4.54 mmol) followed by 1,1,1-trifluoro-N-phenyl-N-(trifluoromethylsulfonyl)methanesulfonamide (1361 mg, 3.81 mmol). The reaction mixture was stirred at room temperature overnight. The reaction mixture was concentrated, and water was added to the residue, and the mixture was extracted with dichloromethane (3×). The organic washes were combined, dried over $Na_2SO_4$, concentrated, and purified by silica gel flash chromatography eluting with methanol (1-10%) in dichloromethane to obtain the title compound.

Example 195B

Trans-8-(benzo[c][1,2,5]oxadiazol-5-yl)-2-methyl-1,2,3,3a,4,5-hexahydrobenzo[c]pyrrolo[3,4-c]azepin-6(10bH)-one The title compound was prepared according to the procedure outlined in Example 227H substituting benzo[c][1,2,5]oxadiazol-5-ylboronic acid for 3-(methylsulfonyl)phenylboronic acid and substituting Example 195A for Example 227G. The crude material was purified by reverse phase HPLC to afford the title compound as the trifluoroacetic acid salt. $^1$H NMR (400 MHz, DMSO-$d_6$) δ ppm 10.37 (d, J=65.5, 1H), 8.38 (s, 1H), 8.23 (d, J=4.5, 1H), 8.18 (d, J=9.5, 1H), 8.12 (dd, J=15.0, 2.0, 1H), 8.08-8.00 (m, 2H), 7.41 (dd, J=25.6, 8.1, 1H), 4.18-3.99 (m, 2H), 3.87-3.31 (m, 3H), 3.31 (m, 2H), 3.09-2.90 (m, 3H), 2.68-2.27 (m, 1H); MS (ESI+) m/z 335.0 $[M+H]^+$.

Example 196

Trans-8-isopropyl-2-methyl-1,2,3,3a,4,5-hexahydrobenzo[c]pyrrolo[3,4-c]azepin-6(10bH)-one Example 196A Trans-2-methyl-8-(prop-1-en-2-yl)-1,2,3,3a,4,5-hexahydrobenzo[c]pyrrolo[3,4-c]azepin-6(10bH)-one The title compound was prepared according to the procedure outlined in Example 75 substituting 2-isopropenyl-4,4,5,5-tetramethyl-1,3,2-dioxaborolane for 4-fluorophenylboronic acid.

Example 196B

Trans-8-isopropyl-2-methyl-1,2,3,3a,4,5-hexahydrobenzo[c]pyrrolo[3,4-c]azepin-6(10bH)-one Example 196A (85 mg, 0.332 mmol) and methanol (10 mL) were added to 5% Pd—C, wet (17.00 mg, 0.160 mmol) in a 50 mL pressure bottle and stirred for 70 minutes under hydrogen (40 psi) at room temperature. The mixture was filtered through a nylon membrane and concentrated. The crude material was purified by reverse phase HPLC to afford the title compound as the trifluoroacetic acid salt. $^1$H NMR (400 MHz, DMSO-$d_6$) δ ppm 10.28 (d, J=56.0, 1H), 8.05 (d, J=3.9, 1H), 7.61-7.49 (m, 1H), 7.44-7.37 (m, 1H), 7.19-7.04 (m, 1H), 3.98 (dt, J=10.6, 8.2, 1H), 3.82-3.19 (m, 4H), 3.19-2.84 (m, 5H), 2.58 (dd, J=17.2, 9.6, 1H), 2.35-2.20 (m, 1H), 1.21 (d, J=6.9, 6H); MS (ESI+) m/z 259.0 $[M+H]^+$.

Example 197

Trans-2-methyl-8-(2-methylprop-1-enyl)-1,2,3,3a,4,5-hexahydrobenzo[c]pyrrolo[3,4-c]azepin-6(10bH)-one The title compound was prepared according to the procedure outlined in Example 75, substituting 2-methylprop-1-enylboronic acid for 4-fluorophenylboronic acid. The crude material was purified by reverse phase HPLC to afford the title compound as the trifluoroacetic acid salt. $^1$H NMR (400 MHz, DMSO-$d_6$) δ ppm 10.28 (d, J=53.1, 1H), 8.06 (d, J=4.3, 1H), 7.60-7.46 (m, 1H), 7.36 (d, J=7.9, 1H), 7.16 (dd, J=22.0, 7.9, 1H), 6.29 (s, 1H), 4.00 (dd, J=14.0, 8.2, 1H), 3.66-3.23 (m, 4H), 3.21-3.02 (m, 2H), 2.93 (dt, J=18.3, 8.9, 3H), 2.60-2.22 (m, 1H), 1.93-1.81 (m, 6H); MS (ESI+) m/z 271.2 $[M+H]^+$.

Example 198

Trans-3-(2-methyl-6-oxo-1,2,3,3a,4,5,6,10b-octahydrobenzo[c]pyrrolo[3,4-c]azepin-8-yl)benzaldehyde The title compound was prepared according to the procedure outlined in Example 227H substituting 3-formylphenylboronic acid for 3-(methylsulfonyl)phenylboronic acid and Example 195A for Example 227G. The crude material was purified by reverse phase HPLC to afford the title compound as the trifluoroacetic acid salt. $^1$H NMR (400 MHz, DMSO-$d_6$) δ ppm 10.12 (m, 2H), 8.35-8.22 (m, 1H), 8.23-8.16 (m, 1H), 8.13-7.99 (m, 2H), 7.98-7.89 (m, 2H), 7.73 (t, J=7.6, 1H), 7.37 (dd, J=24.7, 8.0, 1H), 4.12-4.00 (m, 1H), 3.62-3.45 (m, 3H), 3.44-3.31 (m, 2H), 3.26-3.08 (m, 2H), 3.00 (dd, J=7.7, 5.0, 2H), 2.68-2.30 (m, 1H); MS (ESI+) m/z 321.3 $[M+H]^+$.

Example 199

(3aS,10bS)-8-Chloro-2-methyl-1,2,3,3a,4,5-hexahydrobenzo[c]pyrrolo[3,4-c]azepin-6(10bH)-one A 12 L, 4-neck, flask was fitted with a mechanical stirrer, temperature probe and then charged with dibenzoyl-D-tartaric acid (189.7 g) and methanol (5.5 kg) under an atmosphere of nitrogen. Example 53 (126.3 g) was dissolved in methanol (1.48 kg) in a separate flask. A portion of the solution (13.5%) of Example 53 in methanol was added over a period of 1 hour to the dibenzoyl-D-tartrate/methanol solution. The solution was then seeded (seed crystals are prepared as described below) with product (250 mg). The remainder of the Example 53 solution was added over 7.5 hours. A rinse of methanol (278 mL) was employed to wash any remaining starting material residue from the 2 L Erlenmeyer flask, and the resultant mixture was pumped into the reaction vessel over 1 hour. The reaction was allowed to proceed for 14 hours. The suspension was filtered, washed with tert-butyl methyl ether (0° C., 2 L) and dried under vacuum to provide the title compound as the dibenzoyl-D-tartrate. The product exhibited an ee of 98.2%, as judged by reverse phase chiral HPLC analysis [Method: Isocratic elution: 70% aqueous (with 5 mM phosphate buffer, pH 6.9): 30% acetonitrile for 15 minutes. Column: Chiralpak® AS-RH (4.6 mm×150 mm) Temperature 35° C. The wavelength that is used for calculations was 210 nm.]. The salt was freebased by the addition of ethyl acetate (1 L) and extraction with 15% aqueous $K_3PO_4$ (600 mL) twice. The combined basic aqueous layers were then extracted with ethyl acetate (500 mL). The combined organic layers were then extracted with 20% brine (500 mL) twice. The title compound was obtained by evaporation of the organic layer under vacuum (47.5 g). $^1$H NMR (500 MHz, DMSO-$d_6$) δ ppm 8.12 (s, 1H), 7.81 (d, J=2.0 Hz, 1H), 7.49 (dd, J=2.5, 8.0 Hz, 1H), 7.18 (d, J=8.0 Hz, 1H), 3.26 (m, 1H), 3.20 (m, 1H), 3.11 (m, 1H), 3.08 (m, 1H), 2.84 (dd, J=9.0, 10.5 Hz, 1H), 2.62 (m, 2H), and 2.18 (m, 1H); MS (ESI+) m/z 251 [M+H]$^+$.

Example 199

(3aS,10bS)-8-Chloro-2-methyl-1,2,3,3a,4,5-hexahydrobenzo[c]pyrrolo[3,4-c]azepin-6(10bH)-one: Preparation of seed crystals The seeds used in the experiment described in the patent were obtained from a previous experiment that employed the application of seeds that were obtained in a previous experiment that employed the application of seeds, and so on. The same experiment can be carried out without seeding, to the detriment of the enantiomeric purity of product:

A 4 mL septum-equipped vial was charged with dibenzoyl-D-tartaric acid (72 mg, 0.20 mmol, 1.0 equiv), methanol (0.5 mL) and a magnetic stir bar. To the stirring salt was quickly charged a 0.1 g/mL ethanolic solution of the Example 53 (0.5 mL=50 mg, 0.20 mmol, 1.0 equiv). The solution was allowed to stir overnight. Solid formation made the solution unstirrable, thus methanol was added (2.0 mL). The solid was collected by filtration to provide the title compound as the dibenzoyl-D-tartrate, and the cake and filtrate were analyzed by both chiral and achiral HPLC system. Analysis using the previously described chiral method reveals the desired product to be in 84% ee.

Example 200

(3aS,10bS)-8-Hydroxy-2-methyl-1,2,3,3a,4,5-hexahydrobenzo[c]pyrrolo[3,4-c]azepin-6(10bH)-one Example 200A (3aS,10bS)-8-(Benzyloxy)-2-methyl-1,2,3,3a,4,5-hexahydrobenzo[c]pyrrolo[3,4-c]azepin-6(10bH)-one Palladium(II) acetate (1.075 g, 4.79 mmol), 2-di-tert-butylphosphino-3,4,5,6-tetramethyl-2',4',6'-triisopropyl-1,1'-biphenyl (2.76 g, 5.74 mmol), cesium carbonate (58.5, 179 mmol) and (3aS,10bS)-8-chloro-2-methyl-1,2,3,3a,4,5-hexahydrobenzo[c]pyrrolo[3,4-c]azepin-6(10bH)-one (Example 199, 30.0 g, 120 mmol) were charged to a three-neck 2-L round bottom flask equipped with a magnetic stir bar, thermocouple and a reflux condenser. The flask was purged with argon for about 2 hours. Toluene (240 mL) and benzyl alcohol (248 mL, 2393 mmol) were combined in a separate 1-L round bottom flask that was purged with argon for approximately 60 minutes. This mixture was transferred via cannula to the substrate-containing flask, under argon. The temperature was raised to 95° C. and the reaction solution was stirred at this temperature for 1 hour. The reaction mixture was cooled to room temperature and filtered. The reaction flask and funnel were rinsed with ethyl acetate. The solution was diluted with ethyl acetate (1 L) and then was washed with H$_2$O (210 mL). The organic layer was then washed with a saturated aqueous solution of NaCl (220 mL). The combined aqueous layers were basified with an aqueous solution of 2 M KOH to neutral pH (7) and then seeded (Seed crystals were obtained by the process described for Example 199.) with about 20 mg of product. The solution was then further basified with 2 M KOH to pH=12. The solution was vigorously stirred for 30 minutes and then filtered. The solids were dried under an air flow for 1.5 hours. The solids were then dried under vacuum at room temperature. The material was dissolved in warm methanol and the solution was filtered. The filtrate was concentrated under reduced pressure to give a solid. To the solid was added a mixture of ethyl acetate and tert-butyl methyl ether (100 mL each). After stirring vigorously for 30 minutes, the product was collected by filtration and wased with tert-butyl methyl ether (200 mL) that had been pre-cooled to 0° C. The solids were placed in a vacuum oven, at room temperature, under a nitrogen flow for overnight drying. The solid was harvested to provide the title compound (18.0 g). An alternative preparation of the title compound is described in Example 274. $^1$H NMR (400 MHz, DMSO-$d_6$) δ ppm 7.96 (dd, J=8.9, 5.3, 1H), 7.46-7.28 (m, 6H), 7.08-7.02 (m, 2H), 5.10 (s, 2H), 3.25-3.00 (m, 4H), 2.83 (dd, J=10.3, 8.6, 1H), 2.64-2.55 (m, 2H), 2.35 (s, 3H), 2.18-2.05 (m, 1H).

Example 200B (3aS,10bS)-8-Hydroxy-2-methyl-1,2,3,3a,4,5-hexahydrobenzo[c]pyrrolo[3,4-c]azepin-6(10bH)-one The (3aS,10bS)-8-(benzyloxy)-2-methyl-1,2,3,3a,4,5-hexahydrobenzo[c]pyrrolo[3,4-c]azepin-6(10bH)-one (Example 200A, 18 g, 96.9% potent) and catalyst JM UK #3: 3.54 g (10 wt % dry basis, catalyst is 50.9% water) were placed in a 1.8 L Parr shaker reactor followed by 900 mL of methanol. The reactor was sealed and purged with nitrogen followed by purging with hydrogen. The reactor was pressurized to 30 psi hydrogen. The reaction appeared complete in 5 minutes but was allowed to age overnight. No starting material was observed after overnight age as observed by reverse phase HPLC analysis. The solution was filtered, concentrated under reduced pressure to provide a residue, and then chased twice with 2-methyltetrahydrofuran (150 mL). A final slurry was cooled in an ice bath briefly, and the solid was then harvested by filtration to yield after drying (vacuum, 50° C.) the title compound (12.2 g). $^1$H NMR (400 MHz, DMSO-$d_6$) δ ppm 7.86 (t, J=3.8, 1H), 7.23 (t, J=2.9, 1H), 6.91 (d, J=8.3, 1H), 6.79 (dd, J=8.2, 2.7, 1H), 3.18 (ddd, J=13.3, 6.5, 3.1, 3H), 3.13-2.98 (m, 3H), 2.84-2.76 (m, 1H), 2.64-2.53 (m, 2H), 2.49 (dt, J=3.7, 1.8, 1H), 2.15-2.03 (m, 1H); MS (ESI+) m/z 233.3 [M+H]$^+$.

Example 201

Trans-8-cyclopentenyl-2-methyl-1,2,3,3a,4,5-hexahydrobenzo[c]pyrrolo[3,4-c]azepin-6(10bH)-one The title compound was prepared according to the procedure outlined in Example 227H substituting 2-cyclopentenyl-4,4,5,5-tetramethyl-1,3,2-dioxaborolane for 3-(methylsulfonyl)phenylboronic acid and Example 195A for Example 227G. The crude material was purified by reverse phase HPLC to afford the title compound as the trifluoroacetic acid salt. $^1$H NMR (400 MHz, DMSO-$d_6$) δ ppm 10.28 (d, J=51.9, 1H), 8.10 (s, 1H), 7.70 (dd, J=12.7, 1.8, 1H), 7.65-7.56 (m, 1H), 7.17 (dd, J=22.1, 8.0, 1H), 6.35 (s, 1H), 3.99 (dt, J=10.4, 8.0, 1H), 3.82-3.45 (m, 2H), 3.43-3.22 (m, 2H), 3.21-2.83 (m, 7H), 2.66 (dd, J=10.6, 4.3, 2H), 2.59-2.21 (m, 1H), 2.04-1.92 (m, 2H); MS (ESI+) m/z 283.2 [M+H]+.

Example 202

Trans-2-methyl-8-(3,3,3-trifluoroprop-1-en-2-yl)-1,2,3,3a,4,5-hexahydrobenzo[c]pyrrolo[3,4-c]azepin-6(10bH)-one The title compound was prepared according to the procedure outlined in Example 227H substituting 4,4,6-trimethyl-2-(3,3,3-trifluoroprop-1-en-2-yl)-1,3,2-dioxaborinane for 3-(methylsulfonyl)phenylboronic acid and Example 195A for Example 227G. The crude material was purified by reverse phase HPLC to afford the title compound as the trifluoroacetic acid salt. $^1$H NMR (400 MHz, DMSO-d$_6$) δ ppm 10.23 (d, J=58.0, 1H), 8.21 (d, J=4.4, 1H), 7.78 (d, J=17.8, 1H), 7.67 (dd, J=14.9, 7.7, 1H), 7.39-7.26 (m, 1H), 6.17 (d, J=13.7, 2H), 3.85-3.69 (m, 2H), 3.68-3.44 (m, 2H), 3.39 (dd, J=25.4, 8.3, 2H), 3.24-3.04 (m, 2H), 3.03-2.88 (m, 2H), 2.67 (m, 1H), 2.33 (m, 1H); MS (ESI+) m/z 311.1 [M+H]+.

Example 203

Trans-2-methyl-8-(5-methylfuran-2-yl)-1,2,3,3a,4,5-hexahydrobenzo[c]pyrrolo[3,4-c]azepin-6(10bH)-one The title compound was prepared according to the procedure outlined in Example 75 substituting 5-methylfuran-2-boronic acid pinacol ester for 4-fluorophenylboronic acid. The crude material was purified by reverse phase HPLC to afford the title compound as the trifluoroacetic acid salt. $^1$H NMR (400 MHz, DMSO-d$_6$) δ ppm 10.34-10.08 (m, 1H), 8.19-8.12 (m, 1H), 7.92 (d, J=6.2, 1H), 7.76 (dd, J=8.0, 1.8, 1H), 7.29-7.17 (m, 1H), 6.91 (d, J=3.2, 1H), 6.25-6.17 (m, 1H), 3.23-3.06 (m, 4H), 3.02-2.93 (m, 6H), 2.40-2.31 (m, 3H), 2.2 (m, 1H); MS (ESI+) m/z 297.2 [M+H]+.

Example 204

Trans-8-cyclohexyl-2-methyl-1,2,3,3a,4,5-hexahydrobenzo[c]pyrrolo[3,4-c]azepin-6(10bH)-one Example 204A Trans-8-cyclohexenyl-2-methyl-1,2,3,3a,4,5-hexahydrobenzo[c]pyrrolo[3,4-c]azepin-6(10bH)-one The title compound was prepared according to the procedure outlined in Example 227H substituting 2-cyclohexenyl-4,4,5,5-tetramethyl-1,3,2-dioxaborolane for 3-(methylsulfonyl)phenylboronic acid and Example 195A for Example 227G.

Example 204B

Trans-8-cyclohexyl-2-methyl-1,2,3,3a,4,5-hexahydrobenzo[c]pyrrolo[3,4-c]azepin-6(10bH)-one The title compound was prepared according to the procedure outlined in Example 196B substituting Example 204A for Example 196A. $^1$H NMR (400 MHz, DMSO-d$_6$) δ ppm 8.00 (s, 1H), 7.58 (s, 1H), 7.34 (dd, J=7.8, 1.7, 1H), 7.09 (d, J=7.9, 1H), 3.37 (dd, J=14.4, 7.2, 1H), 3.20-3.08 (m, 3H), 3.01 (q, J=7.2, 3H), 2.73 (s, 3H), 2.33 (s, 1H), 1.91 (s, 1H), 1.82-1.65 (m, 5H), 1.46-1.30 (m, 5H); MS (ESI+) m/z 299.3 [M+H]+.

Example 205

Trans-8-cyclopentyl-2-methyl-1,2,3,3a,4,5-hexahydrobenzo[c]pyrrolo[3,4-c]azepin-6(10bH)-one The title compound was prepared according to the procedure outlined in Example 196B substituting Example 201 for Example 196A. The crude material was purified by reverse phase HPLC to afford the title compound as the trifluoroacetic acid salt. $^1$H NMR (500 MHz, DMSO-d$_6$) δ ppm 10.27 (d, J=71.1, 1H), 8.04 (d, J=4.3, 1H), 7.54 (d, J=18.8, 1H), 7.44-7.37 (m, 1H), 7.18-7.06 (m, 1H), 3.97 (d, J=10.6, 1H), 3.80-3.70 (m, 1H), 3.39-3.22 (m, 3H), 3.19-2.81 (m, 5H), 2.56 (d, J=21.0, 1H), 2.27 (m, 1H), 2.01 (dd, J=14.1, 10.8, 2H), 1.82-1.71 (m, 2H), 1.71-1.61 (m, 2H), 1.57-1.47 (m, 2H); MS (ESI+) m/z 285.2 [M+H]+.

Example 206

(3aS,10bS)-8-(3-Fluorobenzyloxy)-2-methyl-1,2,3,3a,4,5-hexahydrobenzo[c]pyrrolo[3,4-c]azepin-6(10bH)-one The title compound was prepared according to the procedure outlined in Example 118 substituting 3-fluorobenzyl alcohol for (S)-1-phenylpropan-2-ol and substituting Example 200B for Example 117. The crude material was purified by reverse phase HPLC to afford the title compound as the trifluoroacetic acid salt. $^1$H NMR (400 MHz, DMSO-d$_6$) δ ppm 10.01 (d, J=48.2, 1H), 8.09 (d, J=4.1, 1H), 7.45 (dd, J=13.9, 8.1, 1H), 7.35-7.25 (m, 3H), 7.15 (ddd, J=22.5, 14.1, 5.5, 3H), 5.18 (s, 2H), 3.95 (dd, J=10.3, 5.6, 1H), 3.80-3.54 (m, 2H), 3.36-3.04 (m, 3H), 2.92 (ddd, J=29.9, 12.9, 8.2, 4H), 2.60-2.16 (m, 1H); MS (ESI+) m/z 341.2 [M+H]+.

Example 207

(3aS,10bS)-8-(2-Fluorobenzyloxy)-2-methyl-1,2,3,3a,4,5-hexahydrobenzo[c]pyrrolo[3,4-c]azepin-6(10bH)-one The title compound was prepared according to the procedure outlined in Examples 118 substituting 2-fluorobenzyl alcohol for (S)-1-phenylpropan-2-ol and substituting Example 200B for Example 117. The crude material was purified by reverse phase HPLC to afford the title compound as the trifluoroacetic acid salt. $^1$H NMR (400 MHz, DMSO-d$_6$) δ ppm 10.22 (d, J=49.8, 1H), 8.08 (d, J=4.4, 1H), 7.56 (t, J=7.7, 1H), 7.48-7.38 (m, 1H), 7.22 (dddd, J=32.1, 28.8, 21.2, 5.6, 5H), 5.18 (s, 2H), 3.71-3.10 (m, 7H), 3.10-2.82 (m, 3H), 2.61-2.16 (m, 1H); MS (ESI+) m/z 341.2 [M+H]+.

Example 208

(3aS,10bS)-8-(3,5-Difluorobenzyloxy)-2-methyl-1,2,3,3a,4,5-hexahydrobenzo[c]pyrrolo[3,4-c]azepin-6(10bH)-one The title compound was prepared according to the procedure outlined in Examples 118 substituting 3,5-difluorobenzyl alcohol for (S)-1-phenylpropan-2-ol and substituting Example 200B for Example 117. The crude material was purified by reverse phase HPLC to afford the title compound as the trifluoroacetic acid salt. $^1$H NMR (400 MHz, DMSO-$d_6$) δ ppm 10.50-10.22 (m, 1H), 8.10 (t, J=4.9, 1H), 7.21 (m, 6H), 5.19 (s, 2H), 3.83-3.16 (m, 5H), 3.18-2.83 (m, 5H), 2.64-2.16 (m, 1H); MS (ESI+) m/z 359.2 [M+H]$^+$.

Example 209

(3aS,10bS)-8-(2,6-Difluorobenzyloxy)-2-methyl-1,2,3,3a,4,5-hexahydrobenzo[c]pyrrolo[3,4-c]azepin-6(10bH)-one The title compound was prepared according to the procedure outlined in Example 118 substituting (2,6-difluorophenyl)methanol for (S)-1-phenylpropan-2-ol and substituting Example 200B for Example 117. The crude material was purified by reverse phase HPLC to afford the title compound as the trifluoroacetic acid salt. $^1$H NMR (400 MHz, DMSO-$d_6$) δ ppm 10.17 (d, J=48.7, 1H), 8.09 (d, J=4.2, 1H), 7.59-7.48 (m, 1H), 7.31 (dd, J=16.4, 5.5, 1H), 7.25-7.02 (m, 4H), 5.15 (s, 2H), 3.96 (d, J=4.2, 1H), 3.74 (dd, J=14.1, 9.1, 1H), 3.40-3.02 (m, 4H), 3.01-2.81 (m, 4H), 2.62-2.14 (m, 1H); MS (ESI+) m/z 359.1 [M+H]$^+$.

Example 210

(3aS,10bS)-8-(3,4-Difluorobenzyloxy)-2-methyl-1,2,3,3a,4,5-hexahydrobenzo[c]pyrrolo[3,4-c]azepin-6(10bH)-one The title compound was prepared according to the procedure outlined in Example 118 substituting 3,4-difluorobenzyl alcohol for (S)-1-phenylpropan-2-ol and substituting Example 200B for Example 117. The crude material was purified by reverse phase HPLC to afford the title compound as the trifluoroacetic acid salt. $^1$H NMR (400 MHz, DMSO-$d_6$) δ ppm 10.22 (d, J=51.0, 1H), 8.09 (d, J=4.2, 1H), 7.59-7.42 (m, 2H), 7.37-7.28 (m, 2H), 7.20-7.08 (m, 2H), 5.14 (s, 2H), 4.02-3.92 (m, 2H), 3.70-3.41 (m, 4H), 3.40-3.15 (m, 2H), 3.16 (s, 2H), 2.62-2.17 (m, 1H); MS (ESI+) m/z 359.2 [M+H]$^+$.

Example 211

(3aS,10bS)-8-(4-Fluorobenzyloxy)-2-methyl-1,2,3,3a,4,5-hexahydrobenzo[c]pyrrolo[3,4-c]azepin-6(10bH)-one The title compound was prepared according to the procedure outlined in Example 118 substituting 4-fluorobenzyl alcohol for (5)-1-phenylpropan-2-ol and substituting Example 200B for Example 117. The crude material was purified by reverse phase HPLC to afford the title compound as the trifluoroacetic acid salt. $^1$H NMR (400 MHz, DMSO-$d_6$) δ ppm 10.22 (d, J=50.3, 1H), 8.08 (d, J=4.3, 1H), 7.50 (dd, J=8.4, 5.7, 2H), 7.33-7.05 (m, 5H), 5.12 (s, 2H), 4.02-3.89 (m, 1H), 3.62-2.82 (m, 9H), 2.62-2.16 (m, 1H); MS (ESI+) m/z 341.2 [M+H]$^+$.

Example 212

(3aS,10bS)-8-(2,3-Difluorobenzyloxy)-2-methyl-1,2,3,3a,4,5-hexahydrobenzo[c]pyrrolo[3,4-c]azepin-6(10bH)-one The title compound was prepared according to the procedure outlined in Example 118 substituting 2,3-difluorobenzyl alcohol for (S)-1-phenylpropan-2-ol and substituting Example 200B for Example 117. The crude material was purified by reverse phase HPLC to afford the title compound as the trifluoroacetic acid salt. $^1$H NMR (400 MHz, DMSO-$d_6$) δ ppm 10.16 (d, J=47.8, 1H), 8.10 (m, 1H), 7.52-7.36 (m, 2H), 7.28 (ddd, J=19.8, 13.4, 5.4, 2H), 7.23-7.09 (m, 2H), 5.22 (d, J=12.6, 2H), 3.96 (dt, J=12.6, 6.6, 1H), 3.60-3.04 (m, 6H), 2.92 (m, 3H), 2.64-2.15 (m, 1H); MS (ESI+) m/z 359.2 [M+H]$^+$.

Example 213

(3aS,10bS)-2-Methyl-8-(2,3,6-trifluorobenzyloxy)-1,2,3,3a,4,5-hexahydrobenzo[c]pyrrolo[3,4-c]azepin-6(10bH)-one The title compound was prepared according to the procedure outlined in Example 118 substituting 2,3,6-trifluorobenzyl alcohol for (S)-1-phenylpropan-2-ol and substituting Example 200B for Example 117. The crude material was purified by reverse phase HPLC to afford the title compound as the trifluoroacetic acid salt. $^1$H NMR (400 MHz, DMSO-$d_6$) δ ppm 10.25 (d, J=51.2, 1H), 8.10 (d, J=4.3, 1H), 7.61 (qd, J=9.5, 5.1, 1H), 7.38-7.06 (m, 4H), 5.21 (d, J=12.1, 2H), 4.02-3.91 (m, 2H), 3.71-2.80 (m, 8H), 2.63-2.17 (m, 1H); MS (ESI+) m/z 377.2 [M+H]$^+$.

Example 214

Trans-9-bromo-2,3,3a,4,5,10b-hexahydro-1H-[1]benzoxepino[4,5-c]pyrrole

Example 214A tert-Butyl trans-9-bromo-1,3,3a,4,5,10b-hexahydro-2H-[1]benzoxepino[4,5-c]pyrrole-2-carboxylate To a round bottom flask containing Example 94A (0.198 g, 0.684 mmol) in dry N,N-dimethylformamide (5 mL) at 80° C. was added 1-bromopyrrolidine-2,5-dione (0.244 g, 1.368 mmol). The reaction mixture was stirred at 80° C. for 2 hours. The reaction was then diluted with water (30 mL) and extracted with CH$_2$Cl$_2$ (3×30 mL). The organic layers were combined and the solvent was evaporated under vacuum. The resulting oil was purified by silica gel column chromatography eluting with 2:1 hexanes:ethyl acetate to afford the titled compound. $^1$H NMR (400 MHz, DMSO-$d_6$) δ ppm 7.40-7.26 (m, 1H), 7.13 (t, J=15.9, 1H), 7.00-6.88 (m, 1H), 4.42-4.31 (m, 1H), 3.90-3.75 (m, 1H), 3.69-3.43 (m, 3), 3.28-3.15 (m, 1), 3.05-2.95 (m, 1), 2.08-1.9 (m, 2H), 1.9-1.55 (m, 1H), 1.43 (d, J=7.9, 9H).

Example 214B

Trans-9-bromo-2,3,3a,4,5,10b-hexahydro-1H-[1]benzoxepino[4,5-c]pyrrole

To a round bottom flask containing Example 214A (0.062 mg, 0.168 mmol) in dichloromethane (3 mL) was added 4 N HCL in dioxane. This was stirred for 8 hours, then the solvent was evaporated and the product was crystallized out of ethyl acetate to afford the title compound. $^1$H NMR (400 MHz, DMSO-$d_6$) δ ppm 7.37 (ddd, J=8.5, 2.4, 0.5, 1H), 7.23 (dd, J=2.4, 0.9, 1H), 6.96 (d, J=8.5, 1H), 4.46 (ddd, J=12.4, 3.8, 3.0, 1H), 3.86-3.80 (m, 1H), 3.76-3.56 (m, 3), 3.43 (d, J=7.1, 1H), 3.09 (dd, J=11.9, 10.3, 1H), 2.21-2.10 (m, 2), 1.95 (dd, J=8.3, 7.1, 1H); MS (DCI+) m/z 268.1 [M+H]$^+$.

Example 215

Trans-9-phenyl-2,3,3a,4,5,10b-hexahydro-1H-[1]benzoxepino[4,5-c]pyrrole

Example 215A tert-Butyl trans-9-phenyl-1,3,3a,4,5,10b-hexahydro-2H-[1]benzoxepino[4,5-c]pyrrole-2-carboxylate To a microwave vial containing Example 214A (0.08 g, 0.217 mmol) in dimethoxyethane (1 mL) was added phenylboronic acid (0.029 g, 0.239 mmol) followed by 2-dicyclohexylphosphino-2',6'-dimethoxybiphenyl (0.045 g, 0.109 mmol), palladium(II) acetate (4.87 mg, 0.022 mmol), and potassium carbonate (0.217 mL, 0.434 mmol). The mixture was heated in a CEM microwave Explorer® 48, at 150° C. (maximum 300 W) for 25 minutes. After this time, the solvent was removed under reduced pressure and the resulting oil was purified by silica gel column chromatography eluting with 3:1 hexanes:ethyl acetate to afford the title compound. $^1$H NMR (400 MHz, DMSO-$d_6$) δ ppm 7.60 (dd, J=11.9, 7.9, 2H), 7.69-7.51 (m, 3H), 7.42 (d, J=7.7, 1H), 7.32 (t, J=7.0, 1H), 7.05 (d, J=8.2, 1H), 4.37 (t, J=13.2, 1H), 3.93 (m, 1H), 3.77-3.51 (m, 3H), 3.23 (m, 1H), 3.35-2.66 (m, 30H), 3.02 (m, 1H), 2.08-1.92 (m, 2H), 1.91-1.75 9m, 1H), 1.42 (s, 12H).

Example 215B

Trans-9-phenyl-2,3,3a,4,5,10b-hexahydro-1H-[1]benzoxepino[4,5-c]pyrrole

To a round bottom flask containing Example 215A (0.55 mg, 0.150 mmol) in dichloromethane (3 mL) was added 4 N HCl in dioxane. The mixture was stirred for 6 hours, then the solvent was evaporated and the product was crystallized out of ethyl acetate to afford the title compound. $^1$H NMR (400 MHz, DMSO-$d_6$) δ ppm 7.61-7.55 (m, 2H), 7.49-7.38 (m, 3H), 7.35-7.25 (m, 2H), 7.13-7.06 (m, 1H), 4.48 (dt, J=12.4, 3.1, 1H), 3.90 (dd, J=11.0, 6.9, 1H), 3.87-3.70 (m, 2H), 3.68-3.55 (m, 1H), 3.55-3.45 (m, 1H), 3.17-3.08 (m, 1H), 2.23-2.10 (m, 2H), 2.09-1.87 (m, 1H); MS (DCI+) m/z 266.1 [M+H]$^+$.

Example 216

Trans-8-(benzyloxy)-2-methyl-1,2,3,3a,4,5-hexahydrobenzo[c]pyrrolo[3,4-e]azepin-6(10bH)-one To a vial filled with argon was added Example 53 (0.125 g, 5 mmol), 2-di-tert-butylphosphino-3,4,5,6-tetramethyl-2',4',6'-triisopropyl-1,1'-biphenyl (0.019 g, 0.040 mmol), cesium carbonate (0.060 mL, 0.750 mmol), benzyl alcohol (1.035 mL, 10.00 mmol) and toluene (0.1 mL) and argon was bubbled through the suspension. Palladium(II) acetate (4.49 mg, 0.020 mmol) was added, the vial was capped, and the mixture was heated with stirring at 90° C. for 3 hours. The solvents were evaporated and the crude material was dissolved in dimethyl sulfoxide/methanol, filtered and purified by reverse phase HPLC to afford the title compound as the trifluoroacetic acid salt. $^1$H NMR (500 MHz, DMSO-$d_6$) δ ppm 9.98 (m, 1H), 8.07 (s, 1H), 7.47-7.37 (m, 4H), 7.36-7.27 (m, 4H), 7.19-7.08 (m, 2H), 5.22-5.11 (m, 2H), 3.94 (s, 1H), 3.80-3.42 (m, 2H), 3.26-2.79 (m, 8H); MS (ESI+) m/z 323.2 [M+H]$^+$.

Example 217

Trans-8-(3-fluorobenzyloxy)-2-methyl-1,2,3,3a,4,5-hexahydrobenzo[c]pyrrolo[3,4-e]azepin-6(10bH)-one The title compound was prepared according to the procedure outlined in Examples 216 substituting 3-fluorobenzyl alcohol for benzyl alcohol. $^1$H NMR (500 MHz, DMSO-$d_6$) δ ppm 10.09 (m, 1H), 8.09 (m, 1H), 7.48-7.41 (m, 1H), 7.38-7.27 (m, 3H), 7.20-7.01 (m, 4H), 5.18 (s, 2H), 3.95 (m, 1H), 3.80-3.70 (m, 1H), 3.39-2.82 (m, 9H). MS (ESI+) m/z 341.2 [M+H]$^+$

Example 218

Trans-2-benzyl-8-(4-fluorophenyl)-1,2,3,3a,4,5-hexahydrobenzo[c]pyrrolo[3,4-c]azepin-6(10bH)-one The title compound was prepared according to the procedure outlined in Example 75 substituting Example 45 for Example 53. $^1$H NMR (500 MHz, DMSO-$d_6$) δ ppm 8.04 (t, J=4.0 Hz, 1H), 8.01 (m, 1H), 7.68 (m, 3H), 7.36-7.21 (m, 8H), 3.81 (d, J=13.5 Hz, 1H), 3.72 (d, J=13.5, 1H), 3.28-3.15 (m, 3H), 3.09-3.04 (m, 2H), 2.74 (dd, J=9.0, 9.0 Hz, 1H), 2.62 (dd, J=9.0 Hz, 1H), and 2.21 (m, 1H); MS (ESI+) m/z 387 [M+H]$^+$.

Example 219

Trans-8-(4-fluorophenyl)-1,2,3,3a,4,5-hexahydrobenzo[c]pyrrolo[3,4-c]azepin-6(10bH)-one

Example 219A

Trans-tert-butyl 8-(4-fluorophenyl)-6-oxo-1,3a,4,5,6,1013-hexahydrobenzo[c]pyrrolo[3,4-c]azepine-2(3H)-carboxylate The title compound was prepared according to the procedure outlined in Example 94A substituting Example 218 for Example 93.

Example 219B

Trans-8-(4-fluorophenyl)-1,2,3,3a,4,5-hexahydrobenzo[c]pyrrolo[3,4-c]azepin-6(10bH)-one hydrochloride The title compound was prepared as the hydrochloride salt according to the procedure outlined in Example 46B substituting Example 219A for Example 46A. $^1$H NMR (500 MHz, DMSO-$d_6$) δ ppm 9.42 (broad s, 1H), 9.37 (broad s, 1H), 8.18 (dd, J=3.5, 6.5 Hz, 1H), 7.88 (d, J=2.0 Hz, 1H), 7.80 (dd, J=2.0, 8.0 Hz, 1H), 7.74 (m, 2H), 7.36 (d, J=8.0 Hz, 1 Hz), 7.31 (dd, J=8.5, 8.5 Hz, 2H), 3.64 (m, 1H), 3.56 (m, 1H), 3.45 (m, 1H), 3.26 (m, 1H), 3.19 (m, 1H), 3.11 (m, 1H), 2.97 (m, 1H), and 2.28 (m, 1H); MS (ESI+) m/z 297 [M+H]$^+$.

Example 220

(3aR,10bS)-8-(4-Fluorophenyl)-1,2,3,3a,4,5-hexahydrobenzo[c]pyrrolo[3,4-e]azepin-6(10bH)-one

Example 220A (3aS,10bS)-tert-Butyl 8-(4-fluorophenyl)-6-oxo-1,3a,4,5,6,10b-hexahydrobenzo[e]pyrrolo[3,4-c]azepine-2(3H)-carboxylate The title compound was prepared according to the procedure outlined in Example 44 substituting Example 219A for Example 1 (retention time 6.5 minutes).

Example 220B (3aR,10bS)-8-(4-Fluorophenyl)-1,2,3,3a,4,5-hexahydrobenzo[c]pyrrolo[3,4-c]azepin-6(10bH)-one hydrochloride The title compound was prepared as the hydrochloride salt according to the procedure outlined in Example 46B substituting Example 220A for Example 46A. NMR and MS are identical to those of Example 219.

Example 221

(3aS,10bR)-8-(4-Fluorophenyl)-1,2,3,3a,4,5-hexahydrobenzo[c]pyrrolo[3,4-e]azepin-6(10bH)-one

Example 221A (3aR,10bR)-tert-Butyl 8-(4-fluorophenyl)-6-oxo-1,3a,4,5,6,10b-hexahydrobenzo[e]pyrrolo[3,4-c]azepine-2(3H)-carboxylate The title compound was prepared according to the procedure outlined in Example 44 substituting Example 219A for Example 1 (retention time 11.9 minutes).

Example 221B (3aS,10bR)-8-(4-Fluorophenyl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 221A for Example 46A. NMR and MS are identical to those of Example 219B.

Example 222

Trans-2-benzyl-1,2,3,3a,4,10b-hexahydrobenzo[b]pyrrolo[3,4-d]azepin-5(6H)-one

Example 222A (E)-Methyl 4-(2-nitrophenyl)but-3-enoate

A mixture of 2-(2-nitrophenyl)acetaldehyde (760 mg, 4.6 mmol) and methoxylcarbonylmethylenetriphenylphosphorane (1.5 g, 4.6 mmol) in toluene (10 mL) was heated at 110° C. for 3 hours. The crude material was purified by silica gel column chromatography eluting with hexanes and ethyl acetate (2:1) to afford the title compound along with (E)-methyl 4-(2-nitrophenyl)but-2-enoate.

Example 222B

Methyl 2-(trans-1-benzyl-4-(2-nitrophenyl)pyrrolidin-3-yl)acetate

To Example 222A (460 mg, 2.1 mmol) in $CH_2Cl_2$ (5 mL) was added trifluoroacetic acid (5 μl) followed by the addition of N-benzyl-1-methoxy-N-((trimethylsilyl)methyl)methanamine (700 mg, 3.0 mmol) in $CH_2Cl_2$ (3 mL) dropwise. The mixture was stirred at room temperature overnight and then more N-benzyl-1-methoxy-N-((trimethylsilyl)methyl)methanamine (700 mg, 3.0 mmol) was added in batches. The crude material was purified by silica gel column chromatography eluting with hexanes and ethyl acetate (5:1) to afford the title compound. $^1$H NMR (300 MHz, DMSO-$d_6$) δ ppm 7.83 (m, 1H), 7.74 (m, 1H), 7.68 (m, 1H), 7.43 (m, 1H), 7.34 (m, 4H), 7.23 (m, 1H), 3.65 (m, 2H), 3.42 (s, 2H), 3.06 (m, 1H), 2.92 (m, 1H), 2.58 (m, 3H), and 2.45 (m, 1H).

Example 222C

Trans-2-benzyl-1,2,3,3a,4,10b-hexahydrobenzo[b]pyrrolo[3,4-d]azepin-5(6H)-one

To Example 222B (470 mg, 1.3 mmol) in methanol (10 mL) was added to Raney®-nickel 2800 water slurry (470 mg, 8.0 mmol) in a pressure bottle. The mixture was stirred for 16 hours under 30 psi of hydrogen at room temperature. The mixture was filtered through a nylon membrane and concentrated. The crude in methanol (20 mL) was treated with 5 mL of 25% sodium methoxide in methanol, and the mixture was refluxed for 4 hours. The mixture was concentrated and partitioned between ethyl acetate and water. The crude material was purified by silica gel column chromatography eluting with hexanes and ethyl acetate (5:1) to afford the title compound. $^1$H NMR (500 MHz, DMSO-$d_6$) δ ppm 9.67 (s, 1H), 7.33 (m, 4H), 7.25 (m, 1H), 7.12 (t, J=7.0 Hz, 1H), 7.07 (d, J=7.0 Hz, 1H), 7.01 (d, J=7.5 Hz, 1 Hz), 6.95 (t, J=8.0 Hz, 1H), 3.74 (d, J=13.0 Hz, 1H), 3.62 (d, J=13.0 Hz, 1H), 3.19 (m, 1H), 3.13 (m, 1H), 2.85 (t, J=9.0 Hz, 1H), 2.79 (dd, J=5.5, 17.5 Hz, 1H), 2.70 (t, J=9.0 Hz, 1H), 2.64 (dd, J=11, 17.5 Hz, 1H), 2.47 (dd, J=6.5, 9.0 Hz, 1H), and 2.21 (m, 1H); MS (ESI+) m/z 293 [M+H]$^+$.

Example 223

Trans-2-benzyl-1,2,3,3a,4,10b-hexahydrobenzo[d]pyrrolo[3,4-b]azepin-5(6H)-one

Example 223A (E)-tert-Butyl 3-(2-(2-ethoxy-2-oxoethyl)phenyl)acrylate

To a mixture of ethyl 2-(2-bromophenyl)acetate (0.97 g, 4 mmol), t-butyl acrylate (0.51 g, 4 mmol), tris(dibenzylideneacetone)dipalladium(0) (91 mg, 0.1 mmol), dicyclohexylmethylamine (0.98 g, 5 mmol) in dioxane (5 mL) was added tri-tert-butylphosphine (0.2 mL, 1 N in toluene, 0.2 mmol). The mixture was heated at 70° C. for 30 minutes under $N_2$. Ethyl acetate was added, and the mixture was filtered through diatomaceous earth. The filtrate was concentrated and purified by silica gel column chromatography eluting with hexanes and ethyl acetate (10:1) to afford the title compound. $^1$H NMR (300 MHz, DMSO-d$_6$) δ ppm 7.79 (m, 1H), 7.72 (d, J=15.6 Hz, 1H), 7.34 (m, 3H), 6.40 (d, J=15.7 Hz, 1H), 4.06 (q, J=7.2 Hz, 2H), 3.84 (s, 2H), 1.48 (s, 9H), and 1.17 (t, J=2 Hz, 3H).

Example 223B

Trans-tert-butyl 1-benzyl-4-(2-(2-ethoxy-2-oxoethyl) phenyl)pyrrolidine-3-carboxylate To Example 223A (1.3 g, 4.4 mmol) in CH$_2$Cl$_2$ (10 mL) was added trifluoroacetic acid (10 µl) followed by the addition of N-benzyl-1-methoxy-N-((trimethylsilyl)methyl) methanamine (1.0 g, 4.2 mmol) in CH$_2$Cl$_2$ (5 mL) dropwise. The mixture was stirred at room temperature for 2 hours and purified by silica gel column chromatography eluting with hexanes and ethyl acetate (5:1) to afford the title compound. $^1$H NMR (300 MHz, DMSO-d$_6$) δ ppm 7.49 (d, J=7.7 Hz, 1H), 7.31 (m, 4H), 7.25 (m, 2H), 7.14 (m, 2H), 4.03 (q, J=7.2 Hz, 2H), 3.86 (d, J=16.2 Hz, 1H), 3.80 (d, J=16.5 Hz, 1H), 3.55 (d, J=12.9 Hz, 1H), 3.66 (d, J=12.9 Hz, 1H), 2.98 (m, 2H), 2.84 (t, J=8.6 Hz, 1H), 2.75 (m, 1H), 1.34 (s, 9H), and 1.17 (t, J=7.2 Hz, 3H).

Example 223C

Ethyl 2-(2-(trans-1-benzyl-4-(tert-butoxycarbonylamino)pyrrolidin-3-yl)phenyl)acetate To Example 223B (1.2 g, 2.83 mmol) in dioxane (3 mL) was added HCl (3 mL, 4 N in dioxane). The mixture was stirred at room temperature for 24 hours and concentrated to provide the carboxylic acid intermediate (1 g, 96%). To this carboxylic acid (1 g, 2.5 mmol) in CH$_3$CN (10 mL) was added triethylamine (1 mL, 7.2 mmol) and diphenylphosphoryl azide (0.69 g, 2.5 mmol) at 0° C. The mixture was stirred for 1 hour and concentrated. To this crude material was added toluene (3 mL), and the mixture was heated at 115° C. for 30 minutes followed by addition of t-butanol (1 mL). The mixture was stirred for 20 minutes followed by the addition of ethyl acetate and 1 N NaOH$_{(aq)}$. The crude material was purified by silica gel column chromatography eluting with hexanes and ethyl acetate (5:1) to afford the title compound. $^1$H NMR (300 MHz, DMSO-d$_6$) δ ppm 7.45 (m, 1H), 7.31 (m, 4H), 7.25 (m, 2H), 7.12 (m, 2H), 3.99 (q, J=7.2 Hz, 2H), 3.94 (m, 1H), 3.61 (m, 2H), 3.27 (s, 2H), 2.98 (m, 1H), 2.82 (m, 1H), 2.44 (m, 2H), 1.32 (s, 9H), 1.12 (t, J=7.2 Hz, 3H), 1.07 (m, 1H).

Example 223D

Trans-2-benzyl-1,2,3,3a,4,10b-hexahydrobenzo[d] pyrrolo[3,4-b]azepin-5(6H)-one

To Example 223C (240 mg, 0.55 mmol) in dioxane (1 mL) was added HCl (1.5 mL, 4 N in dioxane). The mixture was stirred for 6 hours and concentrated. The crude material was dissolved in methanol (2 mL) followed by 25% sodium methoxide in methanol (3 mL). The mixture was stirred for 1 hour and concentrated. Ethyl acetate was added and the mixture was washed with water. The crude material was purified by silica gel column chromatography eluting with ethyl acetate to afford the title compound. $^1$H NMR (500 MHz, DMSO-d$_6$) δ ppm 7.88 (d, J=4.5 Hz, 1H), 7.33 (m, 4H), 7.24 (m, 1H), 7.14 (m, 3H), 7.06 (d, J=7.0 Hz, 1H), 4.13 (d, J=15.5 Hz, 1 Hz), 4.04 (m, 1H), 3.83 (d, J=13.5 Hz, 1H), 3.68 (d, J=13.0 Hz, 1H), 3.57 (d, J=16.0 Hz, 1H), 3.43 (m, 1H), 3.33 (m, 1H), 2.88 (t, J=9.0 Hz, 1H), 2.84 (t, J=9.5 Hz, 1H), 2.81 (t, J=9.0 Hz, 1H); MS (ESI+) m/z 293 [M+H]$^+$.

Example 224

Trans-8-fluoro-5-methyl-1,2,3,3a,4,5-hexahydrobenzo[c]pyrrolo[3,4-e]azepin-6(10bH)-one Example 224A Trans-tert-butyl 8-fluoro-6-oxo-1,3a,4,5,6,10b-hexahydrobenzo[c]pyrrolo[3,4-e]azepine-2(3H)-carboxylate To Example 57 (4.0 g, 12.9 mmol) in CH$_2$Cl$_2$ (50 mL) was added di-tert-butyl dicarbonate (3.3 g, 15 mmol). The mixture was stirred overnight, concentrated, and triturated in hexanes. The precipitates were collected to afford the title compound.

Example 224B

Trans-tert-butyl 8-fluoro-5-methyl-6-oxo-1,3a,4,5,6,10b-hexahydrobenzo[c]pyrrolo[3,4-e]azepine-2(3H)-carboxylate To a suspension of Example 224A (3.8 g, 11.9 mmol) and iodomethane (2.1 g, 15 mmol) in tetrahydrofuran (15 mL) was added NaH (0.6 g, 60%, 15 mmol) in portions at 0° C. The mixture was stirred for 2 hours and water was then added. The precipitates were collected to afford the title compound. $^1$H NMR (300 MHz, DMSO-d$_6$) δ ppm 7.33 (m, 1H), 7.29 (m, 1H), 7.28 (m, 1H), 3.69 (m, 1H), 3.60 (m, 1H), 3.54 (m, 1H), 3.35 (m, 2H), 3.17 (m, 1H), 3.10 (s, 3H), 3.00 (m, 1H), 2.16 (m, 1H), and 1.43 (s, 9H).

Example 224C

Trans-8-fluoro-5-methyl-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 224B for Example 46A. $^1$H NMR (500 MHz, DMSO-d$_6$) δ ppm 9.43 (broad s, 1H), 9.28 (broad s, 1H), 7.34 (m, 3H), 3.62 (m, 1 Hz), 3.47 (m, 4H), 3.10 (s, 3H), 3.09 (m, 1H), and 2.21 (m, 1H); MS (ESI+) m/z 235 [M+H]$^+$.

Example 225

(3aR,10bS)-8-Fluoro-5-methyl-1,2,3,3a,4,5-hexahydrobenzo[c]pyrrolo[3,4-e]azepin-6(10bH)-one Example 225A (3aS,10bS)-tert-Butyl 8-fluoro-5-methyl-6-oxo-1,3a,4,5,6,10b-hexahydrobenzo[e]pyrrolo[3,4-e]azepine-2 (3H)-carboxylate The title compound was prepared using the chiral chromatography methodology outlined in Example 44 substituting Example 224B for Example 1 (retention time 6.0 minutes).

Example 225B (3aR,10bS)-8-Fluoro-5-methyl-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 225A for Example 46A. The NMR and MS are identical to those of Example 224.

Example 226

(3aS,10bR)-8-Fluoro-5-methyl-1,2,3,3a,4,5-hexahydrobenzo[c]pyrrolo[3,4-e]azepin-6(10bH)-one

Example 226A (3aR,10bR)-tert-Butyl 8-fluoro-5-methyl-6-oxo-1,3a,4,5,6,10b-hexahydrobenzo[e]pyrrolo[3,4-e]azepine-2(3H)-carboxylate The title compound was prepared using the chiral chromatography methodology outlined in Example 44 substituting Example 224B for Example 1 (retention time 6.5 minutes).

Example 226B

S,10bR)-8-Fluoro-5-methyl-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 226A for Example 46A. The NMR and MS are identical to those of Example 224.

Example 227

Trans-8-(3-methylsulfonyl)phenyl-1,2,3,3a,4,5-hexahydrobenzo[c]pyrrolo[3,4-c]azepin-6(10bH)-one

Example 227A

Methyl 5-acetoxy-2-bromobenzoate

To methyl 2-bromo-5-hydroxybenzoate (20 g, 87 mmol) in pyridine (100 mL) was added acetic anhydride (10.2 g, 100 mmol) at 0° C. The mixture was stirred at ambient temperature for 16 hours, concentrated, and ethyl acetate was added. The mixture was washed with saturated NH$_4$Cl(aq) to afford the crude title compound. $^1$H NMR (300 MHz, DMSO-d$_6$) δ ppm 7.79 (d, J=8.7 Hz, 1H), 7.58 (d, J=2.8 Hz, 1H), 7.30 (dd, J=8.7, 2.8 Hz, 1H), 3.86 (s, 3H), and 2.28 (s, 3H).

Example 227B (E)-Methyl 5-acetoxy-2-(2-cyanovinyl)benzoate

The title compound was prepared according to the procedure outlined in Example 223A substituting Example 227A for ethyl 2-(2-bromophenyl)acetate and acrylonitrle for t-butylacrylate.

Example 227C

Methyl 5-acetoxy-2-(trans-1-benzyl-4-cyanopyrrolidin-3-yl)benzoate

The title compound was prepared according to the procedure outlined in Example 223B substituting Example 227B for Example 223A. $^1$H NMR (300 MHz, DMSO-d$_6$) δ ppm 7.71 (d, J=8.6 Hz, 1H), 7.49 (d, J=2.6 Hz, 1H), 7.39 (m, 2H), 7.34 (m, 4H), 7.27 (m, 1H), 4.29 (q, J=6.3 Hz, 1H), 3.85 (s, 2H), 3.40 (m, 1H), 3.15 (m, 1H), 3.02 (m, 1H), 2.82 (dd, J=9.3, 6.2 Hz, 1H), 2.60 (dd, J=9.5, 6.0 Hz, 1H), 2.28 (s, 3H).

Example 227D

Trans-2-benzyl-8-hydroxy-1,2,3,3a,4,5-hexahydrobenzo[c]pyrrolo[3,4-e]azepin-6(10bH)-one The title compound was prepared according to the procedure outlined in Example 1C substituting Example 227C for Example 1B.

Example 227E

Trans-8-hydroxy-1,2,3,3a,4,5-hexahydrobenzo[c]pyrrolo[3,4-e]azepin-6(10bH)-one

The title compound was prepared according to the procedure outlined in Example 2 substituting Example 227D for Example 1. $^1$H NMR (300 MHz, DMSO-d$_6$) δ ppm 9.44 (m, 1H), 7.89 (dd, J=4.9, 4.4 Hz, 1H), 7.10 (d, J=2.7 Hz, 1H), 6.96 (dd, J=7.7, 2.9 Hz, 1H), 6.81 (dd, J=8.2, 2.6 Hz, 1H), 3.14 (m, 2H), 3.04 (m, 1H), 2.96 (m, 2H), 2.85 (dt, J=10.3, 4.0 Hz, 1H), 2.66 (m, 1H), and 1.95 (m, 1H).

Example 227F

Trans-tert-butyl 8-hydroxy-6-oxo-1,3a,4,5,6,10b-hexahydrobenzo[c]pyrrolo[3,4-e]azepine-2(3H)-carboxylate To a slurry of Example 227E (1.1 g, 5.0 mmol) in N,N-dimethylformamide (20 mL) was added di-tert-butyl dicarbonate (1.1 g, 5.0 mmol) in N,N-dimethylformamide (1 mL). The mixture was stirred for 1 hour and water was added. The precipitates were collected to afford the title compound. $^1$H NMR (300 MHz, DMSO-d$_6$) δ ppm 9.54 (s, 1H), 7.92 (m, 1H), 7.03 (d, J=4.8 Hz, 1H), 7.01 (d, J=5.7 Hz, 1H), 6.83 (dt, J=8.4, 2.1 Hz, 1H), 3.65 (dd, J=6.9, 9.6 Hz, 1H), 3.55 (t, J=11.4 Hz, 1H), 3.48 (dd, J=7.5, 9.6 Hz, 1H), 3.04 (m, 4H), 2.10 (m, 1H), and 1.42 (s, 9H).

Example 227G

Trans-tert-butyl 6-oxo-8-(trifluoromethylsulfonyloxy)-1,3a,4,5,6,10b-hexahydrobenzo[e]pyrrolo[3,4-e]azepine-2(3H)-carboxylate To a slurry of Example 227F (0.77 g, 2.4 mmol) in CH$_2$Cl$_2$ (10 mL) was added triethylamine (0.3 g, 3.0 mmol) and 1,1,1-trifluoro-N-phenyl-N-(trifluoromethylsulfonyl)methanesulfonamide (0.9 g, 2.5 mmol). The mixture was stirred overnight, concentrated, and treated with water. The precipitates were collected to afford the title compound. $^1$H NMR (300 MHz, DMSO-d$_6$) δ ppm 8.28 (m, 1H), 7.65 (m, 1H), 7.60 (m, 1H), 7.45 (dd, J=8.4, 3.7 Hz, 1H), 3.75 (dd, J=9.6, 6.9 Hz, 1H), 3.63 (dd, J=21.3, 10.4 Hz, 1H), 3.52 (dd, J=10.0, 7.4 Hz, 1H), 3.19 (d, J=13.6 Hz, 1H), 3.04 (m, 3H), 2.27 (m, 1H), and 1.43 (s, 9H).

Example 227H

Trans-tert-butyl 8-(3-(methylsulfonyl)phenyl)-6-oxo-1,3a,4,5,6,10b-hexahydrobenzo[e]pyrrolo[3,4-e]azepine-2(3H)-carboxylate To a slurry of Example 227G (90 mg, 0.2 mmol) and meta-methylsulfonylphenylboronic acid (40 mg, 0.2 mmol) in dimethoxyethane (0.3 mL) was added tetrakis(triphenylphosphine)palladium(0) (23 mg, 0.02 mmol) and 3 N Na$_2$CO$_{3(aq)}$ (0.2 mL). The mixture was heated at 100° C. for 1 hour and diluted with water after it was cooled to room temperature. The precipitates were collected to afford the title compound. $^1$H NMR (400 MHz, DMSO-d$_6$) δ ppm 8.18 (s, 1H), 8.15 (m, 1H), 8.06 (d, J=7.7 Hz, 1H), 7.98 (s, 1H), 7.93 (d, J=7.9 Hz, 1H), 7.87 (t, J=6.3 Hz, 1H), 7.76 (t, J=7.8 Hz, 1H), 7.31 (m, 1H), 3.76 (m, 1H), 3.67 (m, 1H), 3.53 (m, 1H), 3.24 (m, 1H), 3.07 (m, 3H), 2.25 (m, 1H), 1.45 (s, 4H), and 1.44 (s, 5H).

Example 227I

Trans-8-(3-(methylsulfonyl)phenyl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 227H for Example 46A. $^1$H NMR (400 MHz, DMSO-d$_6$) δ ppm 9.39 (broad s, 1H), 9.35 (broad s, 1H), 8.24 (m, 1H), 8.19 (m, 1H), 8.07 (d, J=8.0 Hz, 1H), 8.01 (d, J=2.0 Hz, 1H), 7.94 (dt, J=2.0, 8.4 Hz, 2 Hz), 7.77 (t, J=8.0 Hz, 1H), 7.43 (d, J=8.0 Hz, 1H), 3.68 (m, 1H), 3.59 (m, 1H), 3.46 (m, 1H), 3.12 (s, 3H), 3.24 (m, 1H), 3.19 (m, 1H), 3.11 (m, 1H), 2.99 (m, 1H), and 2.32 (m, 1H); MS (ESI+) m/z 357 [M+H]$^+$.

Example 228

(3aS,10bS)-2-Methyl-8-(3-(methylsulfonyl)phenyl)-1,2,3,3a,4,5-hexahydrobenzo[c]pyrrolo[3,4-e]azepin-6(10bH)-one

Example 228A

Trans-2-methyl-8-(3-(methylsulfonyl)phenyl)-1,2,3,3a,4,5-hexahydrobenzo[c]pyrrolo[3,4-e]azepin-6(10bH)-one The title compound was prepared according to the procedure outlined in Example 53 substituting Example 227 for Example 46. $^1$H NMR (400 MHz, DMSO-d$_6$) δ ppm 8.19 (d, J=2.1 Hz, 1H), 8.13 (m, 1H), 8.11 (t, J=2.0 Hz, 1H), 8.04 (broad d, J=8.4 Hz, 1H), 7.93 (broad d, J=8.4 Hz, 1H), 7.84 (dd, J=2.0, 7.6 Hz, 1H), 7.76 (t, J=8.0 Hz, 1H), 7.32 (d, J=8.4 Hz, 1H), 3.30 (s, 3H), 3.28 (m, 2H), 3.15 (m, 1H), 3.10 (m, 1H), 2.93 (dd, J=10.4, 10.8 Hz, 1H), 2.65 (m, 1H), 2.63 (m, 1H), 2.39 (s, 3H), and 2.22 (m, 1H); MS (ESI+) m/z 371 [M+H]$^+$.

Example 228B (3aS,10bS)-2-Methyl-8-(3-(methylsulfonyl)phenyl)-1,2,3,3a,4,5-hexahydrobenzo[c]pyrrolo[3,4-e]azepin-6(10bH)-one The title compound was prepared chiral chromatography methodology outlined in Example 44 substituting Example 228A for Example 1. NMR and MS are same as those of Example 228A (retention time 13.3 minutes).

Example 229

(3aR,10bR)-2-Methyl-8-(3-(methylsulfonyl)phenyl)-1,2,3,3a,4,5-hexahydrobenzo[c]pyrrolo[3,4-c]azepin-6(10bH)-one The title compound was prepared chiral chromatography methodology outlined in Example 44 substituting Example 228A for Example 1. NMR and MS are same as those of Example 228A (retention time 18.3 minutes).

Example 230

N,N-Dimethyl-3-(trans-6-oxo-1,2,3,3a,4,5,6,10b-octahydrobenzo[c]pyrrolo[3,4-e]azepin-8-yl)benzamide

Example 230A

Trans-tert-butyl 8-(3-(dimethylcarbamoyl)phenyl)-6-oxo-1,3a,4,5,6,10b-hexahydrobenzo[c]pyrrolo[3,4-e]azepine-2(3H)-carboxylate The title compound was prepared according to the procedure outlined in Example 227H substituting 3-(dimethylcarbamoyl)phenylboronic acid for 3-(methylsulfonyl)phenylboronic acid.

Example 230B

N,N-Dimethyl-3-(trans-6-oxo-1,2,3,3a,4,5,6,10b-octahydrobenzo[c]pyrrolo[3,4-e]azepin-8-yl)benzamide hydrochloride The title compound was prepared as the hydrochloride salt according to the procedure outlined in Example 46B substituting Example 230A for Example 46A. $^1$H NMR (500 MHz, DMSO-d$_6$) δ ppm 9.37 (s, 1H), 9.31 (s, 1H), 8.19 (dd, J=6.6, 3.8 Hz, 1H), 7.92 (d, J=2.0 Hz, 1H), 7.85 (dd, J=8.0, 2.0 Hz, 1H), 7.77 (d, J=8.2 Hz, 1H), 7.68 (s, 1H), 7.55 (t, J=7.7 Hz, 1H), 7.41 (d, J=8.0 Hz, 1H), 7.38 (d, J=8.0 Hz, 1H), 3.66 (m, 1H), 3.57 (m, 1H), 3.46 (m, 1H), 3.26 (m, 2H), 3.20 (m, 1H), 3.13 (m, 1H), 3.01 (s, 3H), 2.94 (s, 3H), and 2.30 (m, 1H); MS (ESI+) m/z 350 [M+H]$^+$.

Example 231

Trans-8-(2-(methylsulfonyl)phenyl)-1,2,3,3a,4,5-hexahydrobenzo[c]pyrrolo[3,4-e]azepin-6(10bH)-one

Example 231A

Trans-tert-butyl 8-(2-(methylsulfonyl)phenyl)-6-oxo-1,3a,4,5,6,10b-hexahydrobenzo[c]pyrrolo[3,4-e]azepine-2(3H)-carboxylate The title compound was prepared according to the procedure outlined in Example 227H substituting 2-(methylsulfonyl)phenylboronic acid for 3-(methylsulfonyl)phenylboronic acid.

Example 231B

Trans-8-(2-(methylsulfonyl)phenyl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 231A for Example 46A. $^1$H NMR (400 MHz, DMSO-$d_6$) δ ppm 9.40 (broad s, 1H), 9.34 (broad s, 1H), 8.18 (dd, J=6.2, 3.6 Hz, 1H), 8.11 (d, J=7.9 Hz, 1H), 7.78 (t, J=7.5 Hz, 1H), 7.70 (t, J=7.7 Hz, 1H), 7.65 (d, J=1.8 Hz, 1H), 7.56 (dd, J=7.9, 1.8 Hz, 1H), 7.41 (d, J=7.3 Hz, 1H), 7.36 (d, J=7.9 Hz, 1H), 3.69 (m, 1H), 3.60 (m, 1H), 3.48 (m, 1H), 3.28 (m, 1H), 3.21 (m, 1H), 3.11 (m, 1H), 2.99 (m, 1H), 2.89 (s, 3H), and 2.33 (m, 1H). MS (ESI+) m/z 357 [M+H]$^+$.

Example 232

Trans-2-methyl-8-(2-(methylsulfonyl)phenyl)-1,2,3,3a,4,5-hexahydrobenzo[c]pyrrolo[3,4-e]azepin-6(10bH)-one The title compound was prepared according to the procedure outlined in Example 53 substituting Example 231 for Example 46. $^1$H NMR (400 MHz, DMSO-$d_6$) δ ppm 8.10 (dd, J=7.9, 1.2 Hz, 1H), 8.04 (s, 1H), 7.86 (d, J=2.0 Hz, 1H), 7.77 (td, J=7.5, 1.3 Hz, 1H), 7.69 (td, J=7.7, 1.3 Hz, 1H), 7.48 (dd, J=7.8, 2.0 Hz, 1H), 7.40 (dd, J=7.5, 1.2 Hz, 1H), 7.24 (d, J=7.9 Hz, 1H), 3.28 (m, 1H), 3.20 (m, 1H), 3.16 (m, 1H), 3.14 (m, 1H), 2.95 (t, J=9.6 Hz, 1H), 2.86 (s, 3H), 2.68 (p, J=9.1 Hz, 2H), 2.41 (s, 3H), and 2.30 (m, 1H). MS (ESI+) m/z 371 [M+H]$^+$.

Example 233

(3aR,10bS)-9-Chloro-2,3,3a,4,5,1013-hexahydro-1H-[1]benzoxepino[4,5-c]pyrrole

Example 233A tert-Butyl (3aR,10bS)-9-chloro-1,3,3a,4,5,10b-hexahydro-2H-[1]benzoxepino[4,5-c]pyrrole-2-carboxylate The title compound was prepared according to the chlorination procedure outlined in Example 95 substituting Example 270A for Example 94A.

Example 233B (3aR,10bS)-9-Chloro-2,3,3a,4,5,1013-hexahydro-1H-[1]benzoxepino[4,5-c]pyrrole hydrochloride The title compound was prepared as the hydrochloride salt according to the procedure outlined in Example 46B substituting Example 233A for Example 46A. $^1$H NMR (400 MHz, DMSO-$d_6$) δ ppm 9.40 (s, 2H), 7.27 (dd, J=8.5, 2.6 Hz, 1H), 7.16 (m, 1H), 7.04 (d, J=8.5 Hz, 1H), 4.40 (dt, J=12.3, 3.5 Hz, 1H), 3.71 (m, 1H), 3.54 (m, 2H), 3.47 (m, 1H), 3.30 (m, 1H), 2.94 (m, 1H), 2.06 (m, 2H), and 1.82 (m, 1H). MS (ESI+) m/z 224, 226 (3:1) [M+H]$^+$.

Example 234

(3aR,10bS)-9-Chloro-2-methyl-2,3,3a,4,5,1013-hexahydro-1H-[1]benzoxepino[4,5-c]pyrrole The title compound was prepared according to the procedure outlined in Example 53 substituting Example 233 for Example 46. $^1$H NMR (400 MHz, DMSO-$d_6$) δ ppm 7.18 (dd, J=8.4, 2.1 Hz, 1H), 7.06 (d, J=1.8 Hz, 1H), 6.97 (d, J=8.5 Hz, 1H), 4.37 (dt, J=12.1, 3.4 Hz, 1H), 3.53 (m, 1H), 3.20 (m, 1H), 3.04 (dd, J=8.7, 6.5 Hz, 1H), 2.77 (m, 1H), 2.67 (t, J=8.9 Hz, 1H), 2.60 (dd, J=9.1, 6.9 Hz, 1H), 2.33 (s, 3H), and 1.88 (m, 3H); MS (ESI+) m/z 238, 240 (3:1) [M+H]$^+$.

Example 235

(3aR,10bS)-2-Methyl-2,3,3a,4,5,10b-hexahydro-1H-[1]benzoxepino[4,5-c]pyrrole

The title compound was prepared as the hydrochloride salt according to the procedure outlined in Example 53 substituting Example 270 for Example 46. $^1$H NMR (500 MHz, DMSO-$d_6$) δ ppm 11.31 (s, 1H), 7.22 (m, 1H), 7.11 (m, 1H), 7.03 (t, J=7.8 Hz, 2H), 4.40 (dt, J=12.3, 3.4 Hz, 1H), 4.04-3.85 (m, 1H), 3.83-3.65 (m, 1H), 3.62-3.43 (m, 4H), 2.90 (m, 3H), 2.31-2.03 (m, 2H), and 1.87 (m, 1H). MS (ESI+) m/z 204 [M+H]$^+$.

Example 236

Trans-8-(3-acetylphenyl)-1,2,3,3a,4,5-hexahydrobenzo[c]pyrrolo[3,4-e]azepin-6(10bH)-one hydrochloride

Example 236A

Trans-tert-butyl 8-(3-acetylphenyl)-6-oxo-1,3a,4,5,6,10b-hexahydrobenzo[c]pyrrolo[3,4-e]azepine-2(3H)-carboxylate The title compound was prepared according to the procedure outlined in Example 227H substituting 3-acetyl phenylboronic acid for 3-(methylsulfonyl)phenylboronic acid.

Example 236B

Trans-8-(3-acetylphenyl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 236A for Example 46A. $^1$H NMR (400 MHz, DMSO-d$_6$) δ ppm 9.29 (s, 2H), 8.21 (m, 2H), 7.98 (m, 3H), 7.89 (m, 1H), 7.65 (t, J=7.7 Hz, 1H), 7.41 (d, J=8.0 Hz, 1H), 3.67 (m, 1H), 3.58 (m, 1H), 3.47 (m, 1), 3.29 (m, 1H), 3.20 (m, 1H), 3.14 (m, 1H), 2.98 (t, J=11.2 Hz, 1H), 2.67 (s, 3H), and 2.30 (m, 1H). MS (ESI+) m/z 321 [M+H]$^+$.

Example 237

Trans-8-(3-acetylphenyl)-2-methyl-1,2,3,3a,4,5-hexahydrobenzo[c]pyrrolo[3,4-e]azepin-6(10bH)-one The title compound was prepared according to the procedure outlined in Example 53 substituting Example 236 for Example 46. $^1$H NMR (400 MHz, DMSO-d$_6$) δ ppm 8.17 (m, 1H), 8.16 (m, 1H), 8.08 (m, 1H), 7.97 (d, J=7.8 Hz, 1H), 7.94 (d, J=8.3 Hz, 1H), 7.81 (dd, J=8.0, 2.1 Hz, 1H), 7.64 (t, J=7.7 Hz, 1H), 7.29 (d, J=8.0 Hz, 1H), 3.28 (m, 3H), 3.13 (m, 2H), 2.92 (t, J=8.8 Hz, 1H), 2.67 (s, 3H), 2.64 (m, 1H), 2.39 (s, 3H), and 2.23 (m, 1H). MS (ESI+) m/z 335 [M+H]$^+$.

Example 238

Trans-8-(3-(1-hydroxyethyl)phenyl)-2-methyl-1,2,3,3a,4,5-hexahydrobenzo[c]pyrrolo[3,4-e]azepin-6(10bH)-one To Example 237 (31 mg, 0.093 mmol) in methanol (0.5 mL) was added NaBH$_4$ (3.5 mg, 0.093 mmol). The mixture was stirred for 10 minutes and then quenched with 1 N HCl$_{(aq)}$. 1 N NaOH$_{(aq)}$ was added to adjust the pH value to 10. The mixture was extracted with ethyl acetate and the crude was triturated in hexanes and ethyl acetate (1:1). The precipitates were collected to afford the title compound. $^1$H NMR (400 MHz, DMSO-d$_6$) δ ppm 8.10 (d, J=2.1 Hz, 1H), 8.05 (m, 1H), 7.72 (dd, J=8.0, 2.1 Hz, 1H), 7.63 (s, 1H), 7.50 (d, J=7.8 Hz, 1H), 7.41 (t, J=7.6 Hz, 1H), 7.33 (d, J=7.6 Hz, 1H), 7.26 (d, J=8.0 Hz, 1H), 5.23 (d, J=4.3 Hz, 1H), 4.79 (m, 1H), 3.27 (m, 2H), 3.16 (m, 1H), 3.10 (m, 1H), 2.94 (t, J=9.2 Hz, 1H), 2.65 (m, 2H), 2.39 (s, 3H), 2.24 (s, 1H), and 1.37 (d, J=6.4 Hz, 3H); MS (ESI+) m/z 336 [M+H]$^+$.

Example 239

3-(Trans-6-oxo-1,2,3,3a,4,5,6,10b-octahydrobenzo[c]pyrrolo[3,4-e]azepin-8-yl)benzonitrile Example 239A Trans-tert-butyl 8-(3-cyanophenyl)-6-oxo-1,3a,4,5,6,10b-hexahydrobenzo[c]pyrrolo[3,4-e]azepine-2(3H)-carboxylate The title compound was prepared according to the procedure outlined in Example 227H substituting 3-cyanophenylboronic acid for 3-(methylsulfonyl)phenylboronic acid.

Example 239B 3-(Trans-6-oxo-1,2,3,3a,4,5,6,10b-octahydrobenzo[c]pyrrolo[3,4-e]azepin-8-yl)benzonitrile hydrochloride The title compound was prepared as the hydrochloride salt according to the procedure outlined in Example 46B substituting Example 239A for Example 46A. $^1$H NMR (400 MHz, DMSO-d$_6$) δ ppm 9.21 (s, 2H), 8.20 (m, 2H), 8.06 (m, 1H), 7.98 (d, J=2.4 Hz, 1H), 7.91 (dt, J=5.4, 2.7 Hz, 1H), 7.86 (dt, J=1.2, 7.6 Hz, 1H), 7.69 (t, J=8.0 Hz, 1H), 7.40 (d, J=8.0, 1H), 3.66 (dd, J=6.8, 8.4 Hz, 1H), 3.57 (t, J=8.4 Hz, 1H), 3.45 (dd, J=7.6, 10.8 Hz, 1H), 3.24 (m, 1H), 3.19 (m, 1H), 3.10 (m, 1H), 2.97 (t, J=11.2 Hz, 1H), and 2.29 (m, 1H); MS (ESI+) m/z 304 [M+H]$^+$.

Example 240

3-(Trans-2-methyl-6-oxo-1,2,3,3a,4,5,6,10b-octahydrobenzo[c]pyrrolo[3,4-e]azepin-8-yl)benzonitrile The title compound was prepared according to the procedure outlined in Example 53 substituting Example 239 for Example 46. $^1$H NMR (400 MHz, DMSO-d$_6$) δ ppm 8.15 (d, J=2.0 Hz, 2H), 8.08 (t, J=3.7 Hz, 1H), 8.05-7.99 (m, 1H), 7.83 (m, 2H), 7.68 (t, J=7.8 Hz, 1H), 7.29 (d, J=8.0 Hz, 1H), 3.30 (m, 1H), 3.26 (m, 1H), 3.14 (m, 1H), 3.09 (m, 1H), 2.93 (dd, J=10.3, 8.9 Hz, 1H), 2.66 (m, 1H), 2.63 (m, 1H), 2.38 (s, 3H), and 2.21 (m, 1H); MS (ESI+) m/z 318 [M+H]$^+$.

Example 241

Trans-8-(3,6-dihydro-2H-pyran-4-yl)-1,2,3,3a,4,5-hexahydrobenzo[c]pyrrolo[3,4-e]azepin-6(10bH)-one Example 241A Trans-tert-butyl 8-(3,6-dihydro-2H-pyran-4-yl)-6-oxo-1,3a,4,5,6,10b-hexahydrobenzo[c]pyrrolo[3,4-e]azepine-2(3H)-carboxylate The title compound was prepared according to the procedure outlined in Example 227H substituting 3,6-dihydro-2H-pyran-4-ylboronic acid for 3-(methylsulfonyl)phenylboronic acid.

Example 241B

Trans-8-(3,6-dihydro-2H-pyran-4-yl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 241A for Example 46A. $^1$H NMR (400 MHz, DMSO-d$_6$) δ ppm 9.27 (m, 2H), 8.10 (m, 1H), 7.69 (m, 1H), 7.58 (dd, J=2.0, 8.0 Hz, 1H), 7.26 (d, J=8.0 Hz, 1H), 6.33 (s, 1H), 4.21 (m, 2H), 3.81 (t, J=5.6 Hz, 2H), 3.60 (dd, J=6.4, 10.4 Hz, 1H), 3.51 (t, J=10.8 Hz, 1H), 3.41 (dd, J=7.2, 10.4 Hz, 1H), 3.16 (m, 2H), 3.05 (m, 1H), 2.92 (d, J=11.5 Hz, 1H), 2.43 (m, 2H) and 2.22 (m, 1H); MS (ESI+) m/z 285 [M+H]$^+$.

Example 242

Trans-8-(3,6-dihydro-2H-pyran-4-yl)-2-methyl-1,2,3,3a,4,5-hexahydrobenzo[c]pyrrolo[3,4-e]azepin-6(10bH)-one The title compound was prepared according to the procedure outlined in Example 53 substituting Example 241 for Example 46. $^1$H NMR (500 MHz, DMSO-d$_6$) δ ppm 7.98 (m, 1H), 7.87 (t, J=4.9 Hz, 1H), 7.52 (dd, J=2.0, 8.0 Hz, 1H), 7.14 (d, J=8.0 Hz, 1H), 6.25 (m, 1H), 4.21 (q, J=2.5 Hz, 2H), 3.82 (t, J=5.5 Hz, 2H), 3.22 (m, 2H), 3.09 (m, 2H), 2.89 (dd, J=1.0, 9.0 Hz, 1H), 2.64 (m, 1H), 2.61 (m, 1H), 2.44 (m, 2H), 2.37 (s, 3H), and 2.16 (m, 1H); MS (ESI+) m/z 299 [M+H]$^+$.

Example 243

Trans-8-(4-fluorophenoxy)-2-methyl-1,2,3,3a,4,5-hexahydrobenzo[c]pyrrolo[3,4-e]azepin-6(10bH)-one A mixture of Example 53 (125 mg, 0.5 mmol), 4-fluorophenol (168 mg, 1.5 mmol), di-tert-butyl(2',4',6'-triisopropyl-3,4,5,6-tetramethylbiphenyl-2-yl)phosphine (24 mg, 0.05 mmol), cesium carbonate (228 mg, 0.7 mmol), and diacetoxypalladium (5.6 mg, 0.025 mmol) in toluene (0.5 mL) was flushed with $N_2$ and heated at 110° C. for 3 hours. Ethyl acetate was added and the mixture was washed with water. The crude material was purified by reverse phase HPLC to afford the title compound as the trifluoroacetic acid salt. $^1$H NMR (500 MHz, DMSO-$d_6$) δ ppm 8.02 (t, J=3.5 Hz, 1H), 7.39 (d, J=2.8 Hz, 1H), 7.24 (m, 2H), 7.16 (d, J=8.4 Hz, 1H), 7.08 (m, 3H), 3.26 (m, 1H), 3.19 (td, J=10.4, 6.4 Hz, 1H), 3.09 (m, 2H), 2.83 (dd, J=10.3, 8.8 Hz, 1H), 2.61 (m, 2H), 2.36 (s, 3H), and 2.18 (m, 1H); MS (ESI+) m/z 327 [M+H]$^+$.

Example 244

Trans-8-isobutyl-2-methyl-1,2,3,3a,4,5-hexahydrobenzo[e]pyrrolo[3,4-c]azepin-6(10bH)-one The title compound was prepared according to the procedure outlined in Example 196B substituting Example 197 for Example 196A. The crude material was purified by reverse phase HPLC to afford the title compound as the trifluoroacetic acid salt. $^1$H NMR (500 MHz, DMSO-$d_6$) δ ppm 10.42-10.15 (m, 1H), 8.10-7.98 (m, 1H), 7.54-7.41 (m, 1H), 7.35-7.27 (m, 1H), 7.18-7.06 (m, 1H), 4.04-3.92 (s, 1H), 3.60 (d, J=1.1, 1H), 3.60-3.22 (m, 2H), 3.20-3.09 (m, 4H), 3.08-2.85 (m, 3H), 2.65-2.21 (m, 2H), 1.89-1.76 (m, 1H), 0.92-0.81 (m, 6H); MS (ESI+) m/z 273.3 [M+H]$^+$.

Example 245

Trans-8-(3,5-dimethylisoxazol-4-yl)-1,2,3,3a,4,5-hexahydrobenzo[c]pyrrolo[3,4-c]azepin-6(10bH)-one Example 245A Trans-tert-butyl 8-(3,5-dimethylisoxazol-4-yl)-6-oxo-1,3a,4,5,6,10b-hexahydrobenzo[e]pyrrolo[3,4-c]azepine-2(3H)-carboxylate The title compound was prepared according to the procedure outlined in Example 227H substituting 3,5-dimethyl-4-(4,4,5,5-tetramethyl-1,3,2-dioxaborolane-2-yl)isoxazole for 3-(methylsulfonyl)phenylboronic acid.

Example 245B

Trans-8-(3,5-dimethylisoxazol-4-yl)-1,2,3,3a,4,5-hexahydrobenzo[e]pyrrolo[3,4-c]azepin-6(10bH)-one To 55 mg (0.138 mmol) of Example 245A was added 1 mL of dichloromethane and 0.3 mL of trifluoroacetic acid. This was stirred at room temperature overnight. Then the mixture was concentrated and the residue was purified by reverse phase HPLC to afford the title compound as the trifluoroacetic acid salt. $^1$H NMR (400 MHz, DMSO) δ ppm 9.06 (d, J=56.1, 2H), 8.18 (dd, J=6.4, 4.0, 1H), 7.61 (d, J=1.9, 1H), 7.54 (dd, J=7.9, 1.9, 1H), 7.37 (d, J=7.9, 1H), 3.74-3.64 (m, 1H), 3.64-3.53 (m, 1H), 3.53-3.43 (m, 1H), 3.19 (qdd, J=10.8, 9.5, 5.3, 2H), 2.99 (dt, J=17.5, 9.7, 1H), 2.41 (s, 3H), 2.32 (ddd, J=19.9, 12.5, 7.4, 1H), 2.23 (s, 3H); MS (ESI+) m/z 298.1 [M+H]$^+$.

Example 246

Trans-8-(4,4-dimethylcyclohexyloxy)-1,2,3,3a,4,5-hexahydrobenzo[e]pyrrolo[3,4-c]azepin-6(10bH)-one Example 246A Trans-tert-butyl 8-(4,4-dimethylcyclohexyloxy)-6-oxo-1,3a,4,5,6,10b-hexahydrobenzo[e]pyrrolo[3,4-c]azepine-2(3H)-carboxylate The title compound was prepared according to the procedure outlined in Example 118 substituting 4,4-dimethylcyclohexanol for (S)-1-phenylpropan-2-ol and substituting Example 227F for Example 117B.

Example 246B

Trans-8-(4,4-dimethylcyclohexyloxy)-1,2,3,3a,4,5-hexahydrobenzo[e]pyrrolo[3,4-c]azepin-6(10bH)-one The title compound was prepared as the hydrochloride salt according to the procedure outlined in Example 46B substituting Example 246A for Example 46A. $^1$H NMR (400 MHz, DMSO) δ ppm 9.23 (s, 2H), 8.08 (dd, J=6.4, 3.9, 1H), 7.18-7.11 (m, 2H), 7.09-7.02 (m, 1H), 4.42-4.28 (m, 1H), 3.67-3.53 (m, 1H), 3.44 (dd, J=31.4, 11.7, 3H), 3.21-3.01 (m, 2H), 2.93 (d, J=6.0, 1H), 2.20 (dd, J=16.3, 9.8, 1H), 1.78 (s, 2H), 1.65-1.51 (m, 2H), 1.44 (d, J=12.0, 2H), 1.28 (t, J=11.4, 2H), 0.93 (d, J=4.3, 6H); MS (ESI+) m/z 329.2 [M+H]$^+$.

Example 247

Trans-8-(3-oxo-2,3-dihydro-1H-inden-5-yl)-1,2,3,3a,4,5-hexahydrobenzo[c]pyrrolo[3,4-e]azepin-6(10bH)-one Example 247A Trans-tert-butyl 6-oxo-8-(3-oxo-2,3-dihydro-1H-inden-5-yl)-1,3a,4,5,6,10b-hexahydrobenzo[c]pyrrolo[3,4-e]azepine-2(3H)-carboxylate The title compound was prepared according to the procedure outlined in Example 227H substituting 6-(4,4,5,5-tetramethyl-1,3,2-dioxaborolan-2-yl)-2,3-dihydro-1H-inden-1-one for 3-(methylsulfonyl)phenylboronic acid.

Example 247B

Trans-8-(3-oxo-2,3-dihydro-1H-inden-5-yl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 247A for Example 46A. ¹H NMR (400 MHz, DMSO-d₆) δ ppm 9.38 (s, 2H), 8.20 (dd, J=6.4, 3.8 Hz, 1H), 8.02 (dd, J=8.0, 1.8 Hz, 1H), 7.94 (d, J=2.0 Hz, 1H), 7.91-7.84 (m, 2H), 7.71 (d, J=8.1 Hz, 1H), 7.39 (d, J=8.0 Hz, 1H), 3.67 (m, 1H), 3.58 (m, 1H), 3.46 (m, 1H), 3.28 (m, 1H), 3.16 (m, 4H), 3.08 (m, 1H), 2.99 (t, J=11.5 Hz, 1H), 2.71 (m, 2H), and 2.30 (m, 1H); MS (ESI+) m/z 333 [M+H]⁺.

Example 248

(3aS,10bS)-8-(3-((S)-1-Hydroxyethyl)phenyl)-2-methyl-1,2,3,3a,4,5-hexahydrobenzo[e]pyrrolo[3,4-c]azepin-6(10bH)-one Example 248A (3aS,10bS)-2-Methyl-6-oxo-1,2,3,3a,4,5,6,10b-octahydrobenzo[e]pyrrolo[3,4-c]azepin-8-yl trifluoromethanesulfonate The title compound was prepared according to the procedure outlined in Example 195A substituting (3aS,10bS)-8-hydroxy-2-methyl-1,2,3,3a,4,5-hexahydrobenzo[c]pyrrolo[3,4-c]azepin-6(10bH)-one (Example 200) for Example 164B.

Example 248B (S)-1-(3-(4,4,5,5-Tetramethyl-1,3,2-dioxaborolan-2-yl)phenyl)ethanol A 100 mL round bottom flask were charged with [1,1'-bis(diphenylphosphino)ferrocene]dichloropalladium(II) (146 mg, 0.199 mmol), potassium acetate (1464 mg, 14.92 mmol), (S)-1-(3-bromophenyl)ethanol (1000 mg, 4.97 mmol), 4,4,4',4',5,5,5',5'-octamethyl-2,2'-bi(1,3,2-dioxaborolane) (1642 mg, 6.47 mmol) and 10 mL of dioxane. The reaction mixture was heated to reflux under nitrogen for 20 hours. Then the reaction mixture was cooled to room temperature. The reaction mixture was partioned between ethyl acetate and water. The organic layer was washed with brine, dried over sodium sulfate, and concentrated. The residue was purified by flash chromatography eluting with 20-40% ethyl acetate/hexane to obtained as title compound.

Example 248C (3aS,10bS)-8-(3-((S)-1-Hydroxyethyl)phenyl)-2-methyl-1,2,3,3a,4,5-hexahydrobenzo[e]pyrrolo[3,4-c]azepin-6(10bH)-one The title compound was prepared according to the procedure outlined in Example 227H substituting Example 248B for 3-(methylsulfonyl)phenylboronic acid and substituting Example 248A for Example 227G ¹H NMR (400 MHz, DMSO) δ ppm 8.14 (t, J=4.5, 1H), 7.98 (d, J=1.7, 1H), 7.79 (dd, J=7.9, 1.8, 1H), 7.65 (s, 1H), 7.53 (d, J=7.7, 1H), 7.42 (t, J=7.6, 1H), 7.35 (d, J=7.6, 1H), 7.29 (d, J=8.0, 1H), 5.24 (d, J=4.1, 1H), 4.88-4.74 (m, 1H), 3.50 (d, J=52.2, 3H), 3.18 (s, 3H), 3.03 (s, 1H), 2.78 (s, 3H), 2.42 (s, 1H), 1.37 (d, J=6.4, 3H); MS (ESI+) m/z 337.2 [M+H]⁺.

Example 249

(3aS,10bS)-8-(3-((R)-1-Hydroxyethyl)phenyl)-2-methyl-1,2,3,3a,4,5-hexahydrobenzo[e]pyrrolo[3,4-c]azepin-6(10bH)-one Example 249A (R)-1-(3-(4,4,5,5-Tetramethyl-1,3,2-dioxaborolan-2-yl)phenyl)ethanol The title compound was prepared according to the procedure outlined in Example 248B substituting (R)-1-(3-bromophenyl)ethanol for (S)-1-(3-bromophenyl)ethanol Example 249B (3aS,10bS)-8-(34(R)-1-Hydroxyethyl)phenyl)-2-methyl-1,2,3,3a,4,5-hexahydrobenzo[e]pyrrolo[3,4-c]azepin-6(10bH)-one The title compound was prepared according to the procedure outlined in Example 227H substituting Example 249A for 3-(methylsulfonyl)phenylboronic acid and substituting Example 248A for Example 227G ¹H NMR (400 MHz, DMSO) δ ppm 8.08 (dd, J=8.1, 4.5, 1H), 8.05 (d, J=2.0, 1H), 7.75 (dd, J=8.0, 2.1, 1H), 7.64 (s, 1H), 7.51 (dd, J=6.3, 1.4, 1H), 7.42 (t, J=7.6, 1H), 7.34 (d, J=7.6, 1H), 7.27 (d, J=8.0, 1H), 5.26 (t, J=14.0, 1H), 4.80 (d, J=4.2, 1H), 3.27-3.07 (m, 5H), 2.91 (t, J=8.9, 1H), 2.80 (t, J=9.3, 1H), 2.56 (s, 3H), 2.37-2.22 (m, 1H), 1.37 (d, J=6.4, 3H); MS (ESI+) m/z 337.2 [M+H]⁺.

Example 250

Trans-8-(3-(ethylsulfonyl)phenyl)-1,2,3,3a,4,5-hexahydrobenzo[c]pyrrolo[3,4-e]azepin-6(10bH)-one Example 250A Trans-tert-butyl 8-(3-(ethylthio)phenyl)-6-oxo-1,3a,4,5,6,10b-hexahydrobenzo[c]pyrrolo[3,4-e]azepine-2(3H)-carboxylate The title compound was prepared according to the procedure outlined in Example 227H substituting 3-(ethylthio)phenylboronic acid for 3-(methylsulfonyl)phenylboronic acid.

Example 250B

Trans-tert-butyl 8-(3-(ethylsulfonyl)phenyl)-6-oxo-1,3a,4,5,6,10b-hexahydrobenzo[c]pyrrolo[3,4-e]azepine-2(3H)-carboxylate To crude 250A (220 mg, 0.5 mmol) in 5 mL CH₂Cl₂ was added m-chloroperoxybenzoic acid (77%, 270 mg, 1.2 mmol), and an exotherm was observed. The mixture was stirred for 30 minutes and diluted with CH₂Cl₂ and washed with 1 N NaOH$_{aq}$. The crude was triturated in hexanes and ethyl acetate (1:1) and the precipitates were collected to afford the title compounds.

Example 250C

Trans-8-(3-(ethylsulfonyl)phenyl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 250B for Example 46A. $^1$H NMR (400 MHz, DMSO) δ ppm 9.23 (s, 1H), 9.19 (w, 1H), 8.23 (m, 1H), 8.13 (d, J=1.7 Hz, 1H), 8.10 (d, J=7.9 Hz, 1H), 8.00 (d, J=2.0 Hz, 1H), 7.92 (m, 2H), 7.78 (t, J=7.8 Hz, 1H), 7.43 (d, J=8.0 Hz, 1H), 3.68 (m, 1H), 3.59 (m 1H), 3.47 (m, 1H), 3.41 (q, J=7.3 Hz, 2H), 3.19 (m, 1H), 3.14 (m, 2H), 2.98 (m, 1H), 2.31 (m, 1H), 1.14 (t, J=7.3 Hz, 3H); MS (ESI+) m/z 371 [M+H]$^+$.

Example 251

Trans-2-methyl-8-(3-oxo-2,3-dihydro-1H-inden-5-yl)-1,2,3,3a,4,5-hexahydrobenzo[c]pyrrolo[3,4-e]azepin-6(10bH)-one The title compound was prepared according to the procedure outlined in Example 53 substituting Example 247 for Example 46. $^1$H NMR (400 MHz, DMSO-d$_6$) δ ppm 8.12 (d, J=2.1 Hz, 1H), 8.08 (m, 1H), 7.99 (dd, J=8.0, 1.9 Hz, 1H), 7.84 (d, J=1.5 Hz, 1H), 7.81 (dd, J=7.9, 2.2 Hz, 1H), 7.70 (d, J=8.2 Hz, 1H), 7.28 (d, J=8.0 Hz, 1H), 3.25 (m, 4H), 3.14 (m, 3H), 3.04 (m, 1H), 2.77 (m, 1H), 2.70 (m, 2H), 2.47 (s, 3H), and 2.27 (m, 1H); MS (ESI+) m/z 347 [M+H]$^+$.

Example 252

Trans-8-(3-(2-hydroxyethyl)phenyl)-1,2,3,3a,4,5-hexahydrobenzo[c]pyrrolo[3,4-e]azepin-6(10bH)-one

Example 252A

Trans-tert-butyl 8-(3-(2-hydroxyethyl)phenyl)-6-oxo-1,3a,4,5,6,10b-hexahydrobenzo[e]pyrrolo[3,4-e]azepine-2(3H)-carboxylate The title compound was prepared according to the procedure outlined in Example 227H substituting 3-(2-hydroxyethyl)phenylboronic acid for 3-(methylsulfonyl)phenylboronic acid.

Example 252B

Trans-8-(3-(2-hydroxyethyl)phenyl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 252A for Example 46A. $^1$H NMR (400 MHz, DMSO-d$_6$) δ ppm 9.36 (s, 1H), 9.29 (m, 1H), 8.17 (m, 1H), 7.89 (d, J=2.0 Hz, 1H), 7.79 (dd, J=8.0, 2.0 Hz, 1H), 7.51 (m, 2H), 7.38 (m, 2H), 7.25 (d, J=7.6 Hz, 1H), 3.66 (t, J=6.9 Hz, 2H), 3.45 (m, 1H), 3.22 (m, 2H), 3.13 (m, 1H), 2.97 (m, 1H), 2.80 (t, J=6.9 Hz, 2H), and 2.29 (m, 1H); MS (ESI+) m/z 323 [M+H]$^+$.

Example 253

Trans-8-(3-(2-hydroxyethyl)phenyl)-2-methyl-1,2,3,3a,4,5-hexahydrobenzo[c]pyrrolo[3,4-e]azepin-6(10bH)-one The title compound was prepared according to the procedure outlined in Example 53 substituting Example 252 for Example 46. $^1$H NMR (400 MHz, DMSO-d$_6$) δ ppm 8.09 (d, J=2.1 Hz, 1H), 8.04 (t, J=3.3 Hz, 1H), 7.71 (dd, J=7.9, 2.1 Hz, 1H), 7.49 (m, 1H), 7.47 (t, J=7.6 Hz, 1H), 7.24 (t, J=8.8 Hz, 1H), 7.27-7.21 (m, 2H), 4.65 (t, J=4.8 Hz, 1H), 3.64 (q, J=6.8 Hz, 2H), 3.26 (m, 2H), 3.12 (m, 2H), 2.92 (dd, J=8.4, 10.4 Hz, 1H), 2.80 (t, J=7.2 Hz, 2H), 2.62 (m, 2H), 2.37 (s, 3H), and 2.20 (m, 1H). MS (ESI+) m/z 337 [M+H]$^+$.

Example 254

Trans-2-benzyl-1,2,3,3a,4,5,6,10b-octahydrobenzo[b]pyrrolo[3,4-d]azepine

To Example 222 in tetrahydrofuran (0.5 mL) was added lithium aluminum hydride (0.2 mL, 1 M in toluene, 0.2 mmol) at −78° C. The mixture was stirred at room temperature for 2 hours and sequentially quenched with ethyl acetate, methanol, and saturated NaHCO$_{3(aq)}$. Ethyl acetate was added and the mixture was filtered through diatomaceous earth. The crude material was purified by silica gel column chromatography eluting with methanol and ethyl acetate (1:10) to afford the title compound. $^1$H NMR (400 MHz, DMSO-d$_6$) δ ppm 7.33 (m, 4H), 7.24 (m, 1H), 6.94 (t, J=7.5 Hz, 1H), 6.89 (d, J=7.6 Hz, 1H), 6.81 (dd, J=7.8, 1.2 Hz, 1H), 6.71 (dt, J=1.2, 7.6 Hz, 1H), 5.19 (d, J=5.3 Hz, 1H), 3.77 (d, J=13.1 Hz, 1H), 3.60 (d, J=13.1 Hz, 1H), 3.27 (m, 1H), 3.14 (m, 1H), 3.01 (m, 1H), 2.84 (dd, J=10.2, 8.6 Hz, 1H), 2.71 (t, J=9.4 Hz, 1H), 2.58 (m, 2H), 1.81 (m, 2H), and 1.50 (m, 1H). MS (ESI+) m/z 279 [M+H]$^+$.

Example 255

Trans-8-(3-(ethylsulfonyl)phenyl)-2-methyl-1,2,3,3a,4,5-hexahydrobenzo[c]pyrrolo[3,4-e]azepin-6(10bH)-one The title compound was prepared according to the procedure outlined in Example 53 substituting Example 250 for Example 46. $^1$H NMR (400 MHz, DMSO) δ ppm 8.18 (d, J=1.9 Hz, 1H), 8.10 (s, 2H), 8.06 (d, J=7.8 Hz, 1H), 7.89 (d, J=7.7 Hz, 1H), 7.84 (dd, J=7.9, 1.9 Hz, 1H), 7.77 (t, J=7.8 Hz, 1H), 7.31 (d, J=8.0 Hz, 1H), 3.40 (q, J=7.3 Hz, 2H), 3.27 (m, 1H), 3.14 (m, 2H), 3.09 (m, 1H), 2.93 (m, 1H), 2.65 (m, 2H), 2.38 (s, 3H), 2.25 (m, 1H), and 1.13 (t, J=7.3 Hz, 3H); MS (ESI+) m/z 385 [M+H]$^+$.

Example 256

Trans-2-benzyl-1,2,3,3a,4,5-hexahydronaphtho[2,3-c]pyrrolo[3,4-e]azepin-6(12bH)-one

Example 256A

Methyl 3-(trifluoromethylsulfonyloxy)-2-naphthoate

To methyl 3-hydroxy-2-naphthoate (0.40 g, 2 mmol) in CH$_2$C$_2$ (3 mL) was added triethylamine (0.25 g, 2.5 mmol) and 1,1,1-trifluoro-N-phenyl-N-(trifluoromethylsulfonyl)methanesulfonamide (0.74 g, 2.1 mmol). The mixture was stirred overnight and purified by silica gel column chromatography eluting with hexanes and ethyl acetate (10:1) to afford the title compound. $^1$H NMR (300 MHz, DMSO-d$_6$) δ ppm 8.80 (s, 1H), 8.26 (d, J=7.9 Hz, 1H), 8.21 (s, 1H), 8.18 (d, J=8.1 Hz, 1H), 7.72 (dt, J=1.5, 6.9 Hz, 1H), 7.75 (dt, J=1.2, 6.9 Hz, 1H), and 3.94 (s, 3H).

Example 256B (E)-Methyl 3-(2-cyanovinyl)-2-naphthoate

The title compound was prepared according to the procedure outlined in Example 97B substituting methyl 3-(trifluoromethylsulfonyloxy)-2-naphthoate for Example 97A (3:1 trans:cis). Trans isomer: $^1$H NMR (300 MHz, DMSO-d$_6$) δ ppm 8.61 (s, 1H), 8.36 (s, 1H), 8.26 (d, J=16.5 Hz, 1H), 8.15 (m, 1H), 8.03 (m, 1H), 7.72 (m, 2H), 6.42 (t, J=9.6 Hz, 1H), and 3.93 (s, 3H).

Example 256C

Methyl 3-(trans-1-benzyl-4-cyanopyrrolidin-3-yl)-2-naphthoate

The title compound was prepared according to the procedure outlined in Example 223B substituting Example 256B for Example 223A. Trans isomer: $^1$H NMR (300 MHz, DMSO-d$_6$) δ ppm 8.44 (s, 1H), 8.18 (s, 1H), 8.06 (d, J=7.7 Hz, 1H), 7.95 (d, J=8.2 Hz, 1H), 7.67 (ddd, J=8.2, 6.9, 1.3 Hz, 1H), 7.59 (ddd, J=8.1, 6.9, 1.3 Hz, 1H), 7.35 (m, 4H), 7.29 (m, 1H), 4.40 (m, 1H), 4.03 (m, 3H), 3.91 (s, 3H), 3.79 (s, 1H), 3.59 (m, 1H), 3.19 (m, 1H), and 2.96 (m, 1H).

Example 256D

Trans-2-benzyl-1,2,3,3a,4,5-hexahydronaphtho[2,3-e]pyrrolo[3,4-e]azepin-6(12bH)-one The title compound was prepared according to the procedure outlined in Example 1C substituting Example 256C for Example 1B. $^1$H NMR (500 MHz, DMSO-d$_6$) δ ppm 8.35 (s, 1H), 8.06 (t, J=5.0 Hz, 1H), 8.00 (d, J=7.9 Hz, 1H), 7.92 (d, J=8.1 Hz, 1H), 7.65 (s, 1H), 7.57 (ddd, J=8.2, 6.9, 1.2 Hz, 1H), 7.51 (ddd, J=8.1, 6.9, 1.2 Hz, 1H), 7.40 (d, J=6.0 Hz, 2H), 7.35 (t, J=8.0 Hz, 2H), 7.26 (dt, J=7.0, 1.5 Hz, 1H), 3.85 (d, J=13.3 Hz, 1H), 3.77 (d, J=13.3 Hz, 1H), 3.39 (m, 1H), 3.22 (m, 2H), 3.18 (m, 1H), 3.10 (dt, J=14.2, 5.2 Hz, 1H), 2.78 (t, J=8.6 Hz, 1H), 2.67 (t, J=8.9 Hz, 1H), and 2.21 (m, 1H). MS (ESI+) m/z 343 [M+H]$^+$.

Example 257

Trans-1,2,3,3a,4,5-hexahydronaphtho[2,3-e]pyrrolo[3,4-e]azepin-6(12bH)-one

Trifluoroethanol (4 mL) was added to Example 256 (411 mg, 1.2 mmol) and 20% Pd(OH)$_2$—C (wet, 40 mg, 0.029 mmol) in a 20 mL pressure bottle. The mixture was stirred under 60 psi of hydrogen at 50° C. for 19 hours. The mixture was filtered through a polypropylene membrane and purified by reversed phase HPLC to afford the title compound and Example 258. $^1$H NMR (400 MHz, DMSO-d$_6$) δ ppm 8.25 (s, 1H), 8.09 (t, J=1.2 Hz, 1H), 8.01 (d, J=8.1 Hz, 1H), 7.94 (d, J=7.8 Hz, 1H), 7.69 (s, 1H), 7.58 (t, J=6.9 Hz, 1H), 7.52 (t, J=6.9 Hz, 1H), 3.36 (m, 2H), 3.12 (m, 4H), 2.77 (t, J=11.6 Hz, 1H), 2.06 (m, 1H); MS (ESI+) m/z 253 [M+H]$^+$.

Example 258

Trans-1,2,3,3a,4,5,8,9,10,11-decahydronaphtho[2,3-c]pyrrolo[3,4-e]azepin-6(12bH)-one Trifluoroethanol (4 mL) was added to Example 256 (411 mg, 1.2 mmol) and 20% Pd(OH)$_2$—C (wet, 40 mg, 0.029 mmol) in a 20 mL pressure bottle. The mixture was stirred under 60 psi of hydrogen at 50° C. for 19 hours. The mixture was filtered through a polypropylene membrane purified by reversed phase HPLC to afford the title compound and Example 257. $^1$H NMR (400 MHz, DMSO-d$_6$) δ ppm 7.86 (t, J=5.2 Hz, 1H), 7.36 (s, 1H), 6.85 (s, 1H), 3.21 (m, 1H), 3.07 (m, 4H), 2.98 (m, 1H), 2.71 (m, 4H), 2.02 (m, 1H), and 1.73 (m, 4H); MS (ESI+) m/z 257 [M+H]$^+$.

Example 259

(3aR,10bS)-9-Methoxy-2,3,3a,4,5,10b-hexahydrobenzo[3,4]cyclohepta[1,2-C]pyrrol-6(1H)-one The title compound was prepared as the hydrochloride salt according to the procedure outlined in Example 94 substituting Example 261 for Example 93. $^1$H NMR (400 MHz, DMSO-d$_6$) δ ppm 9.56 (s, 1H), 9.40 (s, 1H), 7.66 (d, J=8.7 Hz, 1H), 6.97 (dd, J=8.7, 2.4 Hz, 1H), 6.79 (d, J=1.5 Hz, 1H), 4.04 (m, 1H), 3.64 (m, 1H), 3.49 (m, 1H), 3.28 (m, 1H), 3.03 (m, 1H), 2.93 (m, 1H), 2.58 (m, 1H), 2.22 (m, 1H), 2.04 (m, 1H), and 1.76 (m, 1H); MS (ESI+) m/z 232 [M+H]$^+$.

Example 260

2,3,3a,4,5,10b-Hexahydro-1H-pyrrolo[3',4':4,5]oxepino[2,3-b]pyridine

Example 260A (E)-2-Chloro-3-(2-nitrovinyl)pyridine

To 2-chloronicotinaldehyde (2.8 g, 19.8 mmol) in nitromethane (6.1 g) was added ethylamine hydrochloride (100 mg, 1.2 mmol) and NaOH (25 mg) in ethanol (1.5 mL). The mixture was stirred for 1 hour and concentrated. The crude was dissolved in CH$_2$Cl$_2$ (30 mL) and treated with triethylamine (2.8 g, 28 mmol), 4-(dimethylamino)pyridine (20 mg) and acetic anhydride (2.0 g, 20 mmol) at 0° C. The mixture was stirred for 15 minutes and concentrated saturated NaHCO$_{3(aq)}$ was added, and the precipitates were collected to afford the title compound.

Example 260B 2-(2-(tert-Butyldimethylsilyloxy)ethyl)-3-(2-chloropyridin-3-yl)-4-nitrobutanal To Example 260A (1.66 g, 9.0 mmol) in tetrahydrofuran (10 mL) was added 4-(tert-butyldimethylsilyloxy)butanal (1.82 g, 9.0 mmol) and piperidine (0.34 g, 4.0 mmol). The mixture was stirred for 5 hours, and the crude material was purified by silica gel column chromatography eluting with hexanes and ethyl acetate (5:1) to afford the title compound.

Example 260C 3-(1-Benzyl-4-(2-(tert-butyldimethylsilyloxy)ethyl)pyrrolidin-3-yl)-2-chloropyridine To Example 260B in methanol (25 mL) was added water (1 mL) and acetic acid (1 mL) and Zn dust (5×330 mg, 25 mmol)

in portions. The mixture was stirred for 3 hours followed by the addition of NaBH$_3$CN (180 mg, 3 mmol). The mixture was stirred for 15 minutes followed by the addition of benzylaldehyde (1.1 g) and NaBH$_3$CN (180 mg, 3 mmol). The mixture was stirred for 30 minutes and filtered through diatomaceous earth. The filtrate was partitioned between ethyl acetate and 1 N NaOH$_{(aq)}$. The crude material was purified by silica gel column chromatography eluting with hexanes and ethyl acetate (5:1) to afford the title compound.

Example 260D 2-(1-Benzyl-4-(2-chloropyridin-3-yl)pyrrolidin-3-yl)ethanol

To Example 260C (1.8 g, 4.2 mmol) in tetrahydrofuran (10 mL) was added tetrabutylammonium fluoride (1.1 g, 4.2 mmol). The mixture was stirred overnight and concentrated. The crude material was purified by silica gel column chromatography eluting with ethyl acetate to afford the title compound. Fractions of pure trans isomer were combined to make Example 262A.

Example 260E

2-Benzyl-2,3,3a,4,5,10b-hexahydro-1H-pyrrolo[3',4':4,5]oxepino[2,3-b]pyridine

The title compound was prepared according to the procedure outlined in Example 262B substituting Example 260D for Example 262A.

Example 260F 2,3,3a,4,5,10b-Hexahydro-1H-pyrrolo[3',4':4,5]oxepino[2,3-b]pyridine The title compound was prepared as the bis-hydrochloride salt according to the procedure outlined in Example 264 substituting Example 260E for Example 262. 2:1 mixture of trans/cis isomers. Trans isomer: $^1$H NMR (400 MHz, DMSO-d$_6$) δ ppm 9.55 (s, 2H), 8.17 (dd, J=4.9, 1.7 Hz, 1H), 7.72 (d, J=7.5 Hz, 1H), 7.23 (dd, J=7.5, 5.0 Hz, 1H), 4.48 (dt, J=12.4, 3.8 Hz, 1H), 3.87 (ddd, J=2.4, 10.4, 12.3 Hz, 1H), 3.56 (m, 1H), 3.42 (m, 1H), 3.31 (m, 1H), 2.96 (m, 1H), 2.12 (m, 2H), and 1.85 (m, 1H). Cis isomer: 9.75 (s, 1H), 9.45 (s, 1H), 8.24 (dd, J=1.6, 4.8 Hz, 1H), 7.94 (dd, J=1.6, 5.6 Hz, 1H), 7.29 (dd, J=4.0, 6.4 Hz, 1H), 4.35 (dt, J=11.6, 4.4 Hz, 1H), other peaks were buried under the peaks of the trans-isomer. MS (ESI+) m/z 191 [M+H]$^+$.

Example 261

Trans-2-benzyl-9-methoxy-2,3,3a,4,5,10b-hexahydrobenzo[3,4]cyclohepta[1,2-c]pyrrol-6(1H)-one Example 261A (E)-Methyl 3-(3-methoxyphenyl)acrylate A mixture of (E)-3-(3-methoxyphenyl)acrylic acid (3.56 g, 20 mmol). K$_2$CO$_3$ (3.1 g, 22 mmol), and iodomethane (4.0 g, 28 mmol) in acetone (20 mL) was heated to 70° C. for 16 hours. The mixture was concentrated and partitioned between water and ethyl acetate to afford the crude title compound.

Example 261B

Trans-methyl 1-benzyl-4-(3-methoxyphenyl)pyrrolidine-3-carboxylate

The title compound was prepared according to the procedure outlined in Example 223B substituting Example 261A for Example 223A. $^1$H NMR (300 MHz, DMSO-d$_6$) δ ppm 7.33 (d, J=4.4 Hz, 4H), 7.27 (m, 1H), 7.20 (t, J=8.1 Hz, 1H), 6.87 (m, 2H), 6.77 (ddd, J=8.2, 2.4, 0.9 Hz, 1H), 3.73 (s, 3H), 3.67 (d, J=13.0 Hz, 1H), 3.58 (s, 3H), 3.57 (d, J=12.9 Hz, 1H), 3.49 (t, J=7.3 Hz, 1H), 3.09 (dt, J=8.4, 6.6 Hz, 1H), 2.93 (m, 2H), 2.82 (dd, J=9.1, 6.4 Hz, 1H), and 2.55 (dd, J=8.9, 6.9 Hz, 1H).

Example 261C

Trans-1-benzyl-4-(3-methoxyphenyl)pyrrolidine-3-carbaldehyde

To Example 261B (5.7 g, 17.5 mmol) in toluene (40 mL) was added diisobutylaluminum hydride (neat, 2.5 g, 17.5 mmol) at −78° C. The mixture was stirred for 40 minutes and quenched sequentially with methanol and saturated NaHCO$_{3(aq)}$. Ethyl acetate was added and the mixture was filtered through diatomaceous earth. The crude material was purified by silica gel column chromatography eluting with hexanes and ethyl acetate (5:1) to afford the title compound. $^1$H NMR (300 MHz, DMSO-d$_6$) δ ppm 9.64 (d, J=1.6 Hz, 1H), 7.32 (d, J=4.4 Hz, 4H), 7.25 (m, 1H), 7.20 (t, J=8.4 Hz, 1H), 6.89 (m, 2H), 6.78 (ddd, J=8.3, 2.4, 1.0 Hz, 1H), 3.74 (s, 3H), 3.66 (d, J=13.0 Hz, 1H), 3.60 (d, J=12.9 Hz, 1H), 3.57 (dd, J=8.0, 5.6 Hz, 1H), 3.04 (m, 2H), 2.79 (t, J=10.3 Hz, 1H), 2.45 (t, J=8.7 Hz, 1H).

Example 261D (E)-tert-Butyl 3-(trans-1-benzyl-4-(3-methoxyphenyl)pyrrolidin-3-yl)acrylate A mixture of Example 261C (1.86 g, 6.3 mmol) and t-butoxylcarbonylmethylenetriphenylphosphor ne (2.37 g, 6.3 mmol) in toluene (15 mL) was heated at 110° C. for 1 hour. The volatiles were removed and the crude material was purified by silica gel column chromatography eluting with hexanes and ethyl acetate (3:1) to afford the title compound. $^1$H NMR (300 MHz, DMSO-d$_6$) δ ppm 7.32 (m, 4H), 7.25 (m, 1H), 7.18 (d, J=8.4 Hz, 1H), 6.85 (m, 2H), 6.76 (d, J=15.3 Hz, 1H), 5.69-5.61 (m, 1H), 3.73 (s, 3H), 3.70 (d, J=15.0 Hz, 1H), 3.59 (d, J=15.0 Hz, 1H), 3.13 (m, 1H), 2.98 (m, 3H), 2.62 (m, 1H), 2.53 (m, 1H), 1.39 (s, 9H).

Example 261E tert-Butyl 3-(trans-1-benzyl-4-(3-methoxyphenyl)pyrrolidin-3-yl)propanoate To Example 261D (1.85 g, 4.70 mmol) in tetrahydrofuran (20 mL) was added Raney®-nickel 2800 (water slurry, 1.85 g, 31.5 mmol). The mixture was stirred for 2 hours under hydrogen (40 psi) and filtered through a nylon membrane to afford the crude title compound. $^1$H NMR (300 MHz, DMSO-d$_6$) δ ppm 7.32 (m, 4H), 7.24 (m, 1H), 7.18 (d, J=8.1 Hz, 1H), 6.86 (m, 2H), 6.4 (m, 1H), 3.73 (s, 3H), 3.64 (d, J=13.0 Hz, 1H), 3.55 (d, J=13.0 Hz, 1H), 2.89 (t, J=8.2 Hz, 1H), 2.80 (m, 2H), 2.58 (m, 1H), 2.23 (m, 1H), 2.11 (t, J=7.4 Hz, 2H), 2.11 (m, 1H), 1.59 (m, 2H), and 1.28 (s, 9H).

Example 261F

Trans-2-benzyl-9-methoxy-2,3,3a,4,5,10b-hexahydrobenzo[3,4]cyclohepta[1,2-C]pyrrol-6(1H)-one To Example 261E in $CH_2Cl_2$ (20 mL) was added trifluoroacetic acid (10 mL). The mixture was stirred for 2 hours and concentrated. Polyphosphoric acid (50 mL) was added, and the mixture was heated at 100° C. for 30 minutes. The mixture was cooled to room temperature and 1 N $NaOH_{(aq)}$ added to pH=8. The mixture was extracted with ethyl acetate, washed with 1 N $NaOH_{(aq)}$, and purified by silica gel column chromatography eluting with hexanes and ethyl acetate (5:1) to afford the title compound. $^1$H NMR (400 MHz, DMSO-$d_6$) δ ppm 7.66 (d, J=8.4 Hz, 1H), 7.33 (m, 4H), 7.25 (m, 1H), 6.89 (dd, J=8.7, 2.5 Hz, 1H), 6.67 (d, J=2.1 Hz, 1H), 3.80 (s, 3H), 3.75 (d, J=13.2 Hz, 1H), 3.55 (d, J=12.8 Hz, 1H), 3.48 (m, 2H), 3.03 (m, 1H), 2.63 (dd, J=4.4, 9.2 Hz, 1H), 2.55 (m, 1H), 2.53 (m, 2H), 1.96 (m, 2H), 1.65 (m, 1H); MS (ESI+) m/z 322 [M+H]$^+$.

Example 262

Trans-2-benzyl-2,3,3a,4,5,10b-hexahydro-1H-pyrrolo[3',4':4,5]oxepino[2,3-b]pyridine Example 262A 2-(Trans-1-benzyl-4-(2-chloropyridin-3-yl)pyrrolidin-3-yl)ethanol To Example 260C (1.8 g, 4.2 mmol) in tetrahydrofuran (10 mL) was added tetrabutylammonium fluoride (1.1 g, 4.2 mmol). The mixture was stirred overnight and concentrated. The crude material was purified by silica gel column chromatography eluting with ethyl acetate to afford the title compound.

Example 262B

Trans-2-benzyl-2,3,3a,4,5,10b-hexahydro-1H-pyrrolo[3',4':4,5]oxepino[2,3-b]pyridine To Example 262A (680 mg, 2.1 mmol) in dioxane (10 mL) was added potassium tert-butoxide (350 mg, 3.1 mmol). The mixture was heated at 75° C. for 30 minutes and quenched with water. The mixture was extracted with ethyl acetate. The crude material was purified by silica gel column chromatography eluting with ethyl acetate to afford the title compound. $^1$H NMR (400 MHz, DMSO-$d_6$) δ ppm 8.04 (dd, J=4.7, 1.6 Hz, 1H), 7.49 (m, 1H), 7.33 (m, 4H), 7.24 (m, 1H), 7.06 (dd, J=7.4, 4.8 Hz, 1H), 4.41 (dt, J=12.3, 4.1 Hz, 1H), 3.78 (d, J=13.2 Hz, 1H), 3.73 (ddd, J=2.4, 9.6, 12.4 Hz, 1H), 3.65 (d, J=13.2 Hz, 1H), 3.19 (m, 2H), 2.86 (m, 1H), 2.78 (t, J=9.1 Hz, 1H), 2.59 (dd, J=9.3, 7.7 Hz, 1H), 1.99 (m, 2H), and 1.81 (m, 1H). MS (ESI+) m/z 281 [M+H]$^+$.

Example 263

Trans-9-methoxy-1,2,3,3a,4,5,6,10b-octahydrobenzo[3,4]cyclohepta[1,2-c]pyrrole

Example 263A tert-Butyl (trans)-9-methoxy-3,3a,4,5,6,10b-hexahydrobenzo[3,4]cyclohepta[1,2-c]pyrrole-2(1H)-carboxylate To Example 261 (300 mg, 0.93 mmol) in 2,2,2-trifluoroethanol (10 mL) was added 20% Pd(OH)$_2$—C (wet, 60 mg, 0.43 mmol). The mixture was stirred for 36 hours under 30 psi of hydrogen at 50° C. The mixture was filtered through a nylon membrane and the crude was dissolved in $CH_2Cl_2$ (3 mL). Di-tert-butyl dicarbonate (300 mg) was added and the mixture was stirred for 1 hour. The crude material was purified by silica gel column chromatography eluting with hexanes and ethyl acetate (1:1) to afford the title compound and Example 266A.

Example 263B

Trans-9-methoxy-1,2,3,3a,4,5,6,10b-octahydrobenzo[3,4]cyclohepta[1,2-c]pyrrole

The title compound was prepared as the hydrochloride salt according to the procedure outlined in Example 46B substituting Example 263A for Example 46A. $^1$H NMR (400 MHz, DMSO-$d_6$) δ ppm 9.27 (m, 2H), 7.09 (d, J=8.4 Hz, 1H), 6.72 (dd, J=8.2, 2.6 Hz, 1H), 6.62 (d, J=2.4 Hz, 1H), 3.73 (s, 3H), 3.65 (m, 1H), 3.50 (m, 2H), 3.25 (m, 1H), 2.89 (m, 1H), 2.77 (m, 1H), 2.67 (m, 1H), 2.09 (m, 1H), 1.93 (m, 1H), 1.82 (m, 1H), 1.53 (m, 1H), and 1.20 (m, 1H). MS (ESI+) m/z 218 [M+H]$^+$.

Example 264

Trans-2,3,3a,4,5,10b-hexahydro-1H-pyrrolo[3',4':4,5]oxepino[2,3-b]pyridine

The title compound was prepared as the hydrochloride salt according to the procedure outlined in Example 94 substituting Example 262 for Example 93. $^1$H NMR (400 MHz, DMSO-$d_6$) δ ppm 9.55 (s, 2H), 8.17 (dd, J=4.9, 1.7 Hz, 1H), 7.72 (d, J=7.5 Hz, 1H), 7.23 (dd, J=7.5, 5.0 Hz, 1H), 4.48 (dt, J=12.4, 3.8 Hz, 1H), 3.87 (ddd, J=2.4, 10.4, 12.3 Hz, 1H), 3.56 (m, 1H), 3.42 (m, 1H), 3.31 (m, 1H), 2.96 (m, 1H), 2.12 (m, 2H), and 1.85 (m, 1H); MS (ESI+) m/z 191 [M+H]$^+$.

Example 265

Trans-8-(tetrahydro-2H-pyran-4-yl)-1,2,3,3a,4,5-hexahydrobenzo[c]pyrrolo[3,4-e]azepin-6(10bH)-one Example 265A Trans-tert-butyl 6-oxo-8-(tetrahydro-2H-pyran-4-yl)-1,3a,4,5,6,10b-hexahydrobenzo[c]pyrrolo[3,4-e]azepine-2(3H)-carboxylate To Example 241A (160 mg, 0.42 mmol) in tetrahydrofuran (5 mL) and ethanol (5 mL) was added 5% Pd—C (wet, 32.0 mg, 0.30 mmol). The mixture was stirred for 16 hours under 30 psi of hydrogen at room temperature. The mixture was filtered through a nylon membrane to afford the title compound.

Example 265B

Trans-8-(tetrahydro-2H-pyran-4-yl)-1,2,3,3a,4,5-hexahydrobenzo[c]pyrrolo[3,4-e]azepin-6(10bH)-one hydrochloride The title compound was prepared as the hydrochloride salt according to the procedure outlined in Example 46B substituting Example 265A for Example 46A. (78%). $^1$H NMR (400 MHz, DMSO-$d_6$) δ ppm 9.31 (m, 2H), 8.10 (m, 1H), 7.52 (d, J=1.9 Hz, 1H), 7.41 (dd, J=2.0, 8.0 Hz, 1H), 7.20 (d, J=7.9 Hz, 1H), 3.93 (m, 2H), 3.60 (m, 1H), 3.45 (m, 4H), 3.18 (m, 2H), 3.06 (m, 1H), 2.94 (m, 1H), 2.81 (m, 1H), 2.20 (m, 1H), and 1.65 (m, 4H); MS (ESI+) m/z 287 [M+H]$^+$.

Example 266

Trans-9-methoxy-1,2,3,3a,4,10b-hexahydrobenzo[3,4]cyclohepta[1,2-c]pyrrole

Example 266A tert-Butyl (trans)-6-hydroxy-9-methoxy-3,3a,4,5,6,10b-hexahydrobenzo[3,4]cyclohepta[1,2-c]pyrrole-2(1H)-carboxylate To Example 261 (300 mg, 0.93 mmol) in 2,2,2,-trifluoroethanol (10 mL) was added 20% Pd(OH)$_2$—C (wet, 60 mg, 0.43 mmol). The mixture was stirred for 36 hours under 30 psi of hydrogen at 50° C. The mixture was filtered through a nylon membrane and the crude was dissolved in CH$_2$Cl$_2$ (3 mL). Di-tert-butyl dicarbonate (300 mg) was added, and the mixture was stirred for 1 hour. The crude material was purified by silica gel column chromatography eluting with hexanes and ethyl acetate (1:1) to afford the title compound and Example 263A.

Example 266B

Trans-9-methoxy-1,2,3,3a,4,10b-hexahydrobenzo[3,4]cyclohepta[1,2-c]pyrrole

The title compound was prepared as the hydrochloride salt according to the procedure outlined in Example 46B substituting Example 266A for Example 46A. $^1$H NMR (400 MHz, DMSO-$d_6$) δ ppm 9.62 (s, 1H), 9.36 (s, 1H), 7.18 (d, J=8.5 Hz, 1H), 6.82 (dd, J=8.4, 2.5 Hz, 1H), 6.61 (d, J=2.3 Hz, 1H), 6.37 (d, J=12.6 Hz, 1H), 5.68 (ddd, J=12.5, 5.2, 3.1 Hz, 1H), 3.85 (m, 1H), 3.77 (s, 3H), 3.53 (m, 1H), 3.46 (m, 1H), 3.25 (m, 1H), 2.95 (m, 1H), 2.60 (dt, J=18.6, 4.6 Hz, 1H), 2.44 (m, 1H), and 2.31 (m, 1H); MS (ESI+) m/z 216 [M+H]$^+$.

Example 267

Trans-2-methyl-8-(tetrahydro-2H-pyran-4-yl)-1,2,3,3a,4,5-hexahydrobenzo[c]pyrrolo[3,4-e]azepin-6(10bH)-one The title compound was prepared according to the procedure outlined in Example 53 substituting Example 265 for Example 46. $^1$H NMR (500 MHz, DMSO-$d_6$) δ ppm 7.93 (t, J=3.6 Hz, 1H), 7.71 (d, J=1.9 Hz, 1H), 7.32 (dd, J=7.9, 2.0 Hz, 1H), 7.09 (d, J=7.9 Hz, 1H), 3.94 (dd, J=10.8, 3.6 Hz, 2H), 3.43 (td, J=11.5, 2.3 Hz, 2H), 3.21 (m, 2H), 3.07 (m, 2H), 2.87 (dd, J=10.4, 8.9 Hz, 1H), 2.79 (m, 1H), 2.62 (m, 2H), 2.37 (s, 3H), 2.16 (m, 1H), and 1.64 (m, 4H); MS (ESI+) m/z 301 [M+H]$^+$.

Example 268

Trans-2-methyl-2,3,3a,4,5,10b-hexahydro-1H-pyrrolo[3',4':4,5]oxepino[2,3-b]pyridine The title compound was prepared according to the procedure outlined in Example 53 substituting Example 264 for Example 46. $^1$H NMR (400 MHz, DMSO-$d_6$) δ ppm 8.04 (dd, J=4.8, 1.8 Hz, 1H), 7.52 (m, 1H), 7.08 (dd, J=7.5, 4.8 Hz, 1H), 4.41 (dt, J=12.4, 4.1 Hz, 1H), 3.73 (ddd, J=12.4, 9.8, 2.6 Hz, 1H), 3.18 (td, J=10.1, 6.7 Hz, 1H), 3.07 (dd, J=8.7, 6.6 Hz, 1H), 2.77 (dd, J=9.8, 8.9 Hz, 1H), 2.69 (t, J=9.0 Hz, 1H), 2.61 (dd, J=9.1, 7.4 Hz, 1H), 2.34 (s, 3H), 2.03 (m, 1H), 1.94 (m, 1H), and 1.83 (m, 1H); MS (ESI+) m/z 205 [M+H]$^+$.

Example 269

Cis-2-methyl-1,2,3,3a,4,5,6,10b-octahydrobenzo[3,4]cyclohepta[1,2-c]pyrrole

To diisopropylamine (808 mg, 8.0 mmol) in tetrahydrofuran (3 mL) was added n-butyllithium (4.0 mL, 2.0 N in hexanes, 8.0 mmol) at −78° C. followed by the addition of nitromethane (300 mg, 4.0 mmol). The mixture was stirred for 10 min and (Z)-6,7-dihydro-5H-benzo[7]annulene (288 mg, 2.0 mmol) in tetrahydrofuran (1 mL) was added. The mixture was warmed to room temperature for 10 minutes and stirred at room temperature for 4 hours. Water was added and the mixture was extracted with ethyl acetate. The crude material was purified by silica gel column chromatography eluting with ethyl acetate to afford the title compound. $^1$H NMR (500 MHz, DMSO-$d_6$) δ ppm 7.14 (m, 2H), 7.07 (m, 2H), 3.55 (dd, J=17.4, 10.0 Hz, 1H), 3.21 (t, J=8.1 Hz, 1H), 2.97 (t, J=8.3 Hz, 1H), 2.75 (td, J=12.7, 6.9 Hz, 1H), 2.56 (m, 1H), 2.38 (dt, J=11.1, 5.6 Hz, 1H), 2.36 (m, 1H), 2.26 (s, 3H), 1.66 (m, 2H), 1.44 (m, 1H), 1.33 (dd, J=13.7, 6.4 Hz, 1H), and 0.87 (m, 1H); MS (ESI+) m/z 202 [M+H]$^+$.

Example 270

(3aR,10bS)-2,3,3a,4,5,10b-Hexahydro-1H-[1]-benzoxepino[4,5-c]pyrrole

Example 270A tert-Butyl (3aR,10bS)-1,3,3a,4,5,10b-hexahydro-2H-[1]benzoxepino[4,5-c]pyrrole-2-carboxylate Example 94A was resolved using a Kromasil trifunctional (R,R) column (Whelk-O 10 μm, 2.54 mm ID×25 cm) eluting with hexanes and isopropylamine (95/5) at a flow rate of 30 mL/minute using a UV detector (220 nm) to afford the title compound (retention time 4.6 minutes).

Example 270B (3aR,10bS)-2,3,3a,4,5,10b-Hexahydro-1H-[1]benzoxepino[4,5-c]pyrrole hydrochloride The title compound was prepared as the hydrochloride salt according to the procedure outlined in Example 46B substituting Example 270A for Example 46A. $^1$H NMR (400 MHz, DMSO-$d_6$) δ ppm 9.36 (s, 2H), 7.23 (m, 1H), 7.11 (m, 1H), 7.07 (dd, J=7.6, 1.1 Hz, 1H), 7.01 (dd, J=7.9, 1.1 Hz, 1H), 4.40 (dt, J=12.3, 3.5 Hz, 1H), 3.71 (dd, J=11.0, 7.0 Hz, 1H), 3.54 (m, 2H), 3.46 (m, 1H), 3.30 (m, 1H), 2.5 (t, J=10.8 Hz, 1H), 2.09 (m, 1H), 1.99 (m, 1H), and 1.82 (m, 1H); MS (ESI+) m/z 190 [M+H]$^+$.

Example 271

(3aS,10bR)-2,3,3a,4,5,10b-Hexahydro-1H-[1]-benzoxepino[4,5-c]pyrrole

Example 271A tert-Butyl (3aS,10bR)-1,3,3a,4,5,10b-hexahydro-2H-[1]benzoxepino[4,5-c]pyrrole-2-carboxylate Example 94A was resolved using Kromasil trifunctional (R,R) column (Whelk-O 10 µm, 2.54 mm ID×25 cm) eluting with hexanes and isoproylamine (95/5) at a flow rate of 30 mL/minute using a UV detector (220 nm) to afford the title compound (retention time 5.2 minutes).

Example 271B (3aS,10bR)-2,3,3a,4,5,10b-Hexahydro-1H-[1]benzoxepino[4,5-c]pyrrole The title compound was prepared as the hydrochloride salt according to the procedure outlined in Example 46B substituting Example 271A for Example 46A. NMR and MS are identical to those of Example 270.

Example 272

Trans-10-methoxy-2,3,3a,4,5,10b-hexahydro-1H-[1]benzoxepino[4,5-c]pyrrole

Example 272A (E)-3-Methoxy-2-(2-nitrovinyl)phenol

The title compound was prepared according to the procedure outlined in Example 260A substituting 2-hydroxy-6-methoxybenzaldehyde for 2-chloronicotinaldehyde.

Example 272B

Trans-methyl 3-formyl-4-(2-hydroxy-6-methoxyphenyl)-5-nitropentanoate

The title compound was prepared according to the procedure outlined in Example 260B substituting Example 272A for Example 260A and methyl 4-oxobutanoate for 4-(tert-butyldimethylsilyloxy)butanal.

Example 272C

Trans-tert-butyl 3-(2-hydroxy-6-methoxyphenyl)-4-(2-methoxy-2-oxoethyl)pyrrolidine-1-carboxylate To Example 272B in methanol (50 mL), acetic acid (5 mL) and H$_2$O (5 mL) was added zinc dust (5×800 mg) over 1 hour. The mixture was stirred overnight and ethyl acetate (100 mL) was added. Saturated NaHCO$_{3(aq)}$ was added to adjust the pH value to 8. The mixture was filtered through diatomaceous earth and di-tert-butyl dicarbonate (4.36 g, 20 mmol) was added to the filtrate. The mixture was stirred for 1 hour and then partitioned between water and ethyl acetate. The ethyl acetate layer was purified by silica gel column chromatography eluting with hexanes and ethyl acetate (2:1) to afford the titled compound.

Example 272D

Trans-tert-butyl 3-(2-hydroxy-6-methoxyphenyl)-4-(2-hydroxyethyl)pyrrolidine-1-carboxylate To Example 272C (2.4 g, 6.6 mmol) in tetrahydrofuran (15 mL) was added lithium aluminum hydride (5 mL, 2 M in tetrahydrofuran, 1 mmol) at −78° C. The mixture was stirred at room temperature for 1 hour and sequentially quenched with ethyl acetate and saturated NaHCO$_{3(aq)}$. The mixture was filtered through diatomaceous earth and the ethyl acetate layer was concentrated to afford the crude title compound.

Example 272E tert-Butyl (trans)-10-methoxy-1,3,3a,4,5,10b-hexahydro-2H-[1]benzoxepino[4,5-c]pyrrole-2-carboxylate To Example 272D (170 mg, 0.50 mmol) in tetrahydrofuran (3 mL) was added triphenylphosphine (132 mg, 0.50 mmol) and (E)-di-tert-butyl diazene-1,2-dicarboxylate (116 mg, 0.50 mmol). The mixture was stirred for 3 hours. The crude material was purified by silica gel column chromatography eluting with hexanes and ethyl acetate (4:1) to afford the title compound.

Example 272F

Trans-10-methoxy-2,3,3a,4,5,10b-hexahydro-1H-[1]benzoxepino[4,5-c]pyrrole

The title compound was prepared as the hydrochloride salt according to the procedure outlined in Example 46B substituting Example 272E for Example 46A. $^1$H NMR (400 MHz, DMSO-$d_6$) δ ppm 9.26 (s, 1H), 7.12 (t, J=8.2 Hz, 1H), 6.72 (d, J=8.3 Hz, 1H), 6.56 (d, J=8.3 Hz, 1H), 4.11 (m, 1H), 4.05 (m, 1H), 3.97 (m, 1H), 3.76 (s, 3H), 3.44 (m, 2H), 3.11 (m, 1H), 2.85 (m, 1H), 2.43 (m, 1H), 2.26 (m, 1H), and 1.69 (m, 1H); MS (ESI+) m/z 220 [M+H]$^+$.

Example 273

Trans-10-methoxy-2-methyl-2,3,3a,4,5,10b-hexahydro-1H-[1]benzoxepino[4,5-c]pyrrole The title compound was prepared as the hydrochloride salt according to the procedure outlined in Example 53 substituting Example 272 for Example 46. $^1$H NMR (free base): (400 MHz, DMSO-$d_6$) δ ppm 7.04 (dd, J=10.3, 6.0 Hz, 1H), 6.66 (d, J=8.1 Hz, 1H), 6.52 (d, J=8.1 Hz, 1H), 4.13 (m, 1H), 3.87 (m, 1H), 3.70 (s, 3H), 3.23 (m, 3H), 2.73 (m, 1H), 2.54 (m, 1H), 2.21 (m, 1H), 2.08 (m, 1H), and 1.72 (m, 1H); MS (ESI+) m/z 234 [M+H]$^+$.

Example 274

(3aS,10bS)-8-(Benzyloxy)-2-methyl-1,2,3,3a,4,5-hexahydrobenzo[e]pyrrolo[3,4-e]azepin-6(10bH)-one The title compound was prepared according to the procedure outlined in Example 118 substituting benzyl alcohol for (5)-1-phenylpropan-2-ol and substituting Example 200B for Example 117. The crude material was purified by reverse phase HPLC to afford the title compound as the trifluoroacetic acid salt. An alternative preparation of the title compound is described in Example 200A. $^1$H NMR (400 MHz, DMSO-d$_6$) δ ppm 10.28 (d, J=51.0, 1H), 8.08 (d, J=4.4, 1H), 7.52-7.24 (m, 6H), 7.22-7.06 (m, 2H), 5.16 (d, J=12.4, 2H), 3.95 (dt, J=11.2, 6.3, 2H), 3.81-3.68 (m, 1H), 3.66-2.85 (m, 7H), 2.53-2.15 (m, 1H); MS (ESI+) m/z 323.2 [M+H]$^+$.

Example 275

(3aS,10bS)-8-(2-Methoxyphenyl)-2-methyl-1,2,3,3a,4,5-hexahydrobenzo[e]pyrrolo[3,4-c]azepin-6 (10bH)-one The title compound was prepared according to the procedure outlined in Example 75, substituting 2-methoxyphenylboronic acid for 4-fluorophenylboronic acid and substituting Example 199 for Example 53. $^1$H NMR (400 MHz, DMSO-d$_6$) δ ppm 8.03-7.97 (m, 1H), 7.89 (d, J=1.9, 1H), 7.56 (dd, J=7.9, 2.0, 1H), 7.39-7.32 (m, 1H), 7.28 (dd, J=7.5, 1.7, 1H), 7.20 (d, J=8.0, 1H), 7.12 (d, J=7.7, 1H), 7.04 (td, J=7.4, 0.9, 1H), 3.76 (s, 3H), 3.28-3.19 (m, 2H), 3.17-3.05 (m, 3H), 2.91-2.71 (m, 2H), 2.52 (d, J=3.1, 3H), 2.37-2.23 (m, 1H); MS (ESI+) m/z 323.2 [M+H]$^+$.

Example 276

Trans-8-(2,6-difluorophenyl)-1,2,3,3a,4,5-hexahydrobenzo[e]pyrrolo[3,4-c]azepin-6(10bH)-one Example 276A Trans-tert-butyl 8-(2,6-difluorophenyl)-6-oxo-1,3a,4,5,6,10b-hexahydrobenzo[e]pyrrolo[3,4-c]azepine-2(3H)-carboxylate The title compound was prepared according to the procedure outlined in Example 227H substituting 2,6-difluorophenylboronic acid for 3-(methylsulfonyl)phenylboronic acid.

Example 276B

Trans-8-(2,6-difluorophenyl)-1,2,3,3a,4,5-hexahydrobenzo[e]pyrrolo[3,4-c]azepin-6(10bH)-one The title compound was prepared according to the procedure outlined in Example 46B substituting Example 276A for Example 46A. The crude material was purified by reverse phase HPLC to afford the title compound as the trifluoroacetic acid salt. $^1$H NMR (400 MHz, DMSO-d$_6$) δ ppm 9.00 (d, J=52.7, 2H), 8.23-8.16 (m, 1H), 7.72 (s, 1H), 7.62 (d, J=7.9, 1H), 7.51 (tt, J=8.3, 6.6, 1H), 7.42 (d, J=8.0, 1H), 7.30-7.21 (m, 2H), 3.75-3.53 (m, 4H), 3.49 (dd, J=9.4, 6.0, 1H), 3.36-3.10 (m, 3H), 2.98 (dd, J=15.0, 9.4, 1H), 2.35 (dd, J=11.3, 5.9, 1H); MS (ESI+) m/z 323.2 [M+H]$^+$.

Example 277

(3aS,10bS)-8-(Cyclopropylmethoxy)-2-methyl-1,2,3,3a,4,5-hexahydrobenzo[c]pyrrolo[3,4-c]azepin-6 (10bH)-one The title compound was prepared according to the procedure outlined in Example 118 substituting cyclopropanemethanol for (5)-1-phenylpropan-2-ol and substituting Example 200B for Example 117. The crude material was purified by reverse phase HPLC to afford the title compound as the trifluoroacetic acid salt. $^1$H NMR (400 MHz, DMSO-d$_6$) δ ppm 10.10 (s, 1H), 8.06 (t, J=5.0, 1H), 7.17 (s, 1H), 7.08 (s, 2H), 3.94 (s, 1H), 3.89-3.79 (m, 4H), 3.45 (m, 4H), 3.11 (s, 2H), 2.96 (s, 3H), 1.21 (ddd, J=12.7, 7.7, 4.9, 1H), 0.62-0.53 (m, 2H), 0.38-0.29 (m, 2H); MS (ESI+) m/z 287.2 [M+H]$^+$.

Example 278

(3aS,10bS)-8-(3-Acetylphenyl)-2-methyl-1,2,3,3a,4,5-hexahydrobenzo[e]pyrrolo[3,4-e]azepin-6(10bH)-one The title compound was prepared according to the procedure outlined in Example 75, substituting 3-acetylphenylboronic acid for 4-fluorophenylboronic acid and substituting Example 199 for Example 53. $^1$H NMR (400 MHz, DMSO-d$_6$) δ ppm 8.17 (t, J=1.7, 1H), 8.15 (d, J=2.1, 1H), 8.08 (t, J=3.7, 1H), 8.00-7.91 (m, 2H), 7.81 (dd, J=8.0, 2.1, 1H), 7.64 (t, J=7.8, 1H), 7.30 (d, J=8.0, 1H), 3.31-3.23 (m, 1H), 3.22-3.08 (m, 3H), 3.02-2.94 (m, 1H), 2.73-2.62 (m, 6H), 2.42 (s, 3H), 2.24 (dd, J=17.6, 7.1, 1H); MS (ESI+) m/z 335.2 [M+H]$^+$.

Example 279

Cis-8-fluoro-9-methyl-1,2,3,3a,4,5-hexahydrobenzo[c]pyrrolo[3,4-e]azepin-6(10bH)-one The title compound was prepared as described in Example 97 substituting 2-bromo-4-methyl-5-fluorobenzoic acid for 3-bromobenzo[b]thiophene-2-carboxylic acid in Example 97A. $^1$H NMR (300 MHz, DMSO-d$_6$) δ ppm 1.94-2.08 (m, 1H) 2.26 (d, J=1.70 Hz, 3H) 2.66 (t, J=9.83 Hz, 1H) 2.91-3.01 (m, 2H) 3.04-3.13 (m, 3H) 3.15-3.21 (m, 2H) 7.08 (d, J=7.46 Hz, 1H) 7.41 (d, J=10.51 Hz, 1H) 8.03 (s, 1H); MS (+DCI) m/z 235.1 [M+H]$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of formula (I):

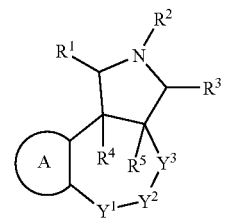

(I)

or a pharmaceutically acceptable salt thereof, wherein A is

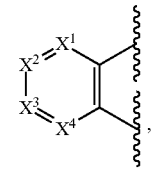

(i)

$R^1$, $R^3$, $R^4$, and $R^5$ are independently selected from the group consisting of hydrogen, alkenyl, alkyl, haloalkyl, $G^1$, $G^2$, —$(CR^{4a}R^{5a})_m$-$G^1$, and —$(CR^{4a}R^{5a})_m$-$G^2$;

$R^{4a}$ and $R^{5a}$, at each occurrence, are each independently hydrogen, halogen, alkyl, or haloalkyl;

$G^1$, at each occurrence, is independently aryl or heteroaryl, wherein each $G^1$ is independently unsubstituted or substituted with 1, 2, 3, 4, or 5 substituents selected from the group consisting of alkyl, alkenyl, alkynyl, halogen, cyano, —$NO_2$, —$OR^{1b}$, —$OC(O)R^{1b}$, —$OC(O)N(R^b)(R^{3b})$, —$SR^{1b}$, —$S(O)R^{2b}$, —$S(O)_2R^{2b}$, —$S(O)_2N(R^b)(R^{3b})$, —$C(O)R^{1b}$, —$C(O)OR^{1b}$, —$C(O)N(R^b)(R^{3b})$, —$N(R^b)(R^{3b})$, —$N(R^a)C(O)R^{1b}$, —$N(R^a)C(O)O(R^{1A})$, —$N(R^a)C(O)N(R^b)(R^{3b})$, —$(CR^{4b}R^{5b})_m$—$NO_2$, —$N(R^b)S(O)_2(R^{2b})$, —$(CR^{4b}R^{5b})_m$—$OR^{1b}$, —$C(OH)[(CR^{4b}R^{5b})_m$—$R^{4b}]_2$, —$(CR^{4b}R^{5b})_m$—$OC(O)R^{1b}$, —$(CR^{4b}R^{5b})_m$—$OC(O)N(R^b)(R^{3b})$, —$(CR^{4b}R^{5b})_m$—$SR^{1b}$, —$(CR^{4b}R^{5b})_m$—$S(O)R^{2b}$, —$(CR^{4b}R^{5b})_m$—$S(O)_2R^{2b}$, —$(CR^{4b}R^{5b})_m$—$S(O)_2N(R^b)(R^{3b})$, —$(CR^{4b}R^{5b})_m$—$C(O)R^{1b}$, —$(CR^{4b}R^{5b})_m$—$C(O)OR^{1b}$, —$(CR^{4b}R^{5b})_m$—$C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, —$(CR^{4b}R^{5b})_m$—$N(R^b)S(O)_2(R^{2b})$, cyanoalkyl, and haloalkyl;

$G^2$ is cycloalkyl, cycloalkenyl, or heterocycle unsubstituted or substituted with 1, 2, 3, 4, or 5 substituents selected from the group consisting of alkyl, alkenyl, alkynyl, halogen, cyano, oxo, —$SR^{1b}$, —$S(O)R^{2b}$, —$S(O)_2R^{2b}$, —$S(O)_2N(R^b)(R^{3b})$, —$C(O)R^{1b}$, —$C(O)OR^{1b}$, —$C(O)N(R^b)(R^{3b})$, —$N(R^b)(R^{3b})$, —$N(R^a)C(O)R^{1b}$, —$N(R^a)C(O)O(R^{1b})$, —$N(R^a)C(O)N(R^b)(R^{3b})$, —$(CR^{4b}R^{5b})_m$—$NO_2$, —$N(R^b)S(O)(R^{2b})$, —$(CR^{4b}R^{5b})_m$—$OR^{1b}$, —$(CR^{4b}R^{5b})_m$—$OC(O)R^{1b}$, —$(CR^{4b}R^{5b})_m$—$OC(O)N(R^b)(R^{3b})$, —$(CR^{4b}R^{5b})_m$—$SR^{1b}$, —$(CR^{4b}R^{5b})_m$—$S(O)R^{2b}$, —$(CR^{4b}R^{5b})_m$—$S(O)_2R^{2b}$, —$(CR^{4b}R^{5b})_m$—$S(O)_2N(R^b)(R^{3b})$, —$(CR^{4b}R^{5b})_m$—$C(O)R^{1b}$, —$(CR^{4b}R^{5b})_m$—$C(O)OR^{1b}$, —$(CR^{4b}R^{5b})_m$—$C(O)N(R^b)(R^{3b})$, —$(CR^{4b}R^{5b})_m$—$N(R^b)(R^{3b})$, —$(CR^{4b}R^{5b})_m$—$N(R^a)C(O)R^{1b}$, —$(CR^{4b}R^{5b})_m$—$N(R^a)C(O)O(R^{1b})$, —$(CR^{4b}R^{5b})_m$—$N(R^a)C(O)N(R^b)(R^{3b})$, —$(CR^{4b}R^{5b})_m$—$N(R^b)S(O)_2(R^{2b})$, cyanoalkyl, and haloalkyl;

$R^a$ and $R^b$, at each occurrence, are each independently hydrogen, alkyl, or haloalkyl;

$R^{1b}$ and $R^{3b}$, at each occurrence, are each independently hydrogen, alkyl, or haloalkyl;

$R^{2b}$, at each occurrence, is independently alkyl or haloalkyl;

$R^{4b}$ and $R^{5b}$, at each occurrence, are each independently hydrogen, halogen, alkyl, or haloalkyl;

m, at each occurrence, is independently 1, 2, 3, 4, or 5;

$R^2$ is selected from the group consisting of hydrogen, alkoxyalkyl, alkyl, alkylcarbonyl, haloalkyl, —$(CR^{4a}R^{5a})_m$-$G^1$, —$(CR^{4a}R^{5a})_p$—O-$G^1$, —C(O)-$G^1$, —$(CR^{4a}R^{5a})_m$-$G^2$, —$(CR^{4a}R^{5a})_p$—O-$G^2$, —C(O)-$G^2$, —$S(O)_2R^6$, and —$C(O)NR^7R^8$;

p, at each occurrence, is independently 2, 3, 4, or 5;

$R^6$ and $R^7$ are independently selected from the group consisting of alkyl, haloalkyl, $G^1$, —$(CR^{4a}R^{5a})_m$-$G^1$, $G^2$ and —$(CR^{4a}R^{5a})_m$-$G^2$;

$R^8$ is selected from the group consisting of hydrogen, alkyl, and haloalkyl; or $R^7$ and $R^8$ taken together with the nitrogen to which they are attached form a heterocycle;

$X^1$ is $CR^9$;

$X^2$ is $CR^{10}$;

$X^3$ is $CR^{11}$;

$X^4$ is $CR^{12}$;

$R^9$, $R^{10}$, $R^{11}$ and $R^{12}$ are each independently hydrogen, alkyl, alkenyl, alkynyl, halogen, cyano, -$G^1$, -$G^2$, —$NO_2$, —$OR^{1a}$, —$OC(O)R^{1a}$, —$OC(O)N(R^b)(R^{3a})$, —$SR^{1a}$, —$S(O)R^{2a}$, —$S(O)_2R^{2a}$, —$S(O)_2N(R^b)(R^{3a})$, —$C(O)R^{1a}$, —$C(O)G^3$, —$C(O)OR^{1a}$, —$C(O)N(R^b)(R^{3a})$, —$N(R^b)(R^{3a})$, —$N(R^a)C(O)R^{1a}$, —$N(R^a)C(O)O(R^{1a})$, —$N(R^a)C(O)N(R^b)(R^{3a})$, —$N(R^a)S(O)_2(R^{2a})$, —$(CR^{4a}R^{5a})_m$—$NO_2$, —$(CR^{4a}R^{5a})_m$—$OR^{1a}$, —$(CR^{4a}R^{5a})_m$—$OC(O)R^{1a}$, —$(CR^{4a}R^{5a})_m$—$OC(O)N(R^b)(R^{3a})$, —$(CR^{4a}R^{5a})_m$—$SR^{1a}$, —$(CR^{4a}R^{5a})_m$—$S(O)R^{2a}$, —$(CR^{4a}R^{5a})_m$—$S(O)_2R^{2a}$, —$(CR^{4a}R^{5a})_m$—$S(O)_2N(R^b)(R^{3a})$, —$(CR^{4a}R^{5a})_m$—$C(O)R^{1a}$, —$(CR^{4a}R^{5a})_m$—$C(O)OR^{1a}$, —$(CR^{4a}R^{5a})_m$—$C(O)N(R^b)(R^{3a})$, —$(CR^{4a}R^{5a})_m$—$N(R^b)(R^{3a})$, —$(CR^{4a}R^{5a})_m$—$N(R^a)C(O)R^{1a}$, —$(CR^{4a}R^{5a})_m$—$N(R^a)C(O)O(R^{1a})$, —$(CR^{4a}R^{5a})_m$—$N(R^a)C(O)N(R^b)(R^{3a})$, —$(CR^{4a}R^{5a})_m$-$G^1$, —$CR^{4a}$=$CR^{5a}$-$G^1$, —$(CR^{4a}R^{5a})_m$-$G^2$, —$CR^{4a}$=$CR^{5a}$-$G^2$, —$CR^{6a}$=$C(R^{7a})_2$, cyanoalkyl, haloalkyl, (v), (vi), (vii) or (vi); wherein (v)

(vi)

(vii)

(viii)

$R^{1a}$ and $R^{3a}$, at each occurrence, are each independently hydrogen, alkyl, haloalkyl, $G^1$, —$(CR^{4a}R^{5a})_m$-G, $G^2$, or —$(CR^{4a}R^{5a})_m$-$G^2$;

$R^2$, at each occurrence, is independently alkyl, haloalkyl, $G^1$, or —$(CR^{4a}R^{5a})_m$-$G^1$;

$R^{6a}$ is alkyl or haloalkyl;

$R^7$, at each occurrence, is independently hydrogen, alkyl, or haloalkyl;

G³ is a heterocyclic ring attached to the adjacent carbonyl moiety through a nitrogen atom contained within the heterocycle;

q is 1 or 2;

$Y^1$ is C(O);

$Y^2$ is $NR^{20}$;

$Y^3$ is $CR^{18}R^{19}$;

$R^{18}$ and $R^{19}$ are independently selected from the group consisting of hydrogen, alkyl, and haloalkyl;

n is 1 or 2; and $R^{20}$ is selected from the group consisting of hydrogen, alkyl, alkylcarbonyl, haloalkyl, —C(O)-G¹, —C(O)NR$^a$-G¹, —S(O)$_n$-G¹, —(CR$^{4a}$R$^{5a}$)$_m$-G¹, —C(O)-G², —C(O)NR$^a$-G², —S(O)$_n$-G², and —(CR$^{4a}$R$^{5a}$)$_m$-G².

2. The compound of claim 1, wherein $R^2$ is selected from the group consisting of hydrogen, alkyl, haloalkyl, —(CR$^{4a}$R$^{5a}$)$_m$-G¹, and —S(O)$_2$R⁶.

3. The compound of claim 1, wherein $R^9$, $R^{10}$, $R^{11}$, and $R^{12}$ are each hydrogen, or wherein one or two of $R^9$, $R^{10}$, $R^{11}$, and $R^{12}$ are each independently alkyl, alkenyl, alkynyl, halogen, cyano, -G¹, -G², —OR$^{1a}$, —NO$_2$, —OC(O)R$^{1a}$, —OC(O)N(R$^b$)(R$^{3a}$), —SR$^{1a}$, —S(O)R$^{2a}$, —S(O)$_2$R$^{2a}$, —S(O)$_2$N(R$^b$)(R$^{3a}$), —C(O)R$^{1a}$, —C(O)G³, —C(O)OR$^{1a}$, —C(O)N(R$^b$)(R$^{3a}$), —N(R$^b$)(R$^{3a}$), —N(R$^a$)C(O)R$^{1a}$, —N(R$^a$)C(O)O(R$^a$), —N(R$^a$)C(O)N(R$^b$)(R$^{3a}$), —N(R$^a$)S(O)$_2$(R$^{2a}$), —(CR$^{4a}$R$^{5a}$)$_m$—NO$_2$, —(CR$^{4a}$R$^{5a}$)$_m$—OR$^{1a}$, —(CR$^{4a}$R$^{5a}$)$_m$—OC(O)R$^{1a}$, —(CR$^{4a}$R$^{5a}$)$_m$—OC(O)N(R$^b$)(R$^{3a}$), —(CR$^{4a}$R$^{5a}$)$_m$—SR$^{1a}$, —(CR$^{4a}$R$^{5a}$)$_m$—S(O)R$^{2a}$, —(CR$^{4a}$R$^{5a}$)$_m$—S(O)$_2$R$^{2a}$, —(CR$^{4a}$R$^{5a}$)$_m$—S(O)$_2$N(R$^b$)(R$^{3a}$), —(CR$^{4a}$R$^{5a}$)$_m$—C(O)R, —(CR$^{4a}$R$^{5a}$)$_m$—C(O)OR$^{1a}$, —(CR$^{4a}$R$^{5a}$)$_m$—C(O)N(R$^b$)(R$^{3a}$), —(CR$^{4a}$R$^{5a}$)$_m$—N(R$^b$)(R$^{3a}$), —(CR$^{4a}$R$^{5a}$)$_m$—N(R$^a$)C(O)R, —(CR$^{4a}$R$^{5a}$)$_m$—N(R$^a$)C(O)O(R$^a$), —(CR$^{4a}$R$^{5a}$)N(R$^a$)C(O)N(R$^b$)(R$^{3a}$), —(CR$^{4a}$R$^{5a}$)$_m$-G¹, —CR$^{4a}$═CR$^{5a}$-G¹, —(CR$^{4a}$R$^{5a}$)$_m$-G², CR$^{4a}$═CR$^{5a}$-G², cyanoalkyl, haloalkyl, (v), (vi), (vii) or (viii), and the others of $R^9$, $R^{10}$, $R^{11}$, and $R^{12}$ are hydrogen (v)

(vi)

(vii)

(viii)

4. The compound of claim 1, wherein the compound is selected from the group consisting of:
trans-2-benzyl-1,2,3,3a,4,5-hexahydrobenzo[c]pyrrolo[3,4-e]azepin-6(10bH)-one;
trans-1,2,3,3a,4,5-hexahydrobenzo[c]pyrrolo[3,4-e]azepin-6(10bH)-one;
cis-2-benzyl-1,2,3,3a,4,5-hexahydrobenzo[c]pyrrolo[3,4-e]azepin-6(10bH)-one;
cis-1,2,3,3a,4,5-hexahydrobenzo[c]pyrrolo[3,4-e]azepin-6(10bH)-one;
trans-2-(3,5-dimethylbenzyl)-1,2,3,3a,4,5-hexahydrobenzo[c]pyrrolo[3,4-e]azepin-6(10bH)-one;
trans-2-(2,5-dimethylbenzyl)-1,2,3,3a,4,5-hexahydrobenzo[c]pyrrolo[3,4-e]azepin-6(10bH)-one;
trans-2-(2,4-dimethylbenzyl)-1,2,3,3a,4,5-hexahydrobenzo[c]pyrrolo[3,4-e]azepin-6(10bH)-one;
trans-2-(3,4-dimethylbenzyl)-1,2,3,3a,4,5-hexahydrobenzo[c]pyrrolo[3,4-e]azepin-6(10bH)-one;
trans-2-(3-methylbenzyl)-1,2,3,3a,4,5-hexahydrobenzo[c]pyrrolo[3,4-e]azepin-6(10bH)-one;
trans-2-(2,3-dimethylbenzyl)-1,2,3,3a,4,5-hexahydrobenzo[c]pyrrolo[3,4-e]azepin-6(10bH)-one;
trans-2-(3-methoxybenzyl)-1,2,3,3a,4,5-hexahydrobenzo[c]pyrrolo[3,4-e]azepin-6(10bH)-one;
trans-2-(2-methoxybenzyl)-1,2,3,3a,4,5-hexahydrobenzo[c]pyrrolo[3,4-e]azepin-6(10bH)-one;
trans-2-(3,5-dichlorobenzyl)-1,2,3,3a,4,5-hexahydrobenzo[c]pyrrolo[3,4-e]azepin-6(10bH)-one;
trans-2-(2,5-dichlorobenzyl)-1,2,3,3a,4,5-hexahydrobenzo[c]pyrrolo[3,4-e]azepin-6(10bH)-one;
trans-2-(3-chlorobenzyl)-1,2,3,3a,4,5-hexahydrobenzo[c]pyrrolo[3,4-e]azepin-6(10bH)-one;
trans-2-(2-chlorobenzyl)-1,2,3,3a,4,5-hexahydrobenzo[c]pyrrolo[3,4-e]azepin-6(10bH)-one;
trans-2-(3-fluorobenzyl)-1,2,3,3a,4,5-hexahydrobenzo[c]pyrrolo[3,4-e]azepin-6(10bH)-one;
trans-2-(2-fluorobenzyl)-1,2,3,3a,4,5-hexahydrobenzo[c]pyrrolo[3,4-e]azepin-6(10bH)-one;
3-((trans-6-oxo-1,3a,4,5,6,10b-hexahydrobenzo[c]pyrrolo[3,4-e]azepin-2(3H)-yl)methyl)benzonitrile;
trans-2-(2,5-dimethoxybenzyl)-1,2,3,3a,4,5-hexahydrobenzo[c]pyrrolo[3,4-e]azepin-6(10bH)-one;
trans-2-(3,5-dimethoxybenzyl)-1,2,3,3a,4,5-hexahydrobenzo[c]pyrrolo[3,4-e]azepin-6(10bH)-one;
cis-2-(3,5-dichlorobenzyl)-1,2,3,3a,4,5-hexahydrobenzo[c]pyrrolo[3,4-e]azepin-6(10bH)-one;
cis-2-(3-chlorobenzyl)-1,2,3,3a,4,5-hexahydrobenzo[c]pyrrolo[3,4-e]azepin-6(10bH)-one;
cis-2-(3-fluorobenzyl)-1,2,3,3a,4,5-hexahydrobenzo[c]pyrrolo[3,4-e]azepin-6(10bH)-one;
cis-2-(naphthalen-1-ylmethyl)-1,2,3,3a,4,5-hexahydrobenzo[c]pyrrlo[3,4-e]azepin-6(10bH)-one;
(3aR,10bS)-1,2,3,3a,4,5-hexahydrobenzo[c]pyrrolo[3,4-e]azepin-6(10bH)-one;
trans-2-benzyl-8-chloro-1,2,3,3a,4,5-hexahydrobenzo[c]pyrrolo[3,4-e]azepin-6(10bH)-one;

trans-8-chloro-1,2,3,3a,4,5-hexahydrobenzo[e]pyrrolo[3,4-c]azepin-6(10bH)-one;
(3aR,10bS)-1,2,3,3a,4,5-hexahydrobenzo[e]pyrrolo[3,4-c]azepin-6(10bH)-one;
trans-2-benzyl-10-chloro-1,2,3,3a,4,5-hexahydrobenzo[e]pyrrolo[3,4-c]azepin-6(1bH)-one;
trans-7-chloro-1,2,3,3a,4,5-hexahydrobenzo[e]pyrrolo[3,4-c]azepin-6(10bH)-one;
trans-2-benzyl-9-chloro-1,2,3,3a,4,5-hexahydrobenzo[e]pyrrolo[3,4-c]azepin-6(10bH)-one;
trans-9-chloro-1,2,3,3a,4,5-hexahydrobenzo[e]pyrrolo[3,4-c]azepin-6(10bH)-one;
trans-8-chloro-2-methyl-1,2,3,3a,4,5-hexahydrobenzo[e]pyrrolo[3,4-c]azepin-6(10bH)-one;
trans-2-benzyl-8-fluoro-1,2,3,3a,4,5-hexahydrobenzo[e]pyrrolo[3,4-c]azepin-6(10bH)-one;
trans-2-benzyl-8,9-dichloro-1,2,3,3a,4,5-hexahydrobenzo[c]pyrrolo[3,4-e]azepin-6(10bH)-one;
trans-8-fluoro-1,2,3,3a,4,5-hexahydrobenzo[c]pyrrolo[3,4-e]azepin-6(10bH)-one;
trans-2-benzyl-7-fluoro-1,2,3,3a,4,5-hexahydrobenzo[e]pyrrolo[3,4-c]azepin-6(10bH)-one;
cis-2-benzyl-7-fluoro-1,2,3,3a,4,5-hexahydrobenzo[c]pyrrolo[3,4-e]azepin-6(10bH)-one;
trans-7-fluoro-1,2,3,3a,4,5-hexahydrobenzo[c]pyrrolo[3,4-e]azepin-6(10bH)-one;
(3aS,10bS)-2-benzyl-8-fluoro-1,2,3,3a,4,5-hexahydrobenzo[c]pyrrolo[3,4-e]azepin-6(10bH)-one;
trans-7-fluoro-1,2,3,3a,4,5-hexahydrobenzo[e]pyrrolo[3,4-c]azepin-6(10bH)-one;
trans-2-benzyl-9-fluoro-1,2,3,3a,4,5-hexahydrobenzo[c]pyrrolo[3,4-e]azepin-6(10bH)-one;
trans-9-fluoro-1,2,3,3a,4,5-hexahydrobenzo[c]pyrrolo[3,4-e]azepin-6(10bH)-one;
trans-2-benzyl-10-fluoro-1,2,3,3a,4,5-hexahydrobenzo[c]pyrrolo[3,4-e]azepin-6(10bH)-one;
cis-2-benzyl-10-fluoro-1,2,3,3a,4,5-hexahydrobenzo[c]pyrrolo[3,4-e]azepin-6(10bH)-one;
trans-10-fluoro-1,2,3,3a,4,5-hexahydrobenzo[c]pyrrolo[3,4-e]azepin-6(10bH)-one;
trans-methyl-3-((6-oxo-1,3a,4,5,6,10b-hexahydrobenzo[e]pyrrolo[3,4-c]azepin-2(3H)-yl)methyl)benzoate;
trans-2-methyl-1,2,3,3a,4,5-hexahydrobenzo[c]pyrrolo[3,4-e]azepin-6(10bH)-one;
trans-2-(5-chloro-2-fluorobenzyl)-1,2,3,3a,4,5-hexahydrobenzo[e]pyrrolo[3,4-c]azepin-6(10bH)-one;
trans-8-(4-fluorophenyl)-2-methyl-1,2,3,3a,4,5-hexahydrobenzo[e]pyrrolo[3,4-c]azepin-6(10bH)-one;
trans-8-(3-fluorophenyl)-2-methyl-1,2,3,3a,4,5-hexahydrobenzo[e]pyrrolo[3,4-c]azepin-6(10bH)-one;
trans-8-(2-fluorophenyl)-2-methyl-1,2,3,3a,4,5-hexahydrobenzo[e]pyrrolo[3,4-c]azepin-6(10bH)-one;
trans-8-(3,4-difluorophenyl)-2-methyl-1,2,3,3a,4,5-hexahydrobenzo[e]pyrrolo[3,4-c]azepin-6(10bH)-one;
trans-2-methyl-8-(4-(trifluoromethyl)phenyl)-1,2,3,3a,4,5-hexahydrobenzo[e]pyrrolo[3,4-c]azepin-6(10bH)-one;
trans-2-methyl-8-(naphthalen-2-yl)-1,2,3,3a,4,5-hexahydrobenzo[e]pyrrolo[3,4-c]azepin-6(10bH)-one;
trans-2-methyl-8-m-tolyl-1,2,3,3a,4,5-hexahydrobenzo[e]pyrrolo[3,4-c]azepin-6(10bH)-one;
trans-2-methyl-8-p-tolyl-1,2,3,3a,4,5-hexahydrobenzo[e]pyrrolo[3,4-c]azepin-6(10bH)-one;
trans-2-methyl-8-(4-(methylsulfonyl)phenyl)-1,2,3,3a,4,5-hexahydrobenzo[e]pyrrolo[3,4-c]azepin-6(10bH)-one;
trans-2-methyl-8-(3-(methylsulfonyl)phenyl)-1,2,3,3a,4,5-hexahydrobenzo[e]pyrrolo[3,4-c]azepin-6(10bH)-one;
trans-2-methyl-8-styryl-1,2,3,3a,4,5-hexahydrobenzo[e]pyrrolo[3,4-c]azepin-6(10bH)-one;
trans-2-methyl-8-phenyl-1,2,3,3a,4,5-hexahydrobenzo[e]pyrrolo[3,4-c]azepin-6(10bH)-one;
trans-2-methyl-8-phenethyl-1,2,3,3a,4,5-hexahydrobenzo[e]pyrrolo[3,4-c]azepin-6(10bH)-one;
trans-methyl 2-methyl-6-oxo-1,2,3,3a,4,5,6,10b-octahydrobenzo[e]pyrrolo[3,4-c]azepine-8-carboxylate;
trans-10-fluoro-2-methyl-1,2,3,3a,4,5-hexahydrobenzo[e]pyrrolo[3,4-c]azepin-6(10bH)-one;
trans-9-fluoro-2-methyl-1,2,3,3a,4,5-hexahydrobenzo[e]pyrrolo[3,4-c]azepin-6(10bH)-one;
trans-8-fluoro-2-methyl-1,2,3,3a,4,5-hexahydrobenzo[e]pyrrolo[3,4-c]azepin-6(10bH)-one;
trans-7-fluoro-2-methyl-1,2,3,3a,4,5-hexahydrobenzo[e]pyrrolo[3,4-c]azepin-6(10bH)-one;
trans-2-benzyl-8,10-dimethoxy-1,2,3,3a,4,5-hexahydrobenzo[c]pyrrolo[3,4-e]azepin-6(10bH)-one;
trans-8,10-dimethoxy-1,2,3,3a,4,5-hexahydrobenzo[c]pyrrolo[3,4-e]azepin-6(10bH)-one;
trans-2-benzyl-7-(trifluoromethoxy)-1,2,3,3a,4,5-hexahydrobenzo[c]pyrrolo[3,4-e]azepin-6(10bH)-one;
trans-7-(trifluoromethoxy)-1,2,3,3a,4,5-hexahydrobenzo[c]pyrrolo[3,4-e]azepin-6(10bH)-one;
(3aS,10bS)-2-benzyl-8,10-difluoro-1,2,3,3a,4,5-hexahydrobenzo[c]pyrrolo[3,4-e]azepin-6(10bH)-one;
(3aR,10bS)-8,10-difluoro-1,2,3,3a,4,5-hexahydrobenzo[c]pyrrolo[3,4-e]azepin-6(10bH)-one;
trans-2-methyl-7-(trifluoromethoxy)-1,2,3,3a,4,5-hexahydrobenzo[c]pyrrolo[3,4-e]azepin-6(10bH)-one;
(3aR,10bR)-2-methyl-7-(trifluoromethoxy)-1,2,3,3a,4,5-hexahydrobenzo[c]pyrrolo[3,4-e]azepin-6(10bH)-one;
(3aS,10bS)-2-methyl-7-(trifluoromethoxy)-1,2,3,3a,4,5-hexahydrobenzo[c]pyrrolo[3,4-e]azepin-6(10bH)-one;
trans-2-methyl-7-phenyl-1,2,3,3a,4,5-hexahydrobenzo[c]pyrrolo[3,4-e]azepin-6(10bH)-one;
(3aS,10bS)-8-(4-fluorophenyl)-2-methyl-1,2,3,3a,4,5-hexahydrobenzo[e]pyrrolo[3,4-c]azepin-6(10bH)-one;
(3aR,10bR)-8-(4-fluorophenyl)-2-methyl-1,2,3,3a,4,5-hexahydrobenzo[e]pyrrolo[3,4-c]azepin-6(10bH)-one;
trans-2-benzyl-8-hydroxy-1,2,3,3a,4,5-hexahydrobenzo[e]pyrrolo[3,4-c]azepin-6(10bH)-one;
trans-2-benzyl-8-((R)-1-phenylpropan-2-yloxy)-1,2,3,3a,4,5-hexahydrobenzo[e]pyrrolo[3,4-c]azepin-6(10bH)-one;
trans-2-benzyl-8-(3-fluorophenethoxy)-1,2,3,3a,4,5-hexahydrobenzo[e]pyrrolo[3,4-c]azepin-6(10bH)-one;
trans-2-benzyl-8-((S)-1-phenylpropan-2-yloxy)-1,2,3,3a,4,5-hexahydrobenzo[e]pyrrolo[3,4-c]azepin-6(10bH)-one;
trans-2-benzyl-8-phenethoxy-1,2,3,3a,4,5-hexahydrobenzo[e]pyrrolo[3,4-c]azepin-6(10bH)-one;
trans-2-methyl-8-(piperidine-1-carbonyl)-1,2,3,3a,4,5-hexahydrobenzo[e]pyrrolo[3,4-c]azepin-6(10bH)-one;
trans-8-phenethoxy-1,2,3,3a,4,5-hexahydrobenzo[e]pyrrolo[3,4-c]azepin-6(10bH)-one;
trans-8-(3-fluorophenethoxy)-1,2,3,3a,4,5-hexahydrobenzo[e]pyrrolo[3,4-c]azepin-6(10bH)-one;
trans-N,2-dimethyl-6-oxo-1,2,3,3a,4,5,6,10b-octahydrobenzo[e]pyrrolo[3,4-c]azepine-8-carboxamide;
trans-2-methyl-6-oxo-N-phenethyl-1,2,3,3a,4,5,6,10b-octahydrobenzo[e]pyrrolo[3,4-c]azepine-8-carboxamide;

trans-2-methyl-6-oxo-N-(3-(trifluoromethyl)phenethyl)-1,2,3,3a,4,5,6,10b-octahydrobenzo[e]pyrrolo[3,4-c]azepine-8-carboxamide;
trans-2-methyl-6-oxo-N-phenyl-1,2,3,3a,4,5,6,10b-octahydrobenzo[e]pyrrolo[3,4-c]azepine-8-carboxamide;
trans-methyl 2-benzyl-6-oxo-1,2,3,3a,4,5,6,10b-octahydrobenzo[e]pyrrolo[3,4-c]azepine-8-carboxylate;
cis-2-benzyl-8-methoxy-1,2,3,3a,4,5-hexahydrobenzo[e]pyrrolo[3,4-c]azepin-6(10bH)-one;
trans-8-(4-methoxyphenyl)-2-methyl-1,2,3,3a,4,5-hexahydrobenzo[e]pyrrolo[3,4-c]azepin-6(10bH)-one;
trans-2-methyl-8-(3-(trifluoromethoxy)phenyl)-1,2,3,3a,4,5-hexahydrobenzo[e]pyrrolo[3,4-c]azepin-6(10bH)-one;
trans-8-(3-methoxyphenyl)-2-methyl-1,2,3,3a,4,5-hexahydrobenzo[e]pyrrolo[3,4-c]azepin-6(10bH)-one;
trans-8-(3-isobutoxyphenyl)-2-methyl-1,2,3,3a,4,5-hexahydrobenzo[e]pyrrolo[3,4-c]azepin-6(10bH)-one;
cis-8-methoxy-1,2,3,3a,4,5-hexahydrobenzo[e]pyrrolo[3,4-c]azepin-6(10bH)-one;
trans-2-benzyl-8-(1,3,4-oxadiazol-2-yl)-1,2,3,3a,4,5-hexahydrobenzo[e]pyrrolo[3,4-c]azepin-6(10bH)-one;
trans-8-(2-methoxyphenyl)-2-methyl-1,2,3,3a,4,5-hexahydrobenzo[e]pyrrolo[3,4-c]azepin-6(10bH)-one;
trans-8-(4-isopropylphenyl)-2-methyl-1,2,3,3a,4,5-hexahydrobenzo[e]pyrrolo[3,4-c]azepin-6(10bH)-one;
trans-8-(4-ethylphenyl)-2-methyl-1,2,3,3a,4,5-hexahydrobenzo[e]pyrrolo[3,4-c]azepin-6(10bH)-one;
trans-2-methyl-8-(4-(trifluoromethoxy)phenyl)-1,2,3,3a,4,5-hexahydrobenzo[e]pyrrolo[3,4-c]azepin-6 (10bH)-one;
trans-8-amino-2-benzyl-1,2,3,3a,4,5-hexahydrobenzo[e]pyrrolo[3,4-c]azepin-6(10bH)-one;
cis-8-amino-2-benzyl-1,2,3,3a,4,5-hexahydrobenzo[e]pyrrolo[3,4-c]azepin-6(10bH)-one;
trans-2-methyl-8-(pyridin-3-yl)-1,2,3,3a,4,5-hexahydrobenzo[e]pyrrolo[3,4-c]azepin-6(10bH)-one;
trans-8-amino-1,2,3,3a,4,5-hexahydrobenzo[e]pyrrolo[3,4-c]azepin-6(10bH)-one;
cis-8-amino-1,2,3,3a,4,5-hexahydrobenzo[e]pyrrolo[3,4-c]azepin-6(10bH)-one;
trans-8-(3-fluorobenzyloxy)-1,2,3,3a,4,5-hexahydrobenzo[e]pyrrolo[3,4-c]azepin-6(10bH)-one;
trans-8-(2-fluorobenzyloxy)-1,2,3,3a,4,5-hexahydrobenzo[e]pyrrolo[3,4-c]azepin-6(10bH)-one;
trans-8-(2-(trifluoromethyl)benzyloxy)-1,2,3,3a,4,5-hexahydrobenzo[e]pyrrolo[3,4-c]azepin-6(10bH)-one;
trans-8-((S)-1-phenylpropan-2-yloxy)-1,2,3,3a,4,5-hexahydrobenzo[e]pyrrolo[3,4-c]azepin-6(10bH)-one;
trans-8-((R)-1-phenylethoxy)-1,2,3,3a,4,5-hexahydrobenzo[e]pyrrolo[3,4-c]azepin-6(10bH)-one;
trans-8-((S)-1-phenylethoxy)-1,2,3,3a,4,5-hexahydrobenzo[e]pyrrolo[3,4-c]azepin-6(10bH)-one;
trans-8-((R)-1-phenylpropan-2-yloxy)-1,2,3,3a,4,5-hexahydrobenzo[e]pyrrolo[3,4-c]azepin-6(10bH)-one;
(3aS,10bS)-8-(4-methoxyphenyl)-2-methyl-1,2,3,3a,4,5-hexahydrobenzo[e]pyrrolo[3,4-c]azepin-6(10bH)-one;
(3aR,10bR)-8-(4-methoxyphenyl)-2-methyl-1,2,3,3a,4,5-hexahydrobenzo[e]pyrrolo[3,4-c]azepin-6(10bH)-one;
(3aS,10 bS)-8-(3-methoxyphenyl)-2-methyl-1,2,3,3a,4,5-hexahydrobenzo[e]pyrrolo[3,4-c]azepin-6(10bH)-one;
(3aR,10bR)-8-(3-methoxyphenyl)-2-methyl-1,2,3,3a,4,5-hexahydrobenzo[e]pyrrolo[3,4-c]azepin-6(10bH)-one;
(3aS,10bS)-8,10-difluoro-2-methyl-1,2,3,3a,4,5-hexahydrobenzo[e]pyrrolo[3,4-c]azepin-6(10bH)-one;
(3aR,10bS)-8-fluoro-2,5-dimethyl-1,2,3,3a,4,5-hexahydrobenzo[e]pyrrolo[3,4-c]azepin-6(10bH)-one;
trans-8-(2-fluorobenzyloxy)-2-methyl-1,2,3,3a,4,5-hexahydrobenzo[e]pyrrolo[3,4-c]azepin-6(10bH)-one;
trans-8-sec-butoxy-1,2,3,3a,4,5-hexahydrobenzo[e]pyrrolo[3,4-c]azepin-6(10bH)-one;
trans-8-isobutoxy-1,2,3,3a,4,5-hexahydrobenzo[e]pyrrolo[3,4-c]azepin-6(10bH)-one;
trans-8-(cyclohexylmethoxy)-1,2,3,3a,4,5-hexahydrobenzo[e]pyrrolo[3,4-c]azepin-6(10bH)-one;
trans-8-(2,6-difluorobenzyloxy)-1,2,3,3a,4,5-hexahydrobenzo[e]pyrrolo[3,4-c]azepin-6(10bH)-one;
trans-8-(isopentyloxy)-1,2,3,3a,4,5-hexahydrobenzo[e]pyrrolo[3,4-c]azepin-6(10bH)-one;
trans-8-sec-butoxy-2-methyl-1,2,3,3a,4,5-hexahydrobenzo[e]pyrrolo[3,4-c]azepin-6(10bH)-one;
trans-8-(isopentyloxy)-2-methyl-1,2,3,3a,4,5-hexahydrobenzo[e]pyrrolo[3,4-c]azepin-6(10bH)-one;
trans-8-isobutoxy-2-methyl-1,2,3,3a,4,5-hexahydrobenzo[e]pyrrolo[3,4-c]azepin-6(10bH)-one;
trans-8-(2-methoxyphenethoxy)-1,2,3,3a,4,5-hexahydrobenzo[e]pyrrolo[3,4-c]azepin-6(10bH)-one;
trans-8-(3-methoxyphenethoxy)-1,2,3,3a,4,5-hexahydrobenzo[e]pyrrolo[3,4-c]azepin-6(10bH)-one;
trans-8-(4-methoxyphenethoxy)-1,2,3,3a,4,5-hexahydrobenzo[e]pyrrolo[3,4-c]azepin-6(10bH)-one;
trans-8-(cyclohexylmethoxy)-2-methyl-1,2,3,3a,4,5-hexahydrobenzo[e]pyrrolo[3,4-c]azepin-6(10bH)-one;
trans-8-(pyridin-4-yl)-1,2,3,3a,4,5-hexahydrobenzo[e]pyrrolo[3,4-c]azepin-6(10bH)-one;
trans-8-(2-methoxypyrimidin-5-yl)-1,2,3,3a,4,5-hexahydrobenzo[e]pyrrolo[3,4-c]azepin-6(10bH)-one;
(3aR,10bS)-8-(2-fluorobenzyloxy)-1,2,3,3a,4,5-hexahydrobenzo[e]pyrrolo[3,4-c]azepin-6(10bH)-one;
(3aS,10bR)-8-(2-fluorobenzyloxy)-1,2,3,3a,4,5-hexahydrobenzo[e]pyrrolo[3,4-c]azepin-6(10bH)-one;
(3aR,10bS)-8-((R)-1-phenylpropan-2-yloxy)-1,2,3,3a,4,5-hexahydrobenzo[e]pyrrolo[3,4-c]azepin-6(10bH)-one;
(3aS,10bR)-8-((R)-1-phenylpropan-2-yloxy)-1,2,3,3a,4,5-hexahydrobenzo[e]pyrrolo[3,4-c]azepin-6(10bH)-one;
trans-8-(2-methoxyphenethoxy)-2-methyl-1,2,3,3a,4,5-hexahydrobenzo[e]pyrrolo[3,4-c]azepin-6(10bH)-one;
trans-8-(thiophen-3-yl)-1,2,3,3a,4,5-hexahydrobenzo[e]pyrrolo[3,4-c]azepin-6 (10bH)-one;
trans-2-methyl-8-(3-(1,1,1-trifluoro-2-hydroxypropan-2-yl)phenyl)-1,2,3,3a,4,5-hexahydrobenzo[e]pyrrolo[3,4-c]azepin-6 (10bH)-one;
trans-8-(3-(2-hydroxypropan-2-yl)phenyl)-2-methyl-1,2,3,3a,4,5-hexahydrobenzo[e]pyrrolo[3,4-c]azepin-6 (10bH)-one;
trans-8-(3-acetylphenyl)-5-methyl-1,2,3,3a,4,5-hexahydrobenzo[e]pyrrolo[3,4-c]azepin-6(10bH)-one;
trans-8-methoxy-5-methyl-1,2,3,3a,4,5-hexahydrobenzo[e]pyrrolo[3,4-c]azepin-6(10bH)-one;
trans-8-(3-(2-hydroxyethyl)phenyl)-5-methyl-1,2,3,3a,4,5-hexahydrobenzo[e]pyrrolo[3,4-c]azepin-6(10bH)-one;
trans-8-methoxy-2,5-dimethyl-1,2,3,3a,4,5-hexahydrobenzo[e]pyrrolo[3,4-c]azepin-6(10bH)-one;
trans-8-(3-acetylphenyl)-2,5-dimethyl-1,2,3,3a,4,5-hexahydrobenzo[e]pyrrolo[3,4-c]azepin-6(10bH)-one;
trans-8-(3-(2-hydroxyethyl)phenyl)-2,5-dimethyl-1,2,3,3a,4,5-hexahydrobenzo[e]pyrrolo[3,4-c]azepin-6 (10bH)-one;
trans-8-(3-(1-hydroxyethyl)phenyl)-2,5-dimethyl-1,2,3,3a,4,5-hexahydrobenzo[e]pyrrolo[3,4-c]azepin-6 (10bH)-one;

trans-8-(3-(2-hydroxypropan-2-yl)phenyl)-2,5-dimethyl-1,2,3,3a,4,5-hexahydrobenzo[e]pyrrolo[3,4-c]azepin-6(10bH)-one;
trans-8-(benzo[e][1,2,5]oxadiazol-5-yl)-2-methyl-1,2,3,3a,4,5-hexahydrobenzo[e]pyrrolo[3,4-c]azepin-6(10bH)-one;
trans-8-isopropyl-2-methyl-1,2,3,3a,4,5-hexahydrobenzo[e]pyrrolo[3,4-c]azepin-6(10bH)-one;
trans-2-methyl-8-(2-methylprop-1-enyl)-1,2,3,3a,4,5-hexahydrobenzo[e]pyrrolo[3,4-c]azepin-6(10bH)-one;
trans-3-(2-methyl-6-oxo-1,2,3,3a,4,5,6,10b-octahydrobenzo[e]pyrrolo[3,4-c]azepin-8-yl)benzaldehyde;
(3aS,10bS)-8-chloro-2-methyl-1,2,3,3a,4,5-hexahydrobenzo[e]pyrrolo[3,4-c]azepin-6(10bH)-one;
(3aS,10bS)-8-hydroxy-2-methyl-1,2,3,3a,4,5-hexahydrobenzo[e]pyrrolo[3,4-c]azepin-6(10bH)-one;
trans-8-cyclopentenyl-2-methyl-1,2,3,3a,4,5-hexahydrobenzo[e]pyrrolo[3,4-c]azepin-6(10bH)-one;
trans-2-methyl-8-(3,3,3-trifluoroprop-1-en-2-yl)-1,2,3,3a,4,5-hexahydrobenzo[e]pyrrolo[3,4-c]azepin-6(10bH)-one;
trans-2-methyl-8-(5-methylfuran-2-yl)-1,2,3,3a,4,5-hexahydrobenzo[e]pyrrolo[3,4-c]azepin-6(10bH)-one;
trans-8-cyclohexyl-2-methyl-1,2,3,3a,4,5-hexahydrobenzo[e]pyrrolo[3,4-c]azepin-6(10bH)-one;
trans-8-cyclopentyl-2-methyl-1,2,3,3a,4,5-hexahydrobenzo[e]pyrrolo[3,4-c]azepin-6(10bH)-one;
(3aS,10bS)-8-(3-fluorobenzyloxy)-2-methyl-1,2,3,3a,4,5-hexahydrobenzo[e]pyrrolo[3,4-c]azepin-6(10bH)-one;
(3aS,10bS)-8-(2-fluorobenzyloxy)-2-methyl-1,2,3,3a,4,5-hexahydrobenzo[e]pyrrolo[3,4-c]azepin-6(10bH)-one;
(3aS,10bS)-8-(3,5-difluorobenzyloxy)-2-methyl-1,2,3,3a,4,5-hexahydrobenzo[e]pyrrolo[3,4-c]azepin-6(10bH)-one;
3aS,10bS)-8-(2,6-difluorobenzyloxy)-2-methyl-1,2,3,3a,4,5-hexahydrobenzo[e]pyrrolo[3,4-c]azepin-6(10bH)-one;
(3aS,10bS)-8-(3,4-difluorobenzyloxy)-2-methyl-1,2,3,3a,4,5-hexahydrobenzo[e]pyrrolo[3,4-c]azepin-6(10bH)-one;
(3aS,10bS)-8-(4-fluorobenzyloxy)-2-methyl-1,2,3,3a,4,5-hexahydrobenzo[e]pyrrolo[3,4-c]azepin-6(10bH)-one;
(3aS,10bS)-8-(2,3-difluorobenzyloxy)-2-methyl-1,2,3,3a,4,5-hexahydrobenzo[e]pyrrolo[3,4-c]azepin-6(10bH)-one;
(3aS,10bS)-2-methyl-8-(2,3,6-trifluorobenzyloxy)-1,2,3,3a,4,5-hexahydrobenzo[e]pyrrolo[3,4-c]azepin-6(10bH)-one;
trans-8-(benzyloxy)-2-methyl-1,2,3,3a,4,5-hexahydrobenzo[c]pyrrolo[3,4-e]azepin-6(10bH)-one;
trans-8-(3-fluorobenzyloxy)-2-methyl-1,2,3,3a,4,5-hexahydrobenzo[c]pyrrolo[3,4-e]azepin-6(10bH)-one;
trans-2-benzyl-8-(4-fluorophenyl)-1,2,3,3a,4,5-hexahydrobenzo[e]pyrrolo[3,4-c]azepin-6(10bH)-one;
trans-8-(4-fluorophenyl)-1,2,3,3a,4,5-hexahydrobenzo[e]pyrrolo[3,4-c]azepin-6(10bH)-one;
(3aR,10bS)-8-(4-fluorophenyl)-1,2,3,3a,4,5-hexahydrobenzo[e]pyrrolo[3,4-c]azepin-6(10bH)-one;
(3aS,10bR)-8-(4-fluorophenyl)-1,2,3,3a,4,5-hexahydrobenzo[e]pyrrolo[3,4-c]azepin-6(10bH)-one;
trans-8-fluoro-5-methyl-1,2,3,3a,4,5-hexahydrobenzo[c]pyrrolo[3,4-e]azepin-6(10bH)-one;
(3aR,10bS)-8-fluoro-5-methyl-1,2,3,3a,4,5-hexahydrobenzo[c]pyrrolo[3,4-e]azepin-6(10bH)-one;
(3aS,10bR)-8-fluoro-5-methyl-1,2,3,3a,4,5-hexahydrobenzo[c]pyrrolo[3,4-e]azepin-6(10bH)-one;
trans-8-(3-(methylsulfonyl)phenyl)-1,2,3,3a,4,5-hexahydrobenzo[c]pyrrolo[3,4-e]azepin-6(10bH)-one;
(3aS,10bS)-2-methyl-8-(3-(methylsulfonyl)phenyl)-1,2,3,3a,4,5-hexahydrobenzo[c]pyrrolo[3,4-e]azepin-6(10bH)-one;
(3aR,10bR)-2-methyl-8-(3-(methylsulfonyl)phenyl)-1,2,3,3a,4,5-hexahydrobenzo[c]pyrrolo[3,4-e]azepin-6(10bH)-one;
N,N-dimethyl-3-(trans-6-oxo-1,2,3,3a,4,5,6,10b-octahydrobenzo[c]pyrrolo[3,4-e]azepin-8-yl)benzamide;
trans-8-(2-(methylsulfonyl)phenyl)-1,2,3,3a,4,5-hexahydrobenzo[c]pyrrolo[3,4-e]azepin-6(10bH)-one;
trans-2-methyl-8-(2-(methylsulfonyl)phenyl)-1,2,3,3a,4,5-hexahydrobenzo[c]pyrrolo[3,4-e]azepin-6(10bH)-one;
trans-8-(3-acetylphenyl)-1,2,3,3a,4,5-hexahydrobenzo[c]pyrrolo[3,4-e]azepin-6(10bH)-one hydrochloride;
trans-8-(3-acetylphenyl)-2-methyl-1,2,3,3a,4,5-hexahydrobenzo[c]pyrrolo[3,4-e]azepin-6(10bH)-one;
trans-8-(3-(1-hydroxyethyl)phenyl)-2-methyl-1,2,3,3a,4,5-hexahydrobenzo[c]pyrrolo[3,4-e]azepin-6(10bH)-one;
3-(trans-6-oxo-1,2,3,3a,4,5,6,10b-octahydrobenzo[c]pyrrolo[3,4-e]azepin-8-yl)benzonitrile;
3-(trans-2-methyl-6-oxo-1,2,3,3a,4,5,6,10b-octahydrobenzo[c]pyrrolo[3,4-e]azepin-8-yl)benzonitrile;
trans-8-(3,6-dihydro-2H-pyran-4-yl)-1,2,3,3a,4,5-hexahydrobenzo[c]pyrrolo[3,4-e]azepin-6(10bH)-one;
trans-8-(3,6-dihydro-2H-pyran-4-yl)-2-methyl-1,2,3,3a,4,5-hexahydrobenzo[c]pyrrolo[3,4-e]azepin-6(10bH)-one;
trans-8-(4-fluorophenoxy)-2-methyl-1,2,3,3a,4,5-hexahydrobenzo[c]pyrrolo[3,4-e]azepin-6(10bH)-one;
trans-8-isobutyl-2-methyl-1,2,3,3a,4,5-hexahydrobenzo[e]pyrrolo[3,4-c]azepin-6(10bH)-one;
trans-8-(3,5-dimethylisoxazol-4-yl)-1,2,3,3a,4,5-hexahydrobenzo[e]pyrrolo[3,4-c]azepin-6(10bH)-one;
trans-8-(4,4-dimethylcyclohexyloxy)-1,2,3,3a,4,5-hexahydrobenzo[e]pyrrolo[3,4-c]azepin-6(10bH)-one;
trans-8-(3-oxo-2,3-dihydro-1H-inden-5-yl)-1,2,3,3a,4,5-hexahydrobenzo[c]pyrrolo[3,4-e]azepin-6(10bH)-one;
(3aS,10bS)-8-(3-((S)-1-hydroxyethyl)phenyl)-2-methyl-1,2,3,3a,4,5-hexahydrobenzo[e]pyrrolo[3,4-c]azepin-6(10bH)-one;
(3aS,10bS)-8-(3-((R)-1-hydroxyethyl)phenyl)-2-methyl-1,2,3,3a,4,5-hexahydrobenzo[e]pyrrolo[3,4-c]azepin-6(10bH)-one;
trans-8-(3-(ethylsulfonyl)phenyl)-1,2,3,3a,4,5-hexahydrobenzo[c]pyrrolo[3,4-e]azepin-6(10bH)-one;
trans-2-methyl-8-(3-oxo-2,3-dihydro-1H-inden-5-yl)-1,2,3,3a,4,5-hexahydrobenzo[c]pyrrolo[3,4-e]azepin-6(10bH)-one;
trans-8-(3-(2-hydroxyethyl)phenyl)-1,2,3,3a,4,5-hexahydrobenzo[c]pyrrolo[3,4-e]azepin-6(10bH)-one;
trans-8-(3-(2-hydroxyethyl)phenyl)-2-methyl-1,2,3,3a,4,5-hexahydrobenzo[c]pyrrolo[3,4-e]azepin-6(10bH)-one;
trans-8-(3-(ethylsulfonyl)phenyl)-2-methyl-1,2,3,3a,4,5-hexahydrobenzo[c]pyrrolo[3,4-e]azepin-6(10bH)-one;
trans-8-(tetrahydro-2H-pyran-4-yl)-1,2,3,3a,4,5-hexahydrobenzo[c]pyrrolo[3,4-e]azepin-6(10bH)-one;
trans-2-methyl-8-(tetrahydro-2H-pyran-4-yl)-1,2,3,3a,4,5-hexahydrobenzo[c]pyrrolo[3,4-e]azepin-6(10bH)-one;

(3aS,10bS)-8-(benzyloxy)-2-methyl-1,2,3,3a,4,5-hexahydrobenzo[e]pyrrolo[3,4-c]azepin-6(10bH)-one;

(3aS,10bS)-8-(2-methoxyphenyl)-2-methyl-1,2,3,3a,4,5-hexahydrobenzo[e]pyrrolo[3,4-c]azepin-6 (10bH)-one;

trans-8-(2,6-difluorophenyl)-1,2,3,3a,4,5-hexahydrobenzo[e]pyrrolo[3,4-c]azepin-6(10bH)-one;

(3aS,10bS)-8-(cyclopropylmethoxy)-2-methyl-1,2,3,3a,4,5-hexahydrobenzo[e]pyrrolo[3,4-c]azepin-6 (10bH)-one;

(3aS,10bS)-8-(3-acetylphenyl)-2-methyl-1,2,3,3a,4,5-hexahydrobenzo[e]pyrrolo[3,4-c]azepin-6(10bH)-one; and cis-8-fluoro-9-methyl-1,2,3,3a,4,5-hexahydrobenzo[c]pyrrolo[3,4-e]azepin-6(10bH)-one;

or a pharmaceutically acceptable salt thereof.

5. The compound according to claim 1 of formula (Ia):

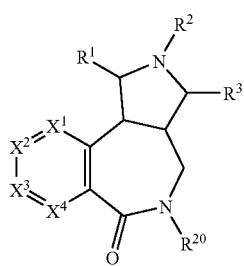

(Ia)

or a pharmaceutically acceptable salt thereof, wherein R$^{20}$ is hydrogen or alkyl.

6. The compound according to claim 5, wherein
R$^1$ and R$^3$ are hydrogen; and
R$^2$ is hydrogen, alkyl, haloalkyl, —(CR$^{4a}$R$^{5a}$)$_m$-G$^1$ or —(CR$^{4a}$R$^{5a}$)$_m$-G$_2$.

7. A method for treating conditions, disorders or deficits modulated by a 5-HT$_{2C}$ receptor, a 5-HT$_6$ receptor or both 5-HT$_{2C}$ and 5-HT$_6$ receptors wherein the condition, disorder or deficit is selected from the group consisting of a cognitive dysfunction, attention deficit/hyperactivity syndrome, personality disorders, affective disorders, motion or motor disorders, migraine, sleep disorders, feeding disorders, gastrointestinal disorders, diseases associated with neurodegeneration, obesity, diabetes, psoriasis, and ocular hypertension, the method comprising administration of a therapeutically effective amount of the compound of claim 4, or a pharmaceutically acceptable salt thereof.

8. A method for treating a disorder or condition modulated by the 5-HT$_2$ receptor selected from the group consisting of bipolar disorder, depression, anxiety, schizophrenia, cognitive deficits of schizophrenia, obsessive compulsive disorder, migraine, epilepsy, eating disorders, obesity, diabetes, sexual dysfunction/erectile dysfunction, sleep disorders, psoriasis, Parkinson's disease, pain and spinal cord injury, pain, bladder dysfunction/urinary incontinence, smoking cessation, ocular hypertension, and Alzheimer's disease, said method comprising the step of administering to a subject in need thereof the compound of claim 4, or a pharmaceutically acceptable salt thereof.

9. The method according to claim 8 wherein the disorder modulated by the 5-HT$_2$ receptor is schizophrenia or cognitive deficits of schizophrenia.

10. A method for treating a disorder modulated by the 5-HT$_6$ receptor selected from the group consisting of deficits in memory and cognition and learning, Alzheimer's disease, age-related cognitive decline, mild cognitive impairment, attention deficit/hyperactivity syndrome, schizophrenia, cognitive deficits of schizophrenia, depression, anxiety, obsessive compulsive disorders, Parkinson's disease, epilepsy, migraine, sleep disorders, anorexia, bulimia, irritable bowel syndrome, stroke, spinal or head trauma and head injuries, and obesity, said method comprising the step of administering to a subject in need thereof the compound of claim 4, or a pharmaceutically acceptable salt thereof.

11. A pharmaceutical composition comprising a therapeutically effective amount of the compound of claim 4, or a pharmaceutically acceptable salt thereof, in combination with one or more pharmaceutically acceptable carriers.

12. A process for making (3aS,10bS)-8-chloro-2-methyl-1,2,3,3a,4,5-hexahydrobenzo[e]pyrrolo[3,4-c]azepin-6 (10bH)-one dibenzyoyl-D-tartrate comprising:
   (a) combining dibenzoyl-D-tartaric acid (1.05 equivalents) and methanol;
   (b) adding a solution of trans-8-chloro-2-methyl-1,2,3,3a,4,5-hexahydrobenzo[e]pyrrolo[3,4-c]azepin-6(10bH)-one (0.10-0.15 equivalents) in methanol;
   (c) seeding the solution with (3aS,10bS)-8-chloro-2-methyl-1,2,3,3a,4,5-hexahydrobenzo[e]pyrrolo[3,4-c]azepin-6(10bH)-one which are obtained in smaller batches of the same sequence iteratively increasing the enantiomeric excess in successive passage;
   (d) slowly adding additional trans-8-chloro-2-methyl-1,2,3,3a,4,5-hexahydrobenzo[e]pyrrolo[3,4-c]azepin-6 (10bH)-one (0.85-0.90 equivalents) dissolved in methanol; and
   (e) stirring the resultant mixture for a period of time resulting in crystallization and isolating the crystalline (3aS,10bS)-8-chloro-2-methyl-1,2,3,3a,4,5-hexahydrobenzo [e]pyrrolo[3,4-c]azepin-6(10bH)-one dibenzyoyl-D-tartrate.

13. A process for making (3aS,10bS)-8-hydroxy-2-methyl-1,2,3,3a,4,5-hexahydrobenzo[e]pyrrolo[3,4-c]azepin-6 (10bH)-one comprising:
   (a) combining palladium(II) acetate (0.04 equivalents), 2-di-tert-butylphosphino-3,4,5,6-tetramethyl-2',4',6'-triisopropyl-1,1'-biphenyl (0.05 equivalents), cesium carbonate (1.5 equivalents) and (3aS,10bS)-8-chloro-2-methyl-1,2,3,3a,4,5-hexahydrobenzo[e]pyrrolo[3,4-c]azepin-6(10bH)-one (1 equivalent);
   (b) adding a solution of benzyl alcohol (20 equivalents) in toluene to the mixture of palladium(II) acetate, 2-di-tert-butylphosphino-3,4,5,6-tetramethyl-2',4',6'-triisopropyl-1,1'-biphenyl, cesium carbonate and (3aS,10bS)-8-chloro-2-methyl-1,2,3,3a,4,5-hexahydrobenzo[e] pyrrolo[3,4-c]azepin-6(10bH)-one;
   (c) isolating the (3aS,10bS)-8-(benzyloxy)-2-methyl-1,2,3,3a,4,5-hexahydrobenzo[e]pyrrolo[3,4-c]azepin-6 (10bH)-one;
   (d) hydrogenating (3aS,10bS)-8-(benzyloxy)-2-methyl-1,2,3,3a,4,5-hexahydrobenzo[e]pyrrolo[3,4-c]azepin-6 (10bH)-one to generate (3aS,10bS)-8-hydroxy-2-methyl-1,2,3,3a,4,5-hexahydrobenzo [e]pyrrolo[3,4-c]azepin-6(10bH)-one; and
   (e) isolating the (3aS,10bS)-8-hydroxy-2-methyl-1,2,3,3a,4,5-hexahydrobenzo[e]pyrrolo[3,4-c]azepin-6(10bH)-one.

* * * * *